(12) United States Patent
Hamel et al.

(10) Patent No.: US 7,074,415 B2
(45) Date of Patent: Jul. 11, 2006

(54) STREPTOCOCCUS ANTIGENS

(75) Inventors: Josée Hamel, Quebec (CA); Catherine Ouellet, Quebec (CA); Nathalie Charland, Quebec (CA); Denis Martin, Quebec (CA); Bernard Brodeur, Quebec (CA)

(73) Assignee: ID Biomedical Corporation, Vancouver (*) Notice: Subject to any disclaimer, the term of this patent is extended or adjusted under 35 U.S.C. 154(b) by 0 days.

(21) Appl. No.: 09/884,465

(22) Filed: Jun. 20, 2001

(65) Prior Publication Data
US 2003/0077293 A1 Apr. 24, 2003

Related U.S. Application Data

(60) Provisional application No. 60/212,683, filed on Jun. 20, 2000.

(51) Int. Cl.
A61K 39/09 (2006.01)
A61K 39/02 (2006.01)
A61K 38/00 (2006.01)
A61K 21/08 (2006.01)

(52) U.S. Cl. .................. 424/244.1; 424/234.1; 530/300; 530/305; 530/324; 530/325

(58) Field of Classification Search .......... 424/234.1, 424/244.1; 530/300, 305, 324, 325
See application file for complete search history.

(56) References Cited

U.S. PATENT DOCUMENTS

| 6,582,706 B1 | 6/2003 | Johnson et al. |
| 6,800,744 B1 | 10/2004 | Doucette-Stamm et al. |
| 2003/0232976 A1 | 12/2003 | Hamel et al. |
| 2004/0081662 A1 | 4/2004 | Hermand et al. |

FOREIGN PATENT DOCUMENTS

| WO | WO/98/18930 | | 5/1998 |
| WO | WO 98/18930 | * | 5/1998 |
| WO | WO/98/18931 | | 5/1998 |
| WO | WO/99/15675 | | 4/1999 |
| WO | WO00/06737 | | 2/2000 |
| WO | WO00/06738 | | 2/2000 |
| WO | WO00/17370 | | 3/2000 |
| WO | 00/37105 | | 6/2000 |
| WO | WO00/39299 | | 7/2000 |
| WO | 00/76540 A2 | | 12/2000 |
| WO | 01/14421 A1 | | 3/2001 |
| WO | WO01/98334 | | 12/2001 |
| WO | WO02/077021 | | 10/2002 |
| WO | WO04/09229 | | 10/2004 |

OTHER PUBLICATIONS

Orihuela et al, Scandinavian Journal of Infectious Diseases, Vo. 35, No. 9, 2003, p. 647-652.*
Whittam et al, Current Opinion in Genetics and Development, Dec. 2002, vol. 12, No. 6.*
Sa-Leao et al, Abstracts of the General Meeting of the American Society for Microbiology, May 20-24, 20.*
Thomas E. Creighton, in his book, "Proteins: Structures and Molecular Properties, 1984", (p. 315).*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second paragraph.*
Oli et al (Infection and Immunity, Dec. 2004, p. 6951-6960).*
Ellis (Vaccines, W.B. Saunders Company, Chapter 29, 1988, pp. 568-574).*
Boslego et al (Vaccines and Immunotherapy, 1991, Chapter 17).*
Swildens et al (Veterinary Microbiology 103, 2004, 29-33).*
Bolton et al (Can J. Microbiol., Jun. 2004, 50(6):423-32). (Abstract only).*
Okamoto et al (Vaccine 22 (2004) 2887-2893).*
Boslego et al. "Vaccines And Immunotherapy" Pergamon Press, 1991, Chapter 17, pp. 211-223.
Ellis, et al. "New Technologies for Making Vaccines," WB Sanders Co., 1988, Chapter 29, pp. 568-575.
Briles D.E. et al, Immunization of Humans with Recombinant Pneumococcal Surface Protein A (rPsspA) Elicits Antibodies that Passively Protect Mice from Fatal Infection with Streptococcus pneumoniae bearing Heterologous PspA J Infectious Disease 182 (Dec. 2000) 1694-1701.
Briles, D.E. et al, Intranasal Immunization of Mice with a Mixture of the Pneumococcal Proteins PsaA and PspA is Highly Protective against Nasopharyngeal Carriage of Streptococcus pneumoniae Infection & Immunity vol. 68 No. 2 (Feb. 2000) p796-800.
Gregor Z. et al, Detection of 23 Immunogenic Pneumococcal Proteins Using Convalescent-Phase Serum Infection & Immunity vol. 68 No. 6 (Jun. 2000) p3740-43 (exact publication date not available).
"Comparison of D1 (Seq ID Nos: 56 and 66) with BVH-11 Seq ID Nos: 7 and 8 of the present invention".
Spellerberg, et al., "Lmb, a Protein with Similarities to the LraI Adhesin Family, Mediates Attachment of Streptococcus agalactiae to Human Laminin", Infection and Immunity, Feb. 1999, p. 871-878.

(Continued)

Primary Examiner—Nita Minnifield
Assistant Examiner—Vanessa L. Ford
(74) Attorney, Agent, or Firm—McDermott Will & Emery LLP

(57) ABSTRACT

Streptococcus polypeptides and polynucleotides encoding them are disclosed. The polypeptides may be useful vaccine components for the prophylaxis or therapy of streptococcus infection in animals. Also disclosed are recombinant methods of producing the protein antigens as well as diagnostic assays for detecting streptococcus bacterial infection.

6 Claims, 22 Drawing Sheets

OTHER PUBLICATIONS

Adamou, et al., "Identification and Characterization of a Novel Family of Pneumococcal Proteins That Are Protective Against Sepsis", Infection and Immunity, Feb. 2001, p. 949-958.

Wizermann, et al., "Use of a Whole Genome Approach to Identify Vaccine Molecules Affording Protection Against *Streptococcus pneumoniae* Infection", Infection and Immunity, Mar. 2001, p. 1593-1598.

Zhang, et al., "Recombinant PhpA Protein, a Unique Histidine Motif-Containing Protein from *Streptococcus pneumoniae*, Protects Mice against Intranasal Pneumococcal Challenge", Infection and Immunity, Jun. 2001, p. 3827-3836.

U.S. Appl. No. 09/471,255, filed Dec. 23, 1999, Josee Hamel et al.

U.S. Appl. No. 09/471,255, filed Dec. 23, 1999, Hamel et al.

Hernandez, et al., "Antigenicity of Chimeric Synthetic Peptides Based on HTLV-1 Antigens and the Impact of Epitope Orientation," Biochemical and Biophysical Research Communication. vol. 276. No. 3, pp. 1085-1088.

Partidos, et al., "The Influence of orientation and number of copies of T and B cell epitopes on the specificity and affinity of antibodies induced by chimeric peptides," Eur. J. Immunol 1992, 22: pp. 2675-2680.

Oishi, et al., "The effect of amino acid spacers on the antigenicity of dimeric peptide-inducing cross-reacting antibodies to a cell surface protein antigen of Streptococcus mutans," Oral Microbiol Immunol.2001: 16: pp. 40-44.

Kurstak, Edouard, Editorial "Recent progress in vaccines development and new trends in immunisation." Vaccine 19 (2001) pp. 2198-2200.

* cited by examiner

```
ATGAAATTTA GTAAAAAATA TATAGCAGCT GGATCAGCTG TTATCGTATC CTTGAGTCTA    60
TGTGCCTATG CACTAAACCA GCATCGTTCG CAGGAAAATA AGGACAATAA TCGTGTCTCT   120
TATGTGGATG GCAGCCAGTC AAGTCAGAAA AGTGAAAACT TGACACCAGA CCAGGTTAGC   180
CAGAAAGAAG GAATTCAGGC TGAGCAAATT GTAATCAAAA TTACAGATCA GGGCTATGTA   240
ACGTCACACG GTGACCACTA TCATTACTAT AATGGGAAAG TTCCTTATGA TGCCCTCTTT   300
AGTGAAGAAC TCTTGATGAA GGATCCAAAC TATCAACTTA AGACGCTGA TATTGTCAAT    360
GAAGTCAAGG GTGGTTATAT CATCAAGGTC GATGGAAAAT ATTATGTCTA CCTGAAAGAT   420
GCAGCTCATG CTGATAATGT TCGAACTAAA GATGAAATCA ATCGTCAAAA ACAAGAACAT   480
GTCAAGATA ATGAGAAGGT TAACTCTAAT GTTGCTGTAG CAAGGTCTCA GGGACGATAT    540
ACGACAAATG ATGGTTATGT CTTTAATCCA GCTGATATTA TCGAAGATAC GGGTAATGCT   600
TATATCGTTC CTCATGGAGG TCACTATCAC TACATTCCCA AAAGCGATTT ATCTGCTAGT   660
GAATTAGCAG CAGCTAAAGC ACATCTGGCT GGAAAAAATA TGCAACCGAG TCAGTTAAGC   720
TATTCTTCAA CAGCTAGTGA CAATAACACG CAATCTGTAG CAAAAGGATC AACTAGCAAG   780
CCAGCAAATA AATCTGAAAA TCTCCAGAGT CTTTTGAAGG AACTCTATGA TTCACCTAGC   840
GCCCAACGTT ACAGTGAATC AGATGGCCTG GTCTTTGACC CTGCTAAGAT TATCAGTCGT   900
ACACCAAATG GAGTTGCGAT TCCGCATGGC GACCATTACC ACTTTATTCC TTACAGCAAG   960
CTTTCTGCTT TAGAAGAAAA GATTGCCAGA ATGGTGCCTA TCAGTGGAAC TGGTTCTACA  1020
GTTTCTACAA ATGCAAAACC TAATGAAGTA GTGTCTAGTC TAGGCAGTCT TTCAAGCAAT  1080
CCTTCTTCTT TAACGACAAG TAAGGAGCTC TCTTCAGCAT CTGATGGTTA TATTTTTAAT  1140
CCAAAAGATA TCGTTGAAGA AACGGCTACA GCTTATATTG TAAGACATGG TGATCATTTC  1200
CATTACATTC CAAAATCAAA TCAAATTGGG CAACCGACTC TTCCAAACAA TAGTCTAGCA  1260
ACACCTTCTC CATCTCTTCC AATCAATCCA GGAACTTCAC ATGAGAAACA TGAAGAAGAT  1320
GGATACGGAT TTGATGCTAA TCGTATTATC GCTGAAGATG AATCAGGTTT TGTCATGAGT  1380
CACGGAGACC ACAATCATTA TTTCTTCAAG AAGGACTTGA CAGAAGAGCA AATTAAGGCT  1440
GCGCAAAAAC ATTTAGAGGA AGTTAAAACT AGTCATAATG GATTAGATTC TTTGTCATCT  1500
CATGAACAGG ATTATCCAGG TAATGCCAAA GAAATGAAAG ATTTAGATAA AAAAATCGAA  1560
GAAAAAATTG CTGGCATTAT GAAACAATAT GGTGTCAAAC GTGAAAGTAT TGTCGTGAAT  1620
AAAGAAAAAA ATGCGATTAT TTATCCGCAT GGAGATCACC ATCATGCAGA TCCGATTGAT  1680
GAACATAAAC CGGTTGGAAT TGGTCATTCT CACAGTAACT ATGAACTGTT TAAACCCGAA  1740
GAAGGAGTTG CTAAAAAAGA AGGGAATAAA GTTTATACTG GAGAAGAATT AACGAATGTT  1800
GTTAATTTGT TAAAAAATAG TACGTTTAAT AATCAAAACT TTACTCTAGC CAATGGTCAA  1860
AAACGCGTTT CTTTTAGTTT TCCGCCTGAA TTGGAGAAAA AATTAGGTAT CAATATGCTA  1920
GTAAAATTAA TAACACCAGA TGGAAAAGTA TTGGAGAAAG TATCTGGTAA AGTATTTGGA  1980
GAAGGAGTAG GGAATATTGC AAACTTTGAA TTAGATCAAC CTTATTTACC AGGACAAACA  2040
TTTAAGTATA CTATCGCTTC AAAAGATTAT CCAGAAGTAA GTTATGATGG TACATTTACA  2100
GTTCCAACCT CTTTAGCTTA CAAAATGGCC AGTCAAACGA TTTTCTATCC TTTCCATGCA  2160
GGGGATACTT ATTTAAGAGT GAACCCTCAA TTTGCAGTGC CTAAAGGAAC TGATGCTTTA  2220
GTCAGAGTGT TTGATGAATT TCATGGAAAT GCTTATTTAG AAAATAACTA TAAAGTTGGT  2280
GAAATCAAAT TACCGATTCC GAAATTAAAC CAAGGAACAA CCAGAACGGC CGGAAATAAA  2340
ATTCCTGTAA CCTTCATGGC AAATGCTTAT TTGGACAATC AATCGACTTA TATTGTGGAA  2400
GTACCTATCT TGGAAAAAGA AAATCAAACT GATAAACCAA GTATTCTACC ACAATTTAAA  2460
AGGAATAAAG CACAAGAAAA CTCAAAACTT GATGAAAGG TAGAAGAACC AAAGACTAGT   2520
GAGAAGGTAG AAAAAGAAAA ACTTTCTGAA ACTGGGAATA GTACTAGTAA TTCAACGTTA  2580
GAAGAAGTTC CTACAGTGGA TCCTGTACAA GAAAAAGTAG CAAAATTTGC TGAAAGTTAT  2640
GGGATGAAGC TAGAAAATGT CTTGTTTAAT ATGGACGGAA CAATTGAATT ATATTTACCA  2700
```

```
TCAGGAGAAG TCATTAAAAA GAATATGGCA GATTTTACAG GAGAAGCACC TCAAGGAAAT      2760
GGTGAAAATA AACCATCTGA AAATGGAAAA GTATCTACTG GAACAGTTGA GAACCAACCA      2820
ACAGAAAATA AACCAGCAGA TTCTTTACCA GAGGCACCAA ACGAAAAACC TGTAAAACCA      2880
GAAAACTCAA CGGATAATGG AATGTTGAAT CCAGAAGGGA ATGTGGGGAG TGACCCTATG      2940
TTAGATCCAG CATTAGAGGA AGCTCCAGCA GTAGATCCTG TACAAGAAAA ATTAGAAAAA      3000
TTTACAGCTA GTTACGGATT AGGCTTAGAT AGTGTTATAT TCAATATGGA TGGAACGATT      3060
GAATTAAGAT TGCCAAGTGG AGAAGTGATA AAAAGAATT TATCTGATTT CATAGCGTAA      3120
(SEQ ID NO: 1)
FIGURE 1

AATTCCTTGT CGGGTAAGTT CCGACCCGCA CGAAAGGCGT AATGATTTGG GCACTGTCTC        60
AACGAGAGAC TCGGTGAAAT TTTAGTACCT GTGAAGATGC AGGTTACCCG CGACAGGACG       120
GAAAGACCCC ATGGAGCTTT ACTGCAGTTT GATATTGAGT GTCTGTACCA CATGTACAGG       180
ATAGGTAGGA GTCTAAGAGA TCGGGACGCC AGTTTCGAAG GAGACGCTGT TGGGATACTA       240
CCCTTGTGTT ATGCCACTC TAACCCAGAT AGGTGATCCC TATCGGAGAC AGTGTCTGAC        300
GGGCAGTTTG ACTGGGGCGG TCGCCTCCTA AAAGGTAACG GAGGCGCCCA AAGGTTCCCT       360
CAGAATGGTT GGAAATCATT CGCAGAGTGT AAAGGTATAA GGGAGCTTGA CTGCGAGAGC       420
TACAACTCGA GCAGGGACGA AAGTCGGGCT TAGTGATCCG GTGGTTCCGT ATGGAAGGGC       480
CATCGCTCAA CGGATAAAAG CTACCCTGGG GATAACAGGC TTATCTCCCC CAAGAGTTCA       540
CATCGACGGG GAGGTTTGGC ACCTCGATGT CGGCTCGTCG CATCCTGGGG CTGTAGTCGG       600
TCCCAAGGGT TGGGCTGTTC GCCCATTAAA GCGGCACGCG AGCTGGGTTC AGAACGTCGT       660
GAGACAGTTC GGTCCCTATC CGTCGCGGGC GTAGGAAATT TGAGAGGATC TGCTCCTAGT       720
ACGAGAGGAC CAGAGTGGAC TTACCGCTGG TGTACCAGTT GTCTTGCCAA AGGCATCGCT       780
GGGTAGCTAT GTAGGGAAGG GATAAACGCT GAAAGCATCT AAGTGTGAAA CCCACCTCAA       840
GATGAGATTT CCCATGATTA TATATCAGTA AGAGCCCTGA GAGATGATCA GGTAGATAGG       900
TTAGAAGTGG AAGTGTGGCG ACACATGTAG CGGACTAATA CTAATAGCTC GAGGACTTAT       960
CCAAAGTAAC TGAGAATATG AAAGCGAACG GTTTTCTTAA ATTGAATAGA TATTCAATTT      1020
TGAGTAGGTA TTACTCAGAG TTAAGTGACG ATAGCCTAGG AGATACACCT GTACCCATGC      1080
CGAACACAGA AGTTAAGCCC TAGAACGCCG GAAGTAGTTG GGGGTTGCCC CCTGTGAGAT      1140
AGGGAAGTCG CTTAGCTCTA GGGAGTTTAG CTCAGCTGGG AGAGCATCTG CCTTACAAGC      1200
AGAGGGTCAG CGGTTCGATC CCGTTAACTC CCAAAGGTCC CGTAGTGTAG CGGTTATCAC      1260
GTCGCCCTGT CACGGCGAAG ATCGCGGGTT CGATTCCCGT CGGGACCGTT TAAGGTAACG      1320
CAAGTTATTT TAGACTCGTT AGCTCAGTTG GTAGAGCAAT TGACTTTTAA TCAATGGGTC      1380
ACTGGTTCGA GCCCAGTACG GGTCATATAT GCGGGTTTGG CGGAATTCTA ATCTCTTTGA      1440
AATCATCTTC TCTCACTTTC CAAAACTCTA TTACCTCTTA TTATACCACA TTTCAATCTT      1500
CAACTTCCCA GTAATATAAG CACCTCTGGC GAAAGAAGTT TCAATGTCCT AAAGTAATAA      1560
GTGAATCCAA TTCAGGAACT CCAAGAACAA AAGAAACATC TGGTGTCACA AGTATTGGAT      1620
GGCACAGAGT CACGTGGTAG TCTGACCCTA GCAGAAATTT TAAATAGTAA ACTATTTACT      1680
GGTTAATTAA ATGGTTAAAT AACCGGTTTA GAAAACTATT TAATAAAGTA AAGAAGTTG       1740
AGAAAAAACT TCATCATTTA TTGAAATGAG GGATTATGA AATTTAGTAA AAAATATATA       1800
GCAGCTGGAT CAGCTGTTAT CGTATCCTTG AGTCTATGTG CCTATGCACT AAACCAGCAT      1860
CGTTCGCAGG AAAATAAGGA CAATAATCGT GTCTCTTATG TGGATGGCAG CCAGTCAAGT      1920
CAGAAAAGTG AAAACTTCAC ACCAGACCAG GTTAGCCAGA AGAAGGAAT TCAGGCTGAG       1980
CAAATTGTAA TCAAAATTAC AGATCAGGGC TATGTAACGT CACACGGTGA CCACTATCAT      2040
```

| | | | | | |
|---|---|---|---|---|---|
| TACTATAATG | GGAAAGTTCC | TTATGATGCC | CTCTTTAGTG | AAGAACTCTT | GATGAAGGAT | 2100
| CCAAACTATC | AACTTAAAGA | CGCTGATATT | GTCAATGAAG | TCAAGGGTGG | TTATATCATC | 2160
| AAGGTCGATG | GAAAATATTA | TGTCTACCTG | AAAGATGCAG | CTCATGCTGA | TAATGTTCGA | 2220
| ACTAAAGATG | AAATCAATCG | TCAAAAACAA | GAACATGTCA | AAGATAATGA | GAAGGTTAAC | 2280
| TCTAATGTTG | CTGTAGCAAG | GTCTCAGGGA | CGATATACGA | CAAATGATGG | TTATGTCTTT | 2340
| AATCCAGCTG | ATATTATCGA | AGATACGGGT | AATGCTTATA | TCGTTCCTCA | TGGAGGTCAC | 2400
| TATCACTACA | TTCCCAAAAG | CGATTTATCT | GCTAGTGAAT | TAGCAGCAGC | TAAAGCACAT | 2460
| CTGGCTGGAA | AAAATATGCA | ACCGAGTCAG | TTAAGCTATT | CTTCAACAGC | TAGTGACAAT | 2520
| AACACGCAAT | CTGTAGCAAA | AGGATCAACT | AGCAAGCCAG | CAAATAAATC | TGAAAATCTC | 2580
| CAGAGTCTTT | TGAAGGAACT | CTATGATTCA | CCTAGCGCCC | AACGTTACAG | TGAATCAGAT | 2640
| GGCCTGGTCT | TTGACCCTGC | TAAGATTATC | AGTCGTACAC | CAAATGGAGT | TGCGATTCCG | 2700
| CATGGCGACC | ATTACCACTT | TATTCCTTAC | AGCAAGCTTT | CTGCTTTAGA | AGAAAAGATT | 2760
| GCCAGAATGG | TGCCTATCAG | TGGAACTGGT | TCTACAGTTT | CTACAAATGC | AAAACCTAAT | 2820
| GAAGTAGTGT | CTAGTCTAGG | CAGTCTTTCA | AGCAATCCTT | CTTCTTTAAC | GACAAGTAAG | 2880
| GAGCTCTCTT | CAGCATCTGA | TGGTTATATT | TTTAATCCAA | AAGATATCGT | TGAAGAAACG | 2940
| GCTACAGCTT | ATATTGTAAG | ACATGGTGAT | CATTTCCATT | ACATTCCAAA | ATCAAATCAA | 3000
| ATTGGGCAAC | CGACTCTTCC | AAACAATAGT | CTAGCAACAC | CTTCTCCATC | TCTTCCAATC | 3060
| AATCCAGGAA | CTTCACATGA | GAAACATGAA | AAGATGGAT | ACGGATTTGA | TGCTAATCGT | 3120
| ATTATCGCTG | AAGATGAATC | AGGTTTTGTC | ATGAGTCACG | GAGACCACAA | TCATTATTTC | 3180
| TTCAAGAAGG | ACTTGACAGA | AGAGCAAATT | AAGGCTGCGC | AAAAACATTT | AGAGGAAGTT | 3240
| AAAACTAGTC | ATAATGGATT | AGATTCTTTG | TCATCTCATG | AACAGGATTA | TCCAGGTAAT | 3300
| GCCAAAGAAA | TGAAAGATTT | AGATAAAAAA | ATCGAAGAAA | AAATTGCTGG | CATTATGAAA | 3360
| CAATATGGTG | TCAAACGTGA | AAGTATTGTC | GTGAATAAAG | AAAAAAATGC | GATTATTTAT | 3420
| CCGCATGGAG | ATCACCATCA | TGCAGATCCG | ATTGATGAAC | ATAAACCGGT | TGGAATTGGT | 3480
| CATTCTCACA | GTAACTATGA | ACTGTTTAAA | CCCGAAGAAG | GAGTTGCTAA | AAAAGAAGGG | 3540
| AATAAAGTTT | ATACTGGAGA | AGAATTAACG | AATGTTGTTA | ATTTGTTAAA | AAATAGTACG | 3600
| TTTAATAATC | AAAACTTTAC | TCTAGCCAAT | GGTCAAAAAC | GCGTTTCTTT | TAGTTTTCCG | 3660
| CCTGAATTGG | AGAAAAAATT | AGCTATCAAT | ATGCTAGTAA | AATTAATAAC | ACCAGATGGA | 3720
| AAAGTATTGG | AGAAAGTATC | TGGTAAAGTA | TTTGGAGAAG | GAGTAGGGAA | TATTGCAAAC | 3780
| TTTGAATTAG | ATCAACCTTA | TTTACCAGGA | CAAACATTTA | AGTATACTAT | CGCTTCAAAA | 3840
| GATTATCCAG | AAGTAAGTTA | TGATGGTACA | TTTACAGTTC | CAACCTCTTT | AGCTTACAAA | 3900
| ATGGCCAGTC | AAACGATTTT | CTATCCTTTC | CATGCAGGGG | ATACTTATTT | AAGAGTGAAC | 3960
| CCTCAATTTG | CAGTGCCTAA | AGGAACTGAT | GCTTTAGTCA | GAGTGTTTGA | TGAATTTCAT | 4020
| GGAAATGCTT | ATTTAGAAAA | TAACTATAAA | GTTGGTGAAA | TCAAATTACC | GATTCCGAAA | 4080
| TTAAACCAAG | GAACAACCAG | AACGGCCGGA | AATAAAATTC | CTGTAACCTT | CATGGCAAAT | 4140
| GCTTATTTGG | ACAATCAATC | GACTTATATT | GTGGAAGTAC | CTATCTTGGA | AAAAGAAAAT | 4200
| CAAACTGATA | AACCAAGTAT | TCTACCACAA | TTTAAAAGGA | ATAAAGCACA | AGAAAACTCA | 4260
| AAACTTGATG | AAAAGGTAGA | AGAACCAAAG | ACTAGTGAGA | AGGTAGAAAA | AGAAAAACTT | 4320
| TCTGAAACTG | GAATAGTAC | TAGTAATTCA | ACGTTAGAAG | AAGTTCCTAC | AGTGGATCCT | 4380
| GTACAAGAAA | AAGTAGCAAA | ATTTGCTGAA | AGTTATGGGA | TGAAGCTAGA | AAATGTCTTG | 4440
| TTTAATATGG | ACGGAACAAT | TGAATTATAT | TTACCATCAG | GAGAAGTCAT | TAAAAAGAAT | 4500
| ATGGCAGATT | TTACAGGAGA | AGCACCTCAA | GGAAATGGTG | AAAATAAACC | ATCTGAAAAT | 4560
| GGAAAAGTAT | CTACTGGAAC | AGTTGAGAAC | CAACCAACAG | AAAATAAACC | AGCAGATTCT | 4620
| TTACCAGAGG | CACCAAACGA | AAAACCTGTA | AAACCAGAAA | ACTCAACGGA | TAATGGAATG | 4680
| TTGAATCCAG | AAGGGAATGT | GGGGAGTGAC | CCTATGTTAG | ATCCAGCATT | AGAGGAAGCT | 4740

```
         CCAGCAGTAG ATCCTGTACA AGAAAAATTA GAAAAATTTA CAGCTAGTTA CGGATTAGGC    4800
         TTAGATAGTG TTATATTCAA TATGGATGGA ACGATTGAAT TAAGATTGCC AAGTGGAGAA    4860
         GTGATAAAAA AGAATTTATC TGATTTCATA GCGTAAGGAA TAGCAGTAGA AAAAGTCTGA    4920
         ATCAAAAATG AAGTTCTCTC AAAAGTTAGA AATAAAACTC TGACTTTGGG AGAATTTCAT    4980
    5    TTTATTATTA ATATATAAAA TTTCTTGACA TACAACTTAA AAAGAGGTGG AATATTTACT    5040
         AGTTAATT   (SEQ ID NO : 2)                                          5048
         FIGURE 2

10    ATGAAAATCA ATAAAAAATA TCTAGCTGGG TCAGTAGCTA CACTTGTTTT AAGTGTCTGT      60
         GCTTATGAAC TAGGTTTGCA TCAAGCTCAA ACTGTAAAAG AAAATAATCG TGTTTCCTAT     120
         ATAGATGGAA AACAAGCGAC GCAAAAAACG GAGAATTTGA CTCCTGATGA GGTTAGCAAG     180
         CGTGAAGGAA TCAACGCCGA ACAAATCGTC ATCAAGATTA CGGATCAAGG TTATGTGACC     240
         TCTCATGGAG ACCATTATCA TTACTATAAT GGCAAGGTCC CTTATGATGC CATCATCAGT     300
   15    GAAGAGCTCC TCATGAAAGA TCCGAATTAT CAGTTGAAGG ATTCAGACAT TGTCAATGAA     360
         ATCAAGGGTG GTTATGTCAT TAAGGTAAAC GGTAAATACT ATGTTTACCT TAAGGATGCA     420
         GCTCATGCGG ATAATGTCCG TACAAAAGAA GAAATCAATC GGCAAAAACA AGAACATAGT     480
         CAGCATCGTG AAGGAGGGAC TTCAGCAAAC GATGGTGCGG TAGCCTTTGC ACGTTCACAG     540
         GGACGCTACA CCACAGATGA TGGTTATATC TTCAATGCAT CTGATATCAT CGAAGATACG     600
   20    GGCGATGCCT ATATCGTTCC TCATGGAGAT CATTACCATT ACATTCCTAA GAATGAGTTA     660
         TCAGCTAGCG AGTTGGCTGC TGCAGAAGCC TTCCTATCTG GTCGGGAAAA TCTGTCAAAT     720
         TTAAGAACCT ATCGCCGACA AAATAGCGAT AACACTCCAA GAACAAACTG GGTACCTTCT     780
         GTAAGCAATC CAGGAACTAC AAATACTAAC ACAAGCAACA ACAGCAACAC TAACAGTCAA     840
         GCAAGTCAAA GTAATGACAT TGATAGTCTC TTGAAACAGC TCTACAAACT GCCTTTGAGT     900
   25    CAACGCCATG TAGAATCTGA TGGCCTTATT TTCGACCCAG CGCAAATCAC AAGTCGAACC     960
         GCCAGAGGTG TAGCTGTCCC TCATGGTAAC CATTACCACT TTATCCCTTA TGAACAAATG    1020
         TCTGAATTGG AAAAACGAAT TGCTCGTATT ATTCCCCTTC GTTATCGTTC AAACCATTGG    1080
         GTACCAGATT CAAGACCAGA AGAACCAAGT CCACAACCGA CTCCAGAACC TAGTCCAAGT    1140
         CCGCAACCTG CACCAAATCC TCAACCAGCT CAAGCAATC CAATTGATGA AAAATTGGTC     1200
   30    AAAGAAGCTG TTCGAAAAGT AGGCGATGGT TATGTCTTTG AGGAGAATGG AGTTTCTCGT    1260
         TATATCCCAG CCAAGAATCT TTCAGCAGAA ACAGCAGCAG GCATTGATAG CAAACTGGCC    1320
         AAGCAGGAAA GTTTATCTCA TAAGCTAGGA GCTAAGAAAA CTGACCTCCC ATCTAGTGAT    1380
         CGAGAATTTT ACAATAAGGC TTATGACTTA CTAGCAAGAA TTCACCAAGA TTTACTTGAT    1440
         AATAAAGGTC GACAAGTTGA TTTTGAGGCT TTGGATAACC TGTTGGAACG ACTCAAGGAT    1500
   35    GTCTCAAGTG ATAAAGTCAA GTTAGTGGAT GATATTCTTG CCTTCTTAGC TCCGATTCGT    1560
         CATCCAGAAC GTTTAGGAAA ACCAAATGCG CAAATTACCT ACACTGATGA TGAGATTCAA    1620
         GTAGCCAAGT TGGCAGGCAA GTACACAACA GAAGACGGTT ATATCTTTGA TCCTCGTGAT    1680
         ATAACCAGTG ATGAGGGGA TGCCTATGTA ACTCCACATA TGACCCATAG CCACTGGATT    1740
         AAAAAGATA GTTTGTCTGA AGCTGAGAGA GCGGCAGCCC AGGCTTATGC TAAAGAGAAA    1800
   40    GGTTTGACCC CTCCTTCGAC AGACCATCAG GATTCAGGAA ATACTGAGGC AAAAGGAGCA    1860
         GAAGCTATCT ACAACCGCGT GAAAGCAGCT AAGAAGGTGC CACTTGATCG TATGCCTTAC    1920
         AATCTTCAAT ATACTGTAGA AGTCAAAAAC GGTAGTTTAA TCATACCTCA TTATGACCAT    1980
         TACCATAACA TCAAATTTGA GTGGTTTGAC GAAGGCCTTT ATGAGGCACC TAAGGGGTAT    2040
         ACTCTTGAGG ATCTTTTGGC GACTGTCAAG TACTATGTCG AACATCCAAA CGAACGTCCG    2100
   45    CATTCAGATA ATGGTTTTGG TAACGCTAGC GACCATGTTC AAAGAAACAA AAATGGTCAA    2160
```

```
GCTGATACCA ATCAAACGGA AAAACCAAGC GAGGAGAAAC CTCAGACAGA AAAACCTGAG     2220
GAAGAAACCC CTCGAGAAGA GAAACCACAA AGCGAGAAAC CAGAGTCTCC AAAACCAACA     2280
GAGGAACCAG AAGAAGAATC ACCAGAGGAA TCAGAAGAAC CTCAGGTCGA GACTGAAAAG     2340
GTTGAAGAAA AACTGAGAGA GGCTGAAGAT TTACTTGGAA AAATCCAGGA TCCAATTATC     2400
AAGTCCAATG CCAAAGAGAC TCTCACAGGA TTAAAAAATA ATTTACTATT TGGCACCCAG     2460
GACAACAATA CTATTATGGC AGAAGCTGAA AAACTATTGG CTTTATTAAA GGAGAGTAAG     2520
TAA     (SEQ ID NO: 3)                                               2523
FIGURE 3
```

```
CAGAGATCTT AGTGAATCAA ATATACTTAA GAAAAGAGGA AAGAATGAAA ATCAATAAAA      60
AATATCTAGC TGGGTCAGTA GCTACACTTG TTTTAAGTGT CTGTGCTTAT GAACTAGGTT     120
TGCATCAAGC TCAAACTGTA AAAGAAAATA ATCGTGTTTC CTATATAGAT GGAAAACAAG     180
CGACGCAAAA AACGGAGAAT TTGACTCCTG ATGAGGTTAG CAAGCGTGAA GGAATCAACG     240
CCGAACAAAT CGTCATCAAG ATTACGGATC AAGGTTATGT GACCTCTCAT GGAGACCATT     300
ATCATTACTA TAATGGCAAG GTCCCTTATG ATGCCATCAT CAGTGAAGAG CTCCTCATGA     360
AAGATCCGAA TTATCAGTTA AAGGATTCAG ACATTGTCAA TGAAATCAAG GGTGGTTATG     420
TCATTAAGGT AAACGGTAAA TACTATGTTT ACCTTAAGGA TGCAGCTCAT GCGGATAATG     480
TCCGTACAAA AGAAGAAATC AATCGGCAAA AACAAGAACA TAGTCAGCAT CGTGAAGGAG     540
GGACTTCAGC AAACGATGGT GCGGTAGCCT TTGCACGTTC ACAGGGACGC TACACCACAG     600
ATGATGGTTA TATCTTCAAT GCATCTGATA TCATCGAAGA TACGGGCGAT GCCTATATCG     660
TTCCTCATGG AGATCATTAC CATTACATTC CTAAGAATGA GTTATCAGCT AGCGAGTTGG     720
CTGCTGCAGA AGCCTTCCTA TCTGGTCGGG AAAATCTGTC AAATTTAAGA ACCTATCGCC     780
GACAAAATAG CGATAACACT CCAAGAACAA ACTGGGTACC TTCTGTAAGC AATCCAGGAA     840
CTACAAATAC TAACACAAGC AACAACAGCA ACACTAACAG TCAAGCAAGT CAAAGTAATG     900
ACATTGATAG TCTCTTGAAA CAGCTCTACA AACTGCCTTT GAGTCAACGC CATGTAGAAT     960
CTGATGGCCT TATTTTCGAC CCAGCGCAAA TCACAAGTCG AACCGCCAGA GGTGTAGCTG    1020
TCCCTCATGG TAACCATTAC CACTTTATCC CTTATGAACA AATGTCTGAA TTGGAAAAAC    1080
GAATTGCTCG TATTATTCCC CTTCGTTATC GTTCAAACCA TTGGGTACCA GATTCAAGAC    1140
CAGAAGAACC AAGTCCACAA CCGACTCCAG AACCTAGTCC AAGTCCGCAA CCTGCACCAA    1200
ATCCTCAACC AGCTCCAAGC AATCCAATTG ATGAGAAATT GGTCAAAGAA GCTGTTCGAA    1260
AAGTAGGCGA TGGTTATGTC TTTGAGGAGA ATGGAGTTTC TCGTTATATC CCAGCCAAGA    1320
ATCTTTCAGC AGAAACAGCA GCAGGCATTG ATAGCAAACT GGCCAAGCAG GAAAGTTTAT    1380
CTCATAAGCT AGGAGCTAAG AAAACTGACC TCCCATCTAG TGATCGAGAA TTTTACAATA    1440
AGGCTTATGA CTTACTAGCA AGAATTCACC AAGATTTACT TGATAATAAA GGTCGACAAG    1500
TTGATTTTGA GGCTTTGGAT AACCTGTTGG AACGACTCAA GGATGTCTCA AGTGATAAAG    1560
TCAAGTTAGT GGATGATATT CTTGCCTTCT TAGCTCCGAT TCGTCATCCA GAACGTTTAG    1620
GAAAACCAAA TGCGCAAATT ACCTACACTG ATGATGAGAT TCAAGTAGCC AAGTTGGCAG    1680
GCAAGTACAC AACAGAAGAC GGTTATATCT TTGATCCTCG TGATATAACC AGTGATGAGG    1740
GGGATGCCTA TGTAACTCCA CATATGACCC ATAGCCACTG GATTAAAAAA GATAGTTTGT    1800
CTGAAGCTGA GAGAGCGGCA GCCCAGGCTT ATGCTAAAGA GAAAGGTTTG ACCCCTCCTT    1860
CGACAGACCA TCAGGATTCA GGAAATACTG AGGCAAAAGG AGCAGAAGCT ATCTACAACC    1920
GCGTGAAAGC AGCTAAGAAG GTGCCACTTG ATCGTATGCC TTACAATCTT CAATATACTG    1980
TAGAAGTCAA AAACGGTAGT TTAATCATAC CTCATTATGA CCATTACCAT AACATCAAAT    2040
TTGAGTGGTT TGACGAAGGC CTTTATGAGG CACCTAAGGG GTATACTCTT GAGGATCTTT    2100
```

```
TGGCGACTGT CAAGTACTAT GTCGAACATC CAAACGAACG TCCGCATTCA GATAATGGTT    2160
TTGGTAACGC TAGCGACCAT GTTCAAAGAA ACAAAAATGG TCAAGCTGAT ACCAATCAAA    2220
CGGAAAAACC AAGCGAGGAG AAACCTCAGA CAGAAAAACC TGAGGAAGAA ACCCCTCGAG    2280
AAGAGAAACC ACAAAGCGAG AAACCAGAGT CTCCAAAACC AACAGAGGAA CCAGAAGAAG    2340
AATCACCAGA GGAATCAGAA GAACCTCAGG TCGAGACTGA AAAGGTTGAA GAAAAACTGA    2400
GAGAGGCTGA AGATTTACTT GGAAAAATCC AGGATCCAAT TATCAAGTCC AATGCCAAAG    2460
AGACTCTCAC AGGATTAAAA AATAATTTAC TATTTGGCAC CCAGGACAAC AATACTATTA    2520
TGGCAGAAGC TGAAAAACTA TTGGCTTTAT TAAAGGAGAG TAAGTAAAGG TAGCAGCATT    2580
TTCTAACTCC TAAAAACAGG ATAGGAGAAC GGGAAAACGA AAAATGAGAG CAGAATGTGA    2640
GTTCTAG     (SEQ ID NO : 4)                                          2647
```
FIGURE 4

```
GGGTCTTAAA ACTCTGAATC CTTTAGAGGC AGACCCACAA AATGACAAGA CCTATTTAGA      60
AAATCTGGAA GAAAATATGA GTGTTCTAGC AGAAGAATTA AAGTGAGGAA AGAATGAAAA     120
TCAATAAAAA ATATCTAGCA GGTTCAGTGG CAGTCCTTGC CCTAAGTGTT TGTTCCTATG     180
AACTTGGTCG TCACCAAGCT GGTCAGGTTA AGAAAGAGTC TAATCGAGTT TCTTATATAG     240
ATGGTCATCA GGCTGGTCAA AAGGCAGAAA ATTTGACACC AGATGAAGTC AGTAAGAGAG     300
AGGGGATCAA CGCCGAACAA ATTGTTATCA AGATTACGGA TCAAGGTTAT GTGACCTCTC     360
ATGGAGACCA TTATCATTAC TATAATGGCA AGGTTCCTTA TGATGCCATC ATCAGTGAAG     420
AACTTCTCAT GAAAGATCCG AATTATCAGT TGAAGGATTC AGACATTGTC AATGAAATCA     480
AGGGTGGCTA TGTGATTAAG GTAGACGGAA AATACTATGT TTACCTTAAA GATGCGGCCC     540
ATGCGGACAA TATTCGGACA AAAGAAGAGA TTAAACGTCA GAAGCAGGAA CACAGTCATA     600
ATCATAACTC AAGAGCAGAT AATGCTGTTG CTGCAGCCAG AGCCCAAGGA CGTTATACAA     660
CGGATGATGG GTATATCTTC AATGCATCTG ATATCATTGA GGACACGGGT GATGCTTATA     720
TCGTTCCTCA CGGCGACCAT TACCATTACA TTCCTAAGAA TGAGTTATCA GCTAGCGAGT     780
TAGCTGCTGC AGAAGCCTAT TGGAATGGGA AGCAGGGATC TCGTCCTTCT TCAAGTTCTA     840
GTTATAATGC AAATCCAGTT CAACCAAGAT TGTCAGAGAA CCACAATCTG ACTGTCACTC     900
CAACTTATCA TCAAAATCAA GGGGAAAACA TTTCAAGCCT TTTACGTGAA TTGTATGCTA     960
AACCCTTATC AGAACGCCAT GTAGAATCTG ATGGCCTTAT TTTCGACCCA GCGCAAATCA    1020
CAAGTCGAAC CGCCAGAGGT GTAGCTGTCC CTCATGGTAA CCATTACCAC TTTATCCCTT    1080
ATGAACAAAT GTCTGAATTG GAAAAACGAA TTGCTCGTAT TATTCCCCTT CGTTATCGTT    1140
CAAACCATTG GGTACCAGAT TCAAGACCAG AACAACCAAG TCCACAATCG ACTCCGGAAC    1200
CTAGTCCAAG TCTGCAACCT GCACCAAATC CTCAACCAGC TCCAAGCAAT CCAATTGATG    1260
AGAAATTGGT CAAAGAAGCT GTTCGAAAAG TAGGCGATGG TTATGTCTTT GAGGAGAATG    1320
GAGTTTCTCG TTATATCCCA GCCAAGGATC TTTCAGCAGA AACAGCAGCA GGCATTGATA    1380
GCAAACTGGC CAAGCAGGAA AGTTTATCTC ATAAGCTAGG AGCTAAGAAA ACTGACCTCC    1440
CATCTAGTGA TCGAGAATTT TACAATAAGG CTTATGACTT ACTAGCAAGA ATTCACCAAG    1500
ATTTACTTGA TAATAAAGGT CGACAAGTTG ATTTGAGGT TTTGGATAAC CTGTTGGAAC    1560
GACTCAAGGA TGTCTCAAGT GATAAAGTCA AGTTAGTGGA TGATATTCTT GCCTTCTTAG    1620
CTCCGATTCG TCATCCAGAA CGTTTAGGAA AACCAAATGC GCAAATTACC TACACTGATG    1680
ATGAGATTCA AGTAGCCAAG TTGGCAGGCA AGTACACAAC AGAAGACGGT TATATCTTTG    1740
ATCCTCGTGA TATAACCAGT GATGAGGGGG ATGCCTATGT AACTCCACAT ATGACCCATA    1800
GCCACTGGAT TAAAAAAGAT AGTTTGTCTG AAGCTGAGAG AGCGGCAGCC AGGCTTATG     1860
CTAAAGAGAA AGGTTTGACC CCTCCTTCGA CAGACCACCA GGATTCAGGA AATACTGAGG    1920
```

```
CAAAAGGAGC AGAAGCTATC TACAACCGCG TGAAAGCAGC TAAGAAGGTG CCACTTGATC    1980
GTATGCCTTA CAATCTTCAA TATACTGTAG AAGTCAAAAA CGGTAGTTTA ATCATACCTC    2040
ATTATGACCA TTACCATAAC ATCAAATTTG AGTGGTTTGA CGAAGGCCTT TATGAGGCAC    2100
CTAAGGGGTA TAGTCTTGAG GATCTTTTGG CGACTGTCAA GTACTATGTC AACATCCAA     2160
ACGAACGTCC GCATTCAGAT AATGGTTTTG GTAACGCTAG TGACCATGTT CGTAAAAATA    2220
AGCAGACCA AGATAGTAAA CCTGATGAAG ATAAGGAACA TGATGAAGTA AGTGAGCCAA     2280
CTCACCCTGA ATCTGATGAA AAAGAGAATC ACGCTGGTTT AAATCCTTCA GCAGATAATC    2340
TTTATAAACC AAGCACTGAT ACGAAGAGA CAGAGGAAGA AGCTGAAGAT ACCACAGATG     2400
AGGCTGAAAT TCCTCAAGTA GAGAATTCTG TTATTAACGC TAAGATAGCA GATGCGGAGG    2460
CCTTGCTAGA AAAAGTAACA GATCCTAGTA TTAGACAAAA TGCTATGGAG ACATTGACTG    2520
GTCTAAAAAG TAGTCTTCTT CTCGGAACGA AAGATAATAA CACTATTTCA GCAGAAGTAG    2580
ATAGTCTCTT GGCTTTGTTA AAAGAAAGTC AACCGGCTCC TATACAGTAG TAAAATGAA     2639
(SEQ ID NO : 5)
FIGURE 5
```

```
MKFSKKYIAA GSAVIVSLSL CAYALNQHRS QENKDNNRVS YVDGSQSSQK      50
SENLTPDQVS QKEGIQAEQI VIKITDQGYV TSHGDHYHYY NGKVPYDALF     100
SEELLMKDPN YQLKDADIVN EVKGGYIIKV DGKYYVYLKD AAHADNVRTK     150
DEINRQKQEH VKDNEKVNSN VAVARSQGRY TTNDGYVFNP ADIIEDTGNA     200
YIVPHGGHYH YIPKSDLSAS ELAAAKAHLA GKNMQPSQLS YSSTASDNNT     250
QSVAKGSTSK PANKSENLQS LLKELYDSPS AQRYSESDGL VFDPAKIISR     300
TPNGVAIPHG DHYHFIPYSK LSALEEKIAR MVPISGTGST VSTNAKPNEV     350
VSSLGSLSSN PSSLTTSKEL SSASDGYIFN PKDIVEETAT AYIVRHGDHF    400
HYIPKSNQIG QPTLPNNSLA TPSPSLPINP GTSHEKHEED GYGFDANRII    450
AEDESGFVMS HGDHNHYFFK KDLTEEQIKA AQKHLEEVKT SHNGLDSLSS     500
HEQDYPGNAK EMKDLDKKIE EKIAGIMKQY GVKRESIVVN KEKNAIIYPH     550
GDHHADPID EHKPVGIGHS HSNYELFKPE EGVAKKEGNK VYTGEELTNV      600
VNLLKNSTFN NQNFTLANGQ KRVSFSFPPE LEKKLGINML VKLITPDGKV     650
LEKVSGKVFG EGVGNIANFE LDQPYLPGQT FKYTIASKDY PEVSYDGTFT    700
VPTSLAYKMA SQTIFYPFHA GDTYLRVNPQ FAVPKGTDAL VRVFDEFHGN     750
AYLENNYKVG EIKLPIPKLN QGTTRTAGNK IPVTFMANAY LDNQSTYIVE     800
VPILEKENQT DKPSILPQFK RNKAQENSKL DEKVEEPKTS EKVEKEKLSE     850
TGNSTSNSTL EEVPTVDPVQ EKVAKFAESY GMKLENVLFN MDGTIELYLP     900
SGEVIKKNMA DFTGEAPQGN GENKPSENGK VSTGTVENQP TENKPADSLP     950
EAPNEKPVKP ENSTDNGMLN PEGNVGSDPM LDPALEEAPA VDPVQEKLEK    1000
FTASYGLGLD SVIFNMDGTI ELRLPSGEVI KKNLSDFIA (SEQ ID NO: 6) 1039
FIGURE 6
```

```
MKINKKYLAG SVATLVLSVC AYELGLHQAQ TVKENNRVSY IDGKQATQKT      50
ENLTPDEVSK REGINAEQIV IKITDQGYVT SHGDHYHYYN GKVPYDAIIS    100
EELLMKDPNY QLKDSDIVNE IKGGYVIKVN GKYYVYLKDA AHADNVRTKE    150
EINRQKQEHS QHREGGTSAN DGAVAFARSQ GRYTTDDGYI FNASDIIEDT   200
GDAYIVPHGD HYHYIPKNEL SASELAAAEA FLSGRENLSN LRTYRRQNSD    250
```

```
NTPRTNWVPS VSNPGTTNTN TSNNSNTNSQ ASQSNDIDSL LKQLYKLPLS    300
QRHVESDGLI FDPAQITSRT ARGVAVPHGN HYHFIPYEQM SELEKRIARI    350
IPLRYRSNHW VPDSRPEEPS PQPTPEPSPS PQPAPNPQPA PSNPIDEKLV    400
KEAVRKVGDG YVFEENGVSR YIPAKNLSAE TAAGIDSKLA KQESLSHKLG    450
AKKTDLPSSD REFYNKAYDL LARIHQDLLD NKGRQVDFEA LDNLLERLKD    500
VSSDKVKLVD DILAFLAPIR HPERLGKPNA QITYTDDEIQ VAKLAGKYTT    550
EDGYIFDPRD ITSDEGDAYV TPHMTHSHWI KKDSLSEAER AAAQAYAKEK    600
GLTPPSTDHQ DSGNTEAKGA EAIYNRVKAA KKVPLDRMPY NLQYTVEVKN    650
GSLIIPHYDH YHNIKFEWFD EGLYEAPKGY TLEDLLATVK YYVEHPNERP    700
HSDNGFGNAS DHVQRNKNGQ ADTNQTEKPS EEKPQTEKPE EETPREEKPQ    750
SEKPESPKPT EEPEEESPEE SEEPQVETEK VEEKLREAED LLGKIQDPII    800
KSNAKETLTG LKNNLLFGTQ DNNTIMAEAE KLLALLKESK (SEQ ID NO: 7) 840
FIGURE 7
```

```
MKINKKYLAG SVAVLALSVC SYELGRHQAG QVKKESNRVS YIDGDQAGQK    50
AENLTPDEVS KREGINAEQI VIKITDQGYV TSHGDHYHYY NGKVPYDAII   100
SEELLMKDPN YQLKDSDIVN EIKGGYVIKV DGKYYVYLKD AAHADNIRTK   150
EEIKRQKQEH SHNHNSRADN AVAAARAQGR YTTDDGYIFN ASDIIEDTGD   200
AYIVPHGDHY HYIPKNELSA SELAAAEAYW NGKQGSRPSS SSSYNANPVQ   250
PRLSENHNLT VTPTYHQNQG ENISSLLREL YAKPLSERHV ESDGLIFDPA   300
QITSRTARGV AVPHGNHYHF IPYEQMSELE KRIARIIPLR YRSNHWVPDS   350
RPEQPSPQST PEPSPSLQPA PNPQPAPSNP IDEKLVKEAV RKVGDGYVFE   400
ENGVSRYIPA KDLSAETAAG IDSKLAKQES LSHKLGAKKT DLPSSDREFY   450
NKAYDLLARI HQDLLDNKGR QVDFEVLDNL LERLKDVSSD KVKLVDDILA   500
FLAPIRHPER LGKPNAQITY TDDEIQVAKL AGKYTTEDGY IFDPRDITSD   550
EGDAYVTPHM THSHWIKKDS LSEAERAAAQ AYAKEKGLTP PSTDHQDSGN   600
TEAKGAEAIY NRVKAAKKVP LDRMPYNLQY TVEVKNGSLI IPHYDHYHNI   650
KFEWFDEGLY EAPKGYSLED LLATVKYYVE HPNERPHSDN GFGNASDHVR   700
KNKADQDSKP DEDKEHDEVS EPTHPESDEK ENHAGLNPSA DNLYKPSTDT   750
EETEEEAEDT TDEAEIPQVE NSVINAKIAD AEALLEKVTD PSIRQNAMET   800
LTGLKSSLLL GTKDNNTISA EVDSLLALLK ESQPAPIQ                838
(SEQ ID NO : 8)
FIGURE 8
```

```
TGTGCCTATG CACTAAACCA GCATCGTTCG CAGGAAAATA AGGACAATAA TCGTGTCTCT    60
TATGTGGATG GCAGCCAGTC AAGTCAGAAA AGTGAAAACT TGACACCAGA CCAGGTTAGC   120
CAGAAAGAAG GAATTCAGGC TGAGCAAATT GTAATCAAAA TTACAGATCA GGGCTATGTA   180
ACGTCACACG GTGATCACTA TCATTACTAT AATGGGAAAG TTCCTTATGA TGCCCTCTTT   240
AGTGAAGAAC TCTTGATGAA GGATCCAAAC TATCAACTTA AAGACGCTGA TATTGTCAAT   300
GAAGTCAAGG GTGGTTATAT CATCAAGGTC GATGGAAAAT ATTATGTCTA CCTGAAAGAT   360
GCAGCTCATG CTGATAATGT TCGAACTAAA GATGAAATCA ATCGTCAAAA ACAAGAACAT   420
GTCAAAGATA ATGAGAAGGT TAACTCTAAT GTTGCTGTAG CAAGGTCTCA GGGACGATAT   480
ACGACAAATG ATGGTTATGT CTTTAATCCA GCTGATATTA TCGAAGATAC GGGTAATGCT   540
```

```
TATATCGTTC CTCATGGAGG TCACTATCAC TACATTCCCA AAAGCGATTT ATCTGCTAGT      600
GAATTAGCAG CAGCTAAAGC ACATCTGGCT GGAAAAAATA TGCAACCGAG TCAGTTAAGC      660
TATTCTTCAA CACCTTCTCC ATCTCTTCCA ATCAATCCAG GAACTTCACA TGAGAAACAT      720
GAAGAAGATG GATACGGATT TGATGCTAAT CGTATTATCG CTGAAGATGA ATCAGGTTTT      780
GTCATGAGTC ACGGAGACCA CAATCATTAT TTCTTCAAGA AGGACTTGAC AGAAGAGCAA      840
ATTAAGGCTG CGCAAAAACA TTTAGAGGAA GTTAAAACTA GTCATAATGG ATTAGATTCT      900
TTGTCATCTC ATGAACAGGA TTATCCAAGT AATGCCAAAG AAATGAAAGA TTTAGATAAA      960
AAAATCGAAG AAAAAATTGC TGGCATTATG AAACAATATG GTGTCAAACG TGAAAGTATT     1020
GTCGTGAATA AGAAAAAAAA TGCGATTATT TATCCGCATG GAGATCACCA TCATGCAGAT     1080
CCGATTGATG AACATAAACC GGTTGGAATT GGTCATTCTC ACAGTAACTA TGAACTGTTT     1140
AAACCCGAAG AAGGAGTTGC TAAAAAAGAA GGGAATAAAG TTTATACTGG AGAAGAATTA     1200
ACGAATGTTG TTAATTTGTT AAAAAATAGT ACGTTTAATA ATCAAAACTT TACTCTAGCC     1260
AATGGTCAAA AACGCGTTTC TTTTAGTTTT CCGCCTGAAT TGGAGAAAAA ATTAGGTATC     1320
AATATGCTAG TAAAATTAAT AACACCAGAT GGAAAAGTAT TGGAGAAAGT ATCTGGTAAA     1380
GTATTTGGAG AAGGAGTAGG GAATATTGCA AACTTTGAAT TAGATCAACC TTATTTACCA     1440
GGACAAACAT TTAAGTATAC TATCGCTTCA AAAGATTATC CAGAAGTAAG TTATGATGGT     1500
ACATTTACAG TTCCAACCTC TTTAGCTTAC AAAATGGCCA GTCAAACGAT TTTCTATCCT     1560
TTCCATGCAG GGATACTTA TTTAAGAGTG AACCCTCAAT TTGCAGTGCC TAAAGGAACT     1620
GATGCTTTAG TCAGAGTGTT TGATGAATTT CATGGAAATG CTTATTTAGA AAATAACTAT     1680
AAAGTTGGTG AAATCAAATT ACCGATTCCG AAATTAAACC AAGGAACAAC CAGAACGGCC     1740
GGAAATAAAA TTCCTGTAAC CTTCATGGCA AATGCTTATT TGGACAATCA ATCGACTTAT     1800
ATTGTGGAAG TACCTATCTT GGAAAAAGAA AATCAAACTG ATAAACCAAG TATTCTACCA     1860
CAATTTAAAA GGAATAAAGC ACAAGAAAAC TCAAAACTTG ATGAAAAGGT AGAAGAACCA     1920
AAGACTAGTG AGAAGGTAGA AAAAGAAAAA CTTTCTGAAA CTGGGAATAG TACTAGTAAT     1980
TCAACGTTAG AAGAAGTTCC TACAGTGGAT CCTGTACAAG AAAAAGTAGC AAAATTTGCT     2040
GAAAGTTATG GGATGAAGCT AGAAAATGTC TTGTTTAATA TGGACGGAAC AATTGAATTA     2100
TATTTACCAT CGGGAGAAGT CATTAAAAAG AATATGGCAG ATTTTACAGG AGAAGCACCT     2160
CAAGGAAATG GTGAAAATAA ACCATCTGAA AATGGAAAAG TATCTACTGG AACAGTTGAG     2220
AACCAACCAA CAGAAAATAA ACCAGCAGAT TCTTTACCAG AGGCACCAAA CGAAAAACCT     2280
GTAAAACCAG AAACTCAAC GGATAATGGA ATGTTGAATC CAGAAGGGAA TGTGGGGAGT     2340
GACCCTATGT TAGATTCAGC ATTAGAGGAA GCTCCAGCAG TAGATCCTGT ACAAGAAAAA     2400
TTAGAAAAAT TTACAGCTAG TTACGGATTA GGCTTAGATA GTGTTATATT CAATATGGAT     2460
GGAACGATTG AATTAAGATT GCCAAGTGGA GAAGTGATAA AAAAGAATTT ATTGATCTCA     2520
TAGCGTAA        (SEQ ID NO : 9)                                       2528
FIGURE 9

CAYALNQHRS QENKDNNRVS YVDGSQSSQK SENLTPDQVS QKEGIQAEQI       50
VIKITDQGYV TSHGDHYHYY NGKVPYDALF SEELLMKDPN YQLKDADIVN      100
EVKGGYIIKV DGKYVVYLKD AAHADNVRTK DEINRQKQEH VKDNEKVNSN      150
VAVARSQGRY TTNDGYVFNP ADIIEDTGNA YIVPHGGHYH YIPKSDLSAS      200
ELAAAKAHLA GKNMQPSQLS YSSTPSPSLP INPGTSHEKH EEDGYGFDAN      250
RIIAEDESGF VMSHGDHNHY FFKKDLTEEQ IKAAQKHLEE VKTSHNGLDS      300
LSSHEQDYPS NAKEMKDLDK KIEEKIAGIM KQYGVKRESI VVNKEKNAII      350
YPHGDHHHAD PIDEHKPVGI GHSHSNYELF KPEEGVAKKE GNKVYTGEEL      400
```

```
TNVVNLLKNS TFNNQNFTLA NGQKRVSFSF PPELEKKLGI NMLVKLITPD    450
GKVLEKVSGK VFGEGVGNIA NFELDQPYLP GQTFKYTIAS KDYPEVSYDG    500
TFTVPTSLAY KMASQTIFYP FHAGDTYLRV NPQFAVPKGT DALVRVFDEF    550
HGNAYLENNY KVGEIKLPIP KLNQGTTRTA GNKIPVTFMA NAYLDNQSTY    600
IVEVPILEKE NQTDKPSILP QFKRNKAQEN SKLDEKVEEP KTSEKVEKEK    650
LSETGNSTSN STLEEVPTVD PVQEKVAKFA ESYGMKLENV LFNMDGTIEL    700
YLPSGEVIKK NMADFTGEAP QGNGENKPSE NGKVSTGTVE NQPTENKPAD    750
SLPEAPNEKP VKPENSTDNG MLNPEGNVGS DPMLDSALEE APAVDPVQEK    800
LEKFTASYGL GLDSVIFNMD GTIELRLPSG EVIKKNLLIS              840
(SEQ ID NO : 10)
```

FIGURE 10

```
DQGYVTSHGD HYHYYNGKVP YDALFSEELL MKDPNYQLKD ADIVNEVKGG YIIKVDGKYY
VYLKDAAHAD NVRTKDEINR QKQEHVKDNE KVNS
(SEQ ID NO: 11)
```

FIGURE 11

```
GIQAEQIVIK ITDQGYVTSH GDHYHYYNGK VPYDALFSEE LL
(SEQ ID NO: 12)
```

FIGURE 12

```
TAYIVRHGDH FHYIPKSNQI GQPTLPNNSL ATPSPSLPI
(SEQ ID NO: 13)
```

FIGURE 13

```
TSNSTLEEVP TVDPVQEKVA KFAESYGMKL ENVLFN
(SEQ ID NO: 14)
```

FIGURE 14

```
MDGTIELRLP SGEVIKKNLS DFIA
(SEQ ID NO: 15)
```

FIGURE 15

```
YGLGLDSVIF NMDGTIELRL PSGEVIKKNL SDFIA
(SEQ ID NO: 16)
```

FIGURE 16

```
PALEEAPAVD PVQEKLEKFT ASYGLGLDSV IFNMDGTIEL RLPSGEVIKK NLSDFIA
(SEQ ID NO: 17)
```

FIGURE 17

KVEEPKTSEK VEKEKLSETG NSTSNSTLEE VPTVDPVQEK
(SEQ ID NO: 18)
FIGURE 18

MKDLDKKIEE KIAGIMKQYG VKRESIVVNK EKNAIIYPHG DHHHADPIDE HKPVGIGHSH
SNYELFKPEE GVAKKEGN
(SEQ ID NO: 19)
FIGURE19

AIIYPHGDHH HADPIDEHKP VGIGHSHSNY ELFKPEEGVA KKEGNKVYTG E
(SEQ ID NO: 20)
FIGURE 20

IQVAKLAGKY TTEDGYIFDP RDITSDEGD
(SEQ ID NO: 21)
FIGURE 21

DHQDSGNTEA KGAEAIYNRV KAAKKVPLDR MPYNLQYTVE VKNGSLIIPH YDHYHNIKFE
WFDEGLYEAP KGYSLEDLLA TVKYYV
(SEQ ID NO: 22)
FIGURE 22

GLYEAPKGYS LEDLLATVKY YVEHPNERPH SDNGFGNASD H
(SEQ ID NO: 23)
FIGURE 23

GLYEAPKGYSLEDLLATVKYYV
(SEQ ID NO: 163)
Figure 24

Epitope Localization on BVH-11-2 Protein

| | | |
|---|---|---|
| leader | NH₂ | |
| | HGDHYH | BVH-3C H11-7G11 H11- |
| conserved | | |
| | HGDHYH | BVH-11A H112-2H7 H112- |
| | | ⌐ 271 |
| | HGNHYH | |
| proline rich (12 P/30 | | NEW18 H112-3A1 H11B-15G2 H11-10B8 |
| | | H112-10D7 * ⌐ 497 |
| | HMTHSH | NEW10 H11B-7E11 ± 520 H11B- |
| | | H112-10G9 * H112-10A2 * H11B-11B8 * H112-3E8 |
| | HYDHYH | |
| | | NEW19 ⌐ 699 |
| charged BVH-11-2-specific | | NEW11 H112-3A4 |
| | PAPIQ-COOH | └─ 838 | non accessible cell-surface exposed

\* Surface-exposed and protection-conferring Mabs

FIGURE 29

```
        BVH-3M   1 CAYALNQHRSQENKDNNRVSYVDGSQSSQKSENLTPDQVSQKEGIQAEQIVIKITDQGYV   60
        BVH3-63  1 CAYALNQHRSQENKDNNRVSYVDGSQSSQKSENLTPDQVSQKEGIQAEQIVIKITDQGYV   60
                   ************************************************************

BVH-3M  61 TSHGDHYHYYNGKVPYDALFSEELLMKDPNYQLKDADIVNEVKGGYIIKVDGKYYVYLKD  120
        BVH3-63 61 TSHGDHYHYYNGKVPYDALFSEELLMKDPNYQLKDADIVNEVKGGYIIKVDGKYYVYLKD  120
                   ************************************************************

BVH-3M  121 AAHADNVRTKDEINRQKQEHVKDNEKVNSNVAVARSQGRYTTNDGYVFNPADIIEDTGNA  180
        BVH3-63 121 AAHADNVRTKDEINRQKQEHVKDNEKVNSNVAVARSQGRYTTNDGYVFNPADIIEDTGNA  180
                    ************************************************************

BVH-3M  181 YIVPHGGHYHYIPKSDLSASELAAAKAHLAGKNMQPSQLSYSSTASDNNTQSVAKGSTSK  240
        BVH3-63 181 YIVPHGGHYHYIPKSDLSASELAAAKAHLAGKNMQPSQLSYSS-----------------  223
                    ******************************************

BVH-3M  241 PANKSENLQSLLKELYDSPSAQRYSESDGLVFDPAKIISRTPNGVAIPHGDHYHFIPYSK  300
        BVH3-63 224 ------------------------------------------------------------  223

BVH-3M  301 LSALEEKIARMVPISGTGSTVSTNAKPNEVVSSLGSLSSNPSSLTTSKELSSASDGYIFN  360
        BVH3-63 224 ------------------------------------------------------------  223

BVH-3M  361 PKDIVEETATAYIVRHGDHFHYIPKSNQIGQPTLPNNSLATPSPSLPINPGTSHEKHEED  420
        BVH3-63 224 ---------------------------------------TPSPSLPINPGTSHEKHEED  243
                                                           ********************

BVH-3M  421 GYGFDANRIIAEDESGFVMSHGDHNHYFFKKDLTEEQIKAAQKHLEEVKTSHNGLDSLSS  480
        BVH3-63 244 GYGFDANRIIAEDESGFVMSHGDHNHYFFKKDLTEEQIKAAQKHLEEVKTSHNGLDSLSS  303
                    ************************************************************

BVH-3M  481 HEQDYPGNAKEMKDLDKKIEEKIAGIMKQYGVKRESIVVNKEKNAIIYPHGDHHHADPID  540
        BVH3-63 304 HEQDYPSNAKEMKDLDKKIEEKIAGIMKQYGVKRESIVVNKEKNAIIYPHGDHHHADPID  363
                    ******  ****************************************************

BVH-3M  541 EHKPVGIGHSHSNYELFKPEEGVAKKEGNKVYTGEELTNVVNLLKNSTFNNQNFTLANGQ  600
        BVH3-63 364 EHKPVGIGHSHSNYELFKPEEGVAKKEGNKVYTGEELTNVVNLLKNSTFNNQNFTLANGQ  423
                    ************************************************************

BVH-3M  601 KRVSFSFPPELEKKLGINMLVKLITPDGKVLEKVSGKVFGEGVGNIANFELDQPYLPGQT  660
        BVH3-63 424 KRVSFSFPPELEKKLGINMLVKLITPDGKVLEKVSGKVFGEGVGNIANFELDQPYLPGQT  483
```

```
BVH-3M    661  FKYTIASKDYPEVSYDGTFTVPTSLAYKMASQTIFYPFHAGDTYLRVNPQFAVPKGTDAL  720
BVH3-63   484  FKYTIASKDYPEVSYDGTFTVPTSLAYKMASQTIFYPFHAGDTYLRVNPQFAVPKGTDAL  543
               ************************************************************

BVH-3M    721  VRVFDEFHGNAYLENNYKVGEIKLPIPKLNQGTTRTAGNKIPVTFMANAYLDNQSTYIVE  780
BVH3-63   544  VRVFDEFHGNAYLENNYKVGEIKLPIPKLNQGTTRTAGNKIPVTFMANAYLDNQSTYIVE  603
               ************************************************************

BVH-3M    781  VPILEKENQTDKPSILPQFKRNKAQENSKLDEKVEEPKTSEKVEKEKLSETGNSTSNSTL  840
BVH3-63   604  VPILEKENQTDKPSILPQFKRNKAQENSKLDEKVEEPKTSEKVEKEKLSETGNSTSNSTL  663
               ************************************************************

BVH-3M    841  EEVPTVDPVQEKVAKFAESYGMKLENVLFNMDGTIELYLPSGEVIKKNMADFTGEAPQGN  900
BVH3-63   664  EEVPTVDPVQEKVAKFAESYGMKLENVLFNMDGTIELYLPSGEVIKKNMADFTGEAPQGN  723
               ************************************************************

BVH-3M    901  GENKPSENGKVSTGTVENQPTENKPADSLPEAPNEKPVKPENSTDNGMLNPEGNVGSDPM  960
BVH3-63   724  GENKPSENGKVSTGTVENQPTENKPADSLPEAPNEKPVKPENSTDNGMLNPEGNVGSDPM  783
               ************************************************************

BVH-3M    961  LDPALEEAPAVDPVQEKLEKFTASYGLGLDSVIFNMDGTIELRLPSGEVIKKNLSDFIA  1019
BVH3-63   784  LDSALEEAPAVDPVQEKLEKFTASYGLGLDSVIFNMDGTIELRLPSGEVIKKNLLIS     840
               ** **********************************************

FIGURE 31

BVH-3     1   MKFSKKYIAAGSAVIVSLSLCAYALNQHRSQENK-DNNRVSYVDGSQSSQKSENLTPDQV  59
BVH-11    1   MKINKKYLAG-SVATLVLSVCAYELGLHQAQTVK-ENNRVSYIDGKQATQKTENLTPDEV  58
BVH-11-2  1   MKINKKYLAG-SVAVLALSVCSYELGRHQAGQVKKESNRVSYIDGDQAGQKAENLTPDEV  59
              **  ***.* *  .**.*.* *. *..  *  . ***** ** *. ** ***** *.*

BVH-3     60  SQKEGIQAEQIVIKITDQGYVTSHGDHYHYYNGKVPYDALFSEELLMKDPNYQLKDADIV  119
BVH-11    59  SKREGINAEQIVIKITDQGYVTSHGDHYHYYNGKVPYDAIISEELLMKDPNYQLKDSDIV  118
BVH-11-2  60  SKREGINAEQIVIKITDQGYVTSHGDHYHYYNGKVPYDAIISEELLMKDPNYQLKDSDIV  119
              *..***.******************************* .***************.***

BVH-3     120 NEVKGGYIIKVDGKYYVYLKDAAHADNVRTKDEINRQKQEHVKDNE----KVNSNVAVAR  175
BVH-11    119 NEIKGGYVIKVNGKYYVYLKDAAHADNVRTKEEINRQKQEHSQHREGGTSANDGAVAFAR  178
BVH-11-2  120 NEIKGGYVIKVDGKYYVYLKDAAHADNIRTKEEIKRQKQEHSHNHN---SRADNAVAAAR  176
              **.****.***.**************.***.**.******.           ** **
```

```
BVH-3      176 SQGRYTTNDGYVFNPADIIEDTGNAYIVPHGGHYHYIPKSDLSASELAAAKAHLAGKNMQ  235
BVH-11     179 SQGRYTTDDGYIFNASDIIEDTGDAYIVPHGDHYHYIPKNELSASELAAAEAFLSGRENL  238
BVH-11-2   177 AQGRYTTDDGYIFNASDIIEDTGDAYIVPHGDHYHYIPKNELSASELAAAEAYWNGKQ--  234
               .****** ***.**  .******* ******* *******  .********* *   *.

BVH-3      236 PSQLSYSSTASDNNTQSVAKGSTSKP------A-N----------KSENLQSLLKELYDSP  279
BVH-11     239 SNLRTYRRQNSDNTPRTNWVPSVSNPGTTNTNTSNNSNTNSQASQSNDIDSLLKQLYKLP   298
BVH-11-2   235 -GSRPSSSSYNANPVQPRLSENHNLTVTPTYHQN---------QGENISSLLRELYAKP   284
                                                 *       .  . ***..**  *

BVH-3      280 SAQRYSESDGLVFDPAKIISRTPNGVAIPHGDHYHFIPYSKLSALEEKIARMVPISGTGS  339
BVH-11     299 LSQRHVESDGLIFDPAQITSRTARGVAVPHGNHYHFIPYEQMSELEKRIARIIPLRYRSN  358
BVH-11-2   285 LSERHVESDGLIFDPAQITSRTARGVAVPHGNHYHFIPYEQMSELEKRIARIIPLRYRSN  344
               ..*  *****.****.* ***  ***.*** ******* ..* **  ***..*..

BVH-3      340 TVSTNAKPNEVVSSLGSLSSNPSSLTTSKELSSASDGYIFNPKDIVEETATAYIVRHGDH  399
BVH-11     359 HWVPDSRP-EEPSPQPTPEPSPS-PQPAPNPQPAPS----NP--IDEKLVKEAVRKVGDG  410
BVH-11-2   345 HWVPDSRP-EQPSPQSTPEPSPS-LQPAPNPQPAPS----NP--IDEKLVKEAVRKVGDG  396
               ..* *  *    .    **    .   *   **  *  .  . **

BVH-3      400 FHYIPKSNQIGQPTLPNNSLATPSPSLPINPGTSHEKHEEDGYGFDANRIIAEDESGFVM  459
BVH-11     411 YVFEE-----------NGVSRYIP--------AKNLSAETAAGIDSKLAKQESLS----  446
BVH-11-2   397 YVFEE-----------NGVSRYIP--------AKDLSAETAAGIDSKLAKQESLS----  432
                . .              * ..   *           .. *     * *.    * *

BVH-3      460 SHGDHNHYFFKKDLTEEQIKAAQKHLEEVKTSHNGLDSLSSHEQDYPGNAKEMKDLDKKI  519
BVH-11     447 ----HKLGAKKTDLPSSDREFYNKAYDLLARIHQDLLDNKGRQVDFEALDNLLERLKDVS  502
BVH-11-2   433 ----HKLGAKKTDLPSSDREFYNKAYDLLARIHQDLLDNKGRQVDFEVLDNLLERLKDVS  488
                   *   *  **     .*  ..  *.  *   .. *.       .  *

BVH-3      520 EEKIAGIMKQYGVKRESIVVNKEKNAIIYPHGDHHHADPIDEHKPVGIGHSHSNYELFKP  579
BVH-11     503 SDKVKLVDDILAFLAP--IRHPER--LGKPNAQITYTDDEIQVAKLAGKYTTEDGYIFDP  558
BVH-11-2   489 SDKVKLVDDILAFLAP--IRHPER--LGKPNAQITYTDDEIQVAKLAGKYTTEDGYIFDP  544
               .*. .              .*.  *.     .*   .       .      .-* *

BVH-3      580 EEGVAKKEGNKVYTGEELTNVVNLLKNSTPNNQNFTLANGQKRVSFSFPPELEKKLGINM  639
BVH-11     559 RD-ITSDEGD-AYVTPHMTHSHWIKKDS-LSEAERAAAQAYAKEKGLTPPSTDHQD---- 611
BVH-11-2   545 RD-ITSDEGD-AYVTPHMTHSHWIKKDS-LSEAERAAAQAYAKEKGLTPPSTDHQD---- 597
                ...  **   *  .*. .  * *    .* . **   **.  .

BVH-3      640 LVKLITPDGKVLEKVSGKVFGEGVGNIANFELDQPYLPGQTFKYTIASKDYPEVSYDGTF  699
BVH-11     612 --------------SGNTEAKGAEAIYNRVKAAKKVPLDRMPYNLQ---YTVEVKNGSL  653
BVH-11-2   598 --------------SGNTEAKGAEAIYNRVKAAKKVPLDRMPYNLQ---YTVEVKNGSL  639
                             **   *  * *    .*   *..   *    *     *.
```

```
BVH-3      700  TVPTSLAYKMASQTIFYPFHAGDTYLRVNPQFAVPKGTDALVRVFDEFHGNAYLENNYKV  759
BVH-11     654  IIP---HYDHYHNIKFEWFDEG--------LYEAPKG--------------YTLEDLLAT  688
BVH-11-2   640  IIP---HYDHYHNIKFEWFDEG--------LYEAPKG--------------YSLEDLLAT  674
                   .*    *  . * * *           . ***               **

BVH-3      760  GEIKLPIPKLNQGTTRTAGNKIPVTFMANAYLDNQSTYIVEVPILEKENQTDKPSILPQF  819
BVH-11     689  VKYYVEHPNERPHSDNGFGN-------ASDHVQRN-----------KNGQADTN------  724
BVH-11-2   675  VKYYVEHPNERPHSDNGFGN-------ASDHVRKN-----------KADQDSKP------  710
                    . *   .   **       *  .  .             * *

BVH-3      820  KRNKAQENSKLDEKVEEPKTSEKVEKEKLSETGNSTSNSTLEEVPTVDPVQEKVAKFAES  879
BVH-11     725  ------QTEKPSEEKPQTEKPE---EE---------------------------------  742
BVH-11-2   711  ------DEDKEHDEVSEPTHPESDEKE---------------------------------  731
                       *  .   *  *

BVH-3      880  YGMKLENVLFNMDGTIELYLPSGEVIKKNMADFTGEAPQGNGENKPSENGKVSTGTVENQ  939
BVH-11     743  -------------------------------TPREEKPQSE---KPES----------PK  758
BVH-11-2   732  ---------------------------------NHAGLNPSADNLYKPSTD--------TE  751
                                                *        **

BVH-3      940  PTENKPADSLPEAPNEKPVKPENSTDNGMLNPEGNVGSDPMLDPALEEAPAVDPVQEKLE  999
BVH-11     759  PTEEPEEESPEES--EEPQVETEKVEEKLREAEDLLGK--IQDPIIKSN-----AKETLT  809
BVH-11-2   752  ETEEEAEDTTDEA--EIPQVENSVINAKIADAEALLEK--VTDPSIRQN-----AMETLT  802
                 **     ..  *.  * *          -  *  .    **  .         * *

BVH-3     1000  KFTASYGLGLDSVIFNMDGTIELRLPSGEVIKKNLSDFIA  1039
BVH-11     810  GLKNNLLFGTQ-----DNNTIMAEAEKLLALLKESK      840
BVH-11-2   803  GLKSSLLLGTK-----DNNTISAEVDSLLALLKESQPAPIQ  838
                 *          .**      . *
```

FIGURE 32

```
  1 ATGCAAATTA CCTACACTGA TGATGAGATT CAGGTAGCCA AGTTGGCAGG CAAGTACACA
 61 ACAGAAGACG GTTATATCTT TGATACTAGT TGGATTAAAA AAGATAGTTT GTCTGAAGCT
121 GAGAGAGCGG CAGCCCAGGC TTATGCTAAA GAGAAAGGTT TGACCCCTCC TTCGACAGAC
181 CACCAGGATT CAGGAAATAC TGAGGCAAAA GGAGCAGAAG CTATCTACAA CCGCGTGAAA
241 GCAGCTAAGA AGGTGCCACT TGATCGTATG CCTTACAATC TTCAGTATAC TGTAGAAGTC
301 AAAAACGGTA GTTTAATCAT ACCTCATTAT GACCATTACC ATAACATCAA ATTTGAGTGG
361 TTTGACGAAG GCCTTTATGA GGCACCTAAG GGGTATAGTC TTGAGGATCT TTTGGCGACT
421 GTCAAGTACT ATGTCGAACC GCGGAACGCT AGTGACCATG TTCGTAAAAA TAAGGCAGAC
481 CAAGATAGTA AACCTGATGA AGATAAGGAA CATGATGAAG TAAGTGAGCC AACTCACCCT
541 GAATCTGATG AAAAAGAGAA TCACGCTGGT TTAAATCCTT CAGCAGATAA TCTTTATAAA
601 CCAAGCACTG ATACGGAAGA GACAGAGGAA GAAGCTGAAG ATACCACAGA TGAGGCTGAA
661 ATTCCTGGTA CCCCTAGTAT TAGACAAAAT GCTATGGAGA CATTGACTGG TCTAAAAAGT
721 AGTCTTCTTC TCGGAACGAA AGATAATAAC ACTATTTCAG CAGAAGTAGA TAGTCTCTTG
781 GCTTTGTTAA AAGAAAGTCA ACCGGCTCCT ATACAGTAG  (SEQ ID NO: 257)
```

FIGURE 33

```
  1 MQITYTDDEI QVAKLAGKYT TEDGYIFDTS WIKKDSLSEA ERAAAQAYAK EKGLTPPSTD
 61 HQDSGNTEAK GAEAIYNRVK AAKKVPLDRM PYNLQYTVEV KNGSLIIPHY DHYHNIKFEW
121 FDEGLYEAPK GYSLEDLLAT VKYYVEPRNA SDHVRKNKAD QDSKPDEDKE HDEVSEPTHP
181 ESDEKENHAG LNPSADNLYK PSTDTEETEE EAEDTTDEAE IPGTPSIRQN AMETLTGLKS
241 SLLLGTKDNN TISAEVDSLL ALLKESQPAP IQ   (SEQ ID NO : 258)
```

FIGURE 34

SEQUENCE LISTING

<160> NUMBER OF SEQ ID NOS: 384

<210> SEQ ID NO 1
<211> LENGTH: 3120
<212> TYPE: DNA
<213> ORGANISM: Streptococcus pneumoniae

<400> SEQUENCE: 1

| | | | | | |
|---|---|---|---|---|---|
| atgaaattta | gtaaaaaata | tatagcagct | ggatcagctg | ttatcgtatc | cttgagtcta | 60 |
| tgtgcctatg | cactaaacca | gcatcgttcg | caggaaaata | aggacaataa | tcgtgtctct | 120 |
| tatgtggatg | gcagccagtc | aagtcagaaa | agtgaaaact | tgacaccaga | ccaggttagc | 180 |
| cagaaagaag | gaattcaggc | tgagcaaatt | gtaatcaaaa | ttacagatca | gggctatgta | 240 |
| acgtcacacg | gtgaccacta | tcattactat | aatgggaaag | ttccttatga | tgccctcttt | 300 |
| agtgaagaac | tcttgatgaa | ggatccaaac | tatcaactta | agacgctga | tattgtcaat | 360 |
| gaagtcaagg | gtggttatat | catcaaggtc | gatggaaaat | attatgtcta | cctgaaagat | 420 |
| gcagctcatg | ctgataatgt | tcgaactaaa | gatgaaatca | atcgtcaaaa | acaagaacat | 480 |
| gtcaaagata | atgagaaggt | taactctaat | gttgctgtag | caaggtctca | gggacgatat | 540 |
| acgacaaatg | atggttatgt | ctttaatcca | gctgatatta | tcgaagatac | gggtaatgct | 600 |
| tatatcgttc | ctcatggagg | tcactataca | tacattccca | aaagcgattt | atctgctagt | 660 |
| gaattagcag | cagctaaagc | acatctggct | ggaaaaaata | tgcaaccgag | tcagttaagc | 720 |
| tattcttcaa | cagctagtga | caataacacg | caatctgtag | caaaaggatc | aactagcaag | 780 |
| ccagcaaata | aatctgaaaa | tctccagagt | cttttgaagg | aactctatga | ttcacctagc | 840 |
| gcccaacgtt | acagtgaatc | agatggcctg | gtctttgacc | ctgctaagat | tatcagtcgt | 900 |
| acaccaaatg | gagttgcgat | tccgcatggc | gaccattacc | actttattcc | ttacagcaag | 960 |
| cttttctgctt | tagaagaaaa | gattgccaga | atggtgccta | tcagtggaac | tggttctaca | 1020 |
| gtttctacaa | atgcaaaacc | taatgaagta | gtgtctagtc | taggcagtct | tcaagcaat | 1080 |
| ccttcttctt | taacgacaag | taaggagctc | tcttcagcat | ctgatggtta | tatttttaat | 1140 |
| ccaaaagata | tcgttgaaga | aacggctaca | gcttatattg | taagcatgg | tgatcatttc | 1200 |
| cattcattc | caaaatcaaa | tcaaattggg | caaccgactc | ttccaaacaa | tagtctagca | 1260 |
| acaccttctc | catctcttcc | aatcaatcca | ggaacttcac | atgagaaaca | tgaagaagat | 1320 |
| ggatacggat | ttgatgctaa | tcgtattatc | gctgaagatg | aatcaggttt | tgtcatgagt | 1380 |
| cacggagacc | acaatcatta | tttcttcaag | aaggacttga | cagaagagca | aattaaggct | 1440 |
| gcgcaaaaac | atttagagga | agttaaaact | agtcataatg | gattagattc | tttgtcatct | 1500 |
| catgaacagg | attatccagg | taatgccaaa | gaaatgaaag | atttagataa | aaaaatcgaa | 1560 |
| gaaaaaattg | ctggcattat | gaaacaatat | ggtgtcaaac | gtgaaagtat | tgtcgtgaat | 1620 |
| aaagaaaaaa | atgcgattat | ttatccgcat | ggagatcacc | atcatgcaga | tccgattgat | 1680 |
| gaacataaac | cggttggaat | tggtcattct | cacagtaact | atgaactgtt | taaacccgaa | 1740 |
| gaaggagttg | ctaaaaaga | agggaataaa | gtttatactg | gagaagaatt | aacgaatgtt | 1800 |
| gttaatttgt | taaaaatag | tacgtttaat | aatcaaaact | ttactctagc | caatggtcaa | 1860 |
| aaacgcgttt | ctttagttt | tccgcctgaa | ttggagaaaa | aattaggtat | caatatgcta | 1920 |
| gtaaaattaa | taacaccaga | tggaaaagta | ttggagaaag | tatctggtaa | agtatttgga | 1980 |
| gaaggagtag | ggaatattgc | aaactttgaa | ttagatcaac | cttatttacc | aggacaaaca | 2040 |

-continued

| | |
|---|---|
| tttaagtata ctatcgcttc aaaagattat ccagaagtaa gttatgatgg tacatttaca | 2100 |
| gttccaacct ctttagctta caaaatggcc agtcaaacga ttttctatcc tttccatgca | 2160 |
| ggggatactt atttaagagt gaaccctcaa tttgcagtgc ctaaaggaac tgatgcttta | 2220 |
| gtcagagtgt tgatgaatt tcatggaaat gcttatttag aaaataacta taaagttggt | 2280 |
| gaaatcaaat taccgattcc gaaattaaac caaggaacaa ccagaacggc cggaaataaa | 2340 |
| attcctgtaa ccttcatggc aaatgcttat ttggacaatc aatcgactta tattgtggaa | 2400 |
| gtacctatct tggaaaaaga aaatcaaact gataaaccaa gtattctacc acaatttaaa | 2460 |
| aggaataaag cacaagaaaa ctcaaaactt gatgaaaagg tagaagaacc aaagactagt | 2520 |
| gagaaggtag aaaaagaaaa actttctgaa actgggaata gtactagtaa ttcaacgtta | 2580 |
| gaagaagttc ctacagtgga tcctgtacaa gaaaagtag caaaatttgc tgaaagttat | 2640 |
| gggatgaagc tagaaaatgt cttgtttaat atggacggaa caattgaatt atatttacca | 2700 |
| tcaggagaag tcattaaaaa gaatatggca gattttacag gagaagcacc tcaaggaaat | 2760 |
| ggtgaaaata aaccatctga aaatggaaaa gtatctactg gaacagttga gaaccaacca | 2820 |
| acagaaaata aaccagcaga ttctttacca gaggcaccaa acgaaaaacc tgtaaaacca | 2880 |
| gaaaactcaa cggataatgg aatgttgaat ccagaaggga atgtggggag tgaccctatg | 2940 |
| ttagatccag cattagagga agctccagca gtagatcctg tacaagaaaa attagaaaaa | 3000 |
| tttacagcta gttacggatt aggcttagat agtgttatat tcaatatgga tggaacgatt | 3060 |
| gaattaagat tgccaagtgg agaagtgata aaaaagaatt tatctgattt catagcgtaa | 3120 |

<210> SEQ ID NO 2
<211> LENGTH: 5048
<212> TYPE: DNA
<213> ORGANISM: Streptococcus pneumoniae

<400> SEQUENCE: 2

| | |
|---|---|
| aattccttgt cgggtaagtt ccgacccgca cgaaaggcgt aatgatttgg gcactgtctc | 60 |
| aacgagagac tcggtgaaat tttagtacct gtgaagatgc aggttacccg cgacaggacg | 120 |
| gaaagacccc atggagcttt actgcagttt gatattgagt gtctgtacca catgtacagg | 180 |
| ataggtagga gtctaagaga tcgggacgcc agtttcgaag gagacgctgt tgggatacta | 240 |
| cccttgtgtt atggccactc taacccagat aggtgatccc tatcggagac agtgtctgac | 300 |
| gggcagtttg actggggcgg tcgcctccta aaaggtaacg gaggcgccca aaggttccct | 360 |
| cagaatggtt ggaaatcatt cgcagagtgt aaaggtataa gggagcttga ctgcgagagc | 420 |
| tacaactcga gcagggacga aagtcgggct tagtgatccg gtggttccgt atggaagggc | 480 |
| catcgctcaa cggataaaag ctaccctggg gataacaggc ttatctcccc caagagttca | 540 |
| catcgacggg gaggtttggc acctcgatgt cggctcgtcg catcctgggg ctgtagtcgg | 600 |
| tcccaagggt tgggctgttc gcccattaaa gcggcacgcg agctgggttc agaacgtcgt | 660 |
| gagacagttc ggtccctatc cgtcgcgggc gtaggaaatt tgagaggatc tgctcctagt | 720 |
| acgagaggac cagagtggac ttaccgctgg tgtaccagtt gtcttgccaa aggcatcgct | 780 |
| gggtagctat gtagggaagg gataaacgct gaaagcatct aagtgtgaaa cccacctcaa | 840 |
| gatgagattt cccatgatta tatatcagta agagccctga gagtgatca ggtagatagg | 900 |
| ttagaagtgg aagtgtggcg acacatgtag cggactaata ctaatagctc gaggacttat | 960 |
| ccaaagtaac tgagaatatg aaagcgaacg gttttcttaa attgaataga tattcaattt | 1020 |

```
tgagtaggta ttactcagag ttaagtgacg atagcctagg agatacacct gtacccatgc    1080
cgaacacaga agttaagccc tagaacgccg gaagtagttg ggggttgccc cctgtgagat    1140
agggaagtcg cttagctcta gggagtttag ctcagctggg agagcatctg ccttacaagc    1200
agagggtcag cggttcgatc ccgttaactc ccaaaggtcc cgtagtgtag cggttatcac    1260
gtcgccctgt cacggcgaag atcgcgggtt cgattcccgt cgggaccgtt taaggtaacg    1320
caagttattt tagactcgtt agctcagttg gtagagcaat tgacttttaa tcaatgggtc    1380
actggttcga gcccagtacg ggtcatatat gcgggtttgg cggaattcta atctctttga    1440
aatcatcttc tctcactttc caaaactcta ttacctctta ttataccaca tttcaatctt    1500
caacttccca gtaatataag cacctctggc gaaagaagtt tcaatgtcct aaagtaataa    1560
gtgaatccaa ttcaggaact ccaagaacaa agaaacatc tggtgtcaca agtattggat    1620
ggcacagagt cacgtggtag tctgacccta gcagaaattt taaatagtaa actatttact    1680
ggttaattaa atggttaaat aaccggttta gaaaactatt taataaagta aaagaagttg    1740
agaaaaaact tcatcattta ttgaaatgag ggatttatga aatttagtaa aaaatatata    1800
gcagctggat cagctgttat cgtatccttg agtctatgtg cctatgcact aaaccagcat    1860
cgttcgcagg aaaataagga caataatcgt gtctcttatg tggatggcag ccagtcaagt    1920
cagaaaagtg aaaacttgac accagaccag gttagccaga agaaggaat tcaggctgag    1980 caaattgtaa tcaaaattac agatcagggc tatgtaacgt cacacggtga ccactatcat    2040
tactataatg ggaaagttcc ttatgatgcc ctctttagtg aagaactctt gatgaaggat    2100
ccaaactatc aacttaaaga cgctgatatt gtcaatgaag tcaagggtgg ttatatcatc    2160
aaggtcgatg gaaatatatta tgtctacctg aaagatgcag ctcatgctga taatgttcga    2220
actaaagatg aaatcaatcg tcaaaaacaa gaacatgtca agataatga aaggttaac    2280 tctaatgttg ctgtagcaag gtctcaggga cgatatacga caaatgatgg ttatgtcttt    2340
aatccagctg atattatcga agatacgggt aatgcttata tcgttcctca tggaggtcac    2400
tatcactaca ttcccaaaag cgatttatct gctagtgaat tagcagcagc taaagcacat    2460
ctggctggaa aaaatatgca accgagtcag ttaagctatt cttcaacagc tagtgacaat    2520
aacacgcaat ctgtagcaaa aggatcaact agcaagccag caaataaatc tgaaaatctc    2580
cagagtcttt tgaaggaact ctatgattca cctagcgccc aacgttacag tgaatcagat    2640
ggcctggtct ttgaccctgc taagattatc agtcgtacac caaatggagt tgcgattccg    2700
catggcgacc attaccactt tattccttac agcaagcttt ctgctttaga agaaaagatt    2760
gccagaatgg tgcctatcag tggaactggt tctacagttt ctacaaatgc aaaacctaat    2820
gaagtagtgt ctagtctagg cagtctttca agcaatcctt cttctttaac gacaagtaag    2880
gagctctctt cagcatctga tggttatatt tttaatccaa agatatcgt tgaagaaacg    2940 gctacagctt atattgtaag acatggtgat catttccatt acattccaaa atcaaatcaa    3000
attgggcaac cgactcttcc aaacaatagt ctagcaacac cttctccatc tcttccaatc    3060
aatccaggaa cttcacatga gaaacatgaa gaagatggat acggatttga tgctaatcgt    3120
attatcgctg aagatgaatc aggttttgtc atgagtcacg gagaccacaa tcattatttc    3180
ttcaagaagg acttgacaga agagcaaatt aaggctgcgc aaaaacattt agaggaagtt    3240
aaaactagtc ataatggatt agattctttg tcatctcatg aacaggatta tccaggtaat    3300
gccaaagaaa tgaagatttt agataaaaaa atcgaagaaa aaattgctgg cattatgaaa    3360
caatatggtg tcaaacgtga agtattgtc gtgaataaag aaaaaaatgc gattatttat    3420
```

-continued

```
ccgcatggag atcaccatca tgcagatccg attgatgaac ataaaccggt tggaattggt    3480
cattctcaca gtaactatga actgtttaaa cccgaagaag gagttgctaa aaagaaggg     3540
aataaagttt atactggaga agaattaacg aatgttgtta atttgttaaa aaatagtacg    3600
tttaataatc aaaactttac tctagccaat ggtcaaaaac gcgtttcttt tagttttccg    3660
cctgaattgg agaaaaaatt aggtatcaat atgctagtaa aattaataac accagatgga    3720
aaagtattgg agaaagtatc tggtaaagta tttggagaag gagtagggaa tattgcaaac    3780
tttgaattag atcaaccttta tttaccagga caaacattta agtatactat cgcttcaaaa    3840
gattatccag aagtaagtta tgatggtaca tttacagttc caacctcttt agcttacaaa    3900
atggccagtc aaacgatttt ctatcctttc catgcagggg atacttattt aagagtgaac    3960
cctcaatttg cagtgcctaa aggaactgat gctttagtca gagtgtttga tgaatttcat    4020
ggaaatgctt atttagaaaa taactataaa gttggtgaaa tcaaattacc gattccgaaa    4080
ttaaaccaag gaacaaccag aacggccgga ataaaaattc ctgtaacctt catggcaaat    4140
gcttatttgg acaatcaatc gacttatatt gtggaagtac ctatcttgga aaaagaaaat    4200
caaactgata aaccaagtat tctaccacaa tttaaaagga ataaagcaca agaaaactca    4260
aaacttgatg aaaaggtaga agaaccaaag actagtgaga aggtagaaaa agaaaaactt    4320
tctgaaactg ggaatagtac tagtaattca acgttagaag aagttcctac agtggatcct    4380
gtacaagaaa aagtagcaaa atttgctgaa agttatggga tgaagctaga aaatgtcttg    4440
tttaatatgg acggaacaat tgaattatat ttaccatcag gagaagtcat taaaaagaat    4500
atggcagatt ttacaggaga agcacctcaa ggaaatggtg aaaataaacc atctgaaaat    4560
ggaaaagtat ctactggaac agttgagaac caaccaacag aaaataaacc agcagattct    4620
ttaccagagg caccaaacga aaaacctgta aaaccagaaa actcaacgga taatggaatg    4680
ttgaatccag aagggaatgt ggggagtgac cctatgttaa tccagcatt agaggaagct    4740
ccagcagtag atcctgtaca agaaaaatta gaaaaattta cagctagtta cggattaggc    4800
ttagatagtg ttatattcaa tatggatgga acgattgaat taagattgcc aagtggagaa    4860
gtgataaaaa agaatttatc tgatttcata gcgtaaggaa tagcagtaga aaaagtctga    4920
atcaaaaatg aagttctctc aaaagttaga aataaaactc tgactttggg agaatttcat    4980
tttattatta atatataaaa tttcttgaca tacaacttaa aagaggtgg aatatttact     5040
agttaatt                                                              5048
```

<210> SEQ ID NO 3
<211> LENGTH: 2523
<212> TYPE: DNA
<213> ORGANISM: Streptococcus pneumoniae

<400> SEQUENCE: 3

```
atgaaaatca ataaaaaata tctagctggg tcagtagcta cacttgtttt aagtgtctgt     60
gcttatgaac taggtttgca tcaagctcaa actgtaaaag aaaataatcg tgtttcctat    120
atagatggaa acaagcgac gcaaaaaacg gagaatttga ctcctgatga ggttagcaag    180
cgtgaaggaa tcaacgccga acaaatcgtc atcaagatta cggatcaagg ttatgtgacc    240
tctcatggag accattatca ttactataat ggcaaggtcc cttatgatgc catcatcagt    300
gaagagctcc tcatgaaaga tccgaattat cagttgaagg attcagacat tgtcaatgaa    360
atcaagggtg gttatgtcat taaggtaaac ggtaaatact atgtttacct taaggatgca    420
```

-continued

```
gctcatgcgg ataatgtccg tacaaaagaa gaaatcaatc ggcaaaaaca agaacatagt      480
cagcatcgtg aaggagggac ttcagcaaac gatggtgcgg tagcctttgc acgttcacag      540
ggacgctaca ccacagatga tggttatatc ttcaatgcat ctgatatcat cgaagatacg      600
ggcgatgcct atatcgttcc tcatggagat cattaccatt acattcctaa gaatgagtta      660
tcagctagcg agttggctgc tgcagaagcc ttcctatctg gtcgggaaaa tctgtcaaat      720
ttaagaacct atcgccgaca aaatagcgat aacactccaa gaacaaactg ggtaccttct      780
gtaagcaatc caggaactac aaatactaac acaagcaaca acagcaacac taacagtcaa      840
gcaagtcaaa gtaatgacat tgatagtctc ttgaaacagc tctacaaact gcctttgagt      900
caacgccatg tagaatctga tggccttatt ttcgacccag cgcaaatcac aagtcgaacc      960
gccagaggtg tagctgtccc tcatggtaac cattaccact ttatccctta tgaacaaatg     1020
tctgaattgg aaaaacgaat tgctcgtatt attcccttc gttatcgttc aaaccattgg      1080
gtaccagatt caagaccaga gaaccaagt ccacaaccga ctccagaacc tagtccaagt      1140
ccgcaacctg caccaaatcc tcaaccagct ccaagcaatc caattgatga gaaattggtc     1200
aaagaagctg ttcgaaaagt aggcgatggt tatgtctttg aggagaatgg agtttctcgt     1260
tatatcccag ccaagaatct ttcagcagaa acagcagcag gcattgatag caaactggcc     1320
aagcaggaaa gtttatctca taagctagga gctaagaaaa ctgacctccc atctagtgat     1380
cgagaatttt acaataaggc ttatgactta ctagcaagaa ttcaccaaga tttacttgat     1440
aataaaggtc gacaagttga ttttgaggct ttggataacc tgttggaacg actcaaggat     1500
gtctcaagtg ataaagtcaa gttagtggat gatattcttg ccttcttagc tccgattcgt     1560
catccagaac gtttaggaaa accaaatgcg caaattacct acactgatga tgagattcaa     1620
gtagccaagt tggcaggcaa gtacacaaca gaagacggtt atatctttga tcctcgtgat     1680
ataaccagtg atgaggggga tgcctatgta actccacata tgacccatag ccactggatt     1740
aaaaaagata gtttgtctga agctgagaga gcggcagccc aggcttatgc taaagagaaa     1800
ggtttgaccc ctccttcgac agaccatcag gattcaggaa atactgaggc aaaaggagca     1860
gaagctatct acaaccgcgt gaaagcagct aagaaggtgc cacttgatcg tatgccttac     1920
aatcttcaat atactgtaga agtcaaaaac ggtagtttaa tcatacctca ttatgaccat     1980
taccataaca tcaaatttga gtggtttgac gaaggccttt atgaggcacc taaggggtat     2040
actcttgagg atcttttggc gactgtcaag tactatgtcg aacatccaaa cgaacgtccg     2100
cattcagata atggttttgg taacgctagc gaccatgttc aaagaaacaa aaatggtcaa     2160
gctgatacca atcaaacgga aaaccaagc gaggagaaac ctcagacaga aaaacctgag     2220
gaagaaaccc ctcgagaaga gaaccacaa agcgagaaac cagagtctcc aaaaccaaca     2280
gaggaaccag aagaagaatc accagaggaa tcagaagaac ctcaggtcga gactgaaaag     2340
gttgaagaaa aactgagaga ggctgaagat ttacttggaa aaatccagga tccaattatc     2400
aagtccaatg ccaaagagac tctcacagga ttaaaaaata atttactatt tggcacccag     2460
gacaacaata ctattatggc agaagctgaa aaactattgg ctttattaaa ggagagtaag     2520
taa                                                                    2523
```

<210> SEQ ID NO 4
<211> LENGTH: 2647
<212> TYPE: DNA
<213> ORGANISM: Streptococcus pneumoniae

<400> SEQUENCE: 4

-continued

```
cagagatctt agtgaatcaa atatacttaa gaaaagagga aagaatgaaa atcaataaaa      60
aatatctagc tgggtcagta gctacacttg ttttaagtgt ctgtgcttat gaactaggtt     120
tgcatcaagc tcaaactgta aaagaaaata atcgtgtttc ctatatagat ggaaaacaag     180
cgacgcaaaa aacggagaat ttgactcctg atgaggttag caagcgtgaa ggaatcaacg     240
ccgaacaaat cgtcatcaag attacggatc aaggttatgt gacctctcat ggagaccatt     300
atcattacta taatggcaag gtcccttatg atgccatcat cagtgaagag ctcctcatga     360
aagatccgaa ttatcagttg aaggattcag acattgtcaa tgaaatcaag ggtggttatg     420
tcattaaggt aaacggtaaa tactatgttt accttaagga tgcagctcat gcggataatg     480
tccgtacaaa agaagaaatc aatcggcaaa acaagaaaca tagtcagcat cgtgaaggag     540
ggacttcagc aaacgatggt gcggtagcct ttgcacgttc acaggacgc tacaccacag      600
atgatggtta tatcttcaat gcatctgata tcatcgaaga tacgggcgat gcctatatcg     660
ttcctcatgg agatcattac cattacattc ctaagaatga gttatcagct agcgagttgg     720
ctgctgcaga agccttccta tctggtcggg aaaatctgtc aaatttaaga acctatcgcc     780
gacaaaatag cgataacact ccaagaacaa actgggtacc ttctgtaagc aatccaggaa     840
ctacaaatac taacaaagc aacaacagca cactaacag tcaagcaagt caaagtaatg       900
acattgatag tctcttgaaa cagctctaca aactgccttt gagtcaacgc catgtagaat     960
ctgatggcct tattttcgac ccagcgcaaa tcacaagtcg aaccgccaga ggtgtagctg    1020
tccctcatgg taaccattac cactttatcc cttatgaaca aatgtctgaa ttggaaaaac    1080
gaattgctcg tattattccc cttcgttatc gttcaaacca ttgggtacca gattcaagac    1140
cagaagaacc aagtccacaa ccgactccag aacctagtcc aagtccgcaa cctgcaccaa    1200
atcctcaacc agctccaagc aatccaattg atgagaaatt ggtcaaagaa gctgttcgaa    1260
aagtaggcga tggttatgtc tttgaggaga atggagtttc tcgttatatc ccagccaaga    1320
atctttcagc agaaacagca gcaggcattg atagcaaact ggccaagcag gaaagtttat    1380
ctcataagct aggagctaag aaaactgacc tcccatctag tgatcgagaa ttttacaata    1440
aggcttatga cttactagca agaattcacc aagatttact tgataataaa ggtcgacaag    1500
ttgattttga ggctttggat aacctgttgg aacgactcaa ggatgtctca agtgataaag    1560
tcaagttagt ggatgatatt cttgccttct tagctccgat tcgtcatcca gaacgtttag    1620
gaaaaccaaa tgcgcaaatt acctacactg atgatgagat tcaagtagcc aagttggcag    1680
gcaagtacac aacagaagac ggttatatct ttgatcctcg tgatataacc agtgatgagg    1740
gggatgccta tgtaactcca catatgaccc atagccactg gattaaaaaa gatagtttgt    1800
ctgaagctga gagagcggca gcccaggctt atgctaaaga aaaggttttg accccctcctt   1860
cgacagacca tcaggattca ggaaatactg aggcaaaagg agcagaagct atctacaacc    1920
gcgtgaaagc agctaagaag gtgccacttg atcgtatgcc ttacaatctt caatatactg    1980
tagaagtcaa aaacggtagt ttaatcatac ctcattatga ccattaccat aacatcaaat    2040
ttgagtggtt tgacgaaggc ctttatgagg cacctaaggg gtatactctt gaggatcttt    2100
tggcgactgt caagtactat gtcgaacatc caaacgaacg tccgcattca gataatggtt    2160
ttggtaacgc tagcgaccat gttcaaagaa acaaaaatgg tcaagctgat accaatcaaa    2220
cggaaaaacc aagcgaggag aaacctcaga cagaaaaacc tgaggaagaa acccctcgag    2280
aagagaaacc acaaagcgag aaaccagagt ctccaaaacc aacagaggaa ccagaagaag    2340
```

-continued

```
aatcaccaga ggaatcagaa gaacctcagg tcgagactga aaaggttgaa gaaaaactga      2400
gagaggctga agatttactt ggaaaaatcc aggatccaat tatcaagtcc aatgccaaag      2460
agactctcac aggattaaaa aataatttac tatttggcac ccaggacaac aatactatta      2520
tggcagaagc tgaaaaacta ttggctttat aaaggagag taagtaaagg tagcagcatt      2580
ttctaactcc taaaaacagg ataggagaac gggaaaacga aaatgagag cagaatgtga      2640 gttctag                                                               2647

<210> SEQ ID NO 5
<211> LENGTH: 2639
<212> TYPE: DNA
<213> ORGANISM: Streptococcus pneumoniae

<400> SEQUENCE: 5
gggtcttaaa actctgaatc ctttagaggc agacccacaa aatgacaaga cctatttaga       60
aaatctggaa gaaaatatga gtgttctagc agaagaatta aagtgaggaa agaatgaaaa      120
tcaataaaaa atatctagca ggttcagtgg cagtccttgc cctaagtgtt tgttcctatg      180
aacttggtcg tcaccaagct ggtcaggtta agaaagagtc taatcgagtt tcttatatag      240
atggtgatca ggctggtcaa aaggcagaaa atttgacacc agatgaagtc agtaagagag      300 agggatcaa cgccgaacaa attgttatca agattacgga tcaaggttat gtgacctctc      360
atggagacca ttatcattac tataatggca aggttcctta tgatgccatc atcagtgaag      420
aacttctcat gaaagatccg aattatcagt tgaaggattc agacattgtc aatgaaatca      480
agggtggcta tgtgattaag gtagacggaa aatactatgt ttaccttaaa gatgcggccc      540
atgcggacaa tattcggaca aaagaagaga ttaaacgtca gaagcaggaa cacagtcata      600
atcataactc aagagcagat aatgctgttg ctgcagccag agcccaagga cgttatacaa      660
cggatgatgg gtatatcttc aatgcatctg atatcattga ggacacgggt gatgcttata      720
tcgttcctca cggcgaccat taccattaca ttcctaagaa tgagttatca gctagcgagt      780
tagctgctgc agaagcctat tggaatggga agcagggatc tcgtccttct tcaagttcta      840
gttataatgc aaatccagtt caaccaagat tgtcagagaa ccacaatctg actgtcactc      900
caacttatca tcaaaatcaa ggggaaaaca tttcaagcct tttacgtgaa ttgtatgcta      960 aaccttatc agaacgccat gtagaatctg atggccttat tttcgaccca gcgcaaatca     1020
caagtcgaac cgccagaggt gtagctgtcc ctcatggtaa ccattaccac tttatccctt     1080
atgaacaaat gtctgaattg gaaaaacgaa ttgctcgtat tattcccctt cgttatcgtt     1140
caaaccattg ggtaccagat tcaagaccag aacaaccaag tccacaatcg actccggaac     1200
ctagtccaag tctgcaacct gcaccaaatc ctcaaccagc tccaagcaat ccaattgatg     1260
agaaattggt caagaagct gttcgaaaag taggcgatgg ttatgtcttt gaggagaatg     1320
gagtttctcg ttatatccca gccaaggatc tttcagcaga aacagcagca ggcattgata     1380
gcaaactggc caagcaggaa agtttatctc ataagctagg agctaagaaa actgacctcc     1440
catctagtga tcgagaattt tacaataagg cttatgactt actagcaaga attcaccaag     1500
atttacttga taataaaggt cgacaagttg attttgaggt tttggataac ctgttggaac     1560
gactcaagga tgtctcaagt gataaagtca agttagtgga tgatattctt gccttcttag     1620
ctccgattcg tcatccagaa cgtttaggaa aaccaaatgc gcaaattacc tacactgatg     1680
atgagattca gtagccaag ttggcaggca agtacacaac agaagacggt tatatctttg     1740
atcctcgtga tataaccagt gatgagggg atgcctatgt aactccacat atgacccata     1800
```

-continued

```
gccactggat taaaaaagat agtttgtctg aagctgagag agcggcagcc caggcttatg   1860
ctaaagagaa aggttttgacc cctccttcga cagaccacca ggattcagga aatactgagg   1920
caaaaggagc agaagctatc tacaaccgcg tgaaagcagc taagaaggtg ccacttgatc   1980
gtatgcctta caatcttcaa tatactgtag aagtcaaaaa cggtagttta atcataccct c   2040 attatgacca ttaccataac atcaaatttg agtggtttga cgaaggcctt tatgaggcac   2100
ctaaggggta tagtcttgag gatcttttgg cgactgtcaa gtactatgtc gaacatccaa   2160
acgaacgtcc gcattcagat aatggttttg gtaacgctag tgaccatgtt cgtaaaaata   2220
aggcagacca agatagtaaa cctgatgaag ataaggaaca tgatgaagta agtgagccaa   2280
ctcaccctga atctgatgaa aaagagaatc acgctggttt aaatccttca gcagataatc   2340
tttataaacc aagcactgat acggaagaga cagaggaaga agctgaagat accacagatg   2400
aggctgaaat tcctcaagta gagaattctg ttattaacgc taagatagca gatgcggagg   2460
ccttgctaga aaaagtaaca gatcctagta ttagacaaaa tgctatggag acattgactg   2520
gtctaaaaag tagtcttctt ctcggaacga aagataataa cactatttca gcagaagtag   2580
atagtctctt ggctttgtta aaagaaagtc aaccggctcc tatacagtag taaaatgaa   2639
```

<210> SEQ ID NO 6
<211> LENGTH: 1039
<212> TYPE: PRT
<213> ORGANISM: Streptococcus pneumoniae

<400> SEQUENCE: 6

```
Met Lys Phe Ser Lys Lys Tyr Ile Ala Ala Gly Ser Ala Val Ile Val
1               5                   10                  15

Ser Leu Ser Leu Cys Ala Tyr Ala Leu Asn Gln His Arg Ser Gln Glu
            20                  25                  30

Asn Lys Asp Asn Asn Arg Val Ser Tyr Val Asp Gly Ser Gln Ser Ser
        35                  40                  45

Gln Lys Ser Glu Asn Leu Thr Pro Asp Gln Val Ser Gln Lys Glu Gly
    50                  55                  60

Ile Gln Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Leu Phe Ser Glu Glu Leu Leu Met Lys Asp Pro Asn Tyr Gln
            100                 105                 110

Leu Lys Asp Ala Asp Ile Val Asn Glu Val Lys Gly Gly Tyr Ile Ile
        115                 120                 125

Lys Val Asp Gly Lys Tyr Tyr Val Tyr Leu Lys Asp Ala Ala His Ala
    130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
            180                 185                 190

Ile Ile Glu Asp Thr Gly Asn Ala Tyr Ile Val Pro His Gly Gly His
        195                 200                 205

Tyr His Tyr Ile Pro Lys Ser Asp Leu Ser Ala Ser Glu Leu Ala Ala
    210                 215                 220
```

```
Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
                245                 250                 255

Ser Thr Ser Lys Pro Ala Asn Lys Ser Glu Asn Leu Gln Ser Leu Leu
            260                 265                 270

Lys Glu Leu Tyr Asp Ser Pro Ser Ala Gln Arg Tyr Ser Glu Ser Asp
        275                 280                 285

Gly Leu Val Phe Asp Pro Ala Lys Ile Ile Ser Arg Thr Pro Asn Gly
290                 295                 300

Val Ala Ile Pro His Gly Asp His Tyr His Phe Ile Pro Tyr Ser Lys
305                 310                 315                 320

Leu Ser Ala Leu Glu Glu Lys Ile Ala Arg Met Val Pro Ile Ser Gly
                325                 330                 335

Thr Gly Ser Thr Val Ser Thr Asn Ala Lys Pro Asn Glu Val Val Ser
            340                 345                 350

Ser Leu Gly Ser Leu Ser Ser Asn Pro Ser Ser Leu Thr Thr Ser Lys
        355                 360                 365

Glu Leu Ser Ser Ala Ser Asp Gly Tyr Ile Phe Asn Pro Lys Asp Ile
370                 375                 380

Val Glu Glu Thr Ala Thr Ala Tyr Ile Val Arg His Gly Asp His Phe
385                 390                 395                 400

His Tyr Ile Pro Lys Ser Asn Gln Ile Gly Gln Pro Thr Leu Pro Asn
                405                 410                 415

Asn Ser Leu Ala Thr Pro Ser Pro Ser Leu Pro Ile Asn Pro Gly Thr
            420                 425                 430

Ser His Glu Lys His Glu Glu Asp Gly Tyr Gly Phe Asp Ala Asn Arg
        435                 440                 445

Ile Ile Ala Glu Asp Glu Ser Gly Phe Val Met Ser His Gly Asp His
450                 455                 460

Asn His Tyr Phe Phe Lys Lys Asp Leu Thr Glu Glu Gln Ile Lys Ala
465                 470                 475                 480

Ala Gln Lys His Leu Glu Glu Val Lys Thr Ser His Asn Gly Leu Asp
                485                 490                 495

Ser Leu Ser Ser His Glu Gln Asp Tyr Pro Gly Asn Ala Lys Glu Met
            500                 505                 510

Lys Asp Leu Asp Lys Lys Ile Glu Glu Lys Ile Ala Gly Ile Met Lys
        515                 520                 525

Gln Tyr Gly Val Lys Arg Glu Ser Ile Val Val Asn Lys Glu Lys Asn
530                 535                 540

Ala Ile Ile Tyr Pro His Gly Asp His His Ala Asp Pro Ile Asp
545                 550                 555                 560

Glu His Lys Pro Val Gly Ile Gly His Ser His Ser Asn Tyr Glu Leu
                565                 570                 575

Phe Lys Pro Glu Glu Gly Val Ala Lys Lys Glu Gly Asn Lys Val Tyr
            580                 585                 590

Thr Gly Glu Glu Leu Thr Asn Val Asn Leu Leu Lys Asn Ser Thr
        595                 600                 605

Phe Asn Asn Gln Asn Phe Thr Leu Ala Asn Gly Gln Lys Arg Val Ser
610                 615                 620

Phe Ser Phe Pro Pro Glu Leu Glu Lys Lys Leu Gly Ile Asn Met Leu
625                 630                 635                 640

Val Lys Leu Ile Thr Pro Asp Gly Lys Val Leu Glu Lys Val Ser Gly
```

-continued

```
            645                 650                 655
Lys Val Phe Gly Glu Gly Val Gly Asn Ile Ala Asn Phe Glu Leu Asp
            660                 665                 670
Gln Pro Tyr Leu Pro Gly Gln Thr Phe Lys Tyr Thr Ile Ala Ser Lys
            675                 680                 685
Asp Tyr Pro Glu Val Ser Tyr Asp Gly Thr Phe Thr Val Pro Thr Ser
            690                 695                 700
Leu Ala Tyr Lys Met Ala Ser Gln Thr Ile Phe Tyr Pro Phe His Ala
705                 710                 715                 720
Gly Asp Thr Tyr Leu Arg Val Asn Pro Gln Phe Ala Val Pro Lys Gly
            725                 730                 735
Thr Asp Ala Leu Val Arg Val Phe Asp Glu Phe His Gly Asn Ala Tyr
            740                 745                 750
Leu Glu Asn Asn Tyr Lys Val Gly Glu Ile Lys Leu Pro Ile Pro Lys
            755                 760                 765
Leu Asn Gln Gly Thr Thr Arg Thr Ala Gly Asn Lys Ile Pro Val Thr
            770                 775                 780
Phe Met Ala Asn Ala Tyr Leu Asp Asn Gln Ser Thr Tyr Ile Val Glu
785                 790                 795                 800
Val Pro Ile Leu Glu Lys Glu Asn Gln Thr Asp Lys Pro Ser Ile Leu
            805                 810                 815
Pro Gln Phe Lys Arg Asn Lys Ala Gln Glu Asn Ser Lys Leu Asp Glu
            820                 825                 830
Lys Val Glu Glu Pro Lys Thr Ser Glu Lys Val Glu Lys Glu Lys Leu
            835                 840                 845
Ser Glu Thr Gly Asn Ser Thr Ser Asn Ser Thr Leu Glu Glu Val Pro
            850                 855                 860
Thr Val Asp Pro Val Gln Glu Lys Val Ala Lys Phe Ala Glu Ser Tyr
865                 870                 875                 880
Gly Met Lys Leu Glu Asn Val Leu Phe Asn Met Asp Gly Thr Ile Glu
            885                 890                 895
Leu Tyr Leu Pro Ser Gly Glu Val Ile Lys Lys Asn Met Ala Asp Phe
            900                 905                 910
Thr Gly Glu Ala Pro Gln Gly Asn Gly Glu Asn Lys Pro Ser Glu Asn
            915                 920                 925
Gly Lys Val Ser Thr Gly Thr Val Glu Asn Gln Pro Thr Glu Asn Lys
            930                 935                 940
Pro Ala Asp Ser Leu Pro Glu Ala Pro Asn Glu Lys Pro Val Lys Pro
945                 950                 955                 960
Glu Asn Ser Thr Asp Asn Gly Met Leu Asn Pro Glu Gly Asn Val Gly
            965                 970                 975
Ser Asp Pro Met Leu Asp Pro Ala Leu Glu Glu Ala Pro Ala Val Asp
            980                 985                 990
Pro Val Gln Glu Lys Leu Glu Lys  Phe Thr Ala Ser Tyr  Gly Leu Gly
            995                 1000                1005
Leu Asp  Ser Val Ile Phe Asn  Met Asp Gly Thr Ile  Glu Leu Arg
            1010                1015               1020
Leu Pro  Ser Gly Glu Val Ile  Lys Lys Asn Leu Ser  Asp Phe Ile
            1025                1030               1035
Ala

<210> SEQ ID NO 7
<211> LENGTH: 840
```

```
<212> TYPE: PRT
<213> ORGANISM: Streptococcus pneumoniae

<400> SEQUENCE: 7

Met Lys Ile Asn Lys Lys Tyr Leu Ala Gly Ser Val Ala Thr Leu Val
1               5                   10                  15

Leu Ser Val Cys Ala Tyr Glu Leu Gly Leu His Gln Ala Gln Thr Val
                20                  25                  30

Lys Glu Asn Asn Arg Val Ser Tyr Ile Asp Gly Lys Gln Ala Thr Gln
            35                  40                  45

Lys Thr Glu Asn Leu Thr Pro Asp Glu Val Ser Lys Arg Glu Gly Ile
    50                  55                  60

Asn Ala Glu Gln Ile Val Ile Lys Ile Thr Asp Gln Gly Tyr Val Thr
65                  70                  75                  80

Ser His Gly Asp His Tyr His Tyr Asn Gly Lys Val Pro Tyr Asp
                85                  90                  95

Ala Ile Ile Ser Glu Glu Leu Leu Met Lys Asp Pro Asn Tyr Gln Leu
                100                 105                 110

Lys Asp Ser Asp Ile Val Asn Glu Ile Lys Gly Gly Tyr Val Ile Lys
            115                 120                 125

Val Asn Gly Lys Tyr Tyr Val Tyr Leu Lys Asp Ala Ala His Ala Asp
    130                 135                 140

Asn Val Arg Thr Lys Glu Glu Ile Asn Arg Gln Lys Gln Glu His Ser
145                 150                 155                 160

Gln His Arg Glu Gly Gly Thr Ser Ala Asn Asp Gly Ala Val Ala Phe
                165                 170                 175

Ala Arg Ser Gln Gly Arg Tyr Thr Thr Asp Asp Gly Tyr Ile Phe Asn
                180                 185                 190

Ala Ser Asp Ile Ile Glu Asp Thr Gly Asp Ala Tyr Ile Val Pro His
            195                 200                 205

Gly Asp His Tyr His Tyr Ile Pro Lys Asn Glu Leu Ser Ala Ser Glu
    210                 215                 220

Leu Ala Ala Ala Glu Ala Phe Leu Ser Gly Arg Glu Asn Leu Ser Asn
225                 230                 235                 240

Leu Arg Thr Tyr Arg Arg Gln Asn Ser Asp Asn Thr Pro Arg Thr Asn
                245                 250                 255

Trp Val Pro Ser Val Ser Asn Pro Gly Thr Thr Asn Thr Asn Thr Ser
                260                 265                 270

Asn Asn Ser Asn Thr Asn Ser Gln Ala Ser Gln Ser Asn Asp Ile Asp
            275                 280                 285

Ser Leu Leu Lys Gln Leu Tyr Lys Leu Pro Leu Ser Gln Arg His Val
    290                 295                 300

Glu Ser Asp Gly Leu Ile Phe Asp Pro Ala Gln Ile Thr Ser Arg Thr
305                 310                 315                 320

Ala Arg Gly Val Ala Val Pro His Gly Asn His Tyr His Phe Ile Pro
                325                 330                 335

Tyr Glu Gln Met Ser Glu Leu Glu Lys Arg Ile Ala Arg Ile Ile Pro
                340                 345                 350

Leu Arg Tyr Arg Ser Asn His Trp Val Pro Asp Ser Arg Pro Glu Glu
            355                 360                 365

Pro Ser Pro Gln Pro Thr Pro Glu Pro Ser Pro Gln Pro Ala
    370                 375                 380

Pro Asn Pro Gln Pro Ala Pro Ser Asn Pro Ile Asp Glu Lys Leu Val
385                 390                 395                 400
```

-continued

Lys Glu Ala Val Arg Lys Val Gly Asp Gly Tyr Val Phe Glu Glu Asn
            405                 410                 415

Gly Val Ser Arg Tyr Ile Pro Ala Lys Asn Leu Ser Ala Glu Thr Ala
        420                 425                 430

Ala Gly Ile Asp Ser Lys Leu Ala Lys Gln Glu Ser Leu Ser His Lys
            435                 440                 445

Leu Gly Ala Lys Lys Thr Asp Leu Pro Ser Ser Asp Arg Glu Phe Tyr
450                 455                 460

Asn Lys Ala Tyr Asp Leu Leu Ala Arg Ile His Gln Asp Leu Leu Asp
465                 470                 475                 480

Asn Lys Gly Arg Gln Val Asp Phe Glu Ala Leu Asp Asn Leu Leu Glu
            485                 490                 495

Arg Leu Lys Asp Val Ser Ser Asp Lys Val Lys Leu Val Asp Asp Ile
            500                 505                 510

Leu Ala Phe Leu Ala Pro Ile Arg His Pro Glu Arg Leu Gly Lys Pro
        515                 520                 525

Asn Ala Gln Ile Thr Tyr Thr Asp Asp Glu Ile Gln Val Ala Lys Leu
530                 535                 540

Ala Gly Lys Tyr Thr Thr Glu Asp Gly Tyr Ile Phe Asp Pro Arg Asp
545                 550                 555                 560

Ile Thr Ser Asp Glu Gly Asp Ala Tyr Val Thr Pro His Met Thr His
                565                 570                 575

Ser His Trp Ile Lys Lys Asp Ser Leu Ser Glu Ala Glu Arg Ala Ala
            580                 585                 590

Ala Gln Ala Tyr Ala Lys Glu Lys Gly Leu Thr Pro Pro Ser Thr Asp
        595                 600                 605

His Gln Asp Ser Gly Asn Thr Glu Ala Lys Gly Ala Glu Ala Ile Tyr
        610                 615                 620

Asn Arg Val Lys Ala Ala Lys Lys Val Pro Leu Asp Arg Met Pro Tyr
625                 630                 635                 640

Asn Leu Gln Tyr Thr Val Glu Val Lys Asn Gly Ser Leu Ile Ile Pro
                645                 650                 655

His Tyr Asp His Tyr His Asn Ile Lys Phe Glu Trp Phe Asp Glu Gly
            660                 665                 670

Leu Tyr Glu Ala Pro Lys Gly Tyr Thr Leu Glu Asp Leu Leu Ala Thr
        675                 680                 685

Val Lys Tyr Tyr Val Glu His Pro Asn Glu Arg Pro His Ser Asp Asn
    690                 695                 700

Gly Phe Gly Asn Ala Ser Asp His Val Gln Arg Asn Lys Asn Gly Gln
705                 710                 715                 720

Ala Asp Thr Asn Gln Thr Glu Lys Pro Ser Glu Lys Pro Gln Thr
                725                 730                 735

Glu Lys Pro Glu Glu Glu Thr Pro Arg Glu Glu Lys Pro Gln Ser Glu
            740                 745                 750

Lys Pro Glu Ser Pro Lys Pro Thr Glu Glu Pro Glu Glu Glu Ser Pro
        755                 760                 765

Glu Glu Ser Glu Glu Pro Gln Val Glu Thr Glu Lys Val Glu Glu Lys
        770                 775                 780

Leu Arg Glu Ala Glu Asp Leu Leu Gly Lys Ile Gln Asp Pro Ile Ile
785                 790                 795                 800

Lys Ser Asn Ala Lys Glu Thr Leu Thr Gly Leu Lys Asn Asn Leu Leu
                805                 810                 815

```
Phe Gly Thr Gln Asp Asn Asn Thr Ile Met Ala Glu Ala Glu Lys Leu
            820                 825                 830

Leu Ala Leu Leu Lys Glu Ser Lys
            835                 840

<210> SEQ ID NO 8
<211> LENGTH: 838
<212> TYPE: PRT
<213> ORGANISM: Streptococcus pneumoniae

<400> SEQUENCE: 8

Met Lys Ile Asn Lys Lys Tyr Leu Ala Gly Ser Val Ala Val Leu Ala
1               5                   10                  15

Leu Ser Val Cys Ser Tyr Glu Leu Gly Arg His Gln Ala Gly Gln Val
            20                  25                  30

Lys Lys Glu Ser Asn Arg Val Ser Tyr Ile Asp Gly Asp Gln Ala Gly
        35                  40                  45

Gln Lys Ala Glu Asn Leu Thr Pro Asp Glu Val Ser Lys Arg Glu Gly
    50                  55                  60

Ile Asn Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Ile Ile Ser Glu Glu Leu Leu Met Lys Asp Pro Asn Tyr Gln
            100                 105                 110

Leu Lys Asp Ser Asp Ile Val Asn Glu Ile Lys Gly Gly Tyr Val Ile
        115                 120                 125

Lys Val Asp Gly Lys Tyr Tyr Val Tyr Leu Lys Asp Ala Ala His Ala
    130                 135                 140

Asp Asn Ile Arg Thr Lys Glu Glu Ile Lys Arg Gln Lys Gln Glu His
145                 150                 155                 160

Ser His Asn His Asn Ser Arg Ala Asp Asn Ala Val Ala Ala Ala Arg
                165                 170                 175

Ala Gln Gly Arg Tyr Thr Thr Asp Asp Gly Tyr Ile Phe Asn Ala Ser
            180                 185                 190

Asp Ile Ile Glu Asp Thr Gly Asp Ala Tyr Ile Val Pro His Gly Asp
        195                 200                 205

His Tyr His Tyr Ile Pro Lys Asn Glu Leu Ser Ala Ser Glu Leu Ala
    210                 215                 220

Ala Ala Glu Ala Tyr Trp Asn Gly Lys Gln Gly Ser Arg Pro Ser Ser
225                 230                 235                 240

Ser Ser Ser Tyr Asn Ala Asn Pro Val Gln Pro Arg Leu Ser Glu Asn
                245                 250                 255

His Asn Leu Thr Val Thr Pro Thr Tyr His Gln Asn Gln Gly Glu Asn
            260                 265                 270

Ile Ser Ser Leu Leu Arg Glu Leu Tyr Ala Lys Pro Leu Ser Glu Arg
        275                 280                 285

His Val Glu Ser Asp Gly Leu Ile Phe Asp Pro Ala Gln Ile Thr Ser
    290                 295                 300

Arg Thr Ala Arg Gly Val Ala Val Pro His Gly Asn His Tyr His Phe
305                 310                 315                 320

Ile Pro Tyr Glu Gln Met Ser Glu Leu Glu Lys Arg Ile Ala Arg Ile
                325                 330                 335

Ile Pro Leu Arg Tyr Arg Ser Asn His Trp Val Pro Asp Ser Arg Pro
            340                 345                 350
```

-continued

```
Glu Gln Pro Ser Pro Gln Ser Thr Pro Glu Pro Ser Pro Ser Leu Gln
            355                 360                 365
Pro Ala Pro Asn Pro Gln Pro Ala Pro Ser Asn Pro Ile Asp Glu Lys
        370                 375                 380
Leu Val Lys Glu Ala Val Arg Lys Val Gly Asp Gly Tyr Val Phe Glu
385                 390                 395                 400
Glu Asn Gly Val Ser Arg Tyr Ile Pro Ala Lys Asp Leu Ser Ala Glu
                405                 410                 415
Thr Ala Ala Gly Ile Asp Ser Lys Leu Ala Lys Gln Glu Ser Leu Ser
            420                 425                 430
His Lys Leu Gly Ala Lys Lys Thr Asp Leu Pro Ser Ser Asp Arg Glu
        435                 440                 445
Phe Tyr Asn Lys Ala Tyr Asp Leu Leu Ala Arg Ile His Gln Asp Leu
    450                 455                 460
Leu Asp Asn Lys Gly Arg Gln Val Asp Phe Glu Val Leu Asp Asn Leu
465                 470                 475                 480
Leu Glu Arg Leu Lys Asp Val Ser Ser Asp Lys Val Lys Leu Val Asp
                485                 490                 495
Asp Ile Leu Ala Phe Leu Ala Pro Ile Arg His Pro Glu Arg Leu Gly
            500                 505                 510
Lys Pro Asn Ala Gln Ile Thr Tyr Thr Asp Asp Glu Ile Gln Val Ala
        515                 520                 525
Lys Leu Ala Gly Lys Tyr Thr Thr Glu Asp Gly Tyr Ile Phe Asp Pro
    530                 535                 540
Arg Asp Ile Thr Ser Asp Glu Gly Asp Ala Tyr Val Thr Pro His Met
545                 550                 555                 560
Thr His Ser His Trp Ile Lys Lys Asp Ser Leu Ser Glu Ala Glu Arg
                565                 570                 575
Ala Ala Ala Gln Ala Tyr Ala Lys Glu Lys Gly Leu Thr Pro Pro Ser
            580                 585                 590
Thr Asp His Gln Asp Ser Gly Asn Thr Glu Ala Lys Gly Ala Glu Ala
        595                 600                 605
Ile Tyr Asn Arg Val Lys Ala Ala Lys Lys Val Pro Leu Asp Arg Met
    610                 615                 620
Pro Tyr Asn Leu Gln Tyr Thr Val Glu Val Lys Asn Gly Ser Leu Ile
625                 630                 635                 640
Ile Pro His Tyr Asp His Tyr His Asn Ile Lys Phe Glu Trp Phe Asp
                645                 650                 655
Glu Gly Leu Tyr Glu Ala Pro Lys Gly Tyr Ser Leu Glu Asp Leu Leu
            660                 665                 670
Ala Thr Val Lys Tyr Tyr Val Glu His Pro Asn Glu Arg Pro His Ser
        675                 680                 685
Asp Asn Gly Phe Gly Asn Ala Ser Asp His Val Arg Lys Asn Lys Ala
    690                 695                 700
Asp Gln Asp Ser Lys Pro Asp Glu Asp Lys Glu His Asp Glu Val Ser
705                 710                 715                 720
Glu Pro Thr His Pro Glu Ser Asp Glu Lys Glu Asn His Ala Gly Leu
                725                 730                 735
Asn Pro Ser Ala Asp Asn Leu Tyr Lys Pro Ser Thr Asp Thr Glu Glu
            740                 745                 750
Thr Glu Glu Glu Ala Glu Asp Thr Thr Asp Glu Ala Glu Ile Pro Gln
        755                 760                 765
```

-continued

| | | | | | | | | | | | |
|---|---|---|---|---|---|---|---|---|---|---|---|
|Val|Glu|Asn|Ser|Val|Ile|Asn|Ala|Lys|Ile|Ala|Asp Ala Glu Ala Leu|
| |770| | |775| | | |780| | | |
|Leu|Glu|Lys|Val|Thr|Asp|Pro|Ser|Ile|Arg|Gln|Asn Ala Met Glu Thr|
|785| | | |790| | | |795| | |800|
|Leu|Thr|Gly|Leu|Lys|Ser|Ser|Leu|Leu|Leu|Gly|Thr Lys Asp Asn Asn|
| | | | |805| | | |810| | |815|
|Thr|Ile|Ser|Ala|Glu|Val|Asp|Ser|Leu|Leu|Ala|Leu Leu Lys Glu Ser|
| | | |820| | | |825| | | |830|
|Gln|Pro|Ala|Pro|Ile|Gln| | | | | | |
| | | |835| | | | | | | | |

<210> SEQ ID NO 9
<211> LENGTH: 2528
<212> TYPE: DNA
<213> ORGANISM: Streptococcus pneumoniae

<400> SEQUENCE: 9

| | |
|---|---|
|tgtgcctatg cactaaacca gcatcgttcg caggaaaata aggacaataa tcgtgtctct|60|
|tatgtggatg gcagccagtc aagtcagaaa agtgaaaact tgacaccaga ccaggttagc|120|
|cagaagaag gaattcaggc tgagcaaatt gtaatcaaaa ttacagatca gggctatgta|180|
|acgtcacacg gtgatcacta tcattactat aatgggaaag ttccttatga tgccctcttt|240|
|agtgaagaac tcttgatgaa ggatccaaac tatcaactta agacgctga tattgtcaat|300|
|gaagtcaagg gtggttatat catcaaggtc gatggaaaat attatgtcta cctgaaagat|360|
|gcagctcatg ctgataatgt tcgaactaaa gatgaaatca atcgtcaaaa acaagaacat|420|
|gtcaaagata tgagaaggt taactctaat gttgctgtag caaggtctca gggacgatat|480|
|acgacaaatg atggttatgt ctttaatcca gctgatatta tcgaagatac gggtaatgct|540|
|tatatcgttc ctcatggagg tcactataca tacattccca aaagcgattt atctgctagt|600|
|gaattagcag cagctaaagc acatctggct ggaaaaaata tgcaaccgag tcagttaagc|660|
|tattcttcaa caccttctcc atctcttcca atcaatccag gaacttcaca tgagaaacat|720|
|gaagaagatg gatacggatt tgatgctaat cgtattatcg ctgaagatga atcaggtttt|780|
|gtcatgagtc acggagacca caatcattat ttcttcaaga aggacttgac agaagagcaa|840|
|attaaggctg cgcaaaaaca tttagaggaa gttaaaacta gtcataatgg attagattct|900|
|ttgtcatctc atgaacagga ttatccaagt aatgccaaag aaatgaaaga tttagataaa|960|
|aaaatcgaag aaaaaattgc tggcattatg aaacaatatg gtgtcaaacg tgaaagtatt|1020|
|gtcgtgaata agaaaaaaa tgcgattatt tatccgcatg gagatcacca tcatgcagat|1080|
|ccgattgatg aacataaacc ggttggaatt ggtcattctc acagtaacta tgaactgttt|1140|
|aaacccgaag aaggagttgc taaaaagaa gggaataaag tttatactgg agaagaatta|1200|
|acgaatgttg ttaatttgtt aaaaaatagt acgtttaata atcaaaactt tactctagcc|1260|
|aatggtcaaa acgcgttttc ttttagtttt ccgcctgaat tggagaaaaa attaggtatc|1320|
|aatatgctag taaaattaat aacaccagat ggaaaagtat tggagaaagt atctggtaaa|1380|
|gtatttggag aaggagtagg gaatattgca actttgaat tagatcaacc ttatttacca|1440|
|ggacaaacat ttaagtatac tatcgcttca aaagattatc cagaagtaag ttatgatggt|1500|
|acatttacag ttccaacctc tttagcttac aaaatggcca gtcaaacgat tttctatcct|1560|
|ttccatgcag gggatactta tttaagagtg aaccctcaat ttgcagtgcc taaaggaact|1620|
|gatgctttag tcagagtgtt tgatgaattt catggaaatg cttatttaga aaataactat|1680|

-continued

```
aaagttggtg aaatcaaatt accgattccg aaattaaacc aaggaacaac cagaacggcc    1740
ggaaataaaa ttcctgtaac cttcatggca atgcttatt  tggacaatca atcgacttat    1800
attgtggaag tacctatctt ggaaaaagaa atcaaactg  ataaaccaag tattctacca    1860
caatttaaaa ggaataaagc acaagaaaac tcaaaacttg atgaaaaggt agaagaacca    1920
aagactagtg agaaggtaga aaagaaaaa  ctttctgaaa ctgggaatag tactagtaat    1980
tcaacgttag aagaagttcc tacagtggat cctgtacaag aaaaagtagc aaaatttgct    2040
gaaagttatg ggatgaagct agaaaatgtc ttgtttaata tggacggaac aattgaatta    2100
tatttaccat cgggagaagt cattaaaaag aatatggcag attttacagg agaagcacct    2160
caaggaaatg gtgaaaataa accatctgaa aatggaaaag tatctactgg aacagttgag    2220
aaccaaccaa cagaaaataa accagcagat tctttaccag aggcaccaaa cgaaaaacct    2280
gtaaaaccag aaaactcaac ggataatgga atgttgaatc cagaagggaa tgtggggagt    2340
gaccctatgt tagattcagc attagaggaa gctccagcag tagatcctgt acaagaaaaa    2400
ttagaaaaat ttacagctag ttacggatta ggcttagata gtgttatatt caatatggat    2460
ggaacgattg aattaagatt gccaagtgga gaagtgataa aaaagaattt attgatctca    2520
tagcgtaa                                                            2528
```

<210> SEQ ID NO 10
<211> LENGTH: 840
<212> TYPE: PRT
<213> ORGANISM: Streptococcus pneumoniae

<400> SEQUENCE: 10

```
Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
    50                  55                  60

Asp His Tyr His Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly Gly His Tyr His Tyr Ile
            180                 185                 190

Pro Lys Ser Asp Leu Ser Ala Ser Glu Leu Ala Ala Ala Lys Ala His
        195                 200                 205

Leu Ala Gly Lys Asn Met Gln Pro Ser Gln Leu Ser Tyr Ser Ser Thr
    210                 215                 220
```

-continued

Pro Ser Pro Ser Leu Pro Ile Asn Pro Gly Thr Ser His Glu Lys His
225                 230                 235                 240

Glu Glu Asp Gly Tyr Gly Phe Asp Ala Asn Arg Ile Ile Ala Glu Asp
            245                 250                 255

Glu Ser Gly Phe Val Met Ser His Gly Asp His Asn His Tyr Phe Phe
            260                 265                 270

Lys Lys Asp Leu Thr Glu Glu Gln Ile Lys Ala Ala Gln Lys His Leu
        275                 280                 285

Glu Glu Val Lys Thr Ser His Asn Gly Leu Asp Ser Leu Ser Ser His
    290                 295                 300

Glu Gln Asp Tyr Pro Ser Asn Ala Lys Glu Met Lys Asp Leu Asp Lys
305                 310                 315                 320

Lys Ile Glu Glu Lys Ile Ala Gly Ile Met Lys Gln Tyr Gly Val Lys
                325                 330                 335

Arg Glu Ser Ile Val Val Asn Lys Glu Lys Asn Ala Ile Ile Tyr Pro
            340                 345                 350

His Gly Asp His His His Ala Asp Pro Ile Asp Glu His Lys Pro Val
        355                 360                 365

Gly Ile Gly His Ser His Ser Asn Tyr Glu Leu Phe Lys Pro Glu Glu
    370                 375                 380

Gly Val Ala Lys Lys Glu Gly Asn Lys Val Tyr Thr Gly Glu Glu Leu
385                 390                 395                 400

Thr Asn Val Val Asn Leu Leu Lys Asn Ser Thr Phe Asn Asn Gln Asn
                405                 410                 415

Phe Thr Leu Ala Asn Gly Gln Lys Arg Val Ser Phe Ser Phe Pro Pro
            420                 425                 430

Glu Leu Glu Lys Lys Leu Gly Ile Asn Met Leu Val Lys Leu Ile Thr
        435                 440                 445

Pro Asp Gly Lys Val Leu Glu Lys Val Ser Gly Lys Val Phe Gly Glu
    450                 455                 460

Gly Val Gly Asn Ile Ala Asn Phe Glu Leu Asp Gln Pro Tyr Leu Pro
465                 470                 475                 480

Gly Gln Thr Phe Lys Tyr Thr Ile Ala Ser Lys Asp Tyr Pro Glu Val
            485                 490                 495

Ser Tyr Asp Gly Thr Phe Thr Val Pro Thr Ser Leu Ala Tyr Lys Met
            500                 505                 510

Ala Ser Gln Thr Ile Phe Tyr Pro Phe His Ala Gly Asp Thr Tyr Leu
        515                 520                 525

Arg Val Asn Pro Gln Phe Ala Val Pro Lys Gly Thr Asp Ala Leu Val
    530                 535                 540

Arg Val Phe Asp Glu Phe His Gly Asn Ala Tyr Leu Glu Asn Asn Tyr
545                 550                 555                 560

Lys Val Gly Glu Ile Lys Leu Pro Ile Pro Lys Leu Asn Gln Gly Thr
                565                 570                 575

Thr Arg Thr Ala Gly Asn Lys Ile Pro Val Thr Phe Met Ala Asn Ala
            580                 585                 590

Tyr Leu Asp Asn Gln Ser Thr Tyr Ile Val Glu Val Pro Ile Leu Glu
        595                 600                 605

Lys Glu Asn Gln Thr Asp Lys Pro Ser Ile Leu Pro Gln Phe Lys Arg
    610                 615                 620

Asn Lys Ala Gln Glu Asn Ser Lys Leu Asp Glu Lys Val Glu Glu Pro
625                 630                 635                 640

```
                                   -continued

Lys Thr Ser Glu Lys Val Glu Lys Leu Ser Glu Thr Gly Asn
                645             650             655

Ser Thr Ser Asn Ser Thr Leu Glu Glu Val Pro Thr Val Asp Pro Val
            660                 665                 670

Gln Glu Lys Val Ala Lys Phe Ala Glu Ser Tyr Gly Met Lys Leu Glu
            675                 680                 685

Asn Val Leu Phe Asn Met Asp Gly Thr Ile Glu Leu Tyr Leu Pro Ser
            690                 695                 700

Gly Glu Val Ile Lys Lys Asn Met Ala Asp Phe Thr Gly Glu Ala Pro
705             710                 715                 720

Gln Gly Asn Gly Glu Asn Lys Pro Ser Glu Asn Gly Lys Val Ser Thr
                725                 730                 735

Gly Thr Val Glu Asn Gln Pro Thr Glu Asn Lys Pro Ala Asp Ser Leu
            740                 745                 750

Pro Glu Ala Pro Asn Glu Lys Pro Val Lys Pro Glu Asn Ser Thr Asp
            755                 760                 765

Asn Gly Met Leu Asn Pro Glu Gly Asn Val Gly Ser Asp Pro Met Leu
            770                 775                 780

Asp Ser Ala Leu Glu Ala Pro Ala Val Asp Pro Val Gln Glu Lys
785             790                 795                 800

Leu Glu Lys Phe Thr Ala Ser Tyr Gly Leu Gly Leu Asp Ser Val Ile
                805                 810                 815

Phe Asn Met Asp Gly Thr Ile Glu Leu Arg Leu Pro Ser Gly Glu Val
            820                 825                 830

Ile Lys Lys Asn Leu Leu Ile Ser
            835                 840

<210> SEQ ID NO 11
<211> LENGTH: 94
<212> TYPE: PRT
<213> ORGANISM: Artificial Sequence
<220> FEATURE:
<223> OTHER INFORMATION: Unknown Organism

<400> SEQUENCE: 11

Asp Gln Gly Tyr Val Thr Ser His Gly Asp His Tyr His Tyr Tyr Asn
1               5                   10                  15

Gly Lys Val Pro Tyr Asp Ala Leu Phe Ser Glu Glu Leu Leu Met Lys
            20                  25                  30

Asp Pro Asn Tyr Gln Leu Lys Asp Ala Asp Ile Val Asn Glu Val Lys
            35                  40                  45

Gly Gly Tyr Ile Ile Lys Val Asp Gly Lys Tyr Tyr Val Tyr Leu Lys
        50                  55                  60

Asp Ala Ala His Ala Asp Asn Val Arg Thr Lys Asp Glu Ile Asn Arg
65                  70                  75                  80

Gln Lys Gln Glu His Val Lys Asp Asn Glu Lys Val Asn Ser
                85                  90

<210> SEQ ID NO 12
<211> LENGTH: 42
<212> TYPE: PRT
<213> ORGANISM: Artificial Sequence
<220> FEATURE:
<223> OTHER INFORMATION: Unknown Organism

<400> SEQUENCE: 12

Gly Ile Gln Ala Glu Gln Ile Val Ile Lys Ile Thr Asp Gln Gly Tyr
1               5                   10                  15
```

Val Thr Ser His Gly Asp His Tyr His Tyr Tyr Asn Gly Lys Val Pro
        20                  25                  30

Tyr Asp Ala Leu Phe Ser Glu Glu Leu Leu
        35                  40

<210> SEQ ID NO 13
<211> LENGTH: 39
<212> TYPE: PRT
<213> ORGANISM: Artificial Sequence
<220> FEATURE:
<223> OTHER INFORMATION: Unknown Organism

<400> SEQUENCE: 13

Thr Ala Tyr Ile Val Arg His Gly Asp His Phe His Tyr Ile Pro Lys
1               5                   10                  15

Ser Asn Gln Ile Gly Gln Pro Thr Leu Pro Asn Asn Ser Leu Ala Thr
        20                  25                  30

Pro Ser Pro Ser Leu Pro Ile
        35

<210> SEQ ID NO 14
<211> LENGTH: 36
<212> TYPE: PRT
<213> ORGANISM: Artificial Sequence
<220> FEATURE:
<223> OTHER INFORMATION: Unknown Organism

<400> SEQUENCE: 14

Thr Ser Asn Ser Thr Leu Glu Glu Val Pro Thr Val Asp Pro Val Gln
1               5                   10                  15

Glu Lys Val Ala Lys Phe Ala Glu Ser Tyr Gly Met Lys Leu Glu Asn
        20                  25                  30

Val Leu Phe Asn
        35

<210> SEQ ID NO 15
<211> LENGTH: 24
<212> TYPE: PRT
<213> ORGANISM: Artificial Sequence
<220> FEATURE:
<223> OTHER INFORMATION: Unknown Organism

<400> SEQUENCE: 15

Met Asp Gly Thr Ile Glu Leu Arg Leu Pro Ser Gly Glu Val Ile Lys
1               5                   10                  15

Lys Asn Leu Ser Asp Phe Ile Ala
        20

<210> SEQ ID NO 16
<211> LENGTH: 35
<212> TYPE: PRT
<213> ORGANISM: Artificial Sequence
<220> FEATURE:
<223> OTHER INFORMATION: Organism Unknown

<400> SEQUENCE: 16

Tyr Gly Leu Gly Leu Asp Ser Val Ile Phe Asn Met Asp Gly Thr Ile
1               5                   10                  15

Glu Leu Arg Leu Pro Ser Gly Glu Val Ile Lys Lys Asn Leu Ser Asp
        20                  25                  30

Phe Ile Ala
        35

```
<210> SEQ ID NO 17
<211> LENGTH: 57
<212> TYPE: PRT
<213> ORGANISM: Artificial Sequence
<220> FEATURE:
<223> OTHER INFORMATION: Unknown Organism

<400> SEQUENCE: 17

Pro Ala Leu Glu Glu Ala Pro Ala Val Asp Pro Val Gln Glu Lys Leu
1               5                   10                  15

Glu Lys Phe Thr Ala Ser Tyr Gly Leu Gly Leu Asp Ser Val Ile Phe
            20                  25                  30

Asn Met Asp Gly Thr Ile Glu Leu Arg Leu Pro Ser Gly Glu Val Ile
        35                  40                  45

Lys Lys Asn Leu Ser Asp Phe Ile Ala
    50                  55

<210> SEQ ID NO 18
<211> LENGTH: 40
<212> TYPE: PRT
<213> ORGANISM: Artificial Sequence
<220> FEATURE:
<223> OTHER INFORMATION: Unknown Organism

<400> SEQUENCE: 18

Lys Val Glu Glu Pro Lys Thr Ser Glu Lys Val Glu Lys Glu Lys Leu
1               5                   10                  15

Ser Glu Thr Gly Asn Ser Thr Ser Asn Ser Thr Leu Glu Glu Val Pro
            20                  25                  30

Thr Val Asp Pro Val Gln Glu Lys
        35                  40

<210> SEQ ID NO 19
<211> LENGTH: 78
<212> TYPE: PRT
<213> ORGANISM: Artificial Sequence
<220> FEATURE:
<223> OTHER INFORMATION: Unknown Organism

<400> SEQUENCE: 19

Met Lys Asp Leu Asp Lys Lys Ile Glu Glu Lys Ile Ala Gly Ile Met
1               5                   10                  15

Lys Gln Tyr Gly Val Lys Arg Glu Ser Ile Val Val Asn Lys Glu Lys
            20                  25                  30

Asn Ala Ile Ile Tyr Pro His Gly Asp His His Ala Asp Pro Ile
        35                  40                  45

Asp Glu His Lys Pro Val Gly Ile Gly His Ser His Ser Asn Tyr Glu
    50                  55                  60

Leu Phe Lys Pro Glu Glu Gly Val Ala Lys Lys Glu Gly Asn
65                  70                  75

<210> SEQ ID NO 20
<211> LENGTH: 51
<212> TYPE: PRT
<213> ORGANISM: Artificial Sequence
<220> FEATURE:
<223> OTHER INFORMATION: Unknown Organism

<400> SEQUENCE: 20

Ala Ile Ile Tyr Pro His Gly Asp His His Ala Asp Pro Ile Asp
1               5                   10                  15
```

```
Glu His Lys Pro Val Gly Ile Gly His Ser His Ser Asn Tyr Glu Leu
            20                  25                  30

Phe Lys Pro Glu Glu Gly Val Ala Lys Lys Glu Gly Asn Lys Val Tyr
        35                  40                  45

Thr Gly Glu
    50

<210> SEQ ID NO 21
<211> LENGTH: 29
<212> TYPE: PRT
<213> ORGANISM: Artificial Sequence
<220> FEATURE:
<223> OTHER INFORMATION: Unknown Organism

<400> SEQUENCE: 21

Ile Gln Val Ala Lys Leu Ala Gly Lys Tyr Thr Thr Glu Asp Gly Tyr
1               5                   10                  15

Ile Phe Asp Pro Arg Asp Ile Thr Ser Asp Glu Gly Asp
            20                  25

<210> SEQ ID NO 22
<211> LENGTH: 86
<212> TYPE: PRT
<213> ORGANISM: Artificial Sequence
<220> FEATURE:
<223> OTHER INFORMATION: Unknown Organism

<400> SEQUENCE: 22

Asp His Gln Asp Ser Gly Asn Thr Glu Ala Lys Gly Ala Glu Ala Ile
1               5                   10                  15

Tyr Asn Arg Val Lys Ala Ala Lys Lys Val Pro Leu Asp Arg Met Pro
            20                  25                  30

Tyr Asn Leu Gln Tyr Thr Val Glu Val Lys Asn Gly Ser Leu Ile Ile
        35                  40                  45

Pro His Tyr Asp His Tyr His Asn Ile Lys Phe Glu Trp Phe Asp Glu
    50                  55                  60

Gly Leu Tyr Glu Ala Pro Lys Gly Tyr Ser Leu Glu Asp Leu Leu Ala
65                  70                  75                  80

Thr Val Lys Tyr Tyr Val
                85

<210> SEQ ID NO 23
<211> LENGTH: 41
<212> TYPE: PRT
<213> ORGANISM: Artificial Sequence
<220> FEATURE:
<223> OTHER INFORMATION: Unknown Organism

<400> SEQUENCE: 23

Gly Leu Tyr Glu Ala Pro Lys Gly Tyr Ser Leu Glu Asp Leu Leu Ala
1               5                   10                  15

Thr Val Lys Tyr Tyr Val Glu His Pro Asn Glu Arg Pro His Ser Asp
            20                  25                  30

Asn Gly Phe Gly Asn Ala Ser Asp His
        35                  40

<210> SEQ ID NO 24
<211> LENGTH: 69
<212> TYPE: PRT
<213> ORGANISM: Artificial Sequence
<220> FEATURE:
```

<223> OTHER INFORMATION: Unknown Organism

<400> SEQUENCE: 24

Val Glu Asn Ser Val Ile Asn Ala Lys Ile Ala Asp Ala Glu Ala Leu
1               5                   10                  15

Leu Glu Lys Val Thr Asp Pro Ser Ile Arg Gln Asn Ala Met Glu Thr
            20                  25                  30

Leu Thr Gly Leu Lys Ser Ser Leu Leu Gly Thr Lys Asp Asn Asn
        35                  40                  45

Thr Ile Ser Ala Glu Val Asp Ser Leu Leu Ala Leu Leu Lys Glu Ser
    50                  55                  60

Gln Pro Ala Pro Ile
65

<210> SEQ ID NO 25
<211> LENGTH: 27
<212> TYPE: DNA
<213> ORGANISM: Artificial Sequence
<220> FEATURE:
<223> OTHER INFORMATION: Unknown Organism

<400> SEQUENCE: 25
cagtagatct gtgcctatgc actaaac                                    27

<210> SEQ ID NO 26
<211> LENGTH: 33
<212> TYPE: DNA
<213> ORGANISM: Artificial Sequence
<220> FEATURE:
<223> OTHER INFORMATION: Unknown Organism

<400> SEQUENCE: 26
gatctctaga ctactgctat tccttacgct atg                             33

<210> SEQ ID NO 27
<211> LENGTH: 30
<212> TYPE: DNA
<213> ORGANISM: Artificial Sequence
<220> FEATURE:
<223> OTHER INFORMATION: Unknown Organism

<400> SEQUENCE: 27
atcactcgag cattacctgg ataatcctgt                                 30

<210> SEQ ID NO 28
<211> LENGTH: 26
<212> TYPE: DNA
<213> ORGANISM: Artificial Sequence
<220> FEATURE:
<223> OTHER INFORMATION: Unknown Organism

<400> SEQUENCE: 28
ctgctaagct tatgaaagat ttagat                                     26

<210> SEQ ID NO 29
<211> LENGTH: 24
<212> TYPE: DNA
<213> ORGANISM: Artificial Sequence
<220> FEATURE:
<223> OTHER INFORMATION: Unknown Organism

<400> SEQUENCE: 29
gatactcgag ctgctattcc ttac                                       24

<210> SEQ ID NO 30
<211> LENGTH: 28
<212> TYPE: DNA
<213> ORGANISM: Artificial Sequence
<220> FEATURE:
<223> OTHER INFORMATION: Unknown Organism

<400> SEQUENCE: 30
gaatctcgag ttaagctgct gctaattc                                28

<210> SEQ ID NO 31
<211> LENGTH: 32
<212> TYPE: DNA
<213> ORGANISM: Artificial Sequence
<220> FEATURE:
<223> OTHER INFORMATION: Unknown Organism

<400> SEQUENCE: 31
gacgctcgag cgctatgaaa tcagataaat tc                           32

<210> SEQ ID NO 32
<211> LENGTH: 37
<212> TYPE: DNA
<213> ORGANISM: Artificial Sequence
<220> FEATURE:
<223> OTHER INFORMATION: Unknown Organism

<400> SEQUENCE: 32
gacgctcgag ggcattacct ggataatcct gttcatg                      37

<210> SEQ ID NO 33
<211> LENGTH: 33
<212> TYPE: DNA
<213> ORGANISM: Artificial Sequence
<220> FEATURE:
<223> OTHER INFORMATION: Unknown Organism

<400> SEQUENCE: 33
cagtagatct cttcatcatt tattgaaaag agg                          33

<210> SEQ ID NO 34
<211> LENGTH: 40
<212> TYPE: DNA
<213> ORGANISM: Artificial Sequence
<220> FEATURE:
<223> OTHER INFORMATION: Unknown Organism

<400> SEQUENCE: 34
ttatttcttc catatggact tgacagaaga gcaaattaag                   40

<210> SEQ ID NO 35
<211> LENGTH: 32
<212> TYPE: DNA
<213> ORGANISM: Artificial Sequence
<220> FEATURE:
<223> OTHER INFORMATION: Organism Unknown

<400> SEQUENCE: 35
cgccaagctt cgctatgaaa tcagataaat tc                           32

<210> SEQ ID NO 36
<211> LENGTH: 34
<212> TYPE: DNA
<213> ORGANISM: Artificial Sequence
<220> FEATURE:
<223> OTHER INFORMATION: Unknown Organism

<400> SEQUENCE: 36
cgccaagctt ttccacaata taagtcgatt gatt                                    34

<210> SEQ ID NO 37
<211> LENGTH: 40
<212> TYPE: DNA
<213> ORGANISM: Artificial Sequence
<220> FEATURE:
<223> OTHER INFORMATION: Unknown Organism

<400> SEQUENCE: 37
ttatttcttc catatggaag tacctatctt ggaaaaagaa                              40

<210> SEQ ID NO 38
<211> LENGTH: 37
<212> TYPE: DNA
<213> ORGANISM: Artificial Sequence
<220> FEATURE:
<223> OTHER INFORMATION: Unknown Organism

<400> SEQUENCE: 38
ttatttcttc catatggtgc ctatgcacta aaccagc                                 37

<210> SEQ ID NO 39
<211> LENGTH: 40
<212> TYPE: DNA
<213> ORGANISM: Artificial Sequence
<220> FEATURE:
<223> OTHER INFORMATION: Unknown Organism

<400> SEQUENCE: 39
ataagaatgc ggccgcttcc acaatataag tcgattgatt                              40

<210> SEQ ID NO 40
<211> LENGTH: 31
<212> TYPE: DNA
<213> ORGANISM: Artificial Sequence
<220> FEATURE:
<223> OTHER INFORMATION: Unknown Organism

<400> SEQUENCE: 40
cagtagatct gtgcttatga actaggtttg c                                       31

<210> SEQ ID NO 41
<211> LENGTH: 32
<212> TYPE: DNA
<213> ORGANISM: Artificial Sequence
<220> FEATURE:
<223> OTHER INFORMATION: Unknown Organism

<400> SEQUENCE: 41
gatcaagctt gctgctacct ttacttactc tc                                      32

<210> SEQ ID NO 42
<211> LENGTH: 26
<212> TYPE: DNA
<213> ORGANISM: Artificial Sequence
<220> FEATURE:
<223> OTHER INFORMATION: Unknown Organism

<400> SEQUENCE: 42
ctgagatatc cgttatcgtt caaacc                                             26

<210> SEQ ID NO 43

```
<211> LENGTH: 28
<212> TYPE: DNA
<213> ORGANISM: Artificial Sequence
<220> FEATURE:
<223> OTHER INFORMATION: Unknown Organism

<400> SEQUENCE: 43
ctgcaagctt ttaaagggga ataatacg                                               28

<210> SEQ ID NO 44
<211> LENGTH: 29
<212> TYPE: DNA
<213> ORGANISM: Artificial Sequence
<220> FEATURE:
<223> OTHER INFORMATION: Unknown Organism

<400> SEQUENCE: 44
cagtagatct gcagaagcct tcctatctg                                              29

<210> SEQ ID NO 45
<211> LENGTH: 33
<212> TYPE: DNA
<213> ORGANISM: Artificial Sequence
<220> FEATURE:
<223> OTHER INFORMATION: Unknown Organism

<400> SEQUENCE: 45
tcgccaagct tcgttatcgt tcaaaccatt ggg                                         33

<210> SEQ ID NO 46
<211> LENGTH: 45
<212> TYPE: DNA
<213> ORGANISM: Artificial Sequence
<220> FEATURE:
<223> OTHER INFORMATION: Unknown Organism

<400> SEQUENCE: 46
ataagaatgc ggccgcctta ctctccttta ataaagccaa tagtt                            45

<210> SEQ ID NO 47
<211> LENGTH: 34
<212> TYPE: DNA
<213> ORGANISM: Artificial Sequence
<220> FEATURE:
<223> OTHER INFORMATION: Unknown Organism

<400> SEQUENCE: 47
catgccatgg acattgatag tctcttgaaa cagc                                        34

<210> SEQ ID NO 48
<211> LENGTH: 37
<212> TYPE: DNA
<213> ORGANISM: Artificial Sequence
<220> FEATURE:
<223> OTHER INFORMATION: Unknown Organism

<400> SEQUENCE: 48
cgccaagctt cttactctcc tttaataaag ccaatag                                     37

<210> SEQ ID NO 49
<211> LENGTH: 31
<212> TYPE: DNA
<213> ORGANISM: Artificial Sequence
<220> FEATURE:
<223> OTHER INFORMATION: Unknown Organism

<400> SEQUENCE: 49
```
cgacaagctt aacatggtcg ctagcgttac c                                        31

<210> SEQ ID NO 50
<211> LENGTH: 30
<212> TYPE: DNA
<213> ORGANISM: Artificial Sequence
<220> FEATURE:
<223> OTHER INFORMATION: Unknown Organism

<400> SEQUENCE: 50
cataccatgg gcctttatga ggcacctaag                                          30

<210> SEQ ID NO 51
<211> LENGTH: 34
<212> TYPE: DNA
<213> ORGANISM: Artificial Sequence
<220> FEATURE:
<223> OTHER INFORMATION: Unknown Organism

<400> SEQUENCE: 51
cgacaagctt aagtaaatct tcagcctctc tcag                                     34

<210> SEQ ID NO 52
<211> LENGTH: 31
<212> TYPE: DNA
<213> ORGANISM: Artificial Sequence
<220> FEATURE:
<223> OTHER INFORMATION: Unknown Organism

<400> SEQUENCE: 52
gataccatgg ctagcgacca tgttcaaaga a                                        31

<210> SEQ ID NO 53
<211> LENGTH: 36
<212> TYPE: DNA
<213> ORGANISM: Artificial Sequence
<220> FEATURE:
<223> OTHER INFORMATION: Unknown Organism

<400> SEQUENCE: 53
cgccaagctt atcatccact aacttgactt tatcac                                   36

<210> SEQ ID NO 54
<211> LENGTH: 33
<212> TYPE: DNA
<213> ORGANISM: Artificial Sequence
<220> FEATURE:
<223> OTHER INFORMATION: Unknown Organism

<400> SEQUENCE: 54
cataccatgg atattcttgc cttcttagct ccg                                      33

<210> SEQ ID NO 55
<211> LENGTH: 30
<212> TYPE: DNA
<213> ORGANISM: Artificial Sequence
<220> FEATURE:
<223> OTHER INFORMATION: Unknown Organism

<400> SEQUENCE: 55
catgccatgg tgcttatgaa ctaggtttgc                                          30

<210> SEQ ID NO 56
<211> LENGTH: 32
<212> TYPE: DNA

```
<213> ORGANISM: Artificial Sequence
<220> FEATURE:
<223> OTHER INFORMATION: Unknown Organism

<400> SEQUENCE: 56
cgccaagctt tagcgttacc aaaaccatta tc                                32

<210> SEQ ID NO 57
<211> LENGTH: 36
<212> TYPE: DNA
<213> ORGANISM: Artificial Sequence
<220> FEATURE:
<223> OTHER INFORMATION: Unknown Organism

<400> SEQUENCE: 57
gtattagatc tgttcctatg aacttggtcg tcacca                            36

<210> SEQ ID NO 58
<211> LENGTH: 28
<212> TYPE: DNA
<213> ORGANISM: Artificial Sequence
<220> FEATURE:
<223> OTHER INFORMATION: Unknown Organism

<400> SEQUENCE: 58
cgcctctaga ctactgtata ggagccgg                                     28

<210> SEQ ID NO 59
<211> LENGTH: 34
<212> TYPE: DNA
<213> ORGANISM: Artificial Sequence
<220> FEATURE:
<223> OTHER INFORMATION: Unknown Organism

<400> SEQUENCE: 59
catgccatgg aaaacatttc aagcctttta cgtg                              34

<210> SEQ ID NO 60
<211> LENGTH: 34
<212> TYPE: DNA
<213> ORGANISM: Artificial Sequence
<220> FEATURE:
<223> OTHER INFORMATION: Unknown Organism

<400> SEQUENCE: 60
cgacaagctt ctgtatagga gccggttgac tttc                              34

<210> SEQ ID NO 61
<211> LENGTH: 34
<212> TYPE: DNA
<213> ORGANISM: Artificial Sequence
<220> FEATURE:
<223> OTHER INFORMATION: Unknown Organism

<400> SEQUENCE: 61
catgccatgg ttcgtaaaaa taaggcagac caag                              34

<210> SEQ ID NO 62
<211> LENGTH: 30
<212> TYPE: DNA
<213> ORGANISM: Artificial Sequence
<220> FEATURE:
<223> OTHER INFORMATION: Unknown Organism

<400> SEQUENCE: 62
catgccatgg aagcctattg gaatgggaag                                   30
```

-continued

<210> SEQ ID NO 63
<211> LENGTH: 31
<212> TYPE: DNA
<213> ORGANISM: Artificial Sequence
<220> FEATURE:
<223> OTHER INFORMATION: Unknown Organism

<400> SEQUENCE: 63
catgccatgg aagcctattg gaatgggaag c					31

<210> SEQ ID NO 64
<211> LENGTH: 31
<212> TYPE: DNA
<213> ORGANISM: Artificial Sequence
<220> FEATURE:
<223> OTHER INFORMATION: Unknown Organism

<400> SEQUENCE: 64
cgccaagctt gtaggtaatt tgcgcatttg g					31

<210> SEQ ID NO 65
<211> LENGTH: 30
<212> TYPE: DNA
<213> ORGANISM: Artificial Sequence
<220> FEATURE:
<223> OTHER INFORMATION: Unknown Organism

<400> SEQUENCE: 65
cgccaagctt ctgtatagga gccggttgac					30

<210> SEQ ID NO 66
<211> LENGTH: 32
<212> TYPE: DNA
<213> ORGANISM: Artificial Sequence
<220> FEATURE:
<223> OTHER INFORMATION: Unknown Organism

<400> SEQUENCE: 66
catgccatgg atattcttgc cttcttagct cc					32

<210> SEQ ID NO 67
<211> LENGTH: 38
<212> TYPE: DNA
<213> ORGANISM: Artificial Sequence
<220> FEATURE:
<223> OTHER INFORMATION: Unknown Organism

<400> SEQUENCE: 67
ttatttcttc catatgcatg gtgatcattt ccattaca				38

<210> SEQ ID NO 68
<211> LENGTH: 34
<212> TYPE: DNA
<213> ORGANISM: Artificial Sequence
<220> FEATURE:
<223> OTHER INFORMATION: Unknown Organism

<400> SEQUENCE: 68
gatgcatatg aatatgcaac cgagtcagtt aagc					34

<210> SEQ ID NO 69
<211> LENGTH: 31
<212> TYPE: DNA
<213> ORGANISM: Artificial Sequence
<220> FEATURE:

```
<223> OTHER INFORMATION: Unknown Organism

<400> SEQUENCE: 69
gatgctcgag agcatcaaat ccgtatccat c                              31

<210> SEQ ID NO 70
<211> LENGTH: 31
<212> TYPE: DNA
<213> ORGANISM: Artificial Sequence
<220> FEATURE:
<223> OTHER INFORMATION: Unknown Organism

<400> SEQUENCE: 70
gatgcatatg gatcatttcc attacattcc a                              31

<210> SEQ ID NO 71
<211> LENGTH: 30
<212> TYPE: DNA
<213> ORGANISM: Artificial Sequence
<220> FEATURE:
<223> OTHER INFORMATION: Unknown Organism

<400> SEQUENCE: 71
gacaagcttg gcattacctg gataatcctg                                30

<210> SEQ ID NO 72
<211> LENGTH: 31
<212> TYPE: DNA
<213> ORGANISM: Artificial Sequence
<220> FEATURE:
<223> OTHER INFORMATION: Unknown Organism

<400> SEQUENCE: 72
catgccatgg aagcctattg gaatgggaag c                              31

<210> SEQ ID NO 73
<211> LENGTH: 38
<212> TYPE: DNA
<213> ORGANISM: Artificial Sequence
<220> FEATURE:
<223> OTHER INFORMATION: Unknown Organism

<400> SEQUENCE: 73
ataagaatgc ggccgccgct atgaaatcag ataaattc                       38

<210> SEQ ID NO 74
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 74

000

<210> SEQ ID NO 75
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:
```

```
<400> SEQUENCE: 75

000

<210> SEQ ID NO 76
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 76

000

<210> SEQ ID NO 77
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 77

000

<210> SEQ ID NO 78
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 78

000

<210> SEQ ID NO 79
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 79

000

<210> SEQ ID NO 80
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 80

000
```

```
<210> SEQ ID NO 81
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 81

000

<210> SEQ ID NO 82
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 82

000

<210> SEQ ID NO 83
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 83

000

<210> SEQ ID NO 84
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 84

000

<210> SEQ ID NO 85
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 85

000

<210> SEQ ID NO 86
<220> FEATURE:
```

```
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 86

000

<210> SEQ ID NO 87
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 87

000

<210> SEQ ID NO 88
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 88

000

<210> SEQ ID NO 89
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 89

000

<210> SEQ ID NO 90
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 90

000

<210> SEQ ID NO 91
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
```

-continued

<211> LENGTH:
<212> TYPE:
<213> ORGANISM:

<400> SEQUENCE: 91

000

<210> SEQ ID NO 92
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 92

000

<210> SEQ ID NO 93
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 93

000

<210> SEQ ID NO 94
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 94

000

<210> SEQ ID NO 95
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 95

000

<210> SEQ ID NO 96
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

```
<400> SEQUENCE: 96

000

<210> SEQ ID NO 97
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 97

000

<210> SEQ ID NO 98
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 98

000

<210> SEQ ID NO 99
<220> FEATURE:
<223> OTHER INFORMATION: Unknown Organism
<221> NAME/KEY: MISC_FEATURE
<222> LOCATION: (1)..(15)
<223> OTHER INFORMATION: Intentionallly skipped sequence
<211> LENGTH:
<212> TYPE:
<213> ORGANISM:

<400> SEQUENCE: 99

000

<210> SEQ ID NO 100
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 100

000

<210> SEQ ID NO 101
<220> FEATURE:
<223> OTHER INFORMATION: Unknow Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 101

000
```

```
<210> SEQ ID NO 102
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 102

000

<210> SEQ ID NO 103
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 103

000

<210> SEQ ID NO 104
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 104

000

<210> SEQ ID NO 105
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 105

000

<210> SEQ ID NO 106
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 106

000

<210> SEQ ID NO 107
<220> FEATURE:
<223> OTHER INFORMATION: Unknown Organism
```

```
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 107

000

<210> SEQ ID NO 108
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 108

000

<210> SEQ ID NO 109
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 109

000

<210> SEQ ID NO 110
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 110

000

<210> SEQ ID NO 111
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 111

000

<210> SEQ ID NO 112
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
```

<212> TYPE:
<213> ORGANISM:

<400> SEQUENCE: 112

000

<210> SEQ ID NO 113
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 113

000

<210> SEQ ID NO 114
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 114

000

<210> SEQ ID NO 115
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 115

000

<210> SEQ ID NO 116
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 116

000

<210> SEQ ID NO 117
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 117

000

<210> SEQ ID NO 118
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 118

000

<210> SEQ ID NO 119
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 119

000

<210> SEQ ID NO 120
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 120

000

<210> SEQ ID NO 121
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 121

000

<210> SEQ ID NO 122
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 122

000

```
<210> SEQ ID NO 123
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 123

000

<210> SEQ ID NO 124
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 124

000

<210> SEQ ID NO 125
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 125

000

<210> SEQ ID NO 126
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 126

000

<210> SEQ ID NO 127
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 127

000

<210> SEQ ID NO 128
<220> FEATURE:
<223> OTHER INFORMATION: Unknown Organism
<221> NAME/KEY: MISC_FEATURE
```

```
<222> LOCATION: (1)..(25)
<223> OTHER INFORMATION: Intentionally skipped sequence
<211> LENGTH:
<212> TYPE:
<213> ORGANISM:

<400> SEQUENCE: 128

000

<210> SEQ ID NO 129
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 129

000

<210> SEQ ID NO 130
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 130

000

<210> SEQ ID NO 131
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 131

000

<210> SEQ ID NO 132
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 132

000

<210> SEQ ID NO 133
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
```

```
<213> ORGANISM:

<400> SEQUENCE: 133

000

<210> SEQ ID NO 134
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 134

000

<210> SEQ ID NO 135
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 135

000

<210> SEQ ID NO 136
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 136

000

<210> SEQ ID NO 137
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 137

000

<210> SEQ ID NO 138
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 138
```

-continued

000

<210> SEQ ID NO 139
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 139

000

<210> SEQ ID NO 140
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 140

000

<210> SEQ ID NO 141
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 141

000

<210> SEQ ID NO 142
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 142

000

<210> SEQ ID NO 143
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 143

000

<210> SEQ ID NO 144

```
<220> FEATURE:
<223> OTHER INFORMATION: Unknown Organism
<221> NAME/KEY: MISC_FEATURE
<222> LOCATION: (1)..(15)
<223> OTHER INFORMATION: Intentionally skipped sequence
<211> LENGTH:
<212> TYPE:
<213> ORGANISM:

<400> SEQUENCE: 144

000

<210> SEQ ID NO 145
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 145

000

<210> SEQ ID NO 146
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 146

000

<210> SEQ ID NO 147
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 147

000

<210> SEQ ID NO 148
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 148

000

<210> SEQ ID NO 149
<220> FEATURE:
<223> OTHER INFORMATION: Unknown Organism
<221> NAME/KEY: MISC_FEATURE
<222> LOCATION: (1)..(25)
```

-continued

```
<223> OTHER INFORMATION: Intentionally skipped sequence
<211> LENGTH:
<212> TYPE:
<213> ORGANISM:

<400> SEQUENCE: 149

000

<210> SEQ ID NO 150
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 150

000

<210> SEQ ID NO 151
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 151

000

<210> SEQ ID NO 152
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 152

000

<210> SEQ ID NO 153
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 153

000

<210> SEQ ID NO 154
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:
```

```
<400> SEQUENCE: 154

000

<210> SEQ ID NO 155
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 155

000

<210> SEQ ID NO 156
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 156

000

<210> SEQ ID NO 157
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 157

000

<210> SEQ ID NO 158
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 158

000

<210> SEQ ID NO 159
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 159

000
```

```
<210> SEQ ID NO 160
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 160

000

<210> SEQ ID NO 161
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 161

000

<210> SEQ ID NO 162
<220> FEATURE:
<223> OTHER INFORMATION: Unknown Organism
<221> NAME/KEY: MISC_FEATURE
<222> LOCATION: (1)..(26)
<223> OTHER INFORMATION: Intentionally skipped sequence
<211> LENGTH:
<212> TYPE:
<213> ORGANISM:

<400> SEQUENCE: 162

000

<210> SEQ ID NO 163
<211> LENGTH: 22
<212> TYPE: PRT
<213> ORGANISM: Artificial Sequence
<220> FEATURE:
<223> OTHER INFORMATION: Unknown Organism

<400> SEQUENCE: 163

Gly Leu Tyr Glu Ala Pro Lys Gly Tyr Ser Leu Glu Asp Leu Leu Ala
 1               5                  10                  15

Thr Val Lys Tyr Tyr Val
             20

<210> SEQ ID NO 164
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 164

000

<210> SEQ ID NO 165
```

```
<220> FEATURE:
<223> OTHER INFORMATION: Unknown Organism
<221> NAME/KEY: MISC_FEATURE
<222> LOCATION: (1)..(25)
<223> OTHER INFORMATION: Intentionally skipped sequence
<211> LENGTH:
<212> TYPE:
<213> ORGANISM:

<400> SEQUENCE: 165

000

<210> SEQ ID NO 166
<220> FEATURE:
<223> OTHER INFORMATION: Unknown Organism
<221> NAME/KEY: MISC_FEATURE
<222> LOCATION: (1)..(31)
<223> OTHER INFORMATION: Intentionally skipped sequence
<211> LENGTH:
<212> TYPE:
<213> ORGANISM:

<400> SEQUENCE: 166

000

<210> SEQ ID NO 167
<220> FEATURE:
<223> OTHER INFORMATION: Unknown Organism
<221> NAME/KEY: MISC_FEATURE
<222> LOCATION: (1)..(21)
<223> OTHER INFORMATION: Intentionally skipped sequence
<211> LENGTH:
<212> TYPE:
<213> ORGANISM:

<400> SEQUENCE: 167

000

<210> SEQ ID NO 168
<211> LENGTH: 34
<212> TYPE: DNA
<213> ORGANISM: Artificial Sequence
<220> FEATURE:
<223> OTHER INFORMATION: Unknown Organism

<400> SEQUENCE: 168
atatgggccc ctgtatagga gccggttgac tttc                     34

<210> SEQ ID NO 169
<211> LENGTH: 34
<212> TYPE: DNA
<213> ORGANISM: Artificial Sequence
<220> FEATURE:
<223> OTHER INFORMATION: Unknown Organism

<400> SEQUENCE: 169
atatgggccc aatatgcaac cgagtcagtt aagc                     34

<210> SEQ ID NO 170
<211> LENGTH: 31
<212> TYPE: DNA
<213> ORGANISM: Artificial Sequence
<220> FEATURE:
<223> OTHER INFORMATION: Unknown Organism

<400> SEQUENCE: 170
atatgggccc aacatggtcg ctagcgttac c                        31
```

<210> SEQ ID NO 171
<211> LENGTH: 34
<212> TYPE: DNA
<213> ORGANISM: Artificial Sequence
<220> FEATURE:
<223> OTHER INFORMATION: Unknown Organism

<400> SEQUENCE: 171
tcccgggccc gacttgacag aagagcaaat taag          34

<210> SEQ ID NO 172
<211> LENGTH: 34
<212> TYPE: DNA
<213> ORGANISM: Artificial Sequence
<220> FEATURE:
<223> OTHER INFORMATION: Unknown Organism

<400> SEQUENCE: 172
catgccatgg gacttgacag aagagcaaat taag          34

<210> SEQ ID NO 173
<211> LENGTH: 32
<212> TYPE: DNA
<213> ORGANISM: Artificial Sequence
<220> FEATURE:
<223> OTHER INFORMATION: Unknown Organism

<400> SEQUENCE: 173
tcccgggccc cgctatgaaa tcagataaat tc          32

<210> SEQ ID NO 174
<211> LENGTH: 35
<212> TYPE: DNA
<213> ORGANISM: Artificial Sequence
<220> FEATURE:
<223> OTHER INFORMATION: Unknown Organism

<400> SEQUENCE: 174
atatgggccc gacattgata gtctcttgaa acagc          35

<210> SEQ ID NO 175
<211> LENGTH: 31
<212> TYPE: DNA
<213> ORGANISM: Artificial Sequence
<220> FEATURE:
<223> OTHER INFORMATION: Unknown Organism

<400> SEQUENCE: 175
cgccaagctt aacatggtcg ctagcgttac c          31

<210> SEQ ID NO 176
<211> LENGTH: 37
<212> TYPE: DNA
<213> ORGANISM: Artificial Sequence
<220> FEATURE:
<223> OTHER INFORMATION: Unknown Organism

<400> SEQUENCE: 176
atatgggccc cttactctcc tttaataaag ccaatag          37

<210> SEQ ID NO 177
<211> LENGTH: 45
<212> TYPE: DNA
<213> ORGANISM: Artificial Sequence
<220> FEATURE:
<223> OTHER INFORMATION: Unknown Organism

<400> SEQUENCE: 177
gaatcaggtt ttgtcatgag ttccggagac cacaatcatt atttc            45

<210> SEQ ID NO 178
<211> LENGTH: 45
<212> TYPE: DNA
<213> ORGANISM: Artificial Sequence
<220> FEATURE:
<223> OTHER INFORMATION: Unknown Organism

<400> SEQUENCE: 178
gaaataatga ttgtggtctc cggaactcat gacaaaacct gattc            45

<210> SEQ ID NO 179
<211> LENGTH: 43
<212> TYPE: DNA
<213> ORGANISM: Artificial Sequence
<220> FEATURE:
<223> OTHER INFORMATION: Unknown Organism

<400> SEQUENCE: 179
gtcatgagtt ccggagactc caatcattat ttcttcaaga agg              43

<210> SEQ ID NO 180
<211> LENGTH: 43
<212> TYPE: DNA
<213> ORGANISM: Artificial Sequence
<220> FEATURE:
<223> OTHER INFORMATION: Unknown Organism

<400> SEQUENCE: 180
ccttcttgaa gaaataatga ttggagtctc cggaactcat gac              43

<210> SEQ ID NO 181
<211> LENGTH: 44
<212> TYPE: DNA
<213> ORGANISM: Artificial Sequence
<220> FEATURE:
<223> OTHER INFORMATION: Unknown Organism

<400> SEQUENCE: 181
atgagttcgg agactccaat tcttatttct tcaagaagga cttg             44

<210> SEQ ID NO 182
<211> LENGTH: 45
<212> TYPE: DNA
<213> ORGANISM: Artificial Sequence
<220> FEATURE:
<223> OTHER INFORMATION: Unknown Organism

<400> SEQUENCE: 182
caagtccttc ttgaagaaat aagaattgga gtctccggaa ctcat            45

<210> SEQ ID NO 183
<211> LENGTH: 35
<212> TYPE: DNA
<213> ORGANISM: Artificial Sequence
<220> FEATURE:
<223> OTHER INFORMATION: Unknown Organism

<400> SEQUENCE: 183
gcgattattt atccgtctgg agatcaccat catgc                       35

<210> SEQ ID NO 184

```
<211> LENGTH: 35
<212> TYPE: DNA
<213> ORGANISM: Artificial Sequence
<220> FEATURE:
<223> OTHER INFORMATION: Unknown Organism

<400> SEQUENCE: 184
gcatgatggt gatctccaga cggataaata atcgc                    35

<210> SEQ ID NO 185
<211> LENGTH: 30
<212> TYPE: DNA
<213> ORGANISM: Artificial Sequence
<220> FEATURE:
<223> OTHER INFORMATION: Unknown Organism

<400> SEQUENCE: 185
ccgtctggag atggccatca tgcagatccg                          30

<210> SEQ ID NO 186
<211> LENGTH: 30
<212> TYPE: DNA
<213> ORGANISM: Artificial Sequence
<220> FEATURE:
<223> OTHER INFORMATION: Unknown Organism

<400> SEQUENCE: 186
cggatctgca tgatggccat ctccagacgg                          30

<210> SEQ ID NO 187
<211> LENGTH: 34
<212> TYPE: DNA
<213> ORGANISM: Artificial Sequence
<220> FEATURE:
<223> OTHER INFORMATION: Unknown Organism

<400> SEQUENCE: 187
ccgcagggag ataagcgtca tgcagatccg attg                     34

<210> SEQ ID NO 188
<211> LENGTH: 34
<212> TYPE: DNA
<213> ORGANISM: Artificial Sequence
<220> FEATURE:
<223> OTHER INFORMATION: Unknown Organism

<400> SEQUENCE: 188
caatcggatc tgcatgacgc ttatctccct gcgg                     34

<210> SEQ ID NO 189
<211> LENGTH: 34
<212> TYPE: DNA
<213> ORGANISM: Artificial Sequence
<220> FEATURE:
<223> OTHER INFORMATION: Unknown Organism

<400> SEQUENCE: 189
ccgtctggag atggcactca tgcagatccg attg                     34

<210> SEQ ID NO 190
<211> LENGTH: 34
<212> TYPE: DNA
<213> ORGANISM: Artificial Sequence
<220> FEATURE:
<223> OTHER INFORMATION: Unknown Organism

<400> SEQUENCE: 190
```

```
caatcggatc tgcatgagtg ccatctccag acgg                               34
```

<210> SEQ ID NO 191
<211> LENGTH: 37
<212> TYPE: DNA
<213> ORGANISM: Artificial Sequence
<220> FEATURE:
<223> OTHER INFORMATION: Unknown Organism

<400> SEQUENCE: 191

```
ccgtctggag atggcacttc tgcagatccg attgatg                            37
```

<210> SEQ ID NO 192
<211> LENGTH: 37
<212> TYPE: DNA
<213> ORGANISM: Artificial Sequence
<220> FEATURE:
<223> OTHER INFORMATION: Unknown Organism

<400> SEQUENCE: 192

```
catcaatcgg atctgcagaa gtgccatctc cagacgg                            37
```

<210> SEQ ID NO 193
<211> LENGTH: 30
<212> TYPE: DNA
<213> ORGANISM: Artificial Sequence
<220> FEATURE:
<223> OTHER INFORMATION: Unknown Organism

<400> SEQUENCE: 193

```
ccgcatggag atggccatca tgcagatccg                                    30
```

<210> SEQ ID NO 194
<211> LENGTH: 30
<212> TYPE: DNA
<213> ORGANISM: Artificial Sequence
<220> FEATURE:
<223> OTHER INFORMATION: Unknown Organism

<400> SEQUENCE: 194

```
cggatctgca tgatggccat ctccatgcgg                                    30
```

<210> SEQ ID NO 195
<211> LENGTH: 43
<212> TYPE: DNA
<213> ORGANISM: Artificial Sequence
<220> FEATURE:
<223> OTHER INFORMATION: Unknown Organism

<400> SEQUENCE: 195

```
gtcatgagtc acggagactc caatcattat ttcttcaaga agg                     43
```

<210> SEQ ID NO 196
<211> LENGTH: 43
<212> TYPE: DNA
<213> ORGANISM: Artificial Sequence
<220> FEATURE:
<223> OTHER INFORMATION: Unknown Organism

<400> SEQUENCE: 196

```
ccttcttgaa gaaataatga ttggagtctc cgtgactcat gac                     43
```

<210> SEQ ID NO 197
<211> LENGTH: 45
<212> TYPE: DNA

```
<213> ORGANISM: Artificial Sequence
<220> FEATURE:
<223> OTHER INFORMATION: Unknown Organism

<400> SEQUENCE: 197
atgagtcacg gagaccacaa ttcttatttc ttcaagaagg acttg                45

<210> SEQ ID NO 198
<211> LENGTH: 45
<212> TYPE: DNA
<213> ORGANISM: Artificial Sequence
<220> FEATURE:
<223> OTHER INFORMATION: Unknown Organism

<400> SEQUENCE: 198
caagtccttc ttgaagaaat aagaattgtg gtctccgtga ctcat                45

<210> SEQ ID NO 199
<211> LENGTH: 45
<212> TYPE: DNA
<213> ORGANISM: Artificial Sequence
<220> FEATURE:
<223> OTHER INFORMATION: Unknown Organism

<400> SEQUENCE: 199
tacctcatta tgactcttac tctaacatca aatttgagtg gtttg                45

<210> SEQ ID NO 200
<211> LENGTH: 45
<212> TYPE: DNA
<213> ORGANISM: Artificial Sequence
<220> FEATURE:
<223> OTHER INFORMATION: Unknown Organism

<400> SEQUENCE: 200
caaaccactc aaatttgatg ttagagtaag agtcataatg aggta                45

<210> SEQ ID NO 201
<211> LENGTH: 45
<212> TYPE: DNA
<213> ORGANISM: Artificial Sequence
<220> FEATURE:
<223> OTHER INFORMATION: Unknown Organism

<400> SEQUENCE: 201
taccttctta tgaccattac tctaacatca aatttgagtg gtttg                45

<210> SEQ ID NO 202
<211> LENGTH: 44
<212> TYPE: DNA
<213> ORGANISM: Artificial Sequence
<220> FEATURE:
<223> OTHER INFORMATION: Unknown Organism

<400> SEQUENCE: 202
aaaccactca aatttgatgt tagagtaatg gtcataagaa ggta                 44

<210> SEQ ID NO 203
<211> LENGTH: 45
<212> TYPE: DNA
<213> ORGANISM: Artificial Sequence
<220> FEATURE:
<223> OTHER INFORMATION: Unknown Organism

<400> SEQUENCE: 203
aacggtagtt taatcatacc ttctaaagac cattaccata acatc                45
```

<210> SEQ ID NO 204
<211> LENGTH: 45
<212> TYPE: DNA
<213> ORGANISM: Artificial Sequence
<220> FEATURE:
<223> OTHER INFORMATION: Unknown Organism

<400> SEQUENCE: 204
gatgttatgg taatggtctt tagaaggtat gattaaacta ccgtt 45

<210> SEQ ID NO 205
<211> LENGTH: 46
<212> TYPE: DNA
<213> ORGANISM: Artificial Sequence
<220> FEATURE:
<223> OTHER INFORMATION: Unknown Organism

<400> SEQUENCE: 205
cggtagttta atcatacctc ataaggactc ttaccataac atcaaa 46

<210> SEQ ID NO 206
<211> LENGTH: 46
<212> TYPE: DNA
<213> ORGANISM: Artificial Sequence
<220> FEATURE:
<223> OTHER INFORMATION: Unknown Organism

<400> SEQUENCE: 206
tttgatgtta tggtaagagt ccttatgagg tatgattaaa ctaccg 46

<210> SEQ ID NO 207
<211> LENGTH: 46
<212> TYPE: DNA
<213> ORGANISM: Artificial Sequence
<220> FEATURE:
<223> OTHER INFORMATION: Unknown Organism

<400> SEQUENCE: 207
aacggtagtt taatcatacc tgaccattac cataacatca aatttg 46

<210> SEQ ID NO 208
<211> LENGTH: 46
<212> TYPE: DNA
<213> ORGANISM: Artificial Sequence
<220> FEATURE:
<223> OTHER INFORMATION: Unknown Organism

<400> SEQUENCE: 208
caaatttgat gttatggtaa tggtcaggta tgattaaact accgtt 46

<210> SEQ ID NO 209
<211> LENGTH: 45
<212> TYPE: DNA
<213> ORGANISM: Artificial Sequence
<220> FEATURE:
<223> OTHER INFORMATION: Unknown Organism

<400> SEQUENCE: 209
aacggtagtt taatcatacc ttaccataac atcaaatttg agtgg 45

<210> SEQ ID NO 210
<211> LENGTH: 45
<212> TYPE: DNA
<213> ORGANISM: Artificial Sequence
<220> FEATURE:

```
<223> OTHER INFORMATION: Unknown Organism

<400> SEQUENCE: 210
ccactcaaat tgatgttat ggtaaggtat gattaaacta ccgtt                    45

<210> SEQ ID NO 211
<211> LENGTH: 45
<212> TYPE: DNA
<213> ORGANISM: Artificial Sequence
<220> FEATURE:
<223> OTHER INFORMATION: Unknown Organism

<400> SEQUENCE: 211
accggtagtt taatcatacc taacatcaaa tttgagtggt ttgac                    45

<210> SEQ ID NO 212
<211> LENGTH: 45
<212> TYPE: DNA
<213> ORGANISM: Artificial Sequence
<220> FEATURE:
<223> OTHER INFORMATION: Unknown Organism

<400> SEQUENCE: 212
gtcaaaccac tcaaatttga tgttaggtat gattaaacta ccgtt                    45

<210> SEQ ID NO 213
<211> LENGTH: 35
<212> TYPE: DNA
<213> ORGANISM: Artificial Sequence
<220> FEATURE:
<223> OTHER INFORMATION: Unknown Organism

<400> SEQUENCE: 213
cctatgtaac tccacatata acccatagcc actgg                              35

<210> SEQ ID NO 214
<211> LENGTH: 35
<212> TYPE: DNA
<213> ORGANISM: Artificial Sequence
<220> FEATURE:
<223> OTHER INFORMATION: Unknown Organism

<400> SEQUENCE: 214
ccagtggcta tgggttatat gtggagttac atagg                              35

<210> SEQ ID NO 215
<211> LENGTH: 36
<212> TYPE: DNA
<213> ORGANISM: Artificial Sequence
<220> FEATURE:
<223> OTHER INFORMATION: Unknown Organism

<400> SEQUENCE: 215
cgtgaaagta ttgtcgtaaa taagaaaaaa aatgcg                             36

<210> SEQ ID NO 216
<211> LENGTH: 36
<212> TYPE: DNA
<213> ORGANISM: Artificial Sequence
<220> FEATURE:
<223> OTHER INFORMATION: Unknown Organism

<400> SEQUENCE: 216 cgcattttt tctttattta cgacaatact ttcacg                              36
```

<210> SEQ ID NO 217
<211> LENGTH: 49
<212> TYPE: DNA
<213> ORGANISM: Artificial Sequence
<220> FEATURE:
<223> OTHER INFORMATION: Unknown Organism

<400> SEQUENCE: 217
catgaagaag atggttacgg tttcgatgct aaccgtatta tcgctgaag                49

<210> SEQ ID NO 218
<211> LENGTH: 48
<212> TYPE: DNA
<213> ORGANISM: Artificial Sequence
<220> FEATURE:
<223> OTHER INFORMATION: Unknown Organism

<400> SEQUENCE: 218
cttcagcgat aatacggtta gcatcgaaac cgtaaccatc ttcttctg                 48

<210> SEQ ID NO 219
<211> LENGTH: 42
<212> TYPE: DNA
<213> ORGANISM: Artificial Sequence
<220> FEATURE:
<223> OTHER INFORMATION: Unknown Organism

<400> SEQUENCE: 219
gaatcaggtt ttgtcatgag tgaccacaat cattatttct tc                       42

<210> SEQ ID NO 220
<211> LENGTH: 42
<212> TYPE: DNA
<213> ORGANISM: Artificial Sequence
<220> FEATURE:
<223> OTHER INFORMATION: Unknown Organism

<400> SEQUENCE: 220
gaagaaataa tgattgtggt cactcatgac aaaacctgat tc                       42

<210> SEQ ID NO 221
<211> LENGTH: 45
<212> TYPE: DNA
<213> ORGANISM: Artificial Sequence
<220> FEATURE:
<223> OTHER INFORMATION: Unknown Organism

<400> SEQUENCE: 221
gaagatgaat caggttttgt catgagtaat cattatttct tcaag                    45

<210> SEQ ID NO 222
<211> LENGTH: 45
<212> TYPE: DNA
<213> ORGANISM: Artificial Sequence
<220> FEATURE:
<223> OTHER INFORMATION: Unknown Organism

<400> SEQUENCE: 222
cttgaagaaa taatgattac tcatgacaaa acctgattca tcttc                    45

<210> SEQ ID NO 223
<211> LENGTH: 45
<212> TYPE: DNA
<213> ORGANISM: Artificial Sequence
<220> FEATURE:
<223> OTHER INFORMATION: Unknown Organism

```
<400> SEQUENCE: 223
gaagatgaat caggttttgt catgagttat ttcttcaaga aggac                45

<210> SEQ ID NO 224
<211> LENGTH: 45
<212> TYPE: DNA
<213> ORGANISM: Artificial Sequence
<220> FEATURE:
<223> OTHER INFORMATION: Unknown Sequence

<400> SEQUENCE: 224
gtccttcttg aagaaataac tcatgacaaa acctgattca tcttc                45

<210> SEQ ID NO 225
<211> LENGTH: 42
<212> TYPE: DNA
<213> ORGANISM: Artificial Sequence
<220> FEATURE:
<223> OTHER INFORMATION: Unknown Organism

<400> SEQUENCE: 225
aaaatgcgat tatttatccg caccatcatg cagatccgat tg                   42

<210> SEQ ID NO 226
<211> LENGTH: 42
<212> TYPE: DNA
<213> ORGANISM: Artificial Sequence
<220> FEATURE:
<223> OTHER INFORMATION: Unknown Organism

<400> SEQUENCE: 226
caatcggatc tgcatgatgg tgcggataaa taatcgcatt tt                   42

<210> SEQ ID NO 227
<211> LENGTH: 45
<212> TYPE: DNA
<213> ORGANISM: Artificial Sequence
<220> FEATURE:
<223> OTHER INFORMATION: Unknown Organism

<400> SEQUENCE: 227
aaaatgcgat tatttatccg gcagatccga ttgatgaaca taaac                45

<210> SEQ ID NO 228
<211> LENGTH: 45
<212> TYPE: DNA
<213> ORGANISM: Artificial Sequence
<220> FEATURE:
<223> OTHER INFORMATION: Unknown Organism

<400> SEQUENCE: 228
gtttatgttc atcaatcgga tctgccggat aaataatcgc atttt                45

<210> SEQ ID NO 229
<211> LENGTH: 45
<212> TYPE: DNA
<213> ORGANISM: Artificial Sequence
<220> FEATURE:
<223> OTHER INFORMATION: Unknown Organism

<400> SEQUENCE: 229
gatgctaacc gtataatcgc cgaagacgaa tcaggttttg tcatg                45

<210> SEQ ID NO 230
<211> LENGTH: 45
```

```
<212> TYPE: DNA
<213> ORGANISM: Artificial Sequence
<220> FEATURE:
<223> OTHER INFORMATION: Unknown Organism

<400> SEQUENCE: 230
catgacaaaa cctgattcgt cttcggcgat tatacggtta gcatc          45

<210> SEQ ID NO 231
<211> LENGTH: 43
<212> TYPE: DNA
<213> ORGANISM: Artificial Sequence
<220> FEATURE:
<223> OTHER INFORMATION: Unknown Organism

<400> SEQUENCE: 231
cgccgaagac gaatccggct ttgtaatgag tcacggagac tcc            43

<210> SEQ ID NO 232
<211> LENGTH: 43
<212> TYPE: DNA
<213> ORGANISM: Artificial Sequence
<220> FEATURE:
<223> OTHER INFORMATION: Unknown Organism

<400> SEQUENCE: 232
ggagtctccg tgactcatta caaagccgga ttcgtcttcg gcg            43

<210> SEQ ID NO 233
<211> LENGTH: 45
<212> TYPE: DNA
<213> ORGANISM: Artificial Sequence
<220> FEATURE:
<223> OTHER INFORMATION: Unknown Organism

<400> SEQUENCE: 233
catctcatga acaggattat cccggcaacg ccaaagaaat gaaag          45

<210> SEQ ID NO 234
<211> LENGTH: 45
<212> TYPE: DNA
<213> ORGANISM: Artificial Sequence
<220> FEATURE:
<223> OTHER INFORMATION: Unknown Organism

<400> SEQUENCE: 234
ctttcatttc tttggcgttg ccgggataat cctgttcatg agatg          45

<210> SEQ ID NO 235
<211> LENGTH: 569
<212> TYPE: PRT
<213> ORGANISM: Artificial Sequence
<220> FEATURE:
<223> OTHER INFORMATION: Unknown Organism

<400> SEQUENCE: 235

Met Asp Leu Thr Glu Glu Gln Ile Lys Ala Ala Gln Lys His Leu Glu
1               5                   10                  15

Glu Val Lys Thr Ser His Asn Gly Leu Asp Ser Leu Ser Ser His Glu
            20                  25                  30

Gln Asp Tyr Pro Gly Asn Ala Lys Glu Met Lys Asp Leu Asp Lys Lys
        35                  40                  45

Ile Glu Glu Lys Ile Ala Gly Ile Met Lys Gln Tyr Gly Val Lys Arg
    50                  55                  60
```

-continued

```
Glu Ser Ile Val Val Asn Lys Glu Lys Asn Ala Ile Ile Tyr Pro His
 65                  70                  75                  80

Gly Asp His His His Ala Asp Pro Ile Asp Glu His Lys Pro Val Gly
                 85                  90                  95

Ile Gly His Ser His Ser Asn Tyr Glu Leu Phe Lys Pro Glu Glu Gly
                100                 105                 110

Val Ala Lys Lys Glu Gly Asn Lys Val Tyr Thr Gly Glu Glu Leu Thr
            115                 120                 125

Asn Val Val Asn Leu Leu Lys Asn Ser Thr Phe Asn Asn Gln Asn Phe
        130                 135                 140

Thr Leu Ala Asn Gly Gln Lys Arg Val Ser Phe Ser Phe Pro Pro Glu
145                 150                 155                 160

Leu Glu Lys Lys Leu Gly Ile Asn Met Leu Val Lys Leu Ile Thr Pro
                165                 170                 175

Asp Gly Lys Val Leu Glu Lys Val Ser Gly Lys Val Phe Gly Glu Gly
                180                 185                 190

Val Gly Asn Ile Ala Asn Phe Glu Leu Asp Gln Pro Tyr Leu Pro Gly
            195                 200                 205

Gln Thr Phe Lys Tyr Thr Ile Ala Ser Lys Asp Tyr Pro Glu Val Ser
        210                 215                 220

Tyr Asp Gly Thr Phe Thr Val Pro Thr Ser Leu Ala Tyr Lys Met Ala
225                 230                 235                 240

Ser Gln Thr Ile Phe Tyr Pro Phe His Ala Gly Asp Thr Tyr Leu Arg
                245                 250                 255

Val Asn Pro Gln Phe Ala Val Pro Lys Gly Thr Asp Ala Leu Val Arg
                260                 265                 270

Val Phe Asp Glu Phe His Gly Asn Ala Tyr Leu Glu Asn Asn Tyr Lys
            275                 280                 285

Val Gly Glu Ile Lys Leu Pro Ile Pro Lys Leu Asn Gln Gly Thr Thr
        290                 295                 300

Arg Thr Ala Gly Asn Lys Ile Pro Val Thr Phe Met Ala Asn Ala Tyr
305                 310                 315                 320

Leu Asp Asn Gln Ser Thr Tyr Ile Val Glu Val Pro Ile Leu Glu Lys
                325                 330                 335

Glu Asn Gln Thr Asp Lys Pro Ser Ile Leu Pro Gln Phe Lys Arg Asn
            340                 345                 350

Lys Ala Gln Glu Asn Ser Lys Leu Asp Glu Lys Val Glu Glu Pro Lys
        355                 360                 365

Thr Ser Glu Lys Val Glu Lys Glu Lys Leu Ser Glu Thr Gly Asn Ser
370                 375                 380

Thr Ser Asn Ser Thr Leu Glu Glu Val Pro Thr Val Asp Pro Val Gln
385                 390                 395                 400

Glu Lys Val Ala Lys Phe Ala Glu Ser Tyr Gly Met Lys Leu Glu Asn
                405                 410                 415

Val Leu Phe Asn Met Asp Gly Thr Ile Glu Leu Tyr Leu Pro Ser Gly
            420                 425                 430

Glu Val Ile Lys Lys Asn Met Ala Asp Phe Thr Gly Glu Ala Pro Gln
        435                 440                 445

Gly Asn Gly Glu Asn Lys Pro Ser Glu Asn Gly Lys Val Ser Thr Gly
    450                 455                 460

Thr Val Glu Asn Gln Pro Thr Glu Asn Lys Pro Ala Asp Ser Leu Pro
465                 470                 475                 480

Glu Ala Pro Asn Glu Lys Pro Val Lys Pro Glu Asn Ser Thr Asp Asn
```

```
                        485                 490                 495
Gly Met Leu Asn Pro Glu Gly Asn Val Gly Ser Asp Pro Met Leu Asp
            500                 505                 510

Pro Ala Leu Glu Glu Ala Pro Ala Val Asp Pro Val Gln Glu Lys Leu
            515                 520                 525

Glu Lys Phe Thr Ala Ser Tyr Gly Leu Gly Leu Asp Ser Val Ile Phe
            530                 535                 540

Asn Met Asp Gly Thr Ile Glu Leu Arg Leu Pro Ser Gly Glu Val Ile
545                 550                 555                 560

Lys Lys Asn Leu Ser Asp Phe Ile Ala
                565
```

<210> SEQ ID NO 236
<220> FEATURE:
<223> OTHER INFORMATION: Unknown Organism
<221> NAME/KEY: MISC_FEATURE
<222> LOCATION: (1)..(569)
<223> OTHER INFORMATION: Intentionally skipped sequence
<211> LENGTH:
<212> TYPE:
<213> ORGANISM:

<400> SEQUENCE: 236

000

<210> SEQ ID NO 237
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 237

000

<210> SEQ ID NO 238
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 238

000

<210> SEQ ID NO 239
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 239

000

<210> SEQ ID NO 240

-continued

```
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 240

000

<210> SEQ ID NO 241
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 241

000

<210> SEQ ID NO 242
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 242

000

<210> SEQ ID NO 243
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 243

000

<210> SEQ ID NO 244
<220> FEATURE:
<223> OTHER INFORMATION: Unknown Organism
<221> NAME/KEY: MISC_FEATURE
<222> LOCATION: (1)..(569)
<223> OTHER INFORMATION: Intentionally skipped sequence
<211> LENGTH:
<212> TYPE:
<213> ORGANISM:

<400> SEQUENCE: 244

000

<210> SEQ ID NO 245
<220> FEATURE:
<223> OTHER INFORMATION: Unknown Organism
<221> NAME/KEY: MISC_FEATURE
<222> LOCATION: (1)..(633)
```

-continued

```
<223> OTHER INFORMATION: Intentionally skipped sequence
<211> LENGTH:
<212> TYPE:
<213> ORGANISM:

<400> SEQUENCE: 245

000

<210> SEQ ID NO 246
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 246

000

<210> SEQ ID NO 247
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 247

000

<210> SEQ ID NO 248
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 248

000

<210> SEQ ID NO 249
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 249

000

<210> SEQ ID NO 250
<220> FEATURE:
<223> OTHER INFORMATION: Unknown Organism
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:
```

```
<400> SEQUENCE: 250

000

<210> SEQ ID NO 251
<220> FEATURE:
<223> OTHER INFORMATION: Unknown Sequence
<221> NAME/KEY: MISC_FEATURE
<222> LOCATION: (1)..(633)
<223> OTHER INFORMATION: Intentionally skipped sequence
<211> LENGTH:
<212> TYPE:
<213> ORGANISM:

<400> SEQUENCE: 251

000

<210> SEQ ID NO 252
<220> FEATURE:
<223> OTHER INFORMATION: Unknown Organism
<221> NAME/KEY: MISC_FEATURE
<222> LOCATION: (1)..(627)
<223> OTHER INFORMATION: Intentionally skipped sequence
<211> LENGTH:
<212> TYPE:
<213> ORGANISM:

<400> SEQUENCE: 252

000

<210> SEQ ID NO 253
<220> FEATURE:
<223> OTHER INFORMATION: Unknown Organism
<221> NAME/KEY: MISC_FEATURE
<222> LOCATION: (1)..(627)
<223> OTHER INFORMATION: Intentionally skipped sequence
<211> LENGTH:
<212> TYPE:
<213> ORGANISM:

<400> SEQUENCE: 253

000

<210> SEQ ID NO 254
<220> FEATURE:
<223> OTHER INFORMATION: Unknown Organism
<221> NAME/KEY: MISC_FEATURE
<222> LOCATION: (1)..(621)
<223> OTHER INFORMATION: Intentionally skipped sequence
<211> LENGTH:
<212> TYPE:
<213> ORGANISM:

<400> SEQUENCE: 254

000

<210> SEQ ID NO 255
<211> LENGTH: 569
<212> TYPE: PRT
<213> ORGANISM: Artificial Sequence
<220> FEATURE:
<223> OTHER INFORMATION: Unknown Organism

<400> SEQUENCE: 255

Met Asp Leu Thr Glu Glu Gln Ile Lys Ala Ala Gln Lys His Leu Glu
1               5                   10                  15

Glu Val Lys Thr Ser His Asn Gly Leu Asp Ser Leu Ser Ser His Glu
```

-continued

```
                    20                  25                  30
Gln Asp Tyr Pro Gly Asn Ala Lys Glu Met Lys Asp Leu Asp Lys Lys
                35                  40                  45
Ile Glu Glu Lys Ile Ala Gly Ile Met Lys Gln Tyr Gly Val Lys Arg
 50                  55                  60
Glu Ser Ile Val Val Asn Lys Glu Lys Asn Ala Ile Ile Tyr Pro His
 65                  70                  75                  80
Gly Asp His His Ala Asp Pro Ile Asp Glu His Lys Pro Val Gly
                 85                  90                  95
Ile Gly His Ser His Ser Asn Tyr Glu Leu Phe Lys Pro Glu Gly
                100                 105                 110
Val Ala Lys Lys Glu Gly Asn Lys Val Tyr Thr Gly Glu Leu Thr
                115                 120                 125
Asn Val Val Asn Leu Leu Lys Asn Ser Thr Phe Asn Gln Asn Phe
130                 135                 140
Thr Leu Ala Asn Gly Gln Lys Arg Val Ser Phe Ser Phe Pro Pro Glu
145                 150                 155                 160
Leu Glu Lys Lys Leu Gly Ile Asn Met Leu Val Lys Leu Ile Thr Pro
                165                 170                 175
Asp Gly Lys Val Leu Glu Lys Val Ser Gly Lys Val Phe Gly Glu Gly
                180                 185                 190
Val Gly Asn Ile Ala Asn Phe Glu Leu Asp Gln Pro Tyr Leu Pro Gly
                195                 200                 205
Gln Thr Phe Lys Tyr Thr Ile Ala Ser Lys Asp Tyr Pro Glu Val Ser
                210                 215                 220
Tyr Asp Gly Thr Phe Thr Val Pro Thr Ser Leu Ala Tyr Lys Met Ala
225                 230                 235                 240
Ser Gln Thr Ile Phe Tyr Pro Phe His Ala Gly Asp Thr Tyr Leu Arg
                245                 250                 255
Val Asn Pro Gln Phe Ala Val Pro Lys Gly Thr Asp Ala Leu Val Arg
                260                 265                 270
Val Phe Asp Glu Phe His Gly Asn Ala Tyr Leu Glu Asn Asn Tyr Lys
                275                 280                 285
Val Gly Glu Ile Lys Leu Pro Ile Pro Lys Leu Asn Gln Gly Thr Thr
                290                 295                 300
Arg Thr Ala Gly Asn Lys Ile Pro Val Thr Phe Met Ala Asn Ala Tyr
305                 310                 315                 320
Leu Asp Asn Gln Ser Thr Tyr Ile Val Glu Val Pro Ile Leu Glu Lys
                325                 330                 335
Glu Asn Gln Thr Asp Lys Pro Ser Ile Leu Pro Gln Phe Lys Arg Asn
                340                 345                 350
Lys Ala Gln Glu Asn Ser Lys Leu Asp Glu Lys Val Glu Glu Pro Lys
                355                 360                 365
Thr Ser Glu Lys Val Glu Lys Glu Leu Ser Glu Thr Gly Asn Ser
                370                 375                 380
Thr Ser Asn Ser Thr Leu Glu Glu Val Pro Thr Val Asp Pro Val Gln
385                 390                 395                 400
Glu Lys Val Ala Lys Phe Ala Glu Ser Tyr Gly Met Lys Leu Glu Asn
                405                 410                 415
Val Leu Phe Asn Met Asp Gly Thr Ile Glu Leu Tyr Leu Pro Ser Gly
                420                 425                 430
Glu Val Ile Lys Lys Asn Met Ala Asp Phe Thr Gly Glu Ala Pro Gln
                435                 440                 445
```

-continued

```
Gly Asn Gly Glu Asn Lys Pro Ser Glu Asn Gly Lys Val Ser Thr Gly
            450                 455                 460
Thr Val Glu Asn Gln Pro Thr Glu Asn Lys Pro Ala Asp Ser Leu Pro
465                 470                 475                 480
Glu Ala Pro Asn Glu Lys Pro Val Lys Pro Glu Asn Ser Thr Asp Asn
                485                 490                 495
Gly Met Leu Asn Pro Glu Gly Asn Val Gly Ser Asp Pro Met Leu Asp
            500                 505                 510
Pro Ala Leu Glu Glu Ala Pro Ala Val Asp Pro Val Gln Glu Lys Leu
            515                 520                 525
Glu Lys Phe Thr Ala Ser Tyr Gly Leu Gly Leu Asp Ser Val Ile Phe
530                 535                 540
Asn Met Asp Gly Thr Ile Glu Leu Arg Leu Pro Ser Gly Glu Val Ile
545                 550                 555                 560
Lys Lys Asn Leu Ser Asp Phe Ile Ala
                565
```

<210> SEQ ID NO 256
<211> LENGTH: 569
<212> TYPE: PRT
<213> ORGANISM: Artificial Sequence
<220> FEATURE:
<223> OTHER INFORMATION: Unknown Sequence

<400> SEQUENCE: 256

```
Met Asp Leu Thr Glu Glu Gln Ile Lys Ala Ala Gln Lys His Leu Glu
1               5                   10                  15
Glu Val Lys Thr Ser His Asn Gly Leu Asp Ser Leu Ser Ser His Glu
            20                  25                  30
Gln Asp Tyr Pro Gly Asn Ala Lys Glu Met Lys Asp Leu Asp Lys Lys
        35                  40                  45
Ile Glu Glu Lys Ile Ala Gly Ile Met Lys Gln Tyr Gly Val Lys Arg
    50                  55                  60
Glu Ser Ile Val Val Asn Lys Glu Lys Asn Ala Ile Ile Tyr Pro Ser
65                  70                  75                  80
Gly Asp Gly Thr Ser Ala Asp Pro Ile Asp Glu His Lys Pro Val Gly
                85                  90                  95
Ile Gly His Ser His Ser Asn Tyr Glu Leu Phe Lys Pro Glu Glu Gly
            100                 105                 110
Val Ala Lys Lys Glu Gly Asn Lys Val Tyr Thr Gly Glu Glu Leu Thr
        115                 120                 125
Asn Val Val Asn Leu Leu Lys Asn Ser Thr Phe Asn Asn Gln Asn Phe
    130                 135                 140
Thr Leu Ala Asn Gly Gln Lys Arg Val Ser Phe Ser Phe Pro Pro Glu
145                 150                 155                 160
Leu Glu Lys Lys Leu Gly Ile Asn Met Leu Val Lys Leu Ile Thr Pro
                165                 170                 175
Asp Gly Lys Val Leu Glu Lys Val Ser Gly Lys Val Phe Gly Glu Gly
            180                 185                 190
Val Gly Asn Ile Ala Asn Phe Glu Leu Asp Gln Pro Tyr Leu Pro Gly
        195                 200                 205
Gln Thr Phe Lys Tyr Thr Ile Ala Ser Lys Asp Tyr Pro Glu Val Ser
    210                 215                 220
Tyr Asp Gly Thr Phe Thr Val Pro Thr Ser Leu Ala Tyr Lys Met Ala
225                 230                 235                 240
```

Ser Gln Thr Ile Phe Tyr Pro Phe His Ala Gly Asp Thr Tyr Leu Arg
            245                 250                 255

Val Asn Pro Gln Phe Ala Val Pro Lys Gly Thr Asp Ala Leu Val Arg
        260                 265                 270

Val Phe Asp Glu Phe His Gly Asn Ala Tyr Leu Glu Asn Asn Tyr Lys
    275                 280                 285

Val Gly Glu Ile Lys Leu Pro Ile Pro Lys Leu Asn Gln Gly Thr Thr
290                 295                 300

Arg Thr Ala Gly Asn Lys Ile Pro Val Thr Phe Met Ala Asn Ala Tyr
305                 310                 315                 320

Leu Asp Asn Gln Ser Thr Tyr Ile Val Glu Val Pro Ile Leu Glu Lys
                325                 330                 335

Glu Asn Gln Thr Asp Lys Pro Ser Ile Leu Pro Gln Phe Lys Arg Asn
            340                 345                 350

Lys Ala Gln Glu Asn Ser Lys Leu Asp Glu Lys Val Glu Glu Pro Lys
        355                 360                 365

Thr Ser Glu Lys Val Glu Lys Glu Lys Leu Ser Glu Thr Gly Asn Ser
    370                 375                 380

Thr Ser Asn Ser Thr Leu Glu Glu Val Pro Thr Val Asp Pro Val Gln
385                 390                 395                 400

Glu Lys Val Ala Lys Phe Ala Glu Ser Tyr Gly Met Lys Leu Glu Asn
                405                 410                 415

Val Leu Phe Asn Met Asp Gly Thr Ile Glu Leu Tyr Leu Pro Ser Gly
            420                 425                 430

Glu Val Ile Lys Lys Asn Met Ala Asp Phe Thr Gly Glu Ala Pro Gln
        435                 440                 445

Gly Asn Gly Glu Asn Lys Pro Ser Glu Asn Gly Lys Val Ser Thr Gly
    450                 455                 460

Thr Val Glu Asn Gln Pro Thr Glu Asn Lys Pro Ala Asp Ser Leu Pro
465                 470                 475                 480

Glu Ala Pro Asn Glu Lys Pro Val Lys Pro Glu Asn Ser Thr Asp Asn
                485                 490                 495

Gly Met Leu Asn Pro Glu Gly Asn Val Gly Ser Asp Pro Met Leu Asp
            500                 505                 510

Pro Ala Leu Glu Glu Ala Pro Ala Val Asp Pro Val Gln Glu Lys Leu
        515                 520                 525

Glu Lys Phe Thr Ala Ser Tyr Gly Leu Gly Leu Asp Ser Val Ile Phe
    530                 535                 540

Asn Met Asp Gly Thr Ile Glu Leu Arg Leu Pro Ser Gly Glu Val Ile
545                 550                 555                 560

Lys Lys Asn Leu Ser Asp Phe Ile Ala
                565

<210> SEQ ID NO 257
<211> LENGTH: 819
<212> TYPE: DNA
<213> ORGANISM: Artificial Sequence
<220> FEATURE:
<223> OTHER INFORMATION: Unknown Organism

<400> SEQUENCE: 257
atgcaaatta cctacactga tgatgagatt caggtagcca agttggcagg caagtacaca      60
acagaagacg gttatatctt tgatactagt tggattaaaa aagatagttt gtctgaagct     120
gagagagcgg cagcccaggc ttatgctaaa gagaaaggtt tgaccctcc ttcgacagac     180

-continued

```
caccaggatt caggaaatac tgaggcaaaa ggagcagaag ctatctacaa ccgcgtgaaa      240
gcagctaaga aggtgccact tgatcgtatg ccttacaatc ttcagtatac tgtagaagtc      300
aaaaacggta gtttaatcat acctcattat gaccattacc ataacatcaa atttgagtgg      360
tttgacgaag gcctttatga ggcacctaag gggtatagtc ttgaggatct tttggcgact      420
gtcaagtact atgtcgaacc gcggaacgct agtgaccatg ttcgtaaaaa taaggcagac      480
caagatagta aacctgatga agataaggaa catgatgaag taagtgagcc aactcaccct      540
gaatctgatg aaaagagaa tcacgctggt ttaaatcctt cagcagataa tctttataaa       600
ccaagcactg atacggaaga gacagaggaa gaagctgaag ataccacaga tgaggctgaa      660
attcctggta cccctagtat tagacaaaat gctatggaga cattgactgg tctaaaaagt      720
agtcttcttc tcggaacgaa agataataac actatttcag cagaagtaga tagtctcttg      780
gctttgttaa agaaagtca accggctcct atacagtag                               819
```

<210> SEQ ID NO 258
<211> LENGTH: 272
<212> TYPE: PRT
<213> ORGANISM: Artificial Sequence
<220> FEATURE:
<223> OTHER INFORMATION: Unknown Organism

<400> SEQUENCE: 258

```
Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
                20                  25                  30

Lys Lys Asp Ser Leu Ser Glu Ala Glu Arg Ala Ala Ala Gln Ala Tyr
            35                  40                  45

Ala Lys Glu Lys Gly Leu Thr Pro Pro Ser Thr Asp His Gln Asp Ser
        50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro His Tyr Asp His
                100                 105                 110

Tyr His Asn Ile Lys Phe Glu Trp Phe Asp Glu Gly Leu Tyr Glu Ala
            115                 120                 125

Pro Lys Gly Tyr Ser Leu Glu Asp Leu Leu Ala Thr Val Lys Tyr Tyr
        130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
```

```
                    245                 250                 255
Asp Ser Leu Leu Ala Leu Leu Lys Glu Ser Gln Pro Ala Pro Ile Gln
        260                 265                 270

<210> SEQ ID NO 259
<211> LENGTH: 36
<212> TYPE: DNA
<213> ORGANISM: Artificial Sequence
<220> FEATURE:
<223> OTHER INFORMATION: Unknown Organism

<400> SEQUENCE: 259
ccgaattcca tatgcaaatt acctacactg atgatg                                 36

<210> SEQ ID NO 260
<211> LENGTH: 29
<212> TYPE: DNA
<213> ORGANISM: Artificial Sequence
<220> FEATURE:
<223> OTHER INFORMATION: Unknown Organism

<400> SEQUENCE: 260
ggactagtat caaagatata accgtcttc                                         29

<210> SEQ ID NO 261
<211> LENGTH: 33
<212> TYPE: DNA
<213> ORGANISM: Artificial Sequence
<220> FEATURE:
<223> OTHER INFORMATION: Unknown Organism

<400> SEQUENCE: 261
ggactagttg gattaaaaaa gatagtttgt ctg                                    33

<210> SEQ ID NO 262
<211> LENGTH: 32
<212> TYPE: DNA
<213> ORGANISM: Artificial Sequence
<220> FEATURE:
<223> OTHER INFORMATION: Unknown Organism

<400> SEQUENCE: 262
ttcccgcggt tcgacatagt acttgacagt cg                                     32

<210> SEQ ID NO 263
<211> LENGTH: 29
<212> TYPE: DNA
<213> ORGANISM: Artificial Sequence
<220> FEATURE:
<223> OTHER INFORMATION: Unknown Organism

<400> SEQUENCE: 263
ttcccgcgga acgctagtga ccatgttcg                                         29

<210> SEQ ID NO 264
<211> LENGTH: 31
<212> TYPE: DNA
<213> ORGANISM: Artificial Sequence
<220> FEATURE:
<223> OTHER INFORMATION: Unknown Organism

<400> SEQUENCE: 264
cggggtacca ggaatttcag cctcatctgt g                                      31

<210> SEQ ID NO 265
```

```
<210> SEQ ID NO 265
<211> LENGTH: 36
<212> TYPE: DNA
<213> ORGANISM: Artificial Sequence
<220> FEATURE:
<223> OTHER INFORMATION: Unknown Organism

<400> SEQUENCE: 265
cccggtaccc ctagtattag acaaaatgct atggag                                36

<210> SEQ ID NO 266
<211> LENGTH: 29
<212> TYPE: DNA
<213> ORGANISM: Artificial Sequence
<220> FEATURE:
<223> OTHER INFORMATION: Unknown Organism

<400> SEQUENCE: 266
ggatcccggg aggtatgatt aaactaccg                                        29

<210> SEQ ID NO 267
<211> LENGTH: 34
<212> TYPE: DNA
<213> ORGANISM: Artificial Sequence
<220> FEATURE:
<223> OTHER INFORMATION: Unknown Organism

<400> SEQUENCE: 267
catgcccggg aacatcaaat ttgagtggtt tgac                                  34

<210> SEQ ID NO 268
<211> LENGTH: 37
<212> TYPE: DNA
<213> ORGANISM: Artificial Sequence
<220> FEATURE:
<223> OTHER INFORMATION: Unknown Organism

<400> SEQUENCE: 268
cttgatcgac atatgttggc aggcaagtac acaacag                               37

<210> SEQ ID NO 269
<211> LENGTH: 45
<212> TYPE: DNA
<213> ORGANISM: Artificial Sequence
<220> FEATURE:
<223> OTHER INFORMATION: Unknown Organism

<400> SEQUENCE: 269
aacggtagtt taatcatacc ttcttatgac cattaccata acatc                      45

<210> SEQ ID NO 270
<211> LENGTH: 45
<212> TYPE: DNA
<213> ORGANISM: Artificial Sequence
<220> FEATURE:
<223> OTHER INFORMATION: Unknown Organism

<400> SEQUENCE: 270
gatgttatgg taatggtcat aagaaggtat gattaaacta ccgtt                      45

<210> SEQ ID NO 271
<211> LENGTH: 45
<212> TYPE: DNA
<213> ORGANISM: Artificial Sequence
<220> FEATURE:
<223> OTHER INFORMATION: Unknown Organism

<400> SEQUENCE: 271
```
aatcatacct tcttatgact cttaccataa catcaaattt gagtg                45

<210> SEQ ID NO 272
<211> LENGTH: 45
<212> TYPE: DNA
<213> ORGANISM: Artificial Sequence
<220> FEATURE:
<223> OTHER INFORMATION: Unknown Organism

<400> SEQUENCE: 272
cactcaaatt tgatgttatg gtaagagtca taagaaggta tgatt                45

<210> SEQ ID NO 273
<211> LENGTH: 45
<212> TYPE: DNA
<213> ORGANISM: Artificial Sequence
<220> FEATURE:
<223> OTHER INFORMATION: Unknown Organism

<400> SEQUENCE: 273
taccttctta tgactcttac tctaacatca aatttgagtg gtttg                45

<210> SEQ ID NO 274
<211> LENGTH: 45
<212> TYPE: DNA
<213> ORGANISM: Artificial Sequence
<220> FEATURE:
<223> OTHER INFORMATION: Unknown Organism

<400> SEQUENCE: 274
caaaccactc aaatttgatg ttagagtaag agtcataaga aggta                45

<210> SEQ ID NO 275
<211> LENGTH: 45
<212> TYPE: DNA
<213> ORGANISM: Artificial Sequence
<220> FEATURE:
<223> OTHER INFORMATION: Unknown Organism

<400> SEQUENCE: 275
aatcatacct cattatgact cttaccataa catcaaattt gagtg                45

<210> SEQ ID NO 276
<211> LENGTH: 45
<212> TYPE: DNA
<213> ORGANISM: Artificial Sequence
<220> FEATURE:
<223> OTHER INFORMATION: Unknown Organism

<400> SEQUENCE: 276
cactcaaatt tgatgttatg gtaagagtca taatgaggta tgatt                45

<210> SEQ ID NO 277
<211> LENGTH: 45
<212> TYPE: DNA
<213> ORGANISM: Artificial Sequence
<220> FEATURE:
<223> OTHER INFORMATION: Unknown Organism

<400> SEQUENCE: 277
tacctcatta tgaccattac tctaacatca aatttgagtg gtttg                45

<210> SEQ ID NO 278
<211> LENGTH: 45
<212> TYPE: DNA

<213> ORGANISM: Artificial Sequence
<220> FEATURE:
<223> OTHER INFORMATION: Unknown Organism

<400> SEQUENCE: 278
caaaccactc aaatttgatg ttagagtaat ggtcataatg aggta       45

<210> SEQ ID NO 279
<211> LENGTH: 45
<212> TYPE: DNA
<213> ORGANISM: Artificial Sequence
<220> FEATURE:
<223> OTHER INFORMATION: Unknown Organism

<400> SEQUENCE: 279
tacctcatta tgactcttac tctaacatca aatttgagtg gtttg       45

<210> SEQ ID NO 280
<211> LENGTH: 45
<212> TYPE: DNA
<213> ORGANISM: Artificial Sequence
<220> FEATURE:
<223> OTHER INFORMATION: Unknown Organism

<400> SEQUENCE: 280
caaaccactc aaatttgatg ttagagtaag agtcataatg aggta       45

<210> SEQ ID NO 281
<211> LENGTH: 45
<212> TYPE: DNA
<213> ORGANISM: Artificial Sequence
<220> FEATURE:
<223> OTHER INFORMATION: Unknown Organism

<400> SEQUENCE: 281
taccttctta tgaccattac tctaacatca aatttgagtg gtttg       45

<210> SEQ ID NO 282
<211> LENGTH: 44
<212> TYPE: DNA
<213> ORGANISM: Artificial Sequence
<220> FEATURE:
<223> OTHER INFORMATION: Unknown Organism

<400> SEQUENCE: 282
aaaccactca aatttgatgt tagagtaatg gtcataagaa ggta       44

<210> SEQ ID NO 283
<211> LENGTH: 45
<212> TYPE: DNA
<213> ORGANISM: Artificial Sequence
<220> FEATURE:
<223> OTHER INFORMATION: Unknown Organism

<400> SEQUENCE: 283
aacggtagtt taatcatacc ttctaaagac cattaccata acatc       45

<210> SEQ ID NO 284
<211> LENGTH: 45
<212> TYPE: DNA
<213> ORGANISM: Artificial Sequence
<220> FEATURE:
<223> OTHER INFORMATION: Unknown Organism

<400> SEQUENCE: 284
gatgttatgg taatggtctt tagaaggtat gattaaacta ccgtt       45

<210> SEQ ID NO 285
<211> LENGTH: 46
<212> TYPE: DNA
<213> ORGANISM: Artificial Sequence
<220> FEATURE:
<223> OTHER INFORMATION: Unknown Organism

<400> SEQUENCE: 285
cggtagttta atcatacctc ataaggactc ttaccataac atcaaa         46

<210> SEQ ID NO 286
<211> LENGTH: 46
<212> TYPE: DNA
<213> ORGANISM: Artificial Sequence
<220> FEATURE:
<223> OTHER INFORMATION: Unknown Organism

<400> SEQUENCE: 286
tttgatgtta tggtaagagt ccttatgagg tatgattaaa ctaccg         46

<210> SEQ ID NO 287
<211> LENGTH: 46
<212> TYPE: DNA
<213> ORGANISM: Artificial Sequence
<220> FEATURE:
<223> OTHER INFORMATION: Unknown Organism

<400> SEQUENCE: 287
aacggtagtt taatcatacc tgaccattac cataacatca aatttg         46

<210> SEQ ID NO 288
<211> LENGTH: 46
<212> TYPE: DNA
<213> ORGANISM: Artificial Sequence
<220> FEATURE:
<223> OTHER INFORMATION: Unknown Organism

<400> SEQUENCE: 288
caaatttgat gttatggtaa tggtcaggta tgattaaact accgtt         46

<210> SEQ ID NO 289
<211> LENGTH: 45
<212> TYPE: DNA
<213> ORGANISM: Artificial Sequence
<220> FEATURE:
<223> OTHER INFORMATION: Unknown Organism

<400> SEQUENCE: 289
aacggtagtt taatcatacc ttaccataac atcaaatttg agtgg          45

<210> SEQ ID NO 290
<211> LENGTH: 45
<212> TYPE: DNA
<213> ORGANISM: Artificial Sequence
<220> FEATURE:
<223> OTHER INFORMATION: Unknown Organism

<400> SEQUENCE: 290
ccactcaaat ttgatgttat ggtaaggtat gattaaacta ccgtt          45

<210> SEQ ID NO 291
<211> LENGTH: 45
<212> TYPE: DNA
<213> ORGANISM: Artificial Sequence
<220> FEATURE:

-continued

<223> OTHER INFORMATION: Unknown Organism

<400> SEQUENCE: 291
accggtagtt taatcatacc taacatcaaa tttgagtggt ttgac          45

<210> SEQ ID NO 292
<211> LENGTH: 45
<212> TYPE: DNA
<213> ORGANISM: Artificial Sequence
<220> FEATURE:
<223> OTHER INFORMATION: Unknown Organism

<400> SEQUENCE: 292
gtcaaaccac tcaaatttga tgttaggtat gattaaacta ccgtt          45

<210> SEQ ID NO 293
<211> LENGTH: 272
<212> TYPE: PRT
<213> ORGANISM: Artificial Sequence
<220> FEATURE:
<223> OTHER INFORMATION: Unknown Organism

<400> SEQUENCE: 293

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
                20                  25                  30

Lys Lys Asp Ser Leu Ser Glu Ala Glu Arg Ala Ala Gln Ala Tyr
            35                  40                  45

Ala Lys Glu Lys Gly Leu Thr Pro Pro Ser Thr Asp His Gln Asp Ser
        50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Ser Tyr Asp His
            100                 105                 110

Tyr His Asn Ile Lys Phe Glu Trp Phe Asp Glu Gly Leu Tyr Glu Ala
        115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

```
<210> SEQ ID NO 294
<211> LENGTH: 272
<212> TYPE: PRT
<213> ORGANISM: Artificial Sequence
<220> FEATURE:
<223> OTHER INFORMATION: Unknown Organism

<400> SEQUENCE: 294
```

| Met | Gln | Ile | Thr | Tyr | Thr | Asp | Asp | Glu | Ile | Gln | Val | Ala | Lys | Leu | Ala |
|---|---|---|---|---|---|---|---|---|---|---|---|---|---|---|---|
| 1 | | | | 5 | | | | | 10 | | | | | 15 | |

| Gly | Lys | Tyr | Thr | Thr | Glu | Asp | Gly | Tyr | Ile | Phe | Asp | Thr | Ser | Trp | Ile |
|---|---|---|---|---|---|---|---|---|---|---|---|---|---|---|---|
| | | | 20 | | | | | 25 | | | | | 30 | | |

| Lys | Lys | Asp | Ser | Leu | Ser | Glu | Ala | Glu | Arg | Ala | Ala | Gln | Ala | Tyr |
|---|---|---|---|---|---|---|---|---|---|---|---|---|---|---|
| | | 35 | | | | | 40 | | | | | 45 | | |

| Ala | Lys | Glu | Lys | Gly | Leu | Thr | Pro | Pro | Ser | Thr | His | Gln | Asp | Ser |
|---|---|---|---|---|---|---|---|---|---|---|---|---|---|---|
| | 50 | | | | | 55 | | | | | 60 | | | |

| Gly | Asn | Thr | Glu | Ala | Lys | Gly | Ala | Glu | Ala | Ile | Tyr | Asn | Arg | Val | Lys |
|---|---|---|---|---|---|---|---|---|---|---|---|---|---|---|---|
| 65 | | | | | 70 | | | | | 75 | | | | | 80 |

| Ala | Ala | Lys | Lys | Val | Pro | Leu | Asp | Arg | Met | Pro | Tyr | Asn | Leu | Gln | Tyr |
|---|---|---|---|---|---|---|---|---|---|---|---|---|---|---|---|
| | | | | 85 | | | | | 90 | | | | | 95 | |

| Thr | Val | Glu | Val | Lys | Asn | Gly | Ser | Leu | Ile | Ile | Pro | His | Tyr | Asp | Ser |
|---|---|---|---|---|---|---|---|---|---|---|---|---|---|---|---|
| | | | | 100 | | | | | 105 | | | | | 110 | |

| Tyr | His | Asn | Ile | Lys | Phe | Glu | Trp | Phe | Asp | Glu | Gly | Leu | Tyr | Glu | Ala |
|---|---|---|---|---|---|---|---|---|---|---|---|---|---|---|---|
| | | | | 115 | | | | | 120 | | | | | 125 | |

| Pro | Lys | Gly | Tyr | Ser | Leu | Glu | Asp | Leu | Leu | Ala | Thr | Val | Lys | Tyr | Tyr |
|---|---|---|---|---|---|---|---|---|---|---|---|---|---|---|---|
| | | 130 | | | | | 135 | | | | | 140 | | | |

| Val | Glu | Pro | Arg | Asn | Ala | Ser | Asp | His | Val | Arg | Lys | Asn | Lys | Ala | Asp |
|---|---|---|---|---|---|---|---|---|---|---|---|---|---|---|---|
| 145 | | | | | 150 | | | | | 155 | | | | | 160 |

| Gln | Asp | Ser | Lys | Pro | Asp | Glu | Asp | Lys | Glu | His | Asp | Glu | Val | Ser | Glu |
|---|---|---|---|---|---|---|---|---|---|---|---|---|---|---|---|
| | | | | 165 | | | | | 170 | | | | | 175 | |

| Pro | Thr | His | Pro | Glu | Ser | Asp | Glu | Lys | Glu | Asn | His | Ala | Gly | Leu | Asn |
|---|---|---|---|---|---|---|---|---|---|---|---|---|---|---|---|
| | | | 180 | | | | | 185 | | | | | 190 | | |

| Pro | Ser | Ala | Asp | Asn | Leu | Tyr | Lys | Pro | Ser | Thr | Asp | Thr | Glu | Glu | Thr |
|---|---|---|---|---|---|---|---|---|---|---|---|---|---|---|---|
| | | | 195 | | | | | 200 | | | | | 205 | | |

| Glu | Glu | Glu | Ala | Glu | Asp | Thr | Thr | Asp | Glu | Ala | Glu | Ile | Pro | Gly | Thr |
|---|---|---|---|---|---|---|---|---|---|---|---|---|---|---|---|
| | 210 | | | | | 215 | | | | | 220 | | | | |

| Pro | Ser | Ile | Arg | Gln | Asn | Ala | Met | Glu | Thr | Leu | Thr | Gly | Leu | Lys | Ser |
|---|---|---|---|---|---|---|---|---|---|---|---|---|---|---|---|
| 225 | | | | | 230 | | | | | 235 | | | | | 240 |

| Ser | Leu | Leu | Leu | Gly | Thr | Lys | Asp | Asn | Asn | Thr | Ile | Ser | Ala | Glu | Val |
|---|---|---|---|---|---|---|---|---|---|---|---|---|---|---|---|
| | | | | 245 | | | | | 250 | | | | | 255 | |

| Asp | Ser | Leu | Leu | Ala | Leu | Leu | Lys | Glu | Ser | Gln | Pro | Ala | Pro | Ile | Gln |
|---|---|---|---|---|---|---|---|---|---|---|---|---|---|---|---|
| | | | 260 | | | | | 265 | | | | | 270 | | |

```
<210> SEQ ID NO 295
<211> LENGTH: 272
<212> TYPE: PRT
<213> ORGANISM: Artificial Sequence
<220> FEATURE:
<223> OTHER INFORMATION: Unknown Organism

<400> SEQUENCE: 295
```

| Met | Gln | Ile | Thr | Tyr | Thr | Asp | Asp | Glu | Ile | Gln | Val | Ala | Lys | Leu | Ala |
|---|---|---|---|---|---|---|---|---|---|---|---|---|---|---|---|
| 1 | | | | 5 | | | | | 10 | | | | | 15 | |

| Gly | Lys | Tyr | Thr | Thr | Glu | Asp | Gly | Tyr | Ile | Phe | Asp | Thr | Ser | Trp | Ile |
|---|---|---|---|---|---|---|---|---|---|---|---|---|---|---|---|
| | | | 20 | | | | | 25 | | | | | 30 | | |

| Lys | Lys | Asp | Ser | Leu | Ser | Glu | Ala | Glu | Arg | Ala | Ala | Gln | Ala | Tyr |
|---|---|---|---|---|---|---|---|---|---|---|---|---|---|---|
| | | 35 | | | | | 40 | | | | | 45 | | |

```
Ala Lys Glu Lys Gly Leu Thr Pro Pro Ser Thr Asp His Gln Asp Ser
         50                  55                  60

Gly Asn Thr Glu Ala Lys Gly Ala Glu Ala Ile Tyr Asn Arg Val Lys
 65                  70                  75                  80

Ala Ala Lys Lys Val Pro Leu Asp Arg Met Pro Tyr Asn Leu Gln Tyr
                 85                  90                  95

Thr Val Glu Val Lys Asn Gly Ser Leu Ile Ile Pro His Tyr Asp His
            100                 105                 110

Tyr Ser Asn Ile Lys Phe Glu Trp Phe Asp Glu Gly Leu Tyr Glu Ala
            115                 120                 125

Pro Lys Gly Tyr Ser Leu Glu Asp Leu Leu Ala Thr Val Lys Tyr Tyr
            130                 135                 140

Val Glu Pro Arg Asn Ala Ser Asp His Val Arg Lys Asn Lys Ala Asp
145                 150                 155                 160

Gln Asp Ser Lys Pro Asp Glu Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
            195                 200                 205

Glu Glu Glu Ala Glu Asp Thr Thr Asp Glu Ala Glu Ile Pro Gly Thr
            210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

<210> SEQ ID NO 296
<211> LENGTH: 272
<212> TYPE: PRT
<213> ORGANISM: Artificial Sequence
<220> FEATURE:
<223> OTHER INFORMATION: Unknown Organism

<400> SEQUENCE: 296

Met Gln Ile Thr Tyr Thr Asp Asp Glu Ile Gln Val Ala Lys Leu Ala
 1               5                  10                  15

Gly Lys Tyr Thr Thr Glu Asp Gly Tyr Ile Phe Asp Thr Ser Trp Ile
                 20                  25                  30

Lys Lys Asp Ser Leu Ser Glu Ala Glu Arg Ala Ala Ala Gln Ala Tyr
             35                  40                  45

Ala Lys Glu Lys Gly Leu Thr Pro Pro Ser Thr Asp His Gln Asp Ser
         50                  55                  60

Gly Asn Thr Glu Ala Lys Gly Ala Glu Ala Ile Tyr Asn Arg Val Lys
 65                  70                  75                  80

Ala Ala Lys Lys Val Pro Leu Asp Arg Met Pro Tyr Asn Leu Gln Tyr
                 85                  90                  95

Thr Val Glu Val Lys Asn Gly Ser Leu Ile Ile Pro Ser Tyr Asp Ser
            100                 105                 110

Tyr His Asn Ile Lys Phe Glu Trp Phe Asp Glu Gly Leu Tyr Glu Ala
            115                 120                 125

Pro Lys Gly Tyr Ser Leu Glu Asp Leu Leu Ala Thr Val Lys Tyr Tyr
            130                 135                 140
```

```
Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
                260                 265                 270
```

<210> SEQ ID NO 297
<211> LENGTH: 272
<212> TYPE: PRT
<213> ORGANISM: Artificial Sequence
<220> FEATURE:
<223> OTHER INFORMATION: Unknown Organism

<400> SEQUENCE: 297

```
Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
                20                  25                  30

Lys Lys Asp Ser Leu Ser Glu Ala Glu Arg Ala Ala Gln Ala Tyr
            35                  40                  45

Ala Lys Glu Lys Gly Leu Thr Pro Pro Ser Thr His Gln Asp Ser
        50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Ser Tyr Asp Ser
                100                 105                 110

Tyr Ser Asn Ile Lys Phe Glu Trp Phe Asp Glu Gly Leu Tyr Glu Ala
            115                 120                 125

Pro Lys Gly Tyr Ser Leu Glu Asp Leu Leu Ala Thr Val Lys Tyr Tyr
        130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240
```

-continued

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

<210> SEQ ID NO 298
<211> LENGTH: 272
<212> TYPE: PRT
<213> ORGANISM: Artificial Sequence
<220> FEATURE:
<223> OTHER INFORMATION: Unknown Organism

<400> SEQUENCE: 298

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Ala Gln Ala Tyr
        35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro His Tyr Asp Ser
            100                 105                 110

Tyr Ser Asn Ile Lys Phe Glu Trp Phe Asp Glu Gly Leu Tyr Glu Ala
        115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

<210> SEQ ID NO 299
<211> LENGTH: 272
<212> TYPE: PRT
<213> ORGANISM: Artificial Sequence
<220> FEATURE:
<223> OTHER INFORMATION: Unknown Organism

<400> SEQUENCE: 299

Met Gln Ile Thr Tyr Thr Asp Asp Glu Ile Gln Val Ala Lys Leu Ala

-continued

```
1               5                   10                  15
Gly Lys Tyr Thr Thr Glu Asp Gly Tyr Ile Phe Asp Thr Ser Trp Ile
                20                  25                  30
Lys Lys Asp Ser Leu Ser Glu Ala Glu Arg Ala Ala Gln Ala Tyr
        35                  40                  45
Ala Lys Glu Lys Gly Leu Thr Pro Pro Ser Thr Asp His Gln Asp Ser
    50                  55                  60
Gly Asn Thr Glu Ala Lys Gly Ala Glu Ala Ile Tyr Asn Arg Val Lys
65                  70                  75                  80
Ala Ala Lys Lys Val Pro Leu Asp Arg Met Pro Tyr Asn Leu Gln Tyr
                85                  90                  95
Thr Val Glu Val Lys Asn Gly Ser Leu Ile Ile Pro Ser Tyr Asp His
                100                 105                 110
Tyr Ser Asn Ile Lys Phe Glu Trp Phe Asp Glu Gly Leu Tyr Glu Ala
                115                 120                 125
Pro Lys Gly Tyr Ser Leu Glu Asp Leu Leu Ala Thr Val Lys Tyr Tyr
            130                 135                 140
Val Glu Pro Arg Asn Ala Ser Asp His Val Arg Lys Asn Lys Ala Asp
145                 150                 155                 160
Gln Asp Ser Lys Pro Asp Glu Asp Lys Glu His Asp Glu Val Ser Glu
                165                 170                 175
Pro Thr His Pro Glu Ser Asp Glu Lys Glu Asn His Ala Gly Leu Asn
                180                 185                 190
Pro Ser Ala Asp Asn Leu Tyr Lys Pro Ser Thr Asp Thr Glu Glu Thr
            195                 200                 205
Glu Glu Glu Ala Glu Asp Thr Thr Asp Glu Ala Glu Ile Pro Gly Thr
210                 215                 220
Pro Ser Ile Arg Gln Asn Ala Met Glu Thr Leu Thr Gly Leu Lys Ser
225                 230                 235                 240
Ser Leu Leu Leu Gly Thr Lys Asp Asn Asn Thr Ile Ser Ala Glu Val
                245                 250                 255
Asp Ser Leu Leu Ala Leu Leu Lys Glu Ser Gln Pro Ala Pro Ile Gln
                260                 265                 270
```

<210> SEQ ID NO 300
<211> LENGTH: 272
<212> TYPE: PRT
<213> ORGANISM: Artificial Sequence
<220> FEATURE:
<223> OTHER INFORMATION: Unknown Organism

<400> SEQUENCE: 300

```
Met Gln Ile Thr Tyr Thr Asp Asp Glu Ile Gln Val Ala Lys Leu Ala
1               5                   10                  15
Gly Lys Tyr Thr Thr Glu Asp Gly Tyr Ile Phe Asp Thr Ser Trp Ile
                20                  25                  30
Lys Lys Asp Ser Leu Ser Glu Ala Glu Arg Ala Ala Gln Ala Tyr
        35                  40                  45
Ala Lys Glu Lys Gly Leu Thr Pro Pro Ser Thr Asp His Gln Asp Ser
    50                  55                  60
Gly Asn Thr Glu Ala Lys Gly Ala Glu Ala Ile Tyr Asn Arg Val Lys
65                  70                  75                  80
Ala Ala Lys Lys Val Pro Leu Asp Arg Met Pro Tyr Asn Leu Gln Tyr
                85                  90                  95
Thr Val Glu Val Lys Asn Gly Ser Leu Ile Ile Pro Ser Lys Asp His
```

```
                    100                 105                 110
Tyr His Asn Ile Lys Phe Glu Trp Phe Asp Glu Gly Leu Tyr Glu Ala
        115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Lys Glu His Asp Glu Val Ser Glu
                165                 170                 175

Pro Thr His Pro Glu Ser Asp Glu Lys Glu Asn His Ala Gly Leu Asn
        180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
        210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
        260                 265                 270
```

<210> SEQ ID NO 301
<211> LENGTH: 272
<212> TYPE: PRT
<213> ORGANISM: Artificial Sequence
<220> FEATURE:
<223> OTHER INFORMATION: Unknown Organism

<400> SEQUENCE: 301

```
Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Gln Ala Tyr
        35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro His Lys Asp Ser
            100                 105                 110

Tyr His Asn Ile Lys Phe Glu Trp Phe Asp Glu Gly Leu Tyr Glu Ala
        115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Lys Glu His Asp Glu Val Ser Glu
                165                 170                 175

Pro Thr His Pro Glu Ser Asp Glu Lys Glu Asn His Ala Gly Leu Asn
        180                 185                 190

Pro Ser Ala Asp Asn Leu Tyr Lys Pro Ser Thr Asp Thr Glu Glu Thr
```

-continued

```
            195                 200                 205
Glu Glu Glu Ala Glu Asp Thr Thr Asp Glu Ala Glu Ile Pro Gly Thr
        210                 215                 220
Pro Ser Ile Arg Gln Asn Ala Met Glu Thr Leu Thr Gly Leu Lys Ser
225                 230                 235                 240
Ser Leu Leu Leu Gly Thr Lys Asp Asn Asn Thr Ile Ser Ala Glu Val
            245                 250                 255
Asp Ser Leu Leu Ala Leu Leu Lys Glu Ser Gln Pro Ala Pro Ile Gln
        260                 265                 270
```

<210> SEQ ID NO 302
<211> LENGTH: 270
<212> TYPE: PRT
<213> ORGANISM: Artificial Sequence
<220> FEATURE:
<223> OTHER INFORMATION: Unknown Organism

<400> SEQUENCE: 302

```
Met Gln Ile Thr Tyr Thr Asp Asp Glu Ile Gln Val Ala Lys Leu Ala
1               5                   10                  15
Gly Lys Tyr Thr Thr Glu Asp Gly Tyr Ile Phe Asp Thr Ser Trp Ile
            20                  25                  30
Lys Lys Asp Ser Leu Ser Glu Ala Glu Arg Ala Ala Ala Gln Ala Tyr
        35                  40                  45
Ala Lys Glu Lys Gly Leu Thr Pro Pro Ser Thr Asp His Gln Asp Ser
    50                  55                  60
Gly Asn Thr Glu Ala Lys Gly Ala Glu Ala Ile Tyr Asn Arg Val Lys
65                  70                  75                  80
Ala Ala Lys Lys Val Pro Leu Asp Arg Met Pro Tyr Asn Leu Gln Tyr
                85                  90                  95
Thr Val Glu Val Lys Asn Gly Ser Leu Ile Ile Pro Asp His Tyr His
            100                 105                 110
Asn Ile Lys Phe Glu Trp Phe Asp Glu Gly Leu Tyr Glu Ala Pro Lys
        115                 120                 125
Gly Tyr Ser Leu Glu Asp Leu Leu Ala Thr Val Lys Tyr Tyr Val Glu
    130                 135                 140
Pro Arg Asn Ala Ser Asp His Val Arg Lys Asn Lys Ala Asp Gln Asp
145                 150                 155                 160
Ser Lys Pro Asp Glu Asp Lys Glu His Asp Glu Val Ser Glu Pro Thr
                165                 170                 175
His Pro Glu Ser Asp Glu Lys Glu Asn His Ala Gly Leu Asn Pro Ser
            180                 185                 190
Ala Asp Asn Leu Tyr Lys Pro Ser Thr Asp Thr Glu Glu Thr Glu Glu
        195                 200                 205
Glu Ala Glu Asp Thr Thr Asp Glu Ala Glu Ile Pro Gly Thr Pro Ser
    210                 215                 220
Ile Arg Gln Asn Ala Met Glu Thr Leu Thr Gly Leu Lys Ser Ser Leu
225                 230                 235                 240
Leu Leu Gly Thr Lys Asp Asn Asn Thr Ile Ser Ala Glu Val Asp Ser
                245                 250                 255
Leu Leu Ala Leu Leu Lys Glu Ser Gln Pro Ala Pro Ile Gln
            260                 265                 270
```

<210> SEQ ID NO 303
<211> LENGTH: 268
<212> TYPE: PRT

```
<213> ORGANISM: Artificial Sequence
<220> FEATURE:
<223> OTHER INFORMATION: Unknown Organism

<400> SEQUENCE: 303

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Gln Ala Tyr
        35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Tyr His Asn Ile
            100                 105                 110

Lys Phe Glu Trp Phe Asp Glu Gly Leu Tyr Glu Ala Pro Lys Gly Tyr
        115                 120                 125

Ser Leu Glu Asp Leu Leu Ala Thr Val Lys Tyr Tyr Val Glu Pro Arg
130                 135                 140

Asn Ala Ser Asp His Val Arg Lys Asn Lys Ala Asp Gln Asp Ser Lys
145                 150                 155                 160

Pro Asp Glu Asp Lys Glu His Asp Glu Val Ser Glu Pro Thr His Pro
                165                 170                 175

Glu Ser Asp Glu Lys Gly Asn His Ala Gly Leu Asn Pro Ser Ala Asp
            180                 185                 190

Asn Leu Tyr Lys Pro Ser Thr Asp Thr Glu Glu Thr Glu Glu Glu Ala
        195                 200                 205

Glu Asp Thr Thr Asp Glu Ala Glu Ile Pro Gly Thr Pro Ser Ile Arg
    210                 215                 220

Gln Asn Ala Met Glu Thr Leu Thr Gly Leu Lys Ser Ser Leu Leu Leu
225                 230                 235                 240

Gly Thr Lys Asp Asn Asn Thr Ile Ser Ala Glu Val Asp Ser Leu Leu
                245                 250                 255

Ala Leu Leu Lys Glu Ser Gln Pro Ala Pro Ile Gln
            260                 265

<210> SEQ ID NO 304
<211> LENGTH: 266
<212> TYPE: PRT
<213> ORGANISM: Artificial Sequence
<220> FEATURE:
<223> OTHER INFORMATION: Unknown Organism

<400> SEQUENCE: 304

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Gln Ala Tyr
        35                  40                  45

Ala Lys Glu Lys Gly Leu Thr Pro Pro Ser Thr Asp His Gln Asp Ser
    50                  55                  60
```

```
Gly Asn Thr Glu Ala Lys Gly Ala Glu Ala Ile Tyr Asn Arg Val Lys
 65                  70                  75                  80

Ala Ala Lys Lys Val Pro Leu Asp Arg Met Pro Tyr Asn Leu Gln Tyr
                 85                  90                  95

Thr Val Glu Val Lys Asn Gly Ser Leu Ile Ile Pro Asn Ile Lys Phe
            100                 105                 110

Glu Trp Phe Asp Glu Gly Leu Tyr Glu Ala Pro Lys Gly Tyr Ser Leu
        115                 120                 125

Glu Asp Leu Leu Ala Thr Val Lys Tyr Tyr Val Glu Pro Arg Asn Ala
    130                 135                 140

Ser Asp His Val Arg Lys Asn Lys Ala Asp Gln Asp Ser Lys Pro Asp
145                 150                 155                 160

Glu Asp Lys Glu His Asp Glu Val Ser Glu Pro Thr His Pro Glu Ser
                165                 170                 175

Asp Glu Lys Glu Asn His Ala Gly Leu Asn Pro Ser Ala Asp Asn Leu
            180                 185                 190

Tyr Lys Pro Ser Thr Asp Thr Glu Glu Thr Glu Glu Ala Glu Asp
        195                 200                 205

Thr Thr Asp Glu Ala Glu Ile Pro Gly Thr Pro Ser Ile Arg Gln Asn
    210                 215                 220

Ala Met Glu Thr Leu Thr Gly Leu Lys Ser Ser Leu Leu Gly Thr
225                 230                 235                 240

Lys Asp Asn Asn Thr Ile Ser Ala Glu Val Asp Ser Leu Leu Ala Leu
                245                 250                 255

Leu Lys Glu Ser Gln Pro Ala Pro Ile Gln
                260                 265

<210> SEQ ID NO 305
<220> FEATURE:
<223> OTHER INFORMATION: Unknown Organism
<221> NAME/KEY: MISC_FEATURE
<222> LOCATION: (1)..(906)
<223> OTHER INFORMATION: Intentionally skipped sequence
<211> LENGTH:
<212> TYPE:
<213> ORGANISM:

<400> SEQUENCE: 305

000

<210> SEQ ID NO 306
<220> FEATURE:
<223> OTHER INFORMATION: Unknown Organism
<221> NAME/KEY: MISC_FEATURE
<222> LOCATION: (1)..(906)
<223> OTHER INFORMATION: Intentionally skipped sequence
<211> LENGTH:
<212> TYPE:
<213> ORGANISM:

<400> SEQUENCE: 306

000

<210> SEQ ID NO 307
<220> FEATURE:
<223> OTHER INFORMATION: Unknown Organism
<221> NAME/KEY: MISC_FEATURE
<222> LOCATION: (1)..(906)
<223> OTHER INFORMATION: Intentionally skipped sequence
<211> LENGTH:
<212> TYPE:
<213> ORGANISM:
```

<400> SEQUENCE: 307

000

<210> SEQ ID NO 308
<220> FEATURE:
<223> OTHER INFORMATION: Unknown Organism
<221> NAME/KEY: MISC_FEATURE
<222> LOCATION: (1)..(906)
<223> OTHER INFORMATION: Intentionally skipped sequence
<211> LENGTH:
<212> TYPE:
<213> ORGANISM:

<400> SEQUENCE: 308

000

<210> SEQ ID NO 309
<220> FEATURE:
<223> OTHER INFORMATION: Unknown Organism
<221> NAME/KEY: MISC_FEATURE
<222> LOCATION: (1)..(906)
<223> OTHER INFORMATION: Intentionally skipped sequence
<211> LENGTH:
<212> TYPE:
<213> ORGANISM:

<400> SEQUENCE: 309

000

<210> SEQ ID NO 310
<220> FEATURE:
<223> OTHER INFORMATION: Unknown Organism
<221> NAME/KEY: MISC_FEATURE
<222> LOCATION: (1)..(906)
<223> OTHER INFORMATION: Intentionally skipped sequence
<211> LENGTH:
<212> TYPE:
<213> ORGANISM:

<400> SEQUENCE: 310

000

<210> SEQ ID NO 311
<220> FEATURE:
<223> OTHER INFORMATION: Unknown Organism
<221> NAME/KEY: MISC_FEATURE
<222> LOCATION: (1)..(900)
<223> OTHER INFORMATION: Intentionally skipped sequence
<211> LENGTH:
<212> TYPE:
<213> ORGANISM:

<400> SEQUENCE: 311

000

<210> SEQ ID NO 312
<220> FEATURE:
<223> OTHER INFORMATION: Unknown Organism
<221> NAME/KEY: MISC_FEATURE
<222> LOCATION: (1)..(900)
<223> OTHER INFORMATION: Intentionally skipped sequence
<211> LENGTH:
<212> TYPE:
<213> ORGANISM:

<400> SEQUENCE: 312

000

<210> SEQ ID NO 313
<220> FEATURE:
<223> OTHER INFORMATION: Unknown Sequence
<221> NAME/KEY: MISC_FEATURE
<222> LOCATION: (1)..(900)
<223> OTHER INFORMATION: Intentionally skipped sequence
<211> LENGTH:
<212> TYPE:
<213> ORGANISM:

<400> SEQUENCE: 313

000

<210> SEQ ID NO 314
<220> FEATURE:
<223> OTHER INFORMATION: Unknown Organism
<221> NAME/KEY: MISC_FEATURE
<222> LOCATION: (1)..(894)
<223> OTHER INFORMATION: Intentionally skipped sequence
<211> LENGTH:
<212> TYPE:
<213> ORGANISM:

<400> SEQUENCE: 314

000

<210> SEQ ID NO 315
<220> FEATURE:
<223> OTHER INFORMATION: Unknown Organism
<221> NAME/KEY: MISC_FEATURE
<222> LOCATION: (1)..(894)
<223> OTHER INFORMATION: Intentionally skipped sequence
<211> LENGTH:
<212> TYPE:
<213> ORGANISM:

<400> SEQUENCE: 315

000

<210> SEQ ID NO 316
<220> FEATURE:
<223> OTHER INFORMATION: Unknown Organism
<221> NAME/KEY: MISC_FEATURE
<222> LOCATION: (1)..(888)
<223> OTHER INFORMATION: Intentionally skipped sequence
<211> LENGTH:
<212> TYPE:
<213> ORGANISM:

<400> SEQUENCE: 316

000

<210> SEQ ID NO 317
<220> FEATURE:
<223> OTHER INFORMATION: Unknown Organism
<221> NAME/KEY: MISC_FEATURE
<222> LOCATION: (1)..(900)
<223> OTHER INFORMATION: Intentionally skipped sequence
<211> LENGTH:
<212> TYPE:
<213> ORGANISM:

<400> SEQUENCE: 317

000

<210> SEQ ID NO 318
<220> FEATURE:

-continued

```
<223> OTHER INFORMATION: Unknown Organism
<221> NAME/KEY: MISC_FEATURE
<222> LOCATION: (1)..(894)
<223> OTHER INFORMATION: Intentionally skipped sequence
<211> LENGTH:
<212> TYPE:
<213> ORGANISM:

<400> SEQUENCE: 318

000

<210> SEQ ID NO 319
<220> FEATURE:
<223> OTHER INFORMATION: Unknown Organism
<221> NAME/KEY: MISC_FEATURE
<222> LOCATION: (1)..(900)
<223> OTHER INFORMATION: Intentionally skipped sequence
<211> LENGTH:
<212> TYPE:
<213> ORGANISM:

<400> SEQUENCE: 319

000

<210> SEQ ID NO 320
<220> FEATURE:
<223> OTHER INFORMATION: Unknown Organism
<221> NAME/KEY: MISC_FEATURE
<222> LOCATION: (1)..(894)
<223> OTHER INFORMATION: Intentionally skipped sequence
<211> LENGTH:
<212> TYPE:
<213> ORGANISM:

<400> SEQUENCE: 320

000

<210> SEQ ID NO 321
<220> FEATURE:
<223> OTHER INFORMATION: Unknown Organism
<221> NAME/KEY: MISC_FEATURE
<222> LOCATION: (1)..(901)
<223> OTHER INFORMATION: Intentionally skipped sequence
<211> LENGTH:
<212> TYPE:
<213> ORGANISM:

<400> SEQUENCE: 321

000

<210> SEQ ID NO 322
<220> FEATURE:
<223> OTHER INFORMATION: Unknown Sequence
<221> NAME/KEY: MISC_FEATURE
<222> LOCATION: (1)..(895)
<223> OTHER INFORMATION: Intentionally skipped sequence
<211> LENGTH:
<212> TYPE:
<213> ORGANISM:

<400> SEQUENCE: 322

000

<210> SEQ ID NO 323
<220> FEATURE:
<223> OTHER INFORMATION: Unknown Organism
<221> NAME/KEY: MISC_FEATURE
<222> LOCATION: (1)..(901)
<223> OTHER INFORMATION: Intentionally skipped sequence
```

```
<211> LENGTH:
<212> TYPE:
<213> ORGANISM:

<400> SEQUENCE: 323

000

<210> SEQ ID NO 324
<220> FEATURE:
<223> OTHER INFORMATION: Unknown Organism
<221> NAME/KEY: MISC_FEATURE
<222> LOCATION: (1)..(895)
<223> OTHER INFORMATION: Intentionally skipped sequence
<211> LENGTH:
<212> TYPE:
<213> ORGANISM:

<400> SEQUENCE: 324

000

<210> SEQ ID NO 325
<220> FEATURE:
<223> OTHER INFORMATION: Unknown Organism
<221> NAME/KEY: MISC_FEATURE
<222> LOCATION: (1)..(895)
<223> OTHER INFORMATION: Intentionally skipped sequence
<211> LENGTH:
<212> TYPE:
<213> ORGANISM:

<400> SEQUENCE: 325

000

<210> SEQ ID NO 326
<220> FEATURE:
<223> OTHER INFORMATION: Unknown Organism
<221> NAME/KEY: MISC_FEATURE
<222> LOCATION: (1)..(889)
<223> OTHER INFORMATION: Intentionally skipped sequence
<211> LENGTH:
<212> TYPE:
<213> ORGANISM:

<400> SEQUENCE: 326

000

<210> SEQ ID NO 327
<211> LENGTH: 41
<212> TYPE: DNA
<213> ORGANISM: Artificial Sequence
<220> FEATURE:
<223> OTHER INFORMATION: Unknown Organism

<400> SEQUENCE: 327
atatgggccc caaattacct acactgatga tgagattcag g        41

<210> SEQ ID NO 328
<211> LENGTH: 43
<212> TYPE: DNA
<213> ORGANISM: Artificial Sequence
<220> FEATURE:
<223> OTHER INFORMATION: Unknown Organism

<400> SEQUENCE: 328
ataagaatgc ggccgcctac tgtataggag ccggttgact ttc        43

<210> SEQ ID NO 329
```

```
<211> LENGTH: 33
<212> TYPE: DNA
<213> ORGANISM: Artificial Sequence
<220> FEATURE:
<223> OTHER INFORMATION: Unknown Organism

<400> SEQUENCE: 329
ccgaattcca tatgcaaatt gggcaaccga ctc                                33

<210> SEQ ID NO 330
<211> LENGTH: 29
<212> TYPE: DNA
<213> ORGANISM: Artificial Sequence
<220> FEATURE:
<223> OTHER INFORMATION: Unknown Organism

<400> SEQUENCE: 330
atatgggccc caaattgggc aaccgactc                                     29

<210> SEQ ID NO 331
<211> LENGTH: 41
<212> TYPE: DNA
<213> ORGANISM: Artificial Sequence
<220> FEATURE:
<223> OTHER INFORMATION: Unknown Organism

<400> SEQUENCE: 331
ataagaatgc ggccgcttac gctatgaaat cagataaatt c                       41

<210> SEQ ID NO 332
<211> LENGTH: 906
<212> TYPE: PRT
<213> ORGANISM: Artificial Sequence
<220> FEATURE:
<223> OTHER INFORMATION: Unknown Organism

<400> SEQUENCE: 332
```

```
Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
                20                  25                  30

Lys Lys Asp Ser Leu Ser Glu Ala Glu Arg Ala Ala Gln Ala Tyr
            35                  40                  45

Ala Lys Glu Lys Gly Leu Thr Pro Pro Ser Thr Asp His Gln Asp Ser
        50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Ser Tyr Asp His
                100                 105                 110

Tyr His Asn Ile Lys Phe Glu Trp Phe Asp Gly Leu Tyr Glu Ala
            115                 120                 125

Pro Lys Gly Tyr Ser Leu Glu Asp Leu Leu Ala Thr Val Lys Tyr Tyr
        130                 135                 140

Val Glu Pro Arg Asn Ala Ser Asp His Val Arg Lys Asn Lys Ala Asp
145                 150                 155                 160

Gln Asp Ser Lys Pro Asp Glu Lys Glu His Asp Glu Val Ser Glu
                165                 170                 175

Pro Thr His Pro Glu Ser Asp Glu Lys Glu Asn His Ala Gly Leu Asn
                180                 185                 190
```

-continued

```
Pro Ser Ala Asp Asn Leu Tyr Lys Pro Ser Thr Asp Thr Glu Glu Thr
            195                 200                 205

Glu Glu Glu Ala Glu Asp Thr Thr Asp Glu Ala Glu Ile Pro Gly Thr
        210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Thr Ile Ser Ala Glu Val
                245                 250                 255

Asp Ser Leu Leu Ala Leu Leu Lys Glu Ser Gln Pro Ala Pro Ile Gln
            260                 265                 270

Gly Pro Gln Ile Gly Gln Pro Thr Leu Pro Asn Asn Ser Leu Ala Thr
            275                 280                 285

Pro Ser Pro Ser Leu Pro Ile Asn Pro Gly Thr Ser His Glu Lys His
        290                 295                 300

Glu Glu Asp Gly Tyr Gly Phe Asp Ala Asn Arg Ile Ile Ala Glu Asp
305                 310                 315                 320

Glu Ser Gly Phe Val Met Ser His Gly Asp Ser Asn His Tyr Phe Phe
                325                 330                 335

Lys Lys Asp Leu Thr Glu Glu Gln Ile Lys Ala Ala Gln Lys His Leu
            340                 345                 350

Glu Glu Val Lys Thr Ser His Asn Gly Leu Asp Ser Leu Ser Ser His
        355                 360                 365

Glu Gln Asp Tyr Pro Gly Asn Ala Lys Glu Met Lys Asp Leu Asp Lys
    370                 375                 380

Lys Ile Glu Glu Lys Ile Ala Gly Ile Met Lys Gln Tyr Gly Val Lys
385                 390                 395                 400

Arg Glu Ser Ile Val Val Asn Lys Glu Lys Asn Ala Ile Ile Tyr Pro
                405                 410                 415

Ser Gly Asp His His His Ala Asp Pro Ile Asp Glu His Lys Pro Val
            420                 425                 430

Gly Ile Gly His Ser His Ser Asn Tyr Glu Leu Phe Lys Pro Glu Glu
        435                 440                 445

Gly Val Ala Lys Lys Glu Gly Asn Lys Val Tyr Thr Gly Glu Glu Leu
    450                 455                 460

Thr Asn Val Val Asn Leu Leu Lys Asn Ser Thr Phe Asn Asn Gln Asn
465                 470                 475                 480

Phe Thr Leu Ala Asn Gly Gln Lys Arg Val Ser Phe Ser Phe Pro Pro
                485                 490                 495

Glu Leu Glu Lys Lys Leu Gly Ile Asn Met Leu Val Lys Leu Ile Thr
            500                 505                 510

Pro Asp Gly Lys Val Leu Glu Lys Val Ser Gly Lys Val Phe Gly Glu
        515                 520                 525

Gly Val Gly Asn Ile Ala Asn Phe Glu Leu Asp Gln Pro Tyr Leu Pro
    530                 535                 540

Gly Gln Thr Phe Lys Tyr Thr Ile Ala Ser Lys Asp Tyr Pro Glu Val
545                 550                 555                 560

Ser Tyr Asp Gly Thr Phe Thr Val Pro Thr Ser Leu Ala Tyr Lys Met
                565                 570                 575

Ala Ser Gln Thr Ile Phe Tyr Pro Phe His Ala Gly Asp Thr Tyr Leu
            580                 585                 590

Arg Val Asn Pro Gln Phe Ala Val Pro Lys Gly Thr Asp Ala Leu Val
        595                 600                 605
```

```
Arg Val Phe Asp Glu Phe His Gly Asn Ala Tyr Leu Glu Asn Asn Tyr
    610                 615                 620

Lys Val Gly Glu Ile Lys Leu Pro Ile Pro Lys Leu Asn Gln Gly Thr
625                 630                 635                 640

Thr Arg Thr Ala Gly Asn Lys Ile Pro Val Thr Phe Met Ala Asn Ala
                645                 650                 655

Tyr Leu Asp Asn Gln Ser Thr Tyr Ile Val Glu Val Pro Ile Leu Glu
                660                 665                 670

Lys Glu Asn Gln Thr Asp Lys Pro Ser Ile Leu Pro Gln Phe Lys Arg
                675                 680                 685

Asn Lys Ala Gln Glu Asn Ser Lys Leu Asp Glu Lys Val Glu Glu Pro
690                 695                 700

Lys Thr Ser Glu Lys Val Glu Lys Glu Lys Leu Ser Glu Thr Gly Asn
705                 710                 715                 720

Ser Thr Ser Asn Ser Thr Leu Glu Glu Val Pro Thr Val Asp Pro Val
                725                 730                 735

Gln Glu Lys Val Ala Lys Phe Ala Glu Ser Tyr Gly Met Lys Leu Glu
                740                 745                 750

Asn Val Leu Phe Asn Met Asp Gly Thr Ile Glu Leu Tyr Leu Pro Ser
                755                 760                 765

Gly Glu Val Ile Lys Lys Asn Met Ala Asp Phe Thr Gly Glu Ala Pro
770                 775                 780

Gln Gly Asn Gly Glu Asn Lys Pro Ser Glu Asn Gly Lys Val Ser Thr
785                 790                 795                 800

Gly Thr Val Glu Asn Gln Pro Thr Glu Asn Lys Pro Ala Asp Ser Leu
                805                 810                 815

Pro Glu Ala Pro Asn Glu Lys Pro Val Lys Pro Glu Asn Ser Thr Asp
                820                 825                 830

Asn Gly Met Leu Asn Pro Glu Gly Asn Val Gly Ser Asp Pro Met Leu
                835                 840                 845

Asp Pro Ala Leu Glu Glu Ala Pro Ala Val Asp Pro Val Gln Glu Lys
                850                 855                 860

Leu Glu Lys Phe Thr Ala Ser Tyr Gly Leu Gly Leu Asp Ser Val Ile
865                 870                 875                 880

Phe Asn Met Asp Gly Thr Ile Glu Leu Arg Leu Pro Ser Gly Glu Val
                885                 890                 895

Ile Lys Lys Asn Leu Ser Asp Phe Ile Ala
                900                 905

<210> SEQ ID NO 333
<211> LENGTH: 900
<212> TYPE: PRT
<213> ORGANISM: Artificial Sequence
<220> FEATURE:
<223> OTHER INFORMATION: Unknown Organism

<400> SEQUENCE: 333

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
                20                  25                  30

Glu Asp Gly Tyr Gly Phe Asp Ala Asn Arg Ile Ile Ala Glu Asp Glu
            35                  40                  45

Ser Gly Phe Val Met Ser His Gly Asp Ser Asn His Tyr Phe Phe Lys
        50                  55                  60
```

-continued

```
Lys Asp Leu Thr Glu Glu Gln Ile Lys Ala Ala Gln Lys His Leu Glu
 65                  70                  75                  80

Glu Val Lys Thr Ser His Asn Gly Leu Asp Ser Leu Ser Ser His Glu
                 85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
    130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
    290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
    370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
            420                 425                 430

Thr Ser Glu Lys Val Glu Lys Glu Leu Ser Glu Thr Gly Asn Ser
        435                 440                 445

Thr Ser Asn Ser Thr Leu Glu Glu Val Pro Thr Val Asp Pro Val Gln
    450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
```

-continued

```
                485                 490                 495
Glu Val Ile Lys Lys Asn Met Ala Asp Phe Thr Gly Glu Ala Pro Gln
            500                 505                 510
Gly Asn Gly Glu Asn Lys Pro Ser Glu Asn Gly Lys Val Ser Thr Gly
        515                 520                 525
Thr Val Glu Asn Gln Pro Thr Glu Asn Lys Pro Ala Asp Ser Leu Pro
    530                 535                 540
Glu Ala Pro Asn Glu Lys Pro Val Lys Pro Glu Asn Ser Thr Asp Asn
545                 550                 555                 560
Gly Met Leu Asn Pro Glu Gly Asn Val Gly Ser Asp Pro Met Leu Asp
            565                 570                 575
Pro Ala Leu Glu Glu Ala Pro Val Asp Pro Val Gln Glu Lys Leu
        580                 585                 590
Glu Lys Phe Thr Ala Ser Tyr Gly Leu Gly Leu Asp Ser Val Ile Phe
    595                 600                 605
Asn Met Asp Gly Thr Ile Glu Leu Arg Leu Pro Ser Gly Glu Val Ile
    610                 615                 620
Lys Lys Asn Leu Ser Asp Phe Ile Ala Gly Pro Gln Ile Thr Tyr Thr
625                 630                 635                 640
Asp Asp Glu Ile Gln Val Ala Lys Leu Ala Gly Lys Tyr Thr Thr Glu
            645                 650                 655
Asp Gly Tyr Ile Phe Asp Thr Ser Trp Ile Lys Lys Asp Ser Leu Ser
            660                 665                 670
Glu Ala Glu Arg Ala Ala Ala Gln Ala Tyr Ala Lys Glu Lys Gly Leu
        675                 680                 685
Thr Pro Pro Ser Thr Asp His Gln Asp Ser Gly Asn Thr Glu Ala Lys
    690                 695                 700
Gly Ala Glu Ala Ile Tyr Asn Arg Val Lys Ala Ala Lys Lys Val Pro
705                 710                 715                 720
Leu Asp Arg Met Pro Tyr Asn Leu Gln Tyr Thr Val Glu Val Lys Asn
            725                 730                 735
Gly Ser Leu Ile Ile Pro Asn Ile Lys Phe Glu Trp Phe Asp Glu Gly
        740                 745                 750
Leu Tyr Glu Ala Pro Lys Gly Tyr Ser Leu Glu Asp Leu Leu Ala Thr
    755                 760                 765
Val Lys Tyr Tyr Val Glu Pro Arg Asn Ala Ser Asp His Val Arg Lys
    770                 775                 780
Asn Lys Ala Asp Gln Asp Ser Lys Pro Asp Glu Asp Lys Glu His Asp
785                 790                 795                 800
Glu Val Ser Glu Pro Thr His Pro Glu Ser Asp Glu Lys Glu Asn His
            805                 810                 815
Ala Gly Leu Asn Pro Ser Ala Asp Asn Leu Tyr Lys Pro Ser Thr Asp
        820                 825                 830
Thr Glu Glu Thr Glu Glu Ala Glu Asp Thr Thr Asp Glu Ala Glu
    835                 840                 845
Ile Pro Gly Thr Pro Ser Ile Arg Gln Asn Ala Met Glu Thr Leu Thr
    850                 855                 860
Gly Leu Lys Ser Ser Leu Leu Gly Thr Lys Asp Asn Asn Thr Ile
865                 870                 875                 880
Ser Ala Glu Val Asp Ser Leu Leu Ala Leu Leu Lys Glu Ser Gln Pro
            885                 890                 895
Ala Pro Ile Gln
            900
```

<210> SEQ ID NO 334
<211> LENGTH: 900
<212> TYPE: PRT
<213> ORGANISM: Artificial Sequence
<220> FEATURE:
<223> OTHER INFORMATION: Unknown Organism

<400> SEQUENCE: 334

```
Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Gln Ala Tyr
        35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Asn Ile Lys Phe
            100                 105                 110

Glu Trp Phe Asp Glu Gly Leu Tyr Glu Ala Pro Lys Gly Tyr Ser Leu
        115                 120                 125

Glu Asp Leu Leu Ala Thr Val Lys Tyr Tyr Val Glu Pro Arg Asn Ala
    130                 135                 140

Ser Asp His Val Arg Lys Asn Lys Ala Asp Gln Asp Ser Lys Pro Asp
145                 150                 155                 160

Glu Asp Lys Glu His Asp Glu Val Ser Glu Pro Thr His Pro Glu Ser
                165                 170                 175

Asp Glu Lys Glu Asn His Ala Gly Leu Asn Pro Ser Ala Asp Asn Leu
            180                 185                 190

Tyr Lys Pro Ser Thr Asp Thr Glu Glu Thr Glu Glu Ala Glu Asp
        195                 200                 205

Thr Thr Asp Glu Ala Glu Ile Pro Gly Thr Pro Ser Ile Arg Gln Asn
    210                 215                 220

Ala Met Glu Thr Leu Thr Gly Leu Lys Ser Ser Leu Leu Leu Gly Thr
225                 230                 235                 240

Lys Asp Asn Asn Thr Ile Ser Ala Glu Val Asp Ser Leu Leu Ala Leu
                245                 250                 255

Leu Lys Glu Ser Gln Pro Ala Pro Ile Gln Gly Pro Gln Ile Gly Gln
            260                 265                 270

Pro Thr Leu Pro Asn Asn Ser Leu Ala Thr Pro Ser Pro Ser Leu Pro
        275                 280                 285

Ile Asn Pro Gly Thr Ser His Glu Lys His Glu Glu Asp Gly Tyr Gly
    290                 295                 300

Phe Asp Ala Asn Arg Ile Ile Ala Glu Asp Glu Ser Gly Phe Val Met
305                 310                 315                 320

Ser His Gly Asp Ser Asn His Tyr Phe Phe Lys Lys Asp Leu Thr Glu
                325                 330                 335

Glu Gln Ile Lys Ala Ala Gln Lys His Leu Glu Glu Val Lys Thr Ser
            340                 345                 350

His Asn Gly Leu Asp Ser Leu Ser Ser His Glu Gln Asp Tyr Pro Gly
        355                 360                 365
```

-continued

```
Asn Ala Lys Glu Met Lys Asp Leu Asp Lys Lys Ile Glu Glu Lys Ile
    370                 375                 380
Ala Gly Ile Met Lys Gln Tyr Gly Val Lys Arg Glu Ser Ile Val Val
385                 390                 395                 400
Asn Lys Glu Lys Asn Ala Ile Ile Tyr Pro Ser Gly Asp His His His
                405                 410                 415
Ala Asp Pro Ile Asp Glu His Lys Pro Val Gly Ile Gly His Ser His
            420                 425                 430
Ser Asn Tyr Glu Leu Phe Lys Pro Glu Glu Gly Val Ala Lys Lys Glu
        435                 440                 445
Gly Asn Lys Val Tyr Thr Gly Glu Glu Leu Thr Asn Val Val Asn Leu
    450                 455                 460
Leu Lys Asn Ser Thr Phe Asn Asn Gln Asn Phe Thr Leu Ala Asn Gly
465                 470                 475                 480
Gln Lys Arg Val Ser Phe Ser Phe Pro Glu Leu Glu Lys Lys Leu
                485                 490                 495
Gly Ile Asn Met Leu Val Lys Leu Ile Thr Pro Asp Gly Lys Val Leu
            500                 505                 510
Glu Lys Val Ser Gly Lys Val Phe Glu Gly Val Gly Asn Ile Ala
        515                 520                 525
Asn Phe Glu Leu Asp Gln Pro Tyr Leu Pro Gly Gln Thr Phe Lys Tyr
    530                 535                 540
Thr Ile Ala Ser Lys Asp Tyr Pro Glu Val Ser Tyr Asp Gly Thr Phe
545                 550                 555                 560
Thr Val Pro Thr Ser Leu Ala Tyr Lys Met Ala Ser Gln Thr Ile Phe
                565                 570                 575
Tyr Pro Phe His Ala Gly Asp Thr Tyr Leu Arg Val Asn Pro Gln Phe
            580                 585                 590
Ala Val Pro Lys Gly Thr Asp Ala Leu Val Arg Val Phe Asp Glu Phe
        595                 600                 605
His Gly Asn Ala Tyr Leu Glu Asn Asn Tyr Lys Val Gly Glu Ile Lys
    610                 615                 620
Leu Pro Ile Pro Lys Leu Asn Gln Gly Thr Thr Arg Thr Ala Gly Asn
625                 630                 635                 640
Lys Ile Pro Val Thr Phe Met Ala Asn Ala Tyr Leu Asp Asn Gln Ser
                645                 650                 655
Thr Tyr Ile Val Glu Val Pro Ile Leu Glu Lys Glu Asn Gln Thr Asp
            660                 665                 670
Lys Pro Ser Ile Leu Pro Gln Phe Lys Arg Asn Lys Ala Gln Glu Asn
        675                 680                 685
Ser Lys Leu Asp Glu Lys Val Glu Pro Lys Thr Ser Glu Lys Val
    690                 695                 700
Glu Lys Glu Lys Leu Ser Glu Thr Gly Asn Ser Thr Ser Asn Ser Thr
705                 710                 715                 720
Leu Glu Glu Val Pro Thr Val Asp Pro Val Gln Glu Lys Val Ala Lys
                725                 730                 735
Phe Ala Glu Ser Tyr Gly Met Lys Leu Glu Asn Val Leu Phe Asn Met
            740                 745                 750
Asp Gly Thr Ile Glu Leu Tyr Leu Pro Ser Gly Glu Val Ile Lys Lys
        755                 760                 765
Asn Met Ala Asp Phe Thr Gly Glu Ala Pro Gln Gly Asn Gly Glu Asn
    770                 775                 780
```

-continued

```
Lys Pro Ser Glu Asn Gly Lys Val Ser Thr Gly Thr Val Glu Asn Gln
785                 790                 795                 800

Pro Thr Glu Asn Lys Pro Ala Asp Ser Leu Pro Glu Ala Pro Asn Glu
            805                 810                 815

Lys Pro Val Lys Pro Glu Asn Ser Thr Asp Asn Gly Met Leu Asn Pro
        820                 825                 830

Glu Gly Asn Val Gly Ser Asp Pro Met Leu Asp Pro Ala Leu Glu Glu
    835                 840                 845

Ala Pro Ala Val Asp Pro Val Gln Glu Lys Leu Glu Lys Phe Thr Ala
850                 855                 860

Ser Tyr Gly Leu Gly Leu Asp Ser Val Ile Phe Asn Met Asp Gly Thr
865                 870                 875                 880

Ile Glu Leu Arg Leu Pro Ser Gly Glu Val Ile Lys Lys Asn Leu Ser
                885                 890                 895

Asp Phe Ile Ala
            900

<210> SEQ ID NO 335
<211> LENGTH: 900
<212> TYPE: PRT
<213> ORGANISM: Artificial Sequence
<220> FEATURE:
<223> OTHER INFORMATION: Unknown Organism

<400> SEQUENCE: 335

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Ala Gln Ala Tyr
        35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Ser Tyr Asp His
            100                 105                 110

Tyr His Asn Ile Lys Phe Glu Trp Phe Asp Glu Gly Leu Tyr Glu Ala
        115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240
```

-continued

```
Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

Gly Pro Gln Ile Gly Gln Pro Thr Leu Pro Asn Asn Ser Leu Ala Thr
        275                 280                 285

Pro Ser Pro Ser Leu Pro Ile Asn Pro Gly Thr Ser His Glu Lys His
    290                 295                 300

Glu Glu Asp Gly Tyr Gly Phe Asp Ala Asn Arg Ile Ile Ala Glu Asp
305                 310                 315                 320

Glu Ser Gly Phe Val Met Ser Tyr Phe Phe Lys Lys Asp Leu Thr Glu
                325                 330                 335

Glu Gln Ile Lys Ala Ala Gln Lys His Leu Glu Glu Val Lys Thr Ser
            340                 345                 350

His Asn Gly Leu Asp Ser Leu Ser Ser His Glu Gln Asp Tyr Pro Gly
        355                 360                 365

Asn Ala Lys Glu Met Lys Asp Leu Asp Lys Lys Ile Glu Glu Lys Ile
    370                 375                 380

Ala Gly Ile Met Lys Gln Tyr Gly Val Lys Arg Glu Ser Ile Val Val
385                 390                 395                 400

Asn Lys Glu Lys Asn Ala Ile Ile Tyr Pro His Gly Asp His His His
                405                 410                 415

Ala Asp Pro Ile Asp Glu His Lys Pro Val Gly Ile Gly His Ser His
            420                 425                 430

Ser Asn Tyr Glu Leu Phe Lys Pro Glu Glu Gly Val Ala Lys Lys Glu
        435                 440                 445

Gly Asn Lys Val Tyr Thr Gly Glu Glu Leu Thr Asn Val Val Asn Leu
    450                 455                 460

Leu Lys Asn Ser Thr Phe Asn Asn Gln Asn Phe Thr Leu Ala Asn Gly
465                 470                 475                 480

Gln Lys Arg Val Ser Phe Ser Phe Pro Pro Glu Leu Glu Lys Lys Leu
                485                 490                 495

Gly Ile Asn Met Leu Val Lys Leu Ile Thr Pro Asp Gly Lys Val Leu
            500                 505                 510

Glu Lys Val Ser Gly Lys Val Phe Gly Glu Gly Val Gly Asn Ile Ala
        515                 520                 525

Asn Phe Glu Leu Asp Gln Pro Tyr Leu Pro Gly Gln Thr Phe Lys Tyr
    530                 535                 540

Thr Ile Ala Ser Lys Asp Tyr Pro Glu Val Ser Tyr Asp Gly Thr Phe
545                 550                 555                 560

Thr Val Pro Thr Ser Leu Ala Tyr Lys Met Ala Ser Gln Thr Ile Phe
                565                 570                 575

Tyr Pro Phe His Ala Gly Asp Thr Tyr Leu Arg Val Asn Pro Gln Phe
            580                 585                 590

Ala Val Pro Lys Gly Thr Asp Ala Leu Val Arg Val Phe Asp Glu Phe
        595                 600                 605

His Gly Asn Ala Tyr Leu Glu Asn Asn Tyr Lys Val Gly Glu Ile Lys
    610                 615                 620

Leu Pro Ile Pro Lys Leu Asn Gln Gly Thr Thr Arg Thr Ala Gly Asn
625                 630                 635                 640

Lys Ile Pro Val Thr Phe Met Ala Asn Ala Tyr Leu Asp Asn Gln Ser
                645                 650                 655

Thr Tyr Ile Val Glu Val Pro Ile Leu Glu Lys Glu Asn Gln Thr Asp
```

```
              660                 665                 670
Lys Pro Ser Ile Leu Pro Gln Phe Lys Arg Asn Lys Ala Gln Glu Asn
            675                 680                 685
Ser Lys Leu Asp Glu Lys Val Glu Pro Lys Thr Ser Glu Lys Val
        690                 695                 700
Glu Lys Glu Lys Leu Ser Glu Thr Gly Asn Ser Thr Asn Ser Thr
705                 710                 715                 720
Leu Glu Glu Val Pro Thr Val Asp Pro Val Gln Glu Lys Val Ala Lys
                725                 730                 735
Phe Ala Glu Ser Tyr Gly Met Lys Leu Glu Asn Val Leu Phe Asn Met
            740                 745                 750
Asp Gly Thr Ile Glu Leu Tyr Leu Pro Ser Gly Glu Val Ile Lys Lys
            755                 760                 765
Asn Met Ala Asp Phe Thr Gly Glu Ala Pro Gln Gly Asn Gly Glu Asn
        770                 775                 780
Lys Pro Ser Glu Asn Gly Lys Val Ser Thr Gly Thr Val Glu Asn Gln
785                 790                 795                 800
Pro Thr Glu Asn Lys Pro Ala Asp Ser Leu Pro Glu Ala Pro Asn Glu
                805                 810                 815
Lys Pro Val Lys Pro Glu Asn Ser Thr Asp Asn Gly Met Leu Asn Pro
            820                 825                 830
Glu Gly Asn Val Gly Ser Asp Pro Met Leu Asp Pro Ala Leu Glu Glu
835                 840                 845
Ala Pro Ala Val Asp Pro Val Gln Glu Lys Leu Glu Lys Phe Thr Ala
        850                 855                 860
Ser Tyr Gly Leu Gly Leu Asp Ser Val Ile Phe Asn Met Asp Gly Thr
865                 870                 875                 880
Ile Glu Leu Arg Leu Pro Ser Gly Glu Val Ile Lys Lys Asn Leu Ser
                885                 890                 895
Asp Phe Ile Ala
        900

<210> SEQ ID NO 336
<211> LENGTH: 894
<212> TYPE: PRT
<213> ORGANISM: Artificial Sequence
<220> FEATURE:
<223> OTHER INFORMATION: Unknown Organism

<400> SEQUENCE: 336

Met Gln Ile Thr Tyr Thr Asp Asp Glu Ile Gln Val Ala Lys Leu Ala
1               5                   10                  15
Gly Lys Tyr Thr Thr Glu Asp Gly Tyr Ile Phe Asp Thr Ser Trp Ile
            20                  25                  30
Lys Lys Asp Ser Leu Ser Glu Ala Glu Arg Ala Ala Ala Gln Ala Tyr
        35                  40                  45
Ala Lys Glu Lys Gly Leu Thr Pro Pro Ser Thr Asp His Gln Asp Ser
    50                  55                  60
Gly Asn Thr Glu Ala Lys Gly Ala Glu Ala Ile Tyr Asn Arg Val Lys
65                  70                  75                  80
Ala Ala Lys Lys Val Pro Leu Asp Arg Met Pro Tyr Asn Leu Gln Tyr
                85                  90                  95
Thr Val Glu Val Lys Asn Gly Ser Leu Ile Ile Pro Ser Tyr Asp His
            100                 105                 110
Tyr His Asn Ile Lys Phe Glu Trp Phe Asp Glu Gly Leu Tyr Glu Ala
```

-continued

```
               115                 120                 125
Pro Lys Gly Tyr Ser Leu Glu Asp Leu Leu Ala Thr Val Lys Tyr Tyr
130                 135                 140
Val Glu Pro Arg Asn Ala Ser Asp His Val Arg Lys Asn Lys Ala Asp
145                 150                 155                 160
Gln Asp Ser Lys Pro Asp Glu Asp Lys Glu His Asp Glu Val Ser Glu
                165                 170                 175
Pro Thr His Pro Glu Ser Asp Glu Lys Glu Asn His Ala Gly Leu Asn
                180                 185                 190
Pro Ser Ala Asp Asn Leu Tyr Lys Pro Ser Thr Asp Thr Glu Glu Thr
                195                 200                 205
Glu Glu Glu Ala Glu Asp Thr Thr Asp Glu Ala Glu Ile Pro Gly Thr
210                 215                 220
Pro Ser Ile Arg Gln Asn Ala Met Glu Thr Leu Thr Gly Leu Lys Ser
225                 230                 235                 240
Ser Leu Leu Leu Gly Thr Lys Asp Asn Thr Ile Ser Ala Glu Val
                245                 250                 255
Asp Ser Leu Leu Ala Leu Leu Lys Glu Ser Gln Pro Ala Pro Ile Gln
                260                 265                 270
Gly Pro Gln Ile Gly Gln Pro Thr Leu Pro Asn Asn Ser Leu Ala Thr
                275                 280                 285
Pro Ser Pro Ser Leu Pro Ile Asn Pro Gly Thr Ser His Glu Lys His
290                 295                 300
Glu Glu Asp Gly Tyr Gly Phe Asp Ala Asn Arg Ile Ile Ala Glu Asp
305                 310                 315                 320
Glu Ser Gly Phe Val Met Ser Tyr Phe Phe Lys Lys Asp Leu Thr Glu
                325                 330                 335
Glu Gln Ile Lys Ala Ala Gln Lys His Leu Glu Glu Val Lys Thr Ser
                340                 345                 350
His Asn Gly Leu Asp Ser Leu Ser Ser His Glu Gln Asp Tyr Pro Gly
                355                 360                 365
Asn Ala Lys Glu Met Lys Asp Leu Asp Lys Lys Ile Glu Glu Lys Ile
370                 375                 380
Ala Gly Ile Met Lys Gln Tyr Gly Val Lys Arg Glu Ser Ile Val Val
385                 390                 395                 400
Asn Lys Glu Lys Asn Ala Ile Ile Tyr Pro Ala Asp Pro Ile Asp Glu
                405                 410                 415
His Lys Pro Val Gly Ile Gly His Ser His Ser Asn Tyr Glu Leu Phe
                420                 425                 430
Lys Pro Glu Glu Gly Val Ala Lys Lys Glu Gly Asn Lys Val Tyr Thr
                435                 440                 445
Gly Glu Glu Leu Thr Asn Val Val Asn Leu Leu Lys Asn Ser Thr Phe
                450                 455                 460
Asn Asn Gln Asn Phe Thr Leu Ala Asn Gly Gln Lys Arg Val Ser Phe
465                 470                 475                 480
Ser Phe Pro Pro Glu Leu Glu Lys Lys Leu Gly Ile Asn Met Leu Val
                485                 490                 495
Lys Leu Ile Thr Pro Asp Gly Lys Val Leu Glu Lys Val Ser Gly Lys
                500                 505                 510
Val Phe Gly Glu Gly Val Gly Asn Ile Ala Asn Phe Glu Leu Asp Gln
                515                 520                 525
Pro Tyr Leu Pro Gly Gln Thr Phe Lys Tyr Thr Ile Ala Ser Lys Asp
530                 535                 540
```

```
Tyr Pro Glu Val Ser Tyr Asp Gly Thr Phe Thr Val Pro Thr Ser Leu
545                 550                 555                 560

Ala Tyr Lys Met Ala Ser Gln Thr Ile Phe Tyr Pro Phe His Ala Gly
                565                 570                 575

Asp Thr Tyr Leu Arg Val Asn Pro Gln Phe Ala Val Pro Lys Gly Thr
            580                 585                 590

Asp Ala Leu Val Arg Val Phe Asp Glu Phe His Gly Asn Ala Tyr Leu
        595                 600                 605

Glu Asn Asn Tyr Lys Val Gly Glu Ile Lys Leu Pro Ile Pro Lys Leu
    610                 615                 620

Asn Gln Gly Thr Thr Arg Thr Ala Gly Asn Lys Ile Pro Val Thr Phe
625                 630                 635                 640

Met Ala Asn Ala Tyr Leu Asp Asn Gln Ser Thr Tyr Ile Val Glu Val
                645                 650                 655

Pro Ile Leu Glu Lys Glu Asn Gln Thr Asp Lys Pro Ser Ile Leu Pro
            660                 665                 670

Gln Phe Lys Arg Asn Lys Ala Gln Glu Asn Ser Lys Leu Asp Glu Lys
        675                 680                 685

Val Glu Glu Pro Lys Thr Ser Glu Lys Val Glu Lys Glu Lys Leu Ser
    690                 695                 700

Glu Thr Gly Asn Ser Thr Ser Asn Ser Thr Leu Glu Glu Val Pro Thr
705                 710                 715                 720

Val Asp Pro Val Gln Glu Lys Val Ala Lys Phe Ala Glu Ser Tyr Gly
                725                 730                 735

Met Lys Leu Glu Asn Val Leu Phe Asn Met Asp Gly Thr Ile Glu Leu
            740                 745                 750

Tyr Leu Pro Ser Gly Glu Val Ile Lys Lys Asn Met Ala Asp Phe Thr
        755                 760                 765

Gly Glu Ala Pro Gln Gly Asn Gly Glu Asn Lys Pro Ser Glu Asn Gly
    770                 775                 780

Lys Val Ser Thr Gly Thr Val Glu Asn Gln Pro Thr Glu Asn Lys Pro
785                 790                 795                 800

Ala Asp Ser Leu Pro Glu Ala Pro Asn Glu Lys Pro Val Lys Pro Glu
                805                 810                 815

Asn Ser Thr Asp Asn Gly Met Leu Asn Pro Glu Gly Asn Val Gly Ser
            820                 825                 830

Asp Pro Met Leu Asp Pro Ala Leu Glu Glu Ala Pro Ala Val Asp Pro
        835                 840                 845

Val Gln Glu Lys Leu Glu Lys Phe Thr Ala Ser Tyr Gly Leu Gly Leu
    850                 855                 860

Asp Ser Val Ile Phe Asn Met Asp Gly Thr Ile Glu Leu Arg Leu Pro
865                 870                 875                 880

Ser Gly Glu Val Ile Lys Lys Asn Leu Ser Asp Phe Ile Ala
                885                 890
```

<210> SEQ ID NO 337
<211> LENGTH: 894
<212> TYPE: PRT
<213> ORGANISM: Artificial Sequence
<220> FEATURE:
<223> OTHER INFORMATION: Unknown Organism

<400> SEQUENCE: 337

```
Met Gln Ile Thr Tyr Thr Asp Asp Glu Ile Gln Val Ala Lys Leu Ala
1               5                   10                  15
```

-continued

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Gln Ala Tyr
        35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Asn Ile Lys Phe
            100                 105                 110

Glu Trp Phe Asp Glu Gly Leu Tyr Glu Ala Pro Lys Gly Tyr Ser Leu
            115                 120                 125

Glu Asp Leu Leu Ala Thr Val Lys Tyr Tyr Val Glu Pro Arg Asn Ala
        130                 135                 140

Ser Asp His Val Arg Lys Asn Lys Ala Asp Gln Asp Ser Lys Pro Asp
145                 150                 155                 160

Glu Asp Lys Glu His Asp Glu Val Ser Glu Pro Thr His Pro Glu Ser
                165                 170                 175

Asp Glu Lys Glu Asn His Ala Gly Leu Asn Pro Ser Ala Asp Asn Leu
            180                 185                 190

Tyr Lys Pro Ser Thr Asp Thr Glu Glu Thr Glu Glu Ala Glu Asp
        195                 200                 205

Thr Thr Asp Glu Ala Glu Ile Pro Gly Thr Pro Ser Ile Arg Gln Asn
    210                 215                 220

Ala Met Glu Thr Leu Thr Gly Leu Lys Ser Ser Leu Leu Leu Gly Thr
225                 230                 235                 240

Lys Asp Asn Asn Thr Ile Ser Ala Glu Val Asp Ser Leu Leu Ala Leu
                245                 250                 255

Leu Lys Glu Ser Gln Pro Ala Pro Ile Gln Gly Pro Gln Ile Gly Gln
            260                 265                 270

Pro Thr Leu Pro Asn Asn Ser Leu Ala Thr Pro Ser Pro Ser Leu Pro
        275                 280                 285

Ile Asn Pro Gly Thr Ser His Glu Lys His Glu Glu Asp Gly Tyr Gly
    290                 295                 300

Phe Asp Ala Asn Arg Ile Ile Ala Glu Asp Glu Ser Gly Phe Val Met
305                 310                 315                 320

Ser Tyr Phe Phe Lys Lys Asp Leu Thr Glu Glu Gln Ile Lys Ala Ala
                325                 330                 335

Gln Lys His Leu Glu Glu Val Lys Thr Ser His Asn Gly Leu Asp Ser
            340                 345                 350

Leu Ser Ser His Glu Gln Asp Tyr Pro Gly Asn Ala Lys Glu Met Lys
        355                 360                 365

Asp Leu Asp Lys Lys Ile Glu Glu Lys Ile Ala Gly Ile Met Lys Gln
    370                 375                 380

Tyr Gly Val Lys Arg Glu Ser Ile Val Val Asn Lys Glu Lys Asn Ala
385                 390                 395                 400

Ile Ile Tyr Pro His Gly Asp His His Ala Asp Pro Ile Asp Glu
                405                 410                 415

His Lys Pro Val Gly Ile Gly His Ser His Ser Asn Tyr Glu Leu Phe
            420                 425                 430

Lys Pro Glu Glu Gly Val Ala Lys Glu Gly Asn Lys Val Tyr Thr
            435                 440                 445

Gly Glu Glu Leu Thr Asn Val Val Asn Leu Leu Lys Asn Ser Thr Phe
    450                 455                 460

Asn Asn Gln Asn Phe Thr Leu Ala Asn Gly Gln Lys Arg Val Ser Phe
465                 470                 475                 480

Ser Phe Pro Pro Glu Leu Glu Lys Lys Leu Gly Ile Asn Met Leu Val
            485                 490                 495

Lys Leu Ile Thr Pro Asp Gly Lys Val Leu Glu Lys Val Ser Gly Lys
            500                 505                 510

Val Phe Gly Glu Gly Val Gly Asn Ile Ala Asn Phe Glu Leu Asp Gln
            515                 520                 525

Pro Tyr Leu Pro Gly Gln Thr Phe Lys Tyr Thr Ile Ala Ser Lys Asp
            530                 535                 540

Tyr Pro Glu Val Ser Tyr Asp Gly Thr Phe Thr Val Pro Thr Ser Leu
545                 550                 555                 560

Ala Tyr Lys Met Ala Ser Gln Thr Ile Phe Tyr Pro Phe His Ala Gly
                565                 570                 575

Asp Thr Tyr Leu Arg Val Asn Pro Gln Phe Ala Val Pro Lys Gly Thr
            580                 585                 590

Asp Ala Leu Val Arg Val Phe Asp Glu Phe His Gly Asn Ala Tyr Leu
            595                 600                 605

Glu Asn Asn Tyr Lys Val Gly Glu Ile Lys Leu Pro Ile Pro Lys Leu
    610                 615                 620

Asn Gln Gly Thr Thr Arg Thr Ala Gly Asn Lys Ile Pro Val Thr Phe
625                 630                 635                 640

Met Ala Asn Ala Tyr Leu Asp Asn Gln Ser Thr Tyr Ile Val Glu Val
                645                 650                 655

Pro Ile Leu Glu Lys Glu Asn Gln Thr Asp Lys Pro Ser Ile Leu Pro
            660                 665                 670

Gln Phe Lys Arg Asn Lys Ala Gln Glu Asn Ser Lys Leu Asp Glu Lys
            675                 680                 685

Val Glu Glu Pro Lys Thr Ser Glu Lys Val Glu Lys Glu Lys Leu Ser
            690                 695                 700

Glu Thr Gly Asn Ser Thr Ser Asn Ser Thr Leu Glu Glu Val Pro Thr
705                 710                 715                 720

Val Asp Pro Val Gln Glu Lys Val Ala Lys Phe Ala Glu Ser Tyr Gly
            725                 730                 735

Met Lys Leu Glu Asn Val Leu Phe Asn Met Asp Gly Thr Ile Glu Leu
            740                 745                 750

Tyr Leu Pro Ser Gly Glu Val Ile Lys Lys Asn Met Ala Asp Phe Thr
            755                 760                 765

Gly Glu Ala Pro Gln Gly Asn Gly Glu Asn Lys Pro Ser Glu Asn Gly
    770                 775                 780

Lys Val Ser Thr Gly Thr Val Glu Asn Gln Pro Thr Glu Asn Lys Pro
785                 790                 795                 800

Ala Asp Ser Leu Pro Glu Ala Pro Asn Glu Lys Pro Val Lys Pro Glu
            805                 810                 815

Asn Ser Thr Asp Asn Gly Met Leu Asn Pro Glu Gly Asn Val Gly Ser
            820                 825                 830

Asp Pro Met Leu Asp Pro Ala Leu Glu Glu Ala Pro Ala Val Asp Pro
            835                 840                 845

Val Gln Glu Lys Leu Glu Lys Phe Thr Ala Ser Tyr Gly Leu Gly Leu

```
                 850                 855                 860
Asp Ser Val Ile Phe Asn Met Asp Gly Thr Ile Glu Leu Arg Leu Pro
865                 870                 875                 880

Ser Gly Glu Val Ile Lys Lys Asn Leu Ser Asp Phe Ile Ala
                885                 890
```

<210> SEQ ID NO 338
<211> LENGTH: 888
<212> TYPE: PRT
<213> ORGANISM: Artificial Sequence
<220> FEATURE:
<223> OTHER INFORMATION: Unknown Organism

<400> SEQUENCE: 338

```
Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
                20                  25                  30

Lys Lys Asp Ser Leu Ser Glu Ala Glu Arg Ala Ala Ala Gln Ala Tyr
            35                  40                  45

Ala Lys Glu Lys Gly Leu Thr Pro Pro Ser Thr Asp His Gln Asp Ser
        50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Asn Ile Lys Phe
                100                 105                 110

Glu Trp Phe Asp Glu Gly Leu Tyr Glu Ala Pro Lys Gly Tyr Ser Leu
            115                 120                 125

Glu Asp Leu Leu Ala Thr Val Lys Tyr Tyr Val Glu Pro Arg Asn Ala
        130                 135                 140

Ser Asp His Val Arg Lys Asn Lys Ala Asp Gln Asp Ser Lys Pro Asp
145                 150                 155                 160

Glu Asp Lys Glu His Asp Glu Val Ser Glu Pro Thr His Pro Glu Ser
                165                 170                 175

Asp Glu Lys Glu Asn His Ala Gly Leu Asn Pro Ser Ala Asp Asn Leu
            180                 185                 190

Tyr Lys Pro Ser Thr Asp Thr Glu Glu Thr Glu Glu Ala Glu Asp
        195                 200                 205

Thr Thr Asp Glu Ala Glu Ile Pro Gly Thr Pro Ser Ile Arg Gln Asn
210                 215                 220

Ala Met Glu Thr Leu Thr Gly Leu Lys Ser Ser Leu Leu Leu Gly Thr
225                 230                 235                 240

Lys Asp Asn Asn Thr Ile Ser Ala Glu Val Asp Ser Leu Leu Ala Leu
                245                 250                 255

Leu Lys Glu Ser Gln Pro Ala Pro Ile Gln Gly Pro Gln Ile Gly Gln
            260                 265                 270

Pro Thr Leu Pro Asn Asn Ser Leu Ala Thr Pro Ser Pro Ser Leu Pro
        275                 280                 285

Ile Asn Pro Gly Thr Ser His Glu Lys His Glu Asp Gly Tyr Gly
        290                 295                 300

Phe Asp Ala Asn Arg Ile Ile Ala Glu Asp Ser Gly Phe Val Met
305                 310                 315                 320

Ser Tyr Phe Phe Lys Lys Asp Leu Thr Glu Glu Gln Ile Lys Ala Ala
```

-continued

```
                325                 330                 335
Gln Lys His Leu Glu Val Lys Thr Ser His Asn Gly Leu Asp Ser
            340                 345                 350
Leu Ser Ser His Glu Gln Asp Tyr Pro Gly Asn Ala Lys Glu Met Lys
            355                 360                 365
Asp Leu Asp Lys Lys Ile Glu Glu Lys Ile Ala Gly Ile Met Lys Gln
370                 375                 380
Tyr Gly Val Lys Arg Glu Ser Ile Val Val Asn Lys Glu Lys Asn Ala
385                 390                 395                 400
Ile Ile Tyr Pro Ala Asp Pro Ile Asp Glu His Lys Pro Val Gly Ile
                405                 410                 415
Gly His Ser His Ser Asn Tyr Glu Leu Phe Lys Pro Glu Glu Gly Val
                420                 425                 430
Ala Lys Lys Glu Gly Asn Lys Val Tyr Thr Gly Glu Glu Leu Thr Asn
            435                 440                 445
Val Val Asn Leu Leu Lys Asn Ser Thr Phe Asn Asn Gln Asn Phe Thr
        450                 455                 460
Leu Ala Asn Gly Gln Lys Arg Val Ser Phe Ser Phe Pro Pro Glu Leu
465                 470                 475                 480
Glu Lys Lys Leu Gly Ile Asn Met Leu Val Lys Leu Ile Thr Pro Asp
                485                 490                 495
Gly Lys Val Leu Glu Lys Val Ser Gly Lys Val Phe Gly Glu Gly Val
            500                 505                 510
Gly Asn Ile Ala Asn Phe Glu Leu Asp Gln Pro Tyr Leu Pro Gly Gln
            515                 520                 525
Thr Phe Lys Tyr Thr Ile Ala Ser Lys Asp Tyr Pro Glu Val Ser Tyr
        530                 535                 540
Asp Gly Thr Phe Thr Val Pro Thr Ser Leu Ala Tyr Lys Met Ala Ser
545                 550                 555                 560
Gln Thr Ile Phe Tyr Pro Phe His Ala Gly Asp Thr Tyr Leu Arg Val
                565                 570                 575
Asn Pro Gln Phe Ala Val Pro Lys Gly Thr Asp Ala Leu Val Arg Val
            580                 585                 590
Phe Asp Glu Phe His Gly Asn Ala Tyr Leu Glu Asn Asn Tyr Lys Val
            595                 600                 605
Gly Glu Ile Lys Leu Pro Ile Pro Lys Leu Asn Gln Gly Thr Thr Arg
        610                 615                 620
Thr Ala Gly Asn Lys Ile Pro Val Thr Phe Met Ala Asn Ala Tyr Leu
625                 630                 635                 640
Asp Asn Gln Ser Thr Tyr Ile Val Glu Val Pro Ile Leu Glu Lys Glu
                645                 650                 655
Asn Gln Thr Asp Lys Pro Ser Ile Leu Pro Gln Phe Lys Arg Asn Lys
            660                 665                 670
Ala Gln Glu Asn Ser Lys Leu Asp Glu Lys Val Glu Pro Lys Thr
            675                 680                 685
Ser Glu Lys Val Glu Lys Glu Lys Leu Ser Thr Gly Asn Ser Thr
        690                 695                 700
Ser Asn Ser Thr Leu Glu Glu Val Pro Thr Val Asp Pro Val Gln Glu
705                 710                 715                 720
Lys Val Ala Lys Phe Ala Glu Ser Tyr Gly Met Lys Leu Glu Asn Val
                725                 730                 735
Leu Phe Asn Met Asp Gly Thr Ile Glu Leu Tyr Leu Pro Ser Gly Glu
            740                 745                 750
```

-continued

Val Ile Lys Lys Asn Met Ala Asp Phe Thr Gly Glu Ala Pro Gln Gly
            755                 760                 765

Asn Gly Glu Asn Lys Pro Ser Glu Asn Gly Lys Val Ser Thr Gly Thr
            770                 775                 780

Val Glu Asn Gln Pro Thr Glu Asn Lys Pro Ala Asp Ser Leu Pro Glu
785                 790                 795                 800

Ala Pro Asn Glu Lys Pro Val Lys Pro Glu Asn Ser Thr Asp Asn Gly
            805                 810                 815

Met Leu Asn Pro Glu Gly Asn Val Gly Ser Asp Pro Met Leu Asp Pro
            820                 825                 830

Ala Leu Glu Glu Ala Pro Ala Val Asp Pro Val Gln Glu Lys Leu Glu
            835                 840                 845

Lys Phe Thr Ala Ser Tyr Gly Leu Gly Leu Asp Ser Val Ile Phe Asn
            850                 855                 860

Met Asp Gly Thr Ile Glu Leu Arg Leu Pro Ser Gly Glu Val Ile Lys
865                 870                 875                 880

Lys Asn Leu Ser Asp Phe Ile Ala
            885

<210> SEQ ID NO 339
<211> LENGTH: 900
<212> TYPE: PRT
<213> ORGANISM: Artificial Sequence
<220> FEATURE:
<223> OTHER INFORMATION: Unknown Organism

<400> SEQUENCE: 339

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Ala Gln Ala Tyr
            35                  40                  45

Ala Lys Glu Lys Gly Leu Thr Pro Pro Ser Thr Asp His Gln Asp Ser
            50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
            85                  90                  95

Thr Val Glu Val Lys Asn Gly Ser Leu Ile Ile Pro Ser Tyr Asp Ser
            100                 105                 110

Tyr His Asn Ile Lys Phe Glu Trp Phe Asp Glu Gly Leu Tyr Glu Ala
            115                 120                 125

Pro Lys Gly Tyr Ser Leu Glu Asp Leu Leu Ala Thr Val Lys Tyr Tyr
            130                 135                 140

Val Glu Pro Arg Asn Ala Ser Asp His Val Arg Lys Asn Lys Ala Asp
145                 150                 155                 160

Gln Asp Ser Lys Pro Asp Glu Lys Glu His Asp Glu Val Ser Glu
            165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
            195                 200                 205

Glu Glu Glu Ala Glu Asp Thr Asp Glu Ala Glu Ile Pro Gly Thr
210                 215                 220

-continued

```
Pro Ser Ile Arg Gln Asn Ala Met Glu Thr Leu Thr Gly Leu Lys Ser
225                 230                 235                 240

Ser Leu Leu Leu Gly Thr Lys Asp Asn Thr Ile Ser Ala Glu Val
            245                 250                 255

Asp Ser Leu Leu Ala Leu Leu Lys Glu Ser Gln Pro Ala Pro Ile Gln
                260                 265                 270

Gly Pro Gln Ile Gly Gln Pro Thr Leu Pro Asn Asn Ser Leu Ala Thr
            275                 280                 285

Pro Ser Pro Ser Leu Pro Ile Asn Pro Gly Thr Ser His Glu Lys His
290                 295                 300

Glu Glu Asp Gly Tyr Gly Phe Asp Ala Asn Arg Ile Ile Ala Glu Asp
305                 310                 315                 320

Glu Ser Gly Phe Val Met Ser Tyr Phe Phe Lys Lys Asp Leu Thr Glu
                325                 330                 335

Glu Gln Ile Lys Ala Ala Gln Lys His Leu Glu Glu Val Lys Thr Ser
            340                 345                 350

His Asn Gly Leu Asp Ser Leu Ser Ser His Glu Gln Asp Tyr Pro Gly
        355                 360                 365

Asn Ala Lys Glu Met Lys Asp Leu Asp Lys Lys Ile Glu Glu Lys Ile
370                 375                 380

Ala Gly Ile Met Lys Gln Tyr Gly Val Lys Arg Glu Ser Ile Val Val
385                 390                 395                 400

Asn Lys Glu Lys Asn Ala Ile Ile Tyr Pro His Gly Asp His His His
            405                 410                 415

Ala Asp Pro Ile Asp Glu His Lys Pro Val Gly Ile Gly His Ser His
            420                 425                 430

Ser Asn Tyr Glu Leu Phe Lys Pro Glu Glu Gly Val Ala Lys Lys Glu
        435                 440                 445

Gly Asn Lys Val Tyr Thr Gly Glu Glu Leu Thr Asn Val Val Asn Leu
450                 455                 460

Leu Lys Asn Ser Thr Phe Asn Asn Gln Asn Phe Thr Leu Ala Asn Gly
465                 470                 475                 480

Gln Lys Arg Val Ser Phe Ser Pro Pro Glu Leu Glu Lys Lys Leu
            485                 490                 495

Gly Ile Asn Met Leu Val Lys Leu Ile Thr Pro Asp Gly Lys Val Leu
            500                 505                 510

Glu Lys Val Ser Gly Lys Val Phe Gly Glu Gly Val Gly Asn Ile Ala
            515                 520                 525

Asn Phe Glu Leu Asp Gln Pro Tyr Leu Pro Gly Gln Thr Phe Lys Tyr
530                 535                 540

Thr Ile Ala Ser Lys Asp Tyr Pro Glu Val Ser Tyr Asp Gly Thr Phe
545                 550                 555                 560

Thr Val Pro Thr Ser Leu Ala Tyr Lys Met Ala Ser Gln Thr Ile Phe
                565                 570                 575

Tyr Pro Phe His Ala Gly Asp Thr Tyr Leu Arg Val Asn Pro Gln Phe
            580                 585                 590

Ala Val Pro Lys Gly Thr Asp Ala Leu Val Arg Val Phe Asp Glu Phe
            595                 600                 605

His Gly Asn Ala Tyr Leu Glu Asn Asn Tyr Lys Val Gly Glu Ile Lys
            610                 615                 620

Leu Pro Ile Pro Lys Leu Asn Gln Gly Thr Thr Arg Thr Ala Gly Asn
625                 630                 635                 640
```

```
Lys Ile Pro Val Thr Phe Met Ala Asn Ala Tyr Leu Asp Asn Gln Ser
                645                 650                 655

Thr Tyr Ile Val Glu Val Pro Ile Leu Glu Lys Glu Asn Gln Thr Asp
            660                 665                 670

Lys Pro Ser Ile Leu Pro Gln Phe Lys Arg Asn Lys Ala Gln Glu Asn
            675                 680                 685

Ser Lys Leu Asp Glu Lys Val Glu Pro Lys Thr Ser Glu Lys Val
690                 695                 700

Glu Lys Glu Lys Leu Ser Glu Thr Gly Asn Ser Thr Ser Asn Ser Thr
705                 710                 715                 720

Leu Glu Glu Val Pro Thr Val Asp Pro Val Gln Glu Lys Val Ala Lys
                725                 730                 735

Phe Ala Glu Ser Tyr Gly Met Lys Leu Glu Asn Val Leu Phe Asn Met
                740                 745                 750

Asp Gly Thr Ile Glu Leu Tyr Leu Pro Ser Gly Glu Val Ile Lys Lys
            755                 760                 765

Asn Met Ala Asp Phe Thr Gly Glu Ala Pro Gln Gly Asn Gly Glu Asn
770                 775                 780

Lys Pro Ser Glu Asn Gly Lys Val Ser Thr Gly Thr Val Glu Asn Gln
785                 790                 795                 800

Pro Thr Glu Asn Lys Pro Ala Asp Ser Leu Pro Glu Ala Pro Asn Glu
                805                 810                 815

Lys Pro Val Lys Pro Glu Asn Ser Thr Asp Asn Gly Met Leu Asn Pro
            820                 825                 830

Glu Gly Asn Val Gly Ser Asp Pro Met Leu Asp Pro Ala Leu Glu Glu
            835                 840                 845

Ala Pro Ala Val Asp Pro Val Gln Glu Lys Leu Glu Lys Phe Thr Ala
850                 855                 860

Ser Tyr Gly Leu Gly Leu Asp Ser Val Ile Phe Asn Met Asp Gly Thr
865                 870                 875                 880

Ile Glu Leu Arg Leu Pro Ser Gly Glu Val Ile Lys Lys Asn Leu Ser
                885                 890                 895

Asp Phe Ile Ala
            900

<210> SEQ ID NO 340
<211> LENGTH: 894
<212> TYPE: PRT
<213> ORGANISM: Artificial Sequence
<220> FEATURE:
<223> OTHER INFORMATION: Unknown Organism

<400> SEQUENCE: 340

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
                20                  25                  30

Lys Lys Asp Ser Leu Ser Glu Ala Glu Arg Ala Ala Ala Gln Ala Tyr
            35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95
```

```
Thr Val Glu Val Lys Asn Gly Ser Leu Ile Ile Pro Ser Tyr Asp Ser
            100                 105                 110

Tyr His Asn Ile Lys Phe Glu Trp Phe Asp Glu Gly Leu Tyr Glu Ala
            115                 120                 125

Pro Lys Gly Tyr Ser Leu Glu Asp Leu Leu Ala Thr Val Lys Tyr Tyr
            130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
            165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
            195                 200                 205

Glu Glu Glu Ala Glu Asp Thr Thr Asp Glu Ala Glu Ile Pro Gly Thr
            210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
            245                 250                 255

Asp Ser Leu Leu Ala Leu Leu Lys Glu Ser Gln Pro Ala Pro Ile Gln
            260                 265                 270

Gly Pro Gln Ile Gly Gln Pro Thr Leu Pro Asn Asn Ser Leu Ala Thr
            275                 280                 285

Pro Ser Pro Ser Leu Pro Ile Asn Pro Gly Thr Ser His Glu Lys His
            290                 295                 300

Glu Glu Asp Gly Tyr Gly Phe Asp Ala Asn Arg Ile Ile Ala Glu Asp
305                 310                 315                 320

Glu Ser Gly Phe Val Met Ser Tyr Phe Lys Lys Asp Leu Thr Glu
            325                 330                 335

Glu Gln Ile Lys Ala Ala Gln Lys His Leu Glu Glu Val Lys Thr Ser
            340                 345                 350

His Asn Gly Leu Asp Ser Leu Ser Ser His Glu Gln Asp Tyr Pro Gly
            355                 360                 365

Asn Ala Lys Glu Met Lys Asp Leu Asp Lys Lys Ile Glu Glu Lys Ile
370                 375                 380

Ala Gly Ile Met Lys Gln Tyr Gly Val Lys Arg Glu Ser Ile Val Val
385                 390                 395                 400

Asn Lys Glu Lys Asn Ala Ile Ile Tyr Pro Ala Asp Pro Ile Asp Glu
            405                 410                 415

His Lys Pro Val Gly Ile Gly His Ser His Ser Asn Tyr Glu Leu Phe
            420                 425                 430

Lys Pro Glu Glu Gly Val Ala Lys Lys Glu Gly Asn Lys Val Tyr Thr
            435                 440                 445

Gly Glu Glu Leu Thr Asn Val Val Asn Leu Leu Lys Asn Ser Thr Phe
            450                 455                 460

Asn Asn Gln Asn Phe Thr Leu Ala Asn Gly Gln Lys Arg Val Ser Phe
465                 470                 475                 480

Ser Phe Pro Pro Glu Leu Glu Lys Lys Leu Gly Ile Asn Met Leu Val
            485                 490                 495

Lys Leu Ile Thr Pro Asp Gly Lys Val Leu Glu Lys Val Ser Gly Lys
            500                 505                 510

Val Phe Gly Glu Gly Val Gly Asn Ile Ala Asn Phe Glu Leu Asp Gln
```

-continued

```
                515                 520                 525
Pro Tyr Leu Pro Gly Gln Thr Phe Lys Tyr Thr Ile Ala Ser Lys Asp
            530                 535                 540
Tyr Pro Glu Val Ser Tyr Asp Gly Thr Phe Thr Val Pro Thr Ser Leu
545                 550                 555                 560
Ala Tyr Lys Met Ala Ser Gln Thr Ile Phe Tyr Pro Phe His Ala Gly
                565                 570                 575
Asp Thr Tyr Leu Arg Val Asn Pro Gln Phe Ala Val Pro Lys Gly Thr
            580                 585                 590
Asp Ala Leu Val Arg Val Phe Asp Glu Phe His Gly Asn Ala Tyr Leu
        595                 600                 605
Glu Asn Asn Tyr Lys Val Gly Glu Ile Lys Leu Pro Ile Pro Lys Leu
    610                 615                 620
Asn Gln Gly Thr Thr Arg Thr Ala Gly Asn Lys Ile Pro Val Thr Phe
625                 630                 635                 640
Met Ala Asn Ala Tyr Leu Asp Asn Gln Ser Thr Tyr Ile Val Glu Val
                645                 650                 655
Pro Ile Leu Glu Lys Glu Asn Gln Thr Asp Lys Pro Ser Ile Leu Pro
            660                 665                 670
Gln Phe Lys Arg Asn Lys Ala Gln Glu Asn Ser Lys Leu Asp Glu Lys
        675                 680                 685
Val Glu Glu Pro Lys Thr Ser Glu Lys Val Glu Lys Glu Lys Leu Ser
    690                 695                 700
Glu Thr Gly Asn Ser Thr Ser Asn Ser Thr Leu Glu Glu Val Pro Thr
705                 710                 715                 720
Val Asp Pro Val Gln Glu Lys Val Ala Lys Phe Ala Glu Ser Tyr Gly
                725                 730                 735
Met Lys Leu Glu Asn Val Leu Phe Asn Met Asp Gly Thr Ile Glu Leu
            740                 745                 750
Tyr Leu Pro Ser Gly Glu Val Ile Lys Lys Asn Met Ala Asp Phe Thr
        755                 760                 765
Gly Glu Ala Pro Gln Gly Asn Gly Glu Asn Lys Pro Ser Glu Asn Gly
    770                 775                 780
Lys Val Ser Thr Gly Thr Val Glu Asn Gln Pro Thr Glu Asn Lys Pro
785                 790                 795                 800
Ala Asp Ser Leu Pro Glu Ala Pro Asn Glu Lys Pro Val Lys Pro Glu
                805                 810                 815
Asn Ser Thr Asp Asn Gly Met Leu Asn Pro Glu Gly Asn Val Gly Ser
            820                 825                 830
Asp Pro Met Leu Asp Pro Ala Leu Glu Glu Ala Pro Ala Val Asp Pro
        835                 840                 845
Val Gln Glu Lys Leu Glu Lys Phe Thr Ala Ser Tyr Gly Leu Gly Leu
    850                 855                 860
Asp Ser Val Ile Phe Asn Met Asp Gly Thr Ile Glu Leu Arg Leu Pro
865                 870                 875                 880
Ser Gly Glu Val Ile Lys Lys Asn Leu Ser Asp Phe Ile Ala
                885                 890

<210> SEQ ID NO 341
<211> LENGTH: 900
<212> TYPE: PRT
<213> ORGANISM: Artificial Sequence
<220> FEATURE:
<223> OTHER INFORMATION: Unknown Organism
```

-continued

<400> SEQUENCE: 341

```
Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Gln Ala Tyr
        35                  40                  45

Ala Lys Glu Lys Gly Leu Thr Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Ser Tyr Asp His
            100                 105                 110

Tyr Ser Asn Ile Lys Phe Glu Trp Phe Asp Gly Leu Tyr Glu Ala
        115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

Gly Pro Gln Ile Gly Gln Pro Thr Leu Pro Asn Asn Ser Leu Ala Thr
        275                 280                 285

Pro Ser Pro Ser Leu Pro Ile Asn Pro Gly Thr Ser His Glu Lys His
    290                 295                 300

Glu Glu Asp Gly Tyr Gly Phe Asp Ala Asn Arg Ile Ile Ala Glu Asp
305                 310                 315                 320

Glu Ser Gly Phe Val Met Ser Tyr Phe Phe Lys Lys Asp Leu Thr Glu
                325                 330                 335

Glu Gln Ile Lys Ala Ala Gln Lys His Leu Glu Val Lys Thr Ser
            340                 345                 350

His Asn Gly Leu Asp Ser Leu Ser Ser His Glu Gln Asp Tyr Pro Gly
        355                 360                 365

Asn Ala Lys Glu Met Lys Asp Leu Asp Lys Lys Ile Glu Glu Lys Ile
    370                 375                 380

Ala Gly Ile Met Lys Gln Tyr Gly Val Lys Arg Glu Ser Ile Val Val
385                 390                 395                 400

Asn Lys Glu Lys Asn Ala Ile Ile Tyr Pro His Gly Asp His His His
                405                 410                 415
```

```
Ala Asp Pro Ile Asp Glu His Lys Pro Val Gly Ile Gly His Ser His
            420                 425                 430

Ser Asn Tyr Glu Leu Phe Lys Pro Glu Glu Gly Val Ala Lys Lys Glu
            435                 440                 445

Gly Asn Lys Val Tyr Thr Gly Glu Glu Leu Thr Asn Val Val Asn Leu
            450                 455                 460

Leu Lys Asn Ser Thr Phe Asn Asn Gln Asn Phe Thr Leu Ala Asn Gly
465                 470                 475                 480

Gln Lys Arg Val Ser Phe Ser Phe Pro Glu Leu Glu Lys Lys Leu
                485                 490                 495

Gly Ile Asn Met Leu Val Lys Leu Ile Thr Pro Asp Gly Lys Val Leu
                500                 505                 510

Glu Lys Val Ser Gly Lys Val Phe Gly Glu Gly Val Gly Asn Ile Ala
                515                 520                 525

Asn Phe Glu Leu Asp Gln Pro Tyr Leu Pro Gly Gln Thr Phe Lys Tyr
            530                 535                 540

Thr Ile Ala Ser Lys Asp Tyr Pro Glu Val Ser Tyr Asp Gly Thr Phe
545                 550                 555                 560

Thr Val Pro Thr Ser Leu Ala Tyr Lys Met Ala Ser Gln Thr Ile Phe
                565                 570                 575

Tyr Pro Phe His Ala Gly Asp Thr Tyr Leu Arg Val Asn Pro Gln Phe
                580                 585                 590

Ala Val Pro Lys Gly Thr Asp Ala Leu Val Arg Val Phe Asp Glu Phe
                595                 600                 605

His Gly Asn Ala Tyr Leu Glu Asn Asn Tyr Lys Val Gly Glu Ile Lys
            610                 615                 620

Leu Pro Ile Pro Lys Leu Asn Gln Gly Thr Thr Arg Thr Ala Gly Asn
625                 630                 635                 640

Lys Ile Pro Val Thr Phe Met Ala Asn Ala Tyr Leu Asp Asn Gln Ser
                645                 650                 655

Thr Tyr Ile Val Glu Val Pro Ile Leu Glu Lys Glu Asn Gln Thr Asp
                660                 665                 670

Lys Pro Ser Ile Leu Pro Gln Phe Lys Arg Asn Lys Ala Gln Glu Asn
            675                 680                 685

Ser Lys Leu Asp Glu Lys Val Glu Glu Pro Lys Thr Ser Glu Lys Val
            690                 695                 700

Glu Lys Glu Lys Leu Ser Glu Thr Gly Asn Ser Thr Ser Asn Ser Thr
705                 710                 715                 720

Leu Glu Glu Val Pro Thr Val Asp Pro Val Gln Glu Lys Val Ala Lys
                725                 730                 735

Phe Ala Glu Ser Tyr Gly Met Lys Leu Glu Asn Val Leu Phe Asn Met
                740                 745                 750

Asp Gly Thr Ile Glu Leu Tyr Leu Pro Ser Gly Glu Val Ile Lys Lys
            755                 760                 765

Asn Met Ala Asp Phe Thr Gly Glu Ala Pro Gln Gly Asn Gly Glu Asn
770                 775                 780

Lys Pro Ser Glu Asn Gly Lys Val Ser Thr Gly Thr Val Glu Asn Gln
785                 790                 795                 800

Pro Thr Glu Asn Lys Pro Ala Asp Ser Leu Pro Glu Ala Pro Asn Glu
                805                 810                 815

Lys Pro Val Lys Pro Glu Asn Ser Thr Asp Asn Gly Met Leu Asn Pro
                820                 825                 830
```

-continued

```
Glu Gly Asn Val Gly Ser Asp Pro Met Leu Asp Pro Ala Leu Glu Glu
        835                 840                 845

Ala Pro Ala Val Asp Pro Val Gln Glu Lys Leu Glu Lys Phe Thr Ala
    850                 855                 860

Ser Tyr Gly Leu Gly Leu Asp Ser Val Ile Phe Asn Met Asp Gly Thr
865                 870                 875                 880

Ile Glu Leu Arg Leu Pro Ser Gly Glu Val Ile Lys Lys Asn Leu Ser
                885                 890                 895

Asp Phe Ile Ala
            900

<210> SEQ ID NO 342
<211> LENGTH: 894
<212> TYPE: PRT
<213> ORGANISM: Artificial Sequence
<220> FEATURE:
<223> OTHER INFORMATION: Unknown Organism

<400> SEQUENCE: 342

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
                20                  25                  30

Lys Lys Asp Ser Leu Ser Glu Ala Glu Arg Ala Ala Ala Gln Ala Tyr
            35                  40                  45

Ala Lys Glu Lys Gly Leu Thr Pro Pro Ser Thr Asp His Gln Asp Ser
        50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Ser Tyr Asp His
                100                 105                 110

Tyr Ser Asn Ile Lys Phe Glu Trp Phe Asp Glu Gly Leu Tyr Glu Ala
            115                 120                 125

Pro Lys Gly Tyr Ser Leu Glu Asp Leu Leu Ala Thr Val Lys Tyr Tyr
        130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

Gly Pro Gln Ile Gly Gln Pro Thr Leu Pro Asn Asn Ser Leu Ala Thr
        275                 280                 285
```

```
Pro Ser Pro Ser Leu Pro Ile Asn Pro Gly Thr Ser His Glu Lys His
    290                 295                 300

Glu Glu Asp Gly Tyr Gly Phe Asp Ala Asn Arg Ile Ile Ala Glu Asp
305                 310                 315                 320

Glu Ser Gly Phe Val Met Ser Tyr Phe Lys Lys Asp Leu Thr Glu
                325                 330                 335

Glu Gln Ile Lys Ala Ala Gln Lys His Leu Glu Glu Val Lys Thr Ser
            340                 345                 350

His Asn Gly Leu Asp Ser Leu Ser Ser His Glu Gln Asp Tyr Pro Gly
        355                 360                 365

Asn Ala Lys Glu Met Lys Asp Leu Asp Lys Lys Ile Glu Glu Lys Ile
    370                 375                 380

Ala Gly Ile Met Lys Gln Tyr Gly Val Lys Arg Glu Ser Ile Val Val
385                 390                 395                 400

Asn Lys Glu Lys Asn Ala Ile Ile Tyr Pro Ala Asp Pro Ile Asp Glu
                405                 410                 415

His Lys Pro Val Gly Ile Gly His Ser His Ser Asn Tyr Glu Leu Phe
            420                 425                 430

Lys Pro Glu Glu Gly Val Ala Lys Lys Glu Gly Asn Lys Val Tyr Thr
        435                 440                 445

Gly Glu Glu Leu Thr Asn Val Val Asn Leu Leu Lys Asn Ser Thr Phe
    450                 455                 460

Asn Asn Gln Asn Phe Thr Leu Ala Asn Gly Gln Lys Arg Val Ser Phe
465                 470                 475                 480

Ser Phe Pro Pro Glu Leu Glu Lys Lys Leu Gly Ile Asn Met Leu Val
                485                 490                 495

Lys Leu Ile Thr Pro Asp Gly Lys Val Leu Glu Lys Val Ser Gly Lys
            500                 505                 510

Val Phe Gly Glu Gly Val Gly Asn Ile Ala Asn Phe Glu Leu Asp Gln
        515                 520                 525

Pro Tyr Leu Pro Gly Gln Thr Phe Lys Tyr Thr Ile Ala Ser Lys Asp
    530                 535                 540

Tyr Pro Glu Val Ser Tyr Asp Gly Thr Phe Thr Val Pro Thr Ser Leu
545                 550                 555                 560

Ala Tyr Lys Met Ala Ser Gln Thr Ile Phe Tyr Pro Phe His Ala Gly
                565                 570                 575

Asp Thr Tyr Leu Arg Val Asn Pro Gln Phe Ala Val Pro Lys Gly Thr
            580                 585                 590

Asp Ala Leu Val Arg Val Phe Asp Glu Phe His Gly Asn Ala Tyr Leu
        595                 600                 605

Glu Asn Asn Tyr Lys Val Gly Glu Ile Lys Leu Pro Ile Pro Lys Leu
    610                 615                 620

Asn Gln Gly Thr Thr Arg Thr Ala Gly Asn Lys Ile Pro Val Thr Phe
625                 630                 635                 640

Met Ala Asn Ala Tyr Leu Asp Asn Gln Ser Thr Tyr Ile Val Glu Val
                645                 650                 655

Pro Ile Leu Glu Lys Glu Asn Gln Thr Asp Lys Pro Ser Ile Leu Pro
            660                 665                 670

Gln Phe Lys Arg Asn Lys Ala Gln Glu Asn Ser Lys Leu Asp Glu Lys
        675                 680                 685

Val Glu Glu Pro Lys Thr Ser Glu Lys Val Glu Lys Glu Lys Leu Ser
    690                 695                 700

Glu Thr Gly Asn Ser Thr Ser Asn Ser Thr Leu Glu Glu Val Pro Thr
```

-continued

```
            705                 710                 715                 720
Val Asp Pro Val Gln Glu Lys Val Ala Lys Phe Ala Glu Ser Tyr Gly
                    725                 730                 735

Met Lys Leu Glu Asn Val Leu Phe Asn Met Asp Gly Thr Ile Glu Leu
                740                 745                 750

Tyr Leu Pro Ser Gly Glu Val Ile Lys Lys Asn Met Ala Asp Phe Thr
            755                 760                 765

Gly Glu Ala Pro Gln Gly Asn Gly Glu Asn Lys Pro Ser Glu Asn Gly
        770                 775                 780

Lys Val Ser Thr Gly Thr Val Glu Asn Gln Pro Thr Glu Asn Lys Pro
785                 790                 795                 800

Ala Asp Ser Leu Pro Glu Ala Pro Asn Glu Lys Pro Val Lys Pro Glu
                805                 810                 815

Asn Ser Thr Asp Asn Gly Met Leu Asn Pro Glu Gly Asn Val Gly Ser
            820                 825                 830

Asp Pro Met Leu Asp Pro Ala Leu Glu Ala Pro Ala Val Asp Pro
        835                 840                 845

Val Gln Glu Lys Leu Glu Lys Phe Thr Ala Ser Tyr Gly Leu Gly Leu
    850                 855                 860

Asp Ser Val Ile Phe Asn Met Asp Gly Thr Ile Glu Leu Arg Leu Pro
865                 870                 875                 880

Ser Gly Glu Val Ile Lys Lys Asn Leu Ser Asp Phe Ile Ala
                885                 890

<210> SEQ ID NO 343
<211> LENGTH: 901
<212> TYPE: PRT
<213> ORGANISM: Artificial Sequence
<220> FEATURE:
<223> OTHER INFORMATION: Unknown Organism

<400> SEQUENCE: 343

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
                20                  25                  30

Lys Lys Asp Ser Leu Ser Glu Ala Glu Arg Ala Ala Ala Gln Ala Tyr
            35                  40                  45

Ala Lys Glu Lys Gly Leu Thr Pro Pro Ser Thr Asp His Gln Asp Ser
        50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro His Tyr Asp His
                100                 105                 110

Tyr His Asn Ile Lys Phe Glu Trp Phe Asp Glu Gly Leu Tyr Glu Ala
            115                 120                 125

Pro Lys Gly Tyr Ser Leu Glu Asp Leu Leu Ala Thr Val Lys Tyr Tyr
        130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
```

-continued

```
                180                 185                 190
Pro Ser Ala Asp Asn Leu Tyr Lys Pro Ser Thr Asp Thr Glu Glu Thr
            195                 200                 205
Glu Glu Glu Ala Glu Asp Thr Thr Asp Glu Ala Glu Ile Pro Gly Thr
210                 215                 220
Pro Ser Ile Arg Gln Asn Ala Met Glu Thr Leu Thr Gly Leu Lys Ser
225                 230                 235                 240
Ser Leu Leu Leu Gly Thr Lys Asp Asn Asn Thr Ile Ser Ala Glu Val
                245                 250                 255
Asp Ser Leu Leu Ala Leu Leu Lys Glu Ser Gln Pro Ala Pro Ile Gln
                260                 265                 270
Ser Gly Pro Gln Ile Gly Gln Pro Thr Leu Pro Asn Asn Ser Leu Ala
            275                 280                 285
Thr Pro Ser Pro Ser Leu Pro Ile Asn Pro Gly Thr Ser His Glu Lys
            290                 295                 300
His Glu Glu Asp Gly Tyr Gly Phe Asp Ala Asn Arg Ile Ile Ala Glu
305                 310                 315                 320
Asp Glu Ser Gly Phe Val Met Ser Tyr Phe Lys Lys Asp Leu Thr
                325                 330                 335
Glu Glu Gln Ile Lys Ala Ala Gln Lys His Leu Glu Glu Val Lys Thr
            340                 345                 350
Ser His Asn Gly Leu Asp Ser Leu Ser Ser His Glu Gln Asp Tyr Pro
            355                 360                 365
Gly Asn Ala Lys Glu Met Lys Asp Leu Asp Lys Lys Ile Glu Glu Lys
            370                 375                 380
Ile Ala Gly Ile Met Lys Gln Tyr Gly Val Lys Arg Glu Ser Ile Val
385                 390                 395                 400
Val Asn Lys Glu Lys Asn Ala Ile Ile Tyr Pro His Gly Asp His His
                405                 410                 415
His Ala Asp Pro Ile Asp Glu His Lys Pro Val Gly Ile Gly His Ser
                420                 425                 430
His Ser Asn Tyr Glu Leu Phe Lys Pro Glu Glu Gly Val Ala Lys Lys
            435                 440                 445
Glu Gly Asn Lys Val Tyr Thr Gly Glu Glu Leu Thr Asn Val Val Asn
            450                 455                 460
Leu Leu Lys Asn Ser Thr Phe Asn Asn Gln Asn Phe Thr Leu Ala Asn
465                 470                 475                 480
Gly Gln Lys Arg Val Ser Phe Ser Phe Pro Pro Glu Leu Glu Lys Lys
                485                 490                 495
Leu Gly Ile Asn Met Leu Val Lys Leu Ile Thr Pro Asp Gly Lys Val
            500                 505                 510
Leu Glu Lys Val Ser Gly Lys Val Phe Gly Glu Gly Val Gly Asn Ile
            515                 520                 525
Ala Asn Phe Glu Leu Asp Gln Pro Tyr Leu Pro Gly Gln Thr Phe Lys
            530                 535                 540
Tyr Thr Ile Ala Ser Lys Asp Tyr Pro Glu Val Ser Tyr Asp Gly Thr
545                 550                 555                 560
Phe Thr Val Pro Thr Ser Leu Ala Tyr Lys Met Ala Ser Gln Thr Ile
                565                 570                 575
Phe Tyr Pro Phe His Ala Gly Asp Thr Tyr Leu Arg Val Asn Pro Gln
            580                 585                 590
Phe Ala Val Pro Lys Gly Thr Asp Ala Leu Val Arg Val Phe Asp Glu
            595                 600                 605
```

-continued

```
Phe His Gly Asn Ala Tyr Leu Glu Asn Asn Tyr Lys Val Gly Glu Ile
    610                 615                 620

Lys Leu Pro Ile Pro Lys Leu Asn Gln Gly Thr Thr Arg Thr Ala Gly
625                 630                 635                 640

Asn Lys Ile Pro Val Thr Phe Met Ala Asn Ala Tyr Leu Asp Asn Gln
                645                 650                 655

Ser Thr Tyr Ile Val Glu Val Pro Ile Leu Lys Glu Asn Gln Thr
            660                 665                 670

Asp Lys Pro Ser Ile Leu Pro Gln Phe Lys Arg Asn Lys Ala Gln Glu
                675                 680                 685

Asn Ser Lys Leu Asp Glu Lys Val Glu Glu Pro Lys Thr Ser Glu Lys
690                 695                 700

Val Glu Lys Glu Lys Leu Ser Glu Thr Gly Asn Ser Thr Ser Asn Ser
705                 710                 715                 720

Thr Leu Glu Glu Val Pro Thr Val Asp Pro Val Gln Glu Lys Val Ala
                725                 730                 735

Lys Phe Ala Glu Ser Tyr Gly Met Lys Leu Glu Asn Val Leu Phe Asn
            740                 745                 750

Met Asp Gly Thr Ile Glu Leu Tyr Leu Pro Ser Gly Glu Val Ile Lys
            755                 760                 765

Lys Asn Met Ala Asp Phe Thr Gly Glu Ala Pro Gln Gly Asn Gly Glu
770                 775                 780

Asn Lys Pro Ser Glu Asn Gly Lys Val Ser Thr Gly Thr Val Glu Asn
785                 790                 795                 800

Gln Pro Thr Glu Asn Lys Pro Ala Asp Ser Leu Pro Glu Ala Pro Asn
                805                 810                 815

Glu Lys Pro Val Lys Pro Glu Asn Ser Thr Asp Asn Gly Met Leu Asn
                820                 825                 830

Pro Glu Gly Asn Val Gly Ser Asp Pro Met Leu Asp Pro Ala Leu Glu
            835                 840                 845

Glu Ala Pro Ala Val Asp Pro Val Gln Glu Lys Leu Glu Lys Phe Thr
850                 855                 860

Ala Ser Tyr Gly Leu Gly Leu Asp Ser Val Ile Phe Asn Met Asp Gly
865                 870                 875                 880

Thr Ile Glu Leu Arg Leu Pro Ser Gly Glu Val Ile Lys Lys Asn Leu
                885                 890                 895

Ser Asp Phe Ile Ala
            900

<210> SEQ ID NO 344
<211> LENGTH: 895
<212> TYPE: PRT
<213> ORGANISM: Artificial Sequence
<220> FEATURE:
<223> OTHER INFORMATION: Unknown Organism

<400> SEQUENCE: 344

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Ala Gln Ala Tyr
        35                  40                  45

Ala Lys Glu Lys Gly Leu Thr Pro Pro Ser Thr Asp His Gln Asp Ser
    50                  55                  60
```

-continued

```
Gly Asn Thr Glu Ala Lys Gly Ala Glu Ala Ile Tyr Asn Arg Val Lys
 65                  70                  75                  80

Ala Ala Lys Lys Val Pro Leu Asp Arg Met Pro Tyr Asn Leu Gln Tyr
                 85                  90                  95

Thr Val Glu Val Lys Asn Gly Ser Leu Ile Ile Pro His Tyr Asp His
            100                 105                 110

Tyr His Asn Ile Lys Phe Glu Trp Phe Asp Glu Gly Leu Tyr Glu Ala
        115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

Ser Gly Pro Gln Ile Gly Gln Pro Thr Leu Pro Asn Asn Ser Leu Ala
        275                 280                 285

Thr Pro Ser Pro Ser Leu Pro Ile Asn Pro Gly Thr Ser His Glu Lys
    290                 295                 300

His Glu Glu Asp Gly Tyr Gly Phe Asp Ala Asn Arg Ile Ile Ala Glu
305                 310                 315                 320

Asp Glu Ser Gly Phe Val Met Ser Tyr Phe Lys Lys Asp Leu Thr
                325                 330                 335

Glu Glu Gln Ile Lys Ala Ala Gln Lys His Leu Glu Glu Val Lys Thr
            340                 345                 350

Ser His Asn Gly Leu Asp Ser Leu Ser Ser His Glu Gln Asp Tyr Pro
        355                 360                 365

Gly Asn Ala Lys Glu Met Lys Asp Leu Asp Lys Lys Ile Glu Glu Lys
    370                 375                 380

Ile Ala Gly Ile Met Lys Gln Tyr Gly Val Lys Arg Glu Ser Ile Val
385                 390                 395                 400

Val Asn Lys Glu Lys Asn Ala Ile Ile Tyr Pro Ala Asp Pro Ile Asp
                405                 410                 415

Glu His Lys Pro Val Gly Ile Gly His Ser His Ser Asn Tyr Glu Leu
            420                 425                 430

Phe Lys Pro Glu Glu Gly Val Ala Lys Lys Glu Gly Asn Lys Val Tyr
        435                 440                 445

Thr Gly Glu Glu Leu Thr Asn Val Val Asn Leu Leu Lys Asn Ser Thr
    450                 455                 460

Phe Asn Asn Gln Asn Phe Thr Leu Ala Asn Gly Gln Lys Arg Val Ser
465                 470                 475                 480
```

-continued

```
Phe Ser Phe Pro Pro Glu Leu Glu Lys Lys Leu Gly Ile Asn Met Leu
            485                 490                 495

Val Lys Leu Ile Thr Pro Asp Gly Lys Val Leu Glu Lys Val Ser Gly
            500                 505                 510

Lys Val Phe Gly Glu Gly Val Gly Asn Ile Ala Asn Phe Glu Leu Asp
            515                 520                 525

Gln Pro Tyr Leu Pro Gly Gln Thr Phe Lys Tyr Thr Ile Ala Ser Lys
            530                 535                 540

Asp Tyr Pro Glu Val Ser Tyr Asp Gly Thr Phe Thr Val Pro Thr Ser
545                 550                 555                 560

Leu Ala Tyr Lys Met Ala Ser Gln Thr Ile Phe Tyr Pro Phe His Ala
            565                 570                 575

Gly Asp Thr Tyr Leu Arg Val Asn Pro Gln Phe Ala Val Pro Lys Gly
            580                 585                 590

Thr Asp Ala Leu Val Arg Val Phe Asp Glu Phe His Gly Asn Ala Tyr
            595                 600                 605

Leu Glu Asn Asn Tyr Lys Val Gly Glu Ile Lys Leu Pro Ile Pro Lys
            610                 615                 620

Leu Asn Gln Gly Thr Thr Arg Thr Ala Gly Asn Lys Ile Pro Val Thr
625                 630                 635                 640

Phe Met Ala Asn Ala Tyr Leu Asp Asn Gln Ser Thr Tyr Ile Val Glu
            645                 650                 655

Val Pro Ile Leu Glu Lys Glu Asn Gln Thr Asp Lys Pro Ser Ile Leu
            660                 665                 670

Pro Gln Phe Lys Arg Asn Lys Ala Gln Glu Asn Ser Lys Leu Asp Glu
            675                 680                 685

Lys Val Glu Glu Pro Lys Thr Ser Glu Lys Val Glu Lys Glu Lys Leu
            690                 695                 700

Ser Glu Thr Gly Asn Ser Thr Ser Asn Ser Thr Leu Glu Glu Val Pro
705                 710                 715                 720

Thr Val Asp Pro Val Gln Glu Lys Val Ala Lys Phe Ala Glu Ser Tyr
            725                 730                 735

Gly Met Lys Leu Glu Asn Val Leu Phe Asn Met Asp Gly Thr Ile Glu
            740                 745                 750

Leu Tyr Leu Pro Ser Gly Glu Val Ile Lys Lys Asn Met Ala Asp Phe
            755                 760                 765

Thr Gly Glu Ala Pro Gln Gly Asn Gly Glu Asn Lys Pro Ser Glu Asn
770                 775                 780

Gly Lys Val Ser Thr Gly Thr Val Glu Asn Gln Pro Thr Glu Asn Lys
785                 790                 795                 800

Pro Ala Asp Ser Leu Pro Glu Ala Pro Asn Glu Lys Pro Val Lys Pro
            805                 810                 815

Glu Asn Ser Thr Asp Asn Gly Met Leu Asn Pro Glu Gly Asn Val Gly
            820                 825                 830

Ser Asp Pro Met Leu Asp Pro Ala Leu Glu Glu Ala Pro Ala Val Asp
            835                 840                 845

Pro Val Gln Glu Lys Leu Glu Lys Phe Thr Ala Ser Tyr Gly Leu Gly
            850                 855                 860

Leu Asp Ser Val Ile Phe Asn Met Asp Gly Thr Ile Glu Leu Arg Leu
865                 870                 875                 880

Pro Ser Gly Glu Val Ile Lys Lys Asn Leu Ser Asp Phe Ile Ala
            885                 890                 895
```

-continued

<210> SEQ ID NO 345
<211> LENGTH: 901
<212> TYPE: PRT
<213> ORGANISM: Artificial Sequence
<220> FEATURE:
<223> OTHER INFORMATION: Unknown Organism

<400> SEQUENCE: 345

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Gln Ala Tyr
        35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro Ser Tyr Asp Ser
            100                 105                 110

Tyr His Asn Ile Lys Phe Glu Trp Phe Asp Glu Gly Leu Tyr Glu Ala
        115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

Ser Gly Pro Gln Ile Gly Gln Pro Thr Leu Pro Asn Asn Ser Leu Ala
        275                 280                 285

Thr Pro Ser Pro Ser Leu Pro Ile Asn Pro Gly Thr Ser His Glu Lys
    290                 295                 300

His Glu Glu Asp Gly Tyr Gly Phe Asp Ala Asn Arg Ile Ile Ala Glu
305                 310                 315                 320

Asp Glu Ser Gly Phe Val Met Ser Tyr Phe Phe Lys Lys Asp Leu Thr
                325                 330                 335

Glu Glu Gln Ile Lys Ala Ala Gln Lys His Leu Glu Glu Val Lys Thr
            340                 345                 350

Ser His Asn Gly Leu Asp Ser Leu Ser Ser His Glu Gln Asp Tyr Pro
        355                 360                 365

Gly Asn Ala Lys Glu Met Lys Asp Leu Asp Lys Lys Ile Glu Glu Lys

```
                370             375             380
Ile Ala Gly Ile Met Lys Gln Tyr Gly Val Lys Arg Glu Ser Ile Val
385             390             395             400
Val Asn Lys Glu Lys Asn Ala Ile Ile Tyr Pro His Gly Asp His His
                405             410             415
His Ala Asp Pro Ile Asp Glu His Lys Pro Val Gly Ile Gly His Ser
            420             425             430
His Ser Asn Tyr Glu Leu Phe Lys Pro Glu Gly Val Ala Lys Lys
            435             440             445
Glu Gly Asn Lys Val Tyr Thr Gly Glu Glu Leu Thr Asn Val Val Asn
450             455             460
Leu Leu Lys Asn Ser Thr Phe Asn Asn Gln Asn Phe Thr Leu Ala Asn
465             470             475             480
Gly Gln Lys Arg Val Ser Phe Ser Phe Pro Glu Leu Glu Lys Lys
                485             490             495
Leu Gly Ile Asn Met Leu Val Lys Leu Ile Thr Pro Asp Gly Lys Val
                500             505             510
Leu Glu Lys Val Ser Gly Lys Val Phe Gly Glu Gly Val Gly Asn Ile
                515             520             525
Ala Asn Phe Glu Leu Asp Gln Pro Tyr Leu Pro Gly Gln Thr Phe Lys
530             535             540
Tyr Thr Ile Ala Ser Lys Asp Tyr Pro Glu Val Ser Tyr Asp Gly Thr
545             550             555             560
Phe Thr Val Pro Thr Ser Leu Ala Tyr Lys Met Ala Ser Gln Thr Ile
                565             570             575
Phe Tyr Pro Phe His Ala Gly Asp Thr Tyr Leu Arg Val Asn Pro Gln
            580             585             590
Phe Ala Val Pro Lys Gly Thr Asp Ala Leu Val Arg Val Phe Asp Glu
            595             600             605
Phe His Gly Asn Ala Tyr Leu Glu Asn Asn Tyr Lys Val Gly Glu Ile
            610             615             620
Lys Leu Pro Ile Pro Lys Leu Asn Gln Gly Thr Thr Arg Thr Ala Gly
625             630             635             640
Asn Lys Ile Pro Val Thr Phe Met Ala Asn Ala Tyr Leu Asp Asn Gln
                645             650             655
Ser Thr Tyr Ile Val Glu Val Pro Ile Leu Glu Lys Glu Asn Gln Thr
                660             665             670
Asp Lys Pro Ser Ile Leu Pro Gln Phe Lys Arg Asn Lys Ala Gln Glu
            675             680             685
Asn Ser Lys Leu Asp Glu Lys Val Glu Pro Lys Thr Ser Glu Lys
            690             695             700
Val Glu Lys Glu Lys Leu Ser Glu Thr Gly Asn Ser Thr Ser Asn Ser
705             710             715             720
Thr Leu Glu Glu Val Pro Thr Val Asp Pro Val Gln Glu Lys Val Ala
                725             730             735
Lys Phe Ala Glu Ser Tyr Gly Met Lys Leu Glu Asn Val Leu Phe Asn
            740             745             750
Met Asp Gly Thr Ile Glu Leu Tyr Leu Pro Ser Gly Glu Val Ile Lys
            755             760             765
Lys Asn Met Ala Asp Phe Thr Gly Glu Ala Pro Gln Gly Asn Gly Glu
            770             775             780
Asn Lys Pro Ser Glu Asn Gly Lys Val Ser Thr Gly Thr Val Glu Asn
785             790             795             800
```

-continued

Gln Pro Thr Glu Asn Lys Pro Ala Asp Ser Leu Pro Glu Ala Pro Asn
              805                 810                 815

Glu Lys Pro Val Lys Pro Glu Asn Ser Thr Asp Asn Gly Met Leu Asn
              820                 825                 830

Pro Glu Gly Asn Val Gly Ser Asp Pro Met Leu Asp Pro Ala Leu Glu
              835                 840                 845

Glu Ala Pro Ala Val Asp Pro Val Gln Glu Lys Leu Gly Lys Phe Thr
    850                 855                 860

Ala Ser Tyr Gly Leu Gly Leu Asp Ser Val Ile Phe Asn Met Asp Gly
865                 870                 875                 880

Thr Ile Glu Leu Arg Leu Pro Ser Gly Glu Val Ile Lys Lys Asn Leu
              885                 890                 895

Ser Asp Phe Ile Ala
              900

<210> SEQ ID NO 346
<211> LENGTH: 895
<212> TYPE: PRT
<213> ORGANISM: Artificial Sequence
<220> FEATURE:
<223> OTHER INFORMATION: Unknown Organism

<400> SEQUENCE: 346

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
              20                  25                  30

Lys Lys Asp Ser Leu Ser Glu Ala Glu Arg Ala Ala Ala Gln Ala Tyr
          35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
              85                  90                  95

Thr Val Glu Val Lys Asn Gly Ser Leu Ile Ile Pro Ser Tyr Asp Ser
              100                 105                 110

Tyr His Asn Ile Lys Phe Glu Trp Phe Asp Glu Gly Leu Tyr Glu Ala
          115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
              165                 170                 175

Pro Thr His Pro Glu Ser Asp Glu Lys Glu Asn His Ala Gly Leu Asn
              180                 185                 190

Pro Ser Ala Asp Asn Leu Tyr Lys Pro Ser Thr Asp Thr Glu Glu Thr
          195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Asn Thr Ile Ser Ala Glu Val
              245                 250                 255

```
Asp Ser Leu Leu Ala Leu Leu Lys Glu Ser Gln Pro Ala Pro Ile Gln
        260                 265                 270

Ser Gly Pro Gln Ile Gly Gln Pro Thr Leu Pro Asn Ser Leu Ala
        275                 280                 285

Thr Pro Ser Pro Ser Leu Pro Ile Asn Pro Gly Thr Ser His Glu Lys
        290                 295                 300

His Glu Glu Asp Gly Tyr Gly Phe Asp Ala Asn Arg Ile Ile Ala Glu
305                 310                 315                 320

Asp Glu Ser Gly Phe Val Met Ser Tyr Phe Lys Lys Asp Leu Thr
                325                 330                 335

Glu Glu Gln Ile Lys Ala Ala Gln Lys His Leu Glu Glu Val Lys Thr
        340                 345                 350

Ser His Asn Gly Leu Asp Ser Leu Ser Ser His Glu Gln Asp Tyr Pro
        355                 360                 365

Gly Asn Ala Lys Glu Met Lys Asp Leu Asp Lys Lys Ile Glu Glu Lys
        370                 375                 380

Ile Ala Gly Ile Met Lys Gln Tyr Gly Val Lys Arg Glu Ser Ile Val
385                 390                 395                 400

Val Asn Lys Glu Lys Asn Ala Ile Ile Tyr Pro Ala Asp Pro Ile Asp
                405                 410                 415

Glu His Lys Pro Val Gly Ile Gly His Ser His Ser Asn Tyr Glu Leu
                420                 425                 430

Phe Lys Pro Glu Glu Gly Val Ala Lys Lys Glu Gly Asn Lys Val Tyr
        435                 440                 445

Thr Gly Glu Glu Leu Thr Asn Val Val Asn Leu Leu Lys Asn Ser Thr
        450                 455                 460

Phe Asn Asn Gln Asn Phe Thr Leu Ala Asn Gly Gln Lys Arg Val Ser
465                 470                 475                 480

Phe Ser Phe Pro Pro Glu Leu Glu Lys Lys Leu Gly Ile Asn Met Leu
                485                 490                 495

Val Lys Leu Ile Thr Pro Asp Gly Lys Val Leu Glu Lys Val Ser Gly
        500                 505                 510

Lys Val Phe Gly Glu Gly Val Gly Asn Ile Ala Asn Phe Glu Leu Asp
        515                 520                 525

Gln Pro Tyr Leu Pro Gly Gln Thr Phe Lys Tyr Thr Ile Ala Ser Lys
        530                 535                 540

Asp Tyr Pro Glu Val Ser Tyr Asp Gly Thr Phe Thr Val Pro Thr Ser
545                 550                 555                 560

Leu Ala Tyr Lys Met Ala Ser Gln Thr Ile Phe Tyr Pro Phe His Ala
                565                 570                 575

Gly Asp Thr Tyr Leu Arg Val Asn Pro Gln Phe Ala Val Pro Lys Gly
                580                 585                 590

Thr Asp Ala Leu Val Arg Val Phe Asp Glu Phe His Gly Asn Ala Tyr
        595                 600                 605

Leu Glu Asn Asn Tyr Lys Val Gly Glu Ile Lys Leu Pro Ile Pro Lys
        610                 615                 620

Leu Asn Gln Gly Thr Thr Arg Thr Ala Gly Asn Lys Ile Pro Val Thr
625                 630                 635                 640

Phe Met Ala Asn Ala Tyr Leu Asp Asn Gln Ser Thr Tyr Ile Val Glu
                645                 650                 655

Val Pro Ile Leu Glu Lys Glu Asn Gln Thr Asp Lys Pro Ser Ile Leu
                660                 665                 670
```

-continued

```
Pro Gln Phe Lys Arg Asn Lys Ala Gln Glu Asn Ser Lys Leu Asp Glu
            675                 680                 685
Lys Val Glu Glu Pro Lys Thr Ser Glu Lys Val Glu Lys Glu Lys Leu
        690                 695                 700
Ser Glu Thr Gly Asn Ser Thr Ser Asn Ser Thr Leu Glu Glu Val Pro
705                 710                 715                 720
Thr Val Asp Pro Val Gln Glu Lys Val Ala Lys Phe Ala Glu Ser Tyr
                725                 730                 735
Gly Met Lys Leu Glu Asn Val Leu Phe Asn Met Asp Gly Thr Ile Glu
            740                 745                 750
Leu Tyr Leu Pro Ser Gly Glu Val Ile Lys Lys Asn Met Ala Asp Phe
        755                 760                 765
Thr Gly Glu Ala Pro Gln Gly Asn Gly Glu Asn Lys Pro Ser Glu Asn
    770                 775                 780
Gly Lys Val Ser Thr Gly Thr Val Glu Asn Gln Pro Thr Glu Asn Lys
785                 790                 795                 800
Pro Ala Asp Ser Leu Pro Glu Ala Pro Asn Glu Lys Pro Val Lys Pro
                805                 810                 815
Glu Asn Ser Thr Asp Asn Gly Met Leu Asn Pro Glu Gly Asn Val Gly
            820                 825                 830
Ser Asp Pro Met Leu Asp Pro Ala Leu Glu Glu Ala Pro Ala Val Asp
        835                 840                 845
Pro Val Gln Glu Lys Leu Glu Lys Phe Thr Ala Ser Tyr Gly Leu Gly
    850                 855                 860
Leu Asp Ser Val Ile Phe Asn Met Asp Gly Thr Ile Glu Leu Arg Leu
865                 870                 875                 880
Pro Ser Gly Glu Val Ile Lys Lys Asn Leu Ser Asp Phe Ile Ala
                885                 890                 895

<210> SEQ ID NO 347
<211> LENGTH: 895
<212> TYPE: PRT
<213> ORGANISM: Artificial Sequence
<220> FEATURE:
<223> OTHER INFORMATION: Unknown Organism

<400> SEQUENCE: 347

Met Gln Ile Thr Tyr Thr Asp Asp Glu Ile Gln Val Ala Lys Leu Ala
1               5                   10                  15
Gly Lys Tyr Thr Thr Glu Asp Gly Tyr Ile Phe Asp Thr Ser Trp Ile
            20                  25                  30
Lys Lys Asp Ser Leu Ser Glu Ala Glu Arg Ala Ala Ala Gln Ala Tyr
        35                  40                  45
Ala Lys Glu Lys Gly Leu Thr Pro Pro Ser Thr Asp His Gln Asp Ser
    50                  55                  60
Gly Asn Thr Glu Ala Lys Gly Ala Glu Ala Ile Tyr Asn Arg Val Lys
65                  70                  75                  80
Ala Ala Lys Lys Val Pro Leu Asp Arg Met Pro Tyr Asn Leu Gln Tyr
                85                  90                  95
Thr Val Glu Val Lys Asn Gly Ser Leu Ile Ile Pro Asn Ile Lys Phe
            100                 105                 110
Glu Trp Phe Asp Glu Gly Leu Tyr Glu Ala Pro Lys Gly Tyr Ser Leu
        115                 120                 125
Glu Asp Leu Leu Ala Thr Val Lys Tyr Tyr Val Glu Pro Arg Asn Ala
    130                 135                 140
```

-continued

```
Ser Asp His Val Arg Lys Asn Lys Ala Asp Gln Asp Ser Lys Pro Asp
145                 150                 155                 160

Glu Asp Lys Glu His Asp Glu Val Ser Glu Pro Thr His Pro Glu Ser
                165                 170                 175

Asp Glu Lys Glu Asn His Ala Gly Leu Asn Pro Ser Ala Asp Asn Leu
            180                 185                 190

Tyr Lys Pro Ser Thr Asp Thr Glu Glu Thr Glu Glu Ala Glu Asp
        195                 200                 205

Thr Thr Asp Glu Ala Glu Ile Pro Gly Thr Pro Ser Ile Arg Gln Asn
    210                 215                 220

Ala Met Glu Thr Leu Thr Gly Leu Lys Ser Ser Leu Leu Leu Gly Thr
225                 230                 235                 240

Lys Asp Asn Asn Thr Ile Ser Ala Glu Val Asp Ser Leu Leu Ala Leu
                245                 250                 255

Leu Lys Glu Ser Gln Pro Ala Pro Ile Gln Ser Gly Pro Gln Ile Gly
            260                 265                 270

Gln Pro Thr Leu Pro Asn Asn Ser Leu Ala Thr Pro Ser Pro Ser Leu
        275                 280                 285

Pro Ile Asn Pro Gly Thr Ser His Glu Lys His Glu Glu Asp Gly Tyr
    290                 295                 300

Gly Phe Asp Ala Asn Arg Ile Ile Ala Glu Asp Glu Ser Gly Phe Val
305                 310                 315                 320

Met Ser Tyr Phe Phe Lys Lys Asp Leu Thr Glu Glu Gln Ile Lys Ala
                325                 330                 335

Ala Gln Lys His Leu Glu Glu Val Lys Thr Ser His Asn Gly Leu Asp
            340                 345                 350

Ser Leu Ser Ser His Glu Gln Asp Tyr Pro Gly Asn Ala Lys Glu Met
        355                 360                 365

Lys Asp Leu Asp Lys Lys Ile Glu Glu Lys Ile Ala Gly Ile Met Lys
    370                 375                 380

Gln Tyr Gly Val Lys Arg Glu Ser Ile Val Val Asn Lys Glu Lys Asn
385                 390                 395                 400

Ala Ile Ile Tyr Pro His Gly Asp His His Ala Asp Pro Ile Asp
                405                 410                 415

Glu His Lys Pro Val Gly Ile Gly His Ser His Ser Asn Tyr Glu Leu
            420                 425                 430

Phe Lys Pro Glu Glu Gly Val Ala Lys Lys Glu Gly Asn Lys Val Tyr
        435                 440                 445

Thr Gly Glu Glu Leu Thr Asn Val Val Asn Leu Leu Lys Asn Ser Thr
    450                 455                 460

Phe Asn Asn Gln Asn Phe Thr Leu Ala Asn Gly Gln Lys Arg Val Ser
465                 470                 475                 480

Phe Ser Phe Pro Pro Glu Leu Glu Lys Lys Leu Gly Ile Asn Met Leu
                485                 490                 495

Val Lys Leu Ile Thr Pro Asp Gly Lys Val Leu Glu Lys Val Ser Gly
            500                 505                 510

Lys Val Phe Gly Glu Gly Val Gly Asn Ile Ala Asn Phe Glu Leu Asp
        515                 520                 525

Gln Pro Tyr Leu Pro Gly Gln Thr Phe Lys Tyr Thr Ile Ala Ser Lys
    530                 535                 540

Asp Tyr Pro Glu Val Ser Tyr Asp Gly Thr Phe Thr Val Pro Thr Ser
545                 550                 555                 560

Leu Ala Tyr Lys Met Ala Ser Gln Thr Ile Phe Tyr Pro Phe His Ala
```

-continued

```
                565                 570                 575
Gly Asp Thr Tyr Leu Arg Val Asn Pro Gln Phe Ala Val Pro Lys Gly
            580                 585                 590

Thr Asp Ala Leu Val Arg Val Phe Asp Glu Phe His Gly Asn Ala Tyr
        595                 600                 605

Leu Glu Asn Asn Tyr Lys Val Gly Glu Ile Lys Leu Pro Ile Pro Lys
    610                 615                 620

Leu Asn Gln Gly Thr Thr Arg Thr Ala Gly Asn Lys Ile Pro Val Thr
625                 630                 635                 640

Phe Met Ala Asn Ala Tyr Leu Asp Asn Gln Ser Thr Tyr Ile Val Glu
                645                 650                 655

Val Pro Ile Leu Glu Lys Glu Asn Gln Thr Asp Lys Pro Ser Ile Leu
            660                 665                 670

Pro Gln Phe Lys Arg Asn Lys Ala Gln Glu Asn Ser Lys Leu Asp Glu
        675                 680                 685

Lys Val Glu Glu Pro Lys Thr Ser Glu Lys Val Lys Glu Lys Leu
    690                 695                 700

Ser Glu Thr Gly Asn Ser Thr Ser Asn Ser Thr Leu Glu Glu Val Pro
705                 710                 715                 720

Thr Val Asp Pro Val Gln Glu Lys Val Ala Lys Phe Ala Glu Ser Tyr
                725                 730                 735

Gly Met Lys Leu Glu Asn Val Leu Phe Asn Met Asp Gly Thr Ile Glu
            740                 745                 750

Leu Tyr Leu Pro Ser Gly Glu Val Ile Lys Lys Asn Met Ala Asp Phe
        755                 760                 765

Thr Gly Glu Ala Pro Gln Gly Asn Gly Glu Asn Lys Pro Ser Glu Asn
    770                 775                 780

Gly Lys Val Ser Thr Gly Thr Val Glu Asn Gln Pro Thr Glu Asn Lys
785                 790                 795                 800

Pro Ala Asp Ser Leu Pro Glu Ala Pro Asn Glu Lys Pro Val Lys Pro
                805                 810                 815

Glu Asn Ser Thr Asp Asn Gly Met Leu Asn Pro Glu Gly Asn Val Gly
            820                 825                 830

Ser Asp Pro Met Leu Asp Pro Ala Leu Glu Glu Ala Pro Ala Val Asp
        835                 840                 845

Pro Val Gln Glu Lys Leu Glu Lys Phe Thr Ala Ser Tyr Gly Leu Gly
    850                 855                 860

Leu Asp Ser Val Ile Phe Asn Met Asp Gly Thr Ile Glu Leu Arg Leu
865                 870                 875                 880

Pro Ser Gly Glu Val Ile Lys Lys Asn Leu Ser Asp Phe Ile Ala
                885                 890                 895
```

<210> SEQ ID NO 348
<211> LENGTH: 889
<212> TYPE: PRT
<213> ORGANISM: Artificial Sequence
<220> FEATURE:
<223> OTHER INFORMATION: Unknown Organism

<400> SEQUENCE: 348

```
Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Ala Gln Ala Tyr
```

-continued

```
               35                  40                  45
Ala Lys Glu Lys Gly Leu Thr Pro Ser Thr Asp His Gln Asp Ser
 50                  55                  60
Gly Asn Thr Glu Ala Lys Gly Ala Glu Ala Ile Tyr Asn Arg Val Lys
 65                  70                  75                  80
Ala Ala Lys Lys Val Pro Leu Asp Arg Met Pro Tyr Asn Leu Gln Tyr
                 85                  90                  95
Thr Val Glu Val Lys Asn Gly Ser Leu Ile Ile Pro Asn Ile Lys Phe
                100                 105                 110
Glu Trp Phe Asp Glu Gly Leu Tyr Glu Ala Pro Lys Gly Tyr Ser Leu
                115                 120                 125
Glu Asp Leu Leu Ala Thr Val Lys Tyr Tyr Val Glu Pro Arg Asn Ala
                130                 135                 140
Ser Asp His Val Arg Lys Asn Lys Ala Asp Gln Asp Ser Lys Pro Asp
145                 150                 155                 160
Glu Asp Lys Glu His Asp Glu Val Ser Glu Pro Thr His Pro Glu Ser
                165                 170                 175
Asp Glu Lys Glu Asn His Ala Gly Leu Asn Pro Ser Ala Asp Asn Leu
                180                 185                 190
Tyr Lys Pro Ser Thr Asp Thr Glu Glu Thr Glu Glu Ala Glu Asp
                195                 200                 205
Thr Thr Asp Glu Ala Glu Ile Pro Gly Thr Pro Ser Ile Arg Gln Asn
210                 215                 220
Ala Met Glu Thr Leu Thr Gly Leu Lys Ser Ser Leu Leu Leu Gly Thr
225                 230                 235                 240
Lys Asp Asn Asn Thr Ile Ser Ala Glu Val Asp Ser Leu Leu Ala Leu
                245                 250                 255
Leu Lys Glu Ser Gln Pro Ala Pro Ile Gln Ser Gly Pro Gln Ile Gly
                260                 265                 270
Gln Pro Thr Leu Pro Asn Asn Ser Leu Ala Thr Pro Ser Pro Ser Leu
                275                 280                 285
Pro Ile Asn Pro Gly Thr Ser His Glu Lys His Glu Glu Asp Gly Tyr
                290                 295                 300
Gly Phe Asp Ala Asn Arg Ile Ile Ala Glu Asp Glu Ser Gly Phe Val
305                 310                 315                 320
Met Ser Tyr Phe Phe Lys Lys Asp Leu Thr Glu Glu Gln Ile Lys Ala
                325                 330                 335
Ala Gln Lys His Leu Glu Glu Val Lys Thr Ser His Asn Gly Leu Asp
                340                 345                 350
Ser Leu Ser Ser His Glu Gln Asp Tyr Pro Gly Asn Ala Lys Glu Met
                355                 360                 365
Lys Asp Leu Asp Lys Lys Ile Glu Glu Lys Ile Ala Gly Ile Met Lys
                370                 375                 380
Gln Tyr Gly Val Lys Arg Glu Ser Ile Val Val Asn Lys Glu Lys Asn
385                 390                 395                 400
Ala Ile Ile Tyr Pro Ala Asp Pro Ile Asp Glu His Lys Pro Val Gly
                405                 410                 415
Ile Gly His Ser His Ser Asn Tyr Glu Leu Phe Lys Pro Glu Glu Gly
                420                 425                 430
Val Ala Lys Lys Glu Gly Asn Lys Val Tyr Thr Gly Glu Glu Leu Thr
                435                 440                 445
Asn Val Val Asn Leu Leu Lys Asn Ser Thr Phe Asn Asn Gln Asn Phe
450                 455                 460
```

-continued

```
Thr Leu Ala Asn Gly Gln Lys Arg Val Ser Phe Ser Phe Pro Pro Glu
465                 470                 475                 480

Leu Glu Lys Lys Leu Gly Ile Asn Met Leu Val Lys Leu Ile Thr Pro
                485                 490                 495

Asp Gly Lys Val Leu Glu Lys Val Ser Gly Lys Val Phe Gly Glu Gly
            500                 505                 510

Val Gly Asn Ile Ala Asn Phe Glu Leu Asp Gln Pro Tyr Leu Pro Gly
        515                 520                 525

Gln Thr Phe Lys Tyr Thr Ile Ala Ser Lys Asp Tyr Pro Glu Val Ser
    530                 535                 540

Tyr Asp Gly Thr Phe Thr Val Pro Thr Ser Leu Ala Tyr Lys Met Ala
545                 550                 555                 560

Ser Gln Thr Ile Phe Tyr Pro Phe His Ala Gly Asp Thr Tyr Leu Arg
                565                 570                 575

Val Asn Pro Gln Phe Ala Val Pro Lys Gly Thr Asp Ala Leu Val Arg
            580                 585                 590

Val Phe Asp Glu Phe His Gly Asn Ala Tyr Leu Glu Asn Asn Tyr Lys
        595                 600                 605

Val Gly Glu Ile Lys Leu Pro Ile Pro Lys Leu Asn Gln Gly Thr Thr
    610                 615                 620

Arg Thr Ala Gly Asn Lys Ile Pro Val Thr Phe Met Ala Asn Ala Tyr
625                 630                 635                 640

Leu Asp Asn Gln Ser Thr Tyr Ile Val Glu Val Pro Ile Leu Glu Lys
                645                 650                 655

Glu Asn Gln Thr Asp Lys Pro Ser Ile Leu Pro Gln Phe Lys Arg Asn
            660                 665                 670

Lys Ala Gln Glu Asn Ser Lys Leu Asp Glu Lys Val Glu Glu Pro Lys
        675                 680                 685

Thr Ser Glu Lys Val Glu Lys Glu Lys Leu Ser Glu Thr Gly Asn Ser
    690                 695                 700

Thr Ser Asn Ser Thr Leu Glu Glu Val Pro Thr Val Asp Pro Val Gln
705                 710                 715                 720

Glu Lys Val Ala Lys Phe Ala Glu Ser Tyr Gly Met Lys Leu Glu Asn
                725                 730                 735

Val Leu Phe Asn Met Asp Gly Thr Ile Glu Leu Tyr Leu Pro Ser Gly
            740                 745                 750

Glu Val Ile Lys Lys Asn Met Ala Asp Phe Thr Gly Glu Ala Pro Gln
        755                 760                 765

Gly Asn Gly Glu Asn Lys Pro Ser Glu Asn Gly Lys Val Ser Thr Gly
    770                 775                 780

Thr Val Glu Asn Gln Pro Thr Glu Asn Lys Pro Ala Asp Ser Leu Pro
785                 790                 795                 800

Glu Ala Pro Asn Glu Lys Pro Val Lys Pro Glu Asn Ser Thr Asp Asn
                805                 810                 815

Gly Met Leu Asn Pro Glu Gly Asn Val Gly Ser Asp Pro Met Leu Asp
            820                 825                 830

Pro Ala Leu Glu Glu Ala Pro Ala Val Asp Pro Val Gln Glu Lys Leu
        835                 840                 845

Glu Lys Phe Thr Ala Ser Tyr Gly Leu Gly Leu Asp Ser Val Ile Phe
    850                 855                 860

Asn Met Asp Gly Thr Ile Glu Leu Arg Leu Pro Ser Gly Glu Val Ile
865                 870                 875                 880
```

Lys Lys Asn Leu Ser Asp Phe Ile Ala
              885

<210> SEQ ID NO 349
<211> LENGTH: 633
<212> TYPE: PRT
<213> ORGANISM: Artificial Sequence
<220> FEATURE:
<223> OTHER INFORMATION: Unknown Organism

<400> SEQUENCE: 349

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser Ser Gly Asp Ser Asn Ser Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
    130                 135                 140

Gly Asp Gly Thr Ser Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
    290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

```
Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
    370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
        435                 440                 445

Thr Ser Asn Ser Thr Leu Glu Glu Val Pro Thr Val Asp Pro Val Gln
    450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
                485                 490                 495

Glu Val Ile Lys Lys Asn Met Ala Asp Phe Thr Gly Glu Ala Pro Gln
            500                 505                 510

Gly Asn Gly Glu Asn Lys Pro Ser Glu Asn Gly Lys Val Ser Thr Gly
        515                 520                 525

Thr Val Glu Asn Gln Pro Thr Glu Asn Lys Pro Ala Asp Ser Leu Pro
    530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
    610                 615                 620

Lys Lys Asn Leu Ser Asp Phe Ile Ala
625                 630

<210> SEQ ID NO 350
<211> LENGTH: 633
<212> TYPE: PRT
<213> ORGANISM: Artificial Sequence
<220> FEATURE:
<223> OTHER INFORMATION: Unknown Organism

<400> SEQUENCE: 350

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser Ser Gly Asp His Asn His Tyr Phe Phe Lys
    50                  55                  60

Lys Asp Leu Thr Glu Glu Gln Ile Lys Ala Ala Gln Lys His Leu Glu
65                  70                  75                  80
```

-continued

```
Glu Val Lys Thr Ser His Asn Gly Leu Asp Ser Leu Ser Ser His Glu
                85                  90                  95
Gln Asp Tyr Pro Gly Asn Ala Lys Glu Met Lys Asp Leu Asp Lys Lys
            100                 105                 110
Ile Glu Glu Lys Ile Ala Gly Ile Met Lys Gln Tyr Gly Val Lys Arg
        115                 120                 125
Glu Ser Ile Val Val Asn Lys Glu Lys Asn Ala Ile Ile Tyr Pro His
    130                 135                 140
Gly Asp His His His Ala Asp Pro Ile Asp Glu His Lys Pro Val Gly
145                 150                 155                 160
Ile Gly His Ser His Ser Asn Tyr Glu Leu Phe Lys Pro Glu Glu Gly
                165                 170                 175
Val Ala Lys Lys Glu Gly Asn Lys Val Tyr Thr Gly Glu Glu Leu Thr
            180                 185                 190
Asn Val Val Asn Leu Leu Lys Asn Ser Thr Phe Asn Asn Gln Asn Phe
        195                 200                 205
Thr Leu Ala Asn Gly Gln Lys Arg Val Ser Phe Ser Phe Pro Pro Glu
    210                 215                 220
Leu Glu Lys Lys Leu Gly Ile Asn Met Leu Val Lys Leu Ile Thr Pro
225                 230                 235                 240
Asp Gly Lys Val Leu Glu Lys Val Ser Gly Lys Val Phe Gly Glu Gly
                245                 250                 255
Val Gly Asn Ile Ala Asn Phe Glu Leu Asp Gln Pro Tyr Leu Pro Gly
            260                 265                 270
Gln Thr Phe Lys Tyr Thr Ile Ala Ser Lys Asp Tyr Pro Glu Val Ser
        275                 280                 285
Tyr Asp Gly Thr Phe Thr Val Pro Thr Ser Leu Ala Tyr Lys Met Ala
    290                 295                 300
Ser Gln Thr Ile Phe Tyr Pro Phe His Ala Gly Asp Thr Tyr Leu Arg
305                 310                 315                 320
Val Asn Pro Gln Phe Ala Val Pro Lys Gly Thr Asp Ala Leu Val Arg
                325                 330                 335
Val Phe Asp Glu Phe His Gly Asn Ala Tyr Leu Glu Asn Asn Tyr Lys
            340                 345                 350
Val Gly Glu Ile Lys Leu Pro Ile Pro Lys Leu Asn Gln Gly Thr Thr
        355                 360                 365
Arg Thr Ala Gly Asn Lys Ile Pro Val Thr Phe Met Ala Asn Ala Tyr
    370                 375                 380
Leu Asp Asn Gln Ser Thr Tyr Ile Val Glu Val Pro Ile Leu Glu Lys
385                 390                 395                 400
Glu Asn Gln Thr Asp Lys Pro Ser Ile Leu Pro Gln Phe Lys Arg Asn
                405                 410                 415
Lys Ala Gln Glu Asn Ser Lys Leu Asp Glu Lys Val Glu Glu Pro Lys
            420                 425                 430
Thr Ser Glu Lys Val Glu Lys Glu Lys Leu Ser Glu Thr Gly Asn Ser
        435                 440                 445
Thr Ser Asn Ser Thr Leu Glu Glu Val Pro Thr Val Asp Pro Val Gln
    450                 455                 460
Glu Lys Val Ala Lys Phe Ala Glu Ser Tyr Gly Met Lys Leu Glu Asn
465                 470                 475                 480
Val Leu Phe Asn Met Asp Gly Thr Ile Glu Leu Tyr Leu Pro Ser Gly
                485                 490                 495
Glu Val Ile Lys Lys Asn Met Ala Asp Phe Thr Gly Glu Ala Pro Gln
```

```
                    500                 505                 510
Gly Asn Gly Glu Asn Lys Pro Ser Glu Asn Gly Lys Val Ser Thr Gly
            515                 520                 525
Thr Val Glu Asn Gln Pro Thr Glu Asn Lys Pro Ala Asp Ser Leu Pro
        530                 535                 540
Glu Ala Pro Asn Glu Lys Pro Val Lys Pro Glu Asn Ser Thr Asp Asn
545                 550                 555                 560
Gly Met Leu Asn Pro Glu Gly Asn Val Gly Ser Asp Pro Met Leu Asp
                565                 570                 575
Pro Ala Leu Glu Glu Ala Pro Ala Val Asp Pro Val Gln Glu Lys Leu
            580                 585                 590
Glu Lys Phe Thr Ala Ser Tyr Gly Leu Gly Leu Asp Ser Val Ile Phe
        595                 600                 605
Asn Met Asp Gly Thr Ile Glu Leu Arg Leu Pro Ser Gly Glu Val Ile
        610                 615                 620
Lys Lys Asn Leu Ser Asp Phe Ile Ala
625                 630

<210> SEQ ID NO 351
<211> LENGTH: 633
<212> TYPE: PRT
<213> ORGANISM: Artificial Sequence
<220> FEATURE:
<223> OTHER INFORMATION: Unknown Organism

<400> SEQUENCE: 351

Met Gln Ile Gly Gln Pro Thr Leu Pro Asn Asn Ser Leu Ala Thr Pro
1               5                   10                  15
Ser Pro Ser Leu Pro Ile Asn Pro Gly Thr Ser His Glu Lys His Glu
            20                  25                  30
Glu Asp Gly Tyr Gly Phe Asp Ala Asn Arg Ile Ile Ala Glu Asp Glu
        35                  40                  45
Ser Gly Phe Val Met Ser Ser Gly Asp Ser Asn His Tyr Phe Phe Lys
    50                  55                  60
Lys Asp Leu Thr Glu Glu Gln Ile Lys Ala Ala Gln Lys His Leu Glu
65                  70                  75                  80
Glu Val Lys Thr Ser His Asn Gly Leu Asp Ser Leu Ser Ser His Glu
                85                  90                  95
Gln Asp Tyr Pro Gly Asn Ala Lys Glu Met Lys Asp Leu Asp Lys Lys
            100                 105                 110
Ile Glu Glu Lys Ile Ala Gly Ile Met Lys Gln Tyr Gly Val Lys Arg
        115                 120                 125
Glu Ser Ile Val Val Asn Lys Glu Lys Asn Ala Ile Ile Tyr Pro His
    130                 135                 140
Gly Asp His His His Ala Asp Pro Ile Asp Glu His Lys Pro Val Gly
145                 150                 155                 160
Ile Gly His Ser His Ser Asn Tyr Glu Leu Phe Lys Pro Glu Glu Gly
                165                 170                 175
Val Ala Lys Lys Glu Gly Asn Lys Val Tyr Thr Gly Glu Glu Leu Thr
            180                 185                 190
Asn Val Val Asn Leu Leu Lys Asn Ser Thr Phe Asn Gln Asn Phe
        195                 200                 205
Thr Leu Ala Asn Gly Gln Lys Arg Val Ser Phe Ser Phe Pro Pro Glu
    210                 215                 220
Leu Glu Lys Lys Leu Gly Ile Asn Met Leu Val Lys Leu Ile Thr Pro
```

-continued

```
        225                 230                 235                 240
Asp Gly Lys Val Leu Glu Lys Val Ser Gly Lys Val Phe Gly Glu Gly
            245                 250                 255
Val Gly Asn Ile Ala Asn Phe Glu Leu Asp Gln Pro Tyr Leu Pro Gly
            260                 265                 270
Gln Thr Phe Lys Tyr Thr Ile Ala Ser Lys Asp Tyr Pro Glu Val Ser
            275                 280                 285
Tyr Asp Gly Thr Phe Thr Val Pro Thr Ser Leu Ala Tyr Lys Met Ala
    290                 295                 300
Ser Gln Thr Ile Phe Tyr Pro Phe His Ala Gly Asp Thr Tyr Leu Arg
305                 310                 315                 320
Val Asn Pro Gln Phe Ala Val Pro Lys Gly Thr Asp Ala Leu Val Arg
            325                 330                 335
Val Phe Asp Glu Phe His Gly Asn Ala Tyr Leu Glu Asn Asn Tyr Lys
            340                 345                 350
Val Gly Glu Ile Lys Leu Pro Ile Pro Lys Leu Asn Gln Gly Thr Thr
            355                 360                 365
Arg Thr Ala Gly Asn Lys Ile Pro Val Thr Phe Met Ala Asn Ala Tyr
    370                 375                 380
Leu Asp Asn Gln Ser Thr Tyr Ile Val Glu Val Pro Ile Leu Glu Lys
385                 390                 395                 400
Glu Asn Gln Thr Asp Lys Pro Ser Ile Leu Pro Gln Phe Lys Arg Asn
            405                 410                 415
Lys Ala Gln Glu Asn Ser Lys Leu Asp Glu Lys Val Glu Glu Pro Lys
            420                 425                 430
Thr Ser Glu Lys Val Glu Lys Glu Lys Leu Ser Glu Thr Gly Asn Ser
            435                 440                 445
Thr Ser Asn Ser Thr Leu Glu Glu Val Pro Thr Val Asp Pro Val Gln
    450                 455                 460
Glu Lys Val Ala Lys Phe Ala Glu Ser Tyr Gly Met Lys Leu Glu Asn
465                 470                 475                 480
Val Leu Phe Asn Met Asp Gly Thr Ile Glu Leu Tyr Leu Pro Ser Gly
            485                 490                 495
Glu Val Ile Lys Lys Asn Met Ala Asp Phe Thr Gly Glu Ala Pro Gln
            500                 505                 510
Gly Asn Gly Glu Asn Lys Pro Ser Glu Asn Gly Lys Val Ser Thr Gly
            515                 520                 525
Thr Val Glu Asn Gln Pro Thr Glu Asn Lys Pro Ala Asp Ser Leu Pro
    530                 535                 540
Glu Ala Pro Asn Glu Lys Pro Val Lys Pro Glu Asn Ser Thr Asp Asn
545                 550                 555                 560
Gly Met Leu Asn Pro Glu Gly Asn Val Gly Ser Asp Pro Met Leu Asp
            565                 570                 575
Pro Ala Leu Glu Glu Ala Pro Ala Val Asp Pro Val Gln Glu Lys Leu
            580                 585                 590
Glu Lys Phe Thr Ala Ser Tyr Gly Leu Gly Leu Asp Ser Val Ile Phe
            595                 600                 605
Asn Met Asp Gly Thr Ile Glu Leu Arg Leu Pro Ser Gly Glu Val Ile
    610                 615                 620
Lys Lys Asn Leu Ser Asp Phe Ile Ala
625                 630

<210> SEQ ID NO 352
```

```
<211> LENGTH: 633
<212> TYPE: PRT
<213> ORGANISM: Artificial Sequence
<220> FEATURE:
<223> OTHER INFORMATION: Unknown Organism

<400> SEQUENCE: 352

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser Ser Gly Asp His Asn His Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
    130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
    275                 280                 285

Tyr Asp Gly Thr Phe Thr Val Pro Thr Ser Leu Ala Tyr Lys Met Ala
290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Tyr Lys
            340                 345                 350

Val Gly Glu Ile Lys Leu Pro Ile Pro Lys Leu Asn Gln Gly Thr Thr
    355                 360                 365

Arg Thr Ala Gly Asn Lys Ile Pro Val Thr Phe Met Ala Asn Ala Tyr
370                 375                 380
```

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
            405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
            435                 440                 445

Thr Ser Asn Ser Thr Leu Glu Glu Val Pro Thr Val Asp Pro Val Gln
450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
            485                 490                 495

Glu Val Ile Lys Lys Asn Met Ala Asp Phe Thr Gly Glu Ala Pro Gln
            500                 505                 510

Gly Asn Gly Glu Asn Lys Pro Ser Glu Asn Gly Lys Val Ser Thr Gly
            515                 520                 525

Thr Val Glu Asn Gln Pro Thr Glu Asn Lys Pro Ala Asp Ser Leu Pro
530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
            565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
            595                 600                 605

Asn Met Asp Gly Thr Ile Glu Leu Arg Leu Pro Ser Gly Glu Val Ile
            610                 615                 620

Lys Lys Asn Leu Ser Asp Phe Ile Ala
625                 630

<210> SEQ ID NO 353
<211> LENGTH: 633
<212> TYPE: PRT
<213> ORGANISM: Artificial Sequence
<220> FEATURE:
<223> OTHER INFORMATION: Unknown Organism

<400> SEQUENCE: 353

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
            35                  40                  45

Ser Gly Phe Val Met Ser Ser Gly Asp Ser Asn His Tyr Phe Phe Lys
        50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

-continued

```
Ile Glu Glu Lys Ile Ala Gly Ile Met Lys Gln Tyr Gly Val Lys Arg
            115                 120                 125
Glu Ser Ile Val Val Asn Lys Glu Lys Asn Ala Ile Ile Tyr Pro Ser
        130                 135                 140
Gly Asp Gly His His Ala Asp Pro Ile Asp Glu His Lys Pro Val Gly
145                 150                 155                 160
Ile Gly His Ser His Ser Asn Tyr Glu Leu Phe Lys Pro Glu Glu Gly
                165                 170                 175
Val Ala Lys Lys Glu Gly Asn Lys Val Tyr Thr Gly Glu Glu Leu Thr
            180                 185                 190
Asn Val Val Asn Leu Leu Lys Asn Ser Thr Phe Asn Gln Asn Phe
        195                 200                 205
Thr Leu Ala Asn Gly Gln Lys Arg Val Ser Phe Ser Pro Pro Glu
    210                 215                 220
Leu Glu Lys Lys Leu Gly Ile Asn Met Leu Val Lys Leu Ile Thr Pro
225                 230                 235                 240
Asp Gly Lys Val Leu Glu Lys Val Ser Gly Lys Val Phe Gly Glu Gly
                245                 250                 255
Val Gly Asn Ile Ala Asn Phe Glu Leu Asp Gln Pro Tyr Leu Pro Gly
            260                 265                 270
Gln Thr Phe Lys Tyr Thr Ile Ala Ser Lys Asp Tyr Pro Glu Val Ser
        275                 280                 285
Tyr Asp Gly Thr Phe Thr Val Pro Thr Ser Leu Ala Tyr Lys Met Ala
290                 295                 300
Ser Gln Thr Ile Phe Tyr Pro Phe His Ala Gly Asp Thr Tyr Leu Arg
305                 310                 315                 320
Val Asn Pro Gln Phe Ala Val Pro Lys Gly Thr Asp Ala Leu Val Arg
                325                 330                 335
Val Phe Asp Glu Phe His Gly Asn Ala Tyr Leu Glu Asn Asn Tyr Lys
            340                 345                 350
Val Gly Glu Ile Lys Leu Pro Ile Pro Lys Leu Asn Gln Gly Thr Thr
        355                 360                 365
Arg Thr Ala Gly Asn Lys Ile Pro Val Thr Phe Met Ala Asn Ala Tyr
    370                 375                 380
Leu Asp Asn Gln Ser Thr Tyr Ile Val Glu Val Pro Ile Leu Glu Lys
385                 390                 395                 400
Glu Asn Gln Thr Asp Lys Pro Ser Ile Leu Pro Gln Phe Lys Arg Asn
                405                 410                 415
Lys Ala Gln Glu Asn Ser Lys Leu Asp Glu Lys Val Glu Pro Lys
            420                 425                 430
Thr Ser Glu Lys Val Glu Lys Glu Lys Leu Ser Glu Thr Gly Asn Ser
        435                 440                 445
Thr Ser Asn Ser Thr Leu Glu Glu Val Pro Thr Val Asp Pro Val Gln
    450                 455                 460
Glu Lys Val Ala Lys Phe Ala Glu Ser Tyr Gly Met Lys Leu Glu Asn
465                 470                 475                 480
Val Leu Phe Asn Met Asp Gly Thr Ile Glu Leu Tyr Leu Pro Ser Gly
                485                 490                 495
Glu Val Ile Lys Lys Asn Met Ala Asp Phe Thr Gly Glu Ala Pro Gln
            500                 505                 510
Gly Asn Gly Glu Asn Lys Pro Ser Glu Asn Gly Lys Val Ser Thr Gly
        515                 520                 525
```

```
Thr Val Glu Asn Gln Pro Thr Glu Asn Lys Pro Ala Asp Ser Leu Pro
    530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
                580                 585                 590

Glu Lys Phe Thr Ala Ser Tyr Gly Leu Gly Leu Asp Ser Val Ile Phe
            595                 600                 605

Asn Met Asp Gly Thr Ile Glu Leu Arg Leu Pro Ser Gly Glu Val Ile
        610                 615                 620

Lys Lys Asn Leu Ser Asp Phe Ile Ala
625                 630

<210> SEQ ID NO 354
<211> LENGTH: 633
<212> TYPE: PRT
<213> ORGANISM: Artificial Sequence
<220> FEATURE:
<223> OTHER INFORMATION: Unknown Organism

<400> SEQUENCE: 354

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp His Asn His Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
            85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
            115                 120                 125

Glu Ser Ile Val Val Asn Lys Glu Lys Asn Ala Ile Ile Tyr Pro Ser
    130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255
```

```
Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
        435                 440                 445

Thr Ser Asn Ser Thr Leu Glu Glu Val Pro Thr Val Asp Pro Val Gln
450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
                485                 490                 495

Glu Val Ile Lys Lys Asn Met Ala Asp Phe Thr Gly Glu Ala Pro Gln
            500                 505                 510

Gly Asn Gly Glu Asn Lys Pro Ser Glu Asn Gly Lys Val Ser Thr Gly
        515                 520                 525

Thr Val Glu Asn Gln Pro Thr Glu Asn Lys Pro Ala Asp Ser Leu Pro
530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
610                 615                 620

Lys Lys Asn Leu Ser Asp Phe Ile Ala
625                 630

<210> SEQ ID NO 355
<211> LENGTH: 633
<212> TYPE: PRT
<213> ORGANISM: Artificial Sequence
<220> FEATURE:
<223> OTHER INFORMATION: Unknown Organism
```

<400> SEQUENCE: 355

```
Met Gln Ile Gly Gln Pro Thr Leu Pro Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp His Asn His Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
    130                 135                 140

Gly Asp Gly His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
    290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
    370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
```

-continued

```
                405                 410                 415
Lys Ala Gln Glu Asn Ser Lys Leu Asp Glu Lys Val Glu Pro Lys
            420                 425                 430

Thr Ser Glu Lys Val Glu Lys Glu Lys Leu Ser Glu Thr Gly Asn Ser
        435                 440                 445

Thr Ser Asn Ser Thr Leu Glu Glu Val Pro Thr Val Asp Pro Val Gln
    450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
                485                 490                 495

Glu Val Ile Lys Lys Asn Met Ala Asp Phe Thr Gly Glu Ala Pro Gln
            500                 505                 510

Gly Asn Gly Glu Asn Lys Pro Ser Glu Asn Gly Lys Val Ser Thr Gly
        515                 520                 525

Thr Val Glu Asn Gln Pro Thr Glu Asn Lys Pro Ala Asp Ser Leu Pro
    530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
    610                 615                 620

Lys Lys Asn Leu Ser Asp Phe Ile Ala
625                 630

<210> SEQ ID NO 356
<211> LENGTH: 569
<212> TYPE: PRT
<213> ORGANISM: Artificial Sequence
<220> FEATURE:
<223> OTHER INFORMATION: Unknown Organism

<400> SEQUENCE: 356

Met Asp Leu Thr Glu Glu Gln Ile Lys Ala Ala Gln Lys His Leu Glu
1               5                   10                  15

Glu Val Lys Thr Ser His Asn Gly Leu Asp Ser Leu Ser Ser His Glu
            20                  25                  30

Gln Asp Tyr Pro Gly Asn Ala Lys Glu Met Lys Asp Leu Asp Lys Lys
        35                  40                  45

Ile Glu Glu Lys Ile Ala Gly Ile Met Lys Gln Tyr Gly Val Lys Arg
    50                  55                  60

Glu Ser Ile Val Val Asn Lys Glu Lys Asn Ala Ile Ile Tyr Pro His
65                  70                  75                  80

Gly Asp Gly His His Ala Asp Pro Ile Asp Glu His Lys Pro Val Gly
                85                  90                  95

Ile Gly His Ser His Ser Asn Tyr Glu Leu Phe Lys Pro Glu Glu Gly
            100                 105                 110

Val Ala Lys Lys Glu Gly Asn Lys Val Tyr Thr Gly Glu Glu Leu Thr
        115                 120                 125

Asn Val Val Asn Leu Leu Lys Asn Ser Thr Phe Asn Asn Gln Asn Phe
```

-continued

```
            130                 135                 140
Thr Leu Ala Asn Gly Gln Lys Arg Val Ser Phe Ser Phe Pro Pro Glu
145                 150                 155                 160
Leu Glu Lys Lys Leu Gly Ile Asn Met Leu Val Lys Leu Ile Thr Pro
                165                 170                 175
Asp Gly Lys Val Leu Glu Lys Val Ser Gly Lys Val Phe Gly Glu Gly
                180                 185                 190
Val Gly Asn Ile Ala Asn Phe Glu Leu Asp Gln Pro Tyr Leu Pro Gly
            195                 200                 205
Gln Thr Phe Lys Tyr Thr Ile Ala Ser Lys Asp Tyr Pro Glu Val Ser
210                 215                 220
Tyr Asp Gly Thr Phe Thr Val Pro Thr Ser Leu Ala Tyr Lys Met Ala
225                 230                 235                 240
Ser Gln Thr Ile Phe Tyr Pro Phe His Ala Gly Asp Thr Tyr Leu Arg
                245                 250                 255
Val Asn Pro Gln Phe Ala Val Pro Lys Gly Thr Asp Ala Leu Val Arg
                260                 265                 270
Val Phe Asp Glu Phe His Gly Asn Ala Tyr Leu Glu Asn Asn Tyr Lys
            275                 280                 285
Val Gly Glu Ile Lys Leu Pro Ile Pro Lys Leu Asn Gln Gly Thr Thr
            290                 295                 300
Arg Thr Ala Gly Asn Lys Ile Pro Val Thr Phe Met Ala Asn Ala Tyr
305                 310                 315                 320
Leu Asp Asn Gln Ser Thr Tyr Ile Val Glu Val Pro Ile Leu Glu Lys
                325                 330                 335
Glu Asn Gln Thr Asp Lys Pro Ser Ile Leu Pro Gln Phe Lys Arg Asn
                340                 345                 350
Lys Ala Gln Glu Asn Ser Lys Leu Asp Glu Lys Val Glu Glu Pro Lys
            355                 360                 365
Thr Ser Glu Lys Val Glu Lys Glu Leu Ser Glu Thr Gly Asn Ser
370                 375                 380
Thr Ser Asn Ser Thr Leu Glu Glu Val Pro Thr Val Asp Pro Val Gln
385                 390                 395                 400
Glu Lys Val Ala Lys Phe Ala Glu Ser Tyr Gly Met Lys Leu Glu Asn
                405                 410                 415
Val Leu Phe Asn Met Asp Gly Thr Ile Glu Leu Tyr Leu Pro Ser Gly
            420                 425                 430
Glu Val Ile Lys Lys Asn Met Ala Asp Phe Thr Gly Glu Ala Pro Gln
            435                 440                 445
Gly Asn Gly Glu Asn Lys Pro Ser Glu Asn Gly Lys Val Ser Thr Gly
450                 455                 460
Thr Val Glu Asn Gln Pro Thr Glu Asn Lys Pro Ala Asp Ser Leu Pro
465                 470                 475                 480
Glu Ala Pro Asn Glu Lys Pro Val Lys Pro Glu Asn Ser Thr Asp Asn
                485                 490                 495
Gly Met Leu Asn Pro Glu Gly Asn Val Gly Ser Asp Pro Met Leu Asp
                500                 505                 510
Pro Ala Leu Glu Glu Ala Pro Ala Val Asp Pro Val Gln Glu Lys Leu
            515                 520                 525
Glu Lys Phe Thr Ala Ser Tyr Gly Leu Gly Leu Asp Ser Val Ile Phe
            530                 535                 540
Asn Met Asp Gly Thr Ile Glu Leu Arg Leu Pro Ser Gly Glu Val Ile
545                 550                 555                 560
```

```
Lys Lys Asn Leu Ser Asp Phe Ile Ala
            565
```

<210> SEQ ID NO 357
<211> LENGTH: 633
<212> TYPE: PRT
<213> ORGANISM: Artificial Sequence
<220> FEATURE:
<223> OTHER INFORMATION: Unknown Organism

<400> SEQUENCE: 357

```
Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp Ser Asn His Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
    130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
    290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350
```

```
Val Gly Glu Ile Lys Leu Pro Ile Pro Lys Leu Asn Gln Gly Thr Thr
            355                 360                 365

Arg Thr Ala Gly Asn Lys Ile Pro Val Thr Phe Met Ala Asn Ala Tyr
        370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
        435                 440                 445

Thr Ser Asn Ser Thr Leu Glu Glu Val Pro Thr Val Asp Pro Val Gln
    450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
                485                 490                 495

Glu Val Ile Lys Lys Asn Met Ala Asp Phe Thr Gly Glu Ala Pro Gln
            500                 505                 510

Gly Asn Gly Glu Asn Lys Pro Ser Glu Asn Gly Lys Val Ser Thr Gly
        515                 520                 525

Thr Val Glu Asn Gln Pro Thr Glu Asn Lys Pro Ala Asp Ser Leu Pro
    530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
    610                 615                 620

Lys Lys Asn Leu Ser Asp Phe Ile Ala
625                 630

<210> SEQ ID NO 358
<211> LENGTH: 633
<212> TYPE: PRT
<213> ORGANISM: Artificial Sequence
<220> FEATURE:
<223> OTHER INFORMATION: Unknown Organism

<400> SEQUENCE: 358

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp Ser Asn His Tyr Phe Phe Lys
    50                  55                  60

Lys Asp Leu Thr Glu Glu Gln Ile Lys Ala Ala Gln Lys His Leu Glu
65                  70                  75                  80
```

```
Glu Val Lys Thr Ser His Asn Gly Leu Asp Ser Leu Ser His Glu
            85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
            115                 120                 125

Glu Ser Ile Val Val Asn Lys Glu Lys Asn Ala Ile Ile Tyr Pro Ser
    130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
    195                 200                 205

Thr Leu Ala Asn Gly Gln Lys Arg Val Ser Phe Ser Phe Pro Pro Glu
210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
            275                 280                 285

Tyr Asp Gly Thr Phe Thr Val Pro Thr Ser Leu Ala Tyr Lys Met Ala
290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
            355                 360                 365

Arg Thr Ala Gly Asn Lys Ile Pro Val Thr Phe Met Ala Asn Ala Tyr
    370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
            435                 440                 445

Thr Ser Asn Ser Thr Leu Glu Glu Val Pro Thr Val Asp Pro Val Gln
    450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
            485                 490                 495
```

-continued

```
Glu Val Ile Lys Lys Asn Met Ala Asp Phe Thr Gly Glu Ala Pro Gln
            500                 505                 510

Gly Asn Gly Glu Asn Lys Pro Ser Glu Asn Gly Lys Val Ser Thr Gly
        515                 520                 525

Thr Val Glu Asn Gln Pro Thr Glu Asn Lys Pro Ala Asp Ser Leu Pro
    530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
    610                 615                 620

Lys Lys Asn Leu Ser Asp Phe Ile Ala
625                 630

<210> SEQ ID NO 359
<211> LENGTH: 633
<212> TYPE: PRT
<213> ORGANISM: Artificial Sequence
<220> FEATURE:
<223> OTHER INFORMATION: Unknown Organism

<400> SEQUENCE: 359

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp Ser Asn His Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
    130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220
```

```
Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
            245                 250                 255

Val Gly Asn Ile Ala Asn Phe Glu Leu Asp Gln Pro Tyr Leu Pro Gly
        260                 265                 270

Gln Thr Phe Lys Tyr Thr Ile Ala Ser Lys Asp Tyr Pro Glu Val Ser
    275                 280                 285

Tyr Asp Gly Thr Phe Thr Val Pro Thr Ser Leu Ala Tyr Lys Met Ala
290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
            325                 330                 335

Val Phe Asp Glu Phe His Gly Asn Ala Tyr Leu Glu Asn Asn Tyr Lys
        340                 345                 350

Val Gly Glu Ile Lys Leu Pro Ile Pro Lys Leu Asn Gln Gly Thr Thr
    355                 360                 365

Arg Thr Ala Gly Asn Lys Ile Pro Val Thr Phe Met Ala Asn Ala Tyr
370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
            405                 410                 415

Lys Ala Gln Glu Asn Ser Lys Leu Asp Glu Lys Val Glu Glu Pro Lys
        420                 425                 430

Thr Ser Glu Lys Val Glu Lys Glu Lys Leu Ser Glu Thr Gly Asn Ser
    435                 440                 445

Thr Ser Asn Ser Thr Leu Glu Glu Val Pro Thr Val Asp Pro Val Gln
450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
            485                 490                 495

Glu Val Ile Lys Lys Asn Met Ala Asp Phe Thr Gly Glu Ala Pro Gln
        500                 505                 510

Gly Asn Gly Glu Asn Lys Pro Ser Glu Asn Gly Lys Val Ser Thr Gly
    515                 520                 525

Thr Val Glu Asn Gln Pro Thr Glu Asn Lys Pro Ala Asp Ser Leu Pro
530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
            565                 570                 575

Pro Ala Leu Glu Glu Ala Pro Ala Val Asp Pro Val Gln Glu Lys Leu
        580                 585                 590

Glu Lys Phe Thr Ala Ser Tyr Gly Leu Gly Leu Asp Ser Val Ile Phe
    595                 600                 605

Asn Met Asp Gly Thr Ile Glu Leu Arg Leu Pro Ser Gly Glu Val Ile
610                 615                 620

Lys Lys Asn Leu Ser Asp Phe Ile Ala
625                 630
```

<210> SEQ ID NO 360
<211> LENGTH: 633
<212> TYPE: PRT
<213> ORGANISM: Artificial Sequence
<220> FEATURE:
<223> OTHER INFORMATION: Unknown Organism

<400> SEQUENCE: 360

```
Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp His Asn Ser Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
    130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
    275                 280                 285

Tyr Asp Gly Thr Phe Thr Val Pro Thr Ser Leu Ala Tyr Lys Met Ala
290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
```

```
                    370                 375                 380
Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
                420                 425                 430

Thr Ser Glu Lys Val Glu Lys Glu Lys Leu Ser Glu Thr Gly Asn Ser
                435                 440                 445

Thr Ser Asn Ser Thr Leu Glu Glu Val Pro Thr Val Asp Pro Val Gln
450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
                485                 490                 495

Glu Val Ile Lys Lys Asn Met Ala Asp Phe Thr Gly Glu Ala Pro Gln
                500                 505                 510

Gly Asn Gly Glu Asn Lys Pro Ser Glu Asn Gly Lys Val Ser Thr Gly
                515                 520                 525

Thr Val Glu Asn Gln Pro Thr Glu Asn Lys Pro Ala Asp Ser Leu Pro
                530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
                580                 585                 590

Glu Lys Phe Thr Ala Ser Tyr Gly Leu Gly Leu Asp Ser Val Ile Phe
                595                 600                 605

Asn Met Asp Gly Thr Ile Glu Leu Arg Leu Pro Ser Gly Glu Val Ile
                610                 615                 620

Lys Lys Asn Leu Ser Asp Phe Ile Ala
625                 630

<210> SEQ ID NO 361
<211> LENGTH: 633
<212> TYPE: PRT
<213> ORGANISM: Artificial Sequence
<220> FEATURE:
<223> OTHER INFORMATION: Unknown Organism

<400> SEQUENCE: 361

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
                20                  25                  30

Glu Asp Gly Tyr Gly Phe Asp Ala Asn Arg Ile Ile Ala Glu Asp Glu
            35                  40                  45

Ser Gly Phe Val Met Ser His Gly Asp Ser Asn His Tyr Phe Phe Lys
        50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
```

-continued

```
            100                 105                 110
Ile Glu Glu Lys Ile Ala Gly Ile Met Lys Gln Tyr Gly Val Lys Arg
            115                 120                 125

Glu Ser Ile Val Val Asn Lys Glu Lys Asn Ala Ile Ile Tyr Pro His
    130                 135                 140

Gly Asp His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
    290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
    370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
        435                 440                 445

Thr Ser Asn Ser Thr Leu Glu Glu Val Pro Thr Val Asp Pro Val Gln
    450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
                485                 490                 495

Glu Val Ile Lys Lys Asn Met Ala Asp Phe Thr Gly Glu Ala Pro Gln
            500                 505                 510

Gly Asn Gly Glu Asn Lys Pro Ser Glu Asn Gly Lys Val Ser Thr Gly
        515                 520                 525
```

-continued

```
Thr Val Glu Asn Gln Pro Thr Glu Asn Lys Pro Ala Asp Ser Leu Pro
        530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
    610                 615                 620

Lys Lys Asn Leu Ser Asp Phe Ile Ala
625                 630

<210> SEQ ID NO 362
<211> LENGTH: 633
<212> TYPE: PRT
<213> ORGANISM: Artificial Sequence
<220> FEATURE:
<223> OTHER INFORMATION: Unknown Organism

<400> SEQUENCE: 362

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp His Asn Ser Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro His
    130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255
```

```
Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
        290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
        435                 440                 445

Thr Ser Asn Ser Thr Leu Glu Glu Val Pro Thr Val Asp Pro Val Gln
    450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
                485                 490                 495

Glu Val Ile Lys Lys Asn Met Ala Asp Phe Thr Gly Glu Ala Pro Gln
            500                 505                 510

Gly Asn Gly Glu Asn Lys Pro Ser Glu Asn Gly Lys Val Ser Thr Gly
        515                 520                 525

Thr Val Glu Asn Gln Pro Thr Glu Asn Lys Pro Ala Asp Ser Leu Pro
    530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
    610                 615                 620

Lys Lys Asn Leu Ser Asp Phe Ile Ala
625                 630

<210> SEQ ID NO 363
<211> LENGTH: 633
<212> TYPE: PRT
<213> ORGANISM: Artificial Sequence
<220> FEATURE:
```

-continued

<223> OTHER INFORMATION: Unknown Organism

<400> SEQUENCE: 363

```
Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp Ser Asn His Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro His
    130                 135                 140

Gly Asp Gly His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
    290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
    370                 375                 380

Leu Asp Asn Gln Ser Thr Tyr Ile Val Glu Val Pro Ile Leu Glu Lys
385                 390                 395                 400
```

```
Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
        435                 440                 445

Thr Ser Asn Ser Thr Leu Glu Glu Val Pro Thr Val Asp Pro Val Gln
    450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
                485                 490                 495

Glu Val Ile Lys Lys Asn Met Ala Asp Phe Thr Gly Glu Ala Pro Gln
            500                 505                 510

Gly Asn Gly Glu Asn Lys Pro Ser Glu Asn Gly Lys Val Ser Thr Gly
        515                 520                 525

Thr Val Glu Asn Gln Pro Thr Glu Asn Lys Pro Ala Asp Ser Leu Pro
    530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
    610                 615                 620

Lys Lys Asn Leu Ser Asp Phe Ile Ala
625                 630

<210> SEQ ID NO 364
<211> LENGTH: 633
<212> TYPE: PRT
<213> ORGANISM: Artificial Sequence
<220> FEATURE:
<223> OTHER INFORMATION: Unknown Organism

<400> SEQUENCE: 364

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp His Asn Ser Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125
```

-continued

```
Glu Ser Ile Val Val Asn Lys Glu Lys Asn Ala Ile Ile Tyr Pro His
    130                 135                 140
Gly Asp Gly His His Ala Asp Pro Ile Asp Glu His Lys Pro Val Gly
145                 150                 155                 160
Ile Gly His Ser His Ser Asn Tyr Glu Leu Phe Lys Pro Glu Glu Gly
                165                 170                 175
Val Ala Lys Lys Glu Gly Asn Lys Val Tyr Thr Gly Glu Glu Leu Thr
            180                 185                 190
Asn Val Val Asn Leu Leu Lys Asn Ser Thr Phe Asn Gln Asn Phe
        195                 200                 205
Thr Leu Ala Asn Gly Gln Lys Arg Val Ser Phe Ser Phe Pro Pro Glu
    210                 215                 220
Leu Glu Lys Lys Leu Gly Ile Asn Met Leu Val Lys Leu Ile Thr Pro
225                 230                 235                 240
Asp Gly Lys Val Leu Glu Lys Val Ser Gly Lys Val Phe Gly Glu Gly
                245                 250                 255
Val Gly Asn Ile Ala Asn Phe Glu Leu Asp Gln Pro Tyr Leu Pro Gly
            260                 265                 270
Gln Thr Phe Lys Tyr Thr Ile Ala Ser Lys Asp Tyr Pro Glu Val Ser
        275                 280                 285
Tyr Asp Gly Thr Phe Thr Val Pro Thr Ser Leu Ala Tyr Lys Met Ala
    290                 295                 300
Ser Gln Thr Ile Phe Tyr Pro Phe His Ala Gly Asp Thr Tyr Leu Arg
305                 310                 315                 320
Val Asn Pro Gln Phe Ala Val Pro Lys Gly Thr Asp Ala Leu Val Arg
                325                 330                 335
Val Phe Asp Glu Phe His Gly Asn Ala Tyr Leu Glu Asn Asn Tyr Lys
            340                 345                 350
Val Gly Glu Ile Lys Leu Pro Ile Pro Lys Leu Asn Gln Gly Thr Thr
        355                 360                 365
Arg Thr Ala Gly Asn Lys Ile Pro Val Thr Phe Met Ala Asn Ala Tyr
    370                 375                 380
Leu Asp Asn Gln Ser Thr Tyr Ile Val Glu Val Pro Ile Leu Glu Lys
385                 390                 395                 400
Glu Asn Gln Thr Asp Lys Pro Ser Ile Leu Pro Gln Phe Lys Arg Asn
                405                 410                 415
Lys Ala Gln Glu Asn Ser Lys Leu Asp Glu Lys Val Glu Glu Pro Lys
            420                 425                 430
Thr Ser Glu Lys Val Glu Lys Glu Lys Leu Ser Glu Thr Gly Asn Ser
        435                 440                 445
Thr Ser Asn Ser Thr Leu Glu Glu Val Pro Thr Val Asp Pro Val Gln
    450                 455                 460
Glu Lys Val Ala Lys Phe Ala Glu Ser Tyr Gly Met Lys Leu Glu Asn
465                 470                 475                 480
Val Leu Phe Asn Met Asp Gly Thr Ile Glu Leu Tyr Leu Pro Ser Gly
                485                 490                 495
Glu Val Ile Lys Lys Asn Met Ala Asp Phe Thr Gly Glu Ala Pro Gln
            500                 505                 510
Gly Asn Gly Glu Asn Lys Pro Ser Glu Asn Gly Lys Val Ser Thr Gly
        515                 520                 525
Thr Val Glu Asn Gln Pro Thr Glu Asn Lys Pro Ala Asp Ser Leu Pro
    530                 535                 540
Glu Ala Pro Asn Glu Lys Pro Val Lys Pro Glu Asn Ser Thr Asp Asn
```

-continued

```
                545                 550                 555                 560
Gly Met Leu Asn Pro Glu Gly Asn Val Gly Ser Asp Pro Met Leu Asp
                565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
    610                 615                 620

Lys Lys Asn Leu Ser Asp Phe Ile Ala
625                 630
```

<210> SEQ ID NO 365
<211> LENGTH: 633
<212> TYPE: PRT
<213> ORGANISM: Artificial Sequence
<220> FEATURE:
<223> OTHER INFORMATION: Unknown Organism

<400> SEQUENCE: 365

```
Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp His Asn Ser Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
    130                 135                 140

Gly Asp Gly His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
```

```
                    275                 280                 285
Tyr Asp Gly Thr Phe Thr Val Pro Thr Ser Leu Ala Tyr Lys Met Ala
            290                 295                 300
Ser Gln Thr Ile Phe Tyr Pro Phe His Ala Gly Asp Thr Tyr Leu Arg
305                 310                 315                 320
Val Asn Pro Gln Phe Ala Val Pro Lys Gly Thr Asp Ala Leu Val Arg
                325                 330                 335
Val Phe Asp Glu Phe His Gly Asn Ala Tyr Leu Glu Asn Asn Tyr Lys
            340                 345                 350
Val Gly Glu Ile Lys Leu Pro Ile Pro Lys Leu Asn Gln Gly Thr Thr
        355                 360                 365
Arg Thr Ala Gly Asn Lys Ile Pro Val Thr Phe Met Ala Asn Ala Tyr
    370                 375                 380
Leu Asp Asn Gln Ser Thr Tyr Ile Val Glu Val Pro Ile Leu Glu Lys
385                 390                 395                 400
Glu Asn Gln Thr Asp Lys Pro Ser Ile Leu Pro Gln Phe Lys Arg Asn
                405                 410                 415
Lys Ala Gln Glu Asn Ser Lys Leu Asp Glu Lys Val Glu Glu Pro Lys
            420                 425                 430
Thr Ser Glu Lys Val Glu Lys Glu Lys Leu Ser Glu Thr Gly Asn Ser
        435                 440                 445
Thr Ser Asn Ser Thr Leu Glu Glu Val Pro Thr Val Asp Pro Val Gln
    450                 455                 460
Glu Lys Val Ala Lys Phe Ala Glu Ser Tyr Gly Met Lys Leu Glu Asn
465                 470                 475                 480
Val Leu Phe Asn Met Asp Gly Thr Ile Glu Leu Tyr Leu Pro Ser Gly
                485                 490                 495
Glu Val Ile Lys Lys Asn Met Ala Asp Phe Thr Gly Glu Ala Pro Gln
            500                 505                 510
Gly Asn Gly Glu Asn Lys Pro Ser Glu Asn Gly Lys Val Ser Thr Gly
        515                 520                 525
Thr Val Glu Asn Gln Pro Thr Glu Asn Lys Pro Ala Asp Ser Leu Pro
    530                 535                 540
Glu Ala Pro Asn Glu Lys Pro Val Lys Pro Glu Asn Ser Thr Asp Asn
545                 550                 555                 560
Gly Met Leu Asn Pro Glu Gly Asn Val Gly Ser Pro Met Leu Asp
                565                 570                 575
Pro Ala Leu Glu Glu Ala Pro Ala Val Asp Pro Val Gln Glu Lys Leu
            580                 585                 590
Glu Lys Phe Thr Ala Ser Tyr Gly Leu Gly Leu Asp Ser Val Ile Phe
        595                 600                 605
Asn Met Asp Gly Thr Ile Glu Leu Arg Leu Pro Ser Gly Glu Val Ile
    610                 615                 620
Lys Lys Asn Leu Ser Asp Phe Ile Ala
625                 630

<210> SEQ ID NO 366
<211> LENGTH: 627
<212> TYPE: PRT
<213> ORGANISM: Artificial Sequence
<220> FEATURE:
<223> OTHER INFORMATION: Unknown Organism

<400> SEQUENCE: 366

Met Gln Ile Gly Gln Pro Thr Leu Pro Asn Asn Ser Leu Ala Thr Pro
```

-continued

```
1               5                   10                  15
Ser Pro Ser Leu Pro Ile Asn Pro Gly Thr Ser His Glu Lys His Glu
                20                  25                  30
Glu Asp Gly Tyr Gly Phe Asp Ala Asn Arg Ile Ile Ala Glu Asp Glu
                35                  40              45
Ser Gly Phe Val Met Ser Tyr Phe Lys Lys Asp Leu Thr Glu Glu
    50              55                  60
Gln Ile Lys Ala Ala Gln Lys His Leu Glu Glu Val Lys Thr Ser His
65                  70                  75                  80
Asn Gly Leu Asp Ser Leu Ser Ser His Glu Gln Asp Tyr Pro Gly Asn
                85                  90                  95
Ala Lys Glu Met Lys Asp Leu Asp Lys Lys Ile Glu Glu Lys Ile Ala
                100                 105                 110
Gly Ile Met Lys Gln Tyr Gly Val Lys Arg Glu Ser Ile Val Val Asn
                115                 120                 125
Lys Glu Lys Asn Ala Ile Ile Tyr Pro His Gly Asp His His His Ala
        130                 135                 140
Asp Pro Ile Asp Glu His Lys Pro Val Gly Ile Gly His Ser His Ser
145                 150                 155                 160
Asn Tyr Glu Leu Phe Lys Pro Glu Glu Gly Val Ala Lys Lys Glu Gly
                165                 170                 175
Asn Lys Val Tyr Thr Gly Glu Glu Leu Thr Asn Val Val Asn Leu Leu
                180                 185                 190
Lys Asn Ser Thr Phe Asn Asn Gln Asn Phe Thr Leu Ala Asn Gly Gln
        195                 200                 205
Lys Arg Val Ser Phe Ser Phe Pro Pro Glu Leu Glu Lys Lys Leu Gly
        210                 215                 220
Ile Asn Met Leu Val Lys Leu Ile Thr Pro Asp Gly Lys Val Leu Glu
225                 230                 235                 240
Lys Val Ser Gly Lys Val Phe Gly Glu Val Gly Asn Ile Ala Asn
                245                 250                 255
Phe Glu Leu Asp Gln Pro Tyr Leu Pro Gly Gln Thr Phe Lys Tyr Thr
                260                 265                 270
Ile Ala Ser Lys Asp Tyr Pro Glu Val Ser Tyr Asp Gly Thr Phe Thr
        275                 280                 285
Val Pro Thr Ser Leu Ala Tyr Lys Met Ala Ser Gln Thr Ile Phe Tyr
        290                 295                 300
Pro Phe His Ala Gly Asp Thr Tyr Leu Arg Val Asn Pro Gln Phe Ala
305                 310                 315                 320
Val Pro Lys Gly Thr Asp Ala Leu Val Arg Val Phe Asp Glu Phe His
                325                 330                 335
Gly Asn Ala Tyr Leu Glu Asn Tyr Lys Val Gly Glu Ile Lys Leu
                340                 345                 350
Pro Ile Pro Lys Leu Asn Gln Gly Thr Thr Arg Thr Ala Gly Asn Lys
        355                 360                 365
Ile Pro Val Thr Phe Met Ala Asn Ala Tyr Leu Asp Asn Gln Ser Thr
        370                 375                 380
Tyr Ile Val Glu Val Pro Ile Leu Glu Lys Glu Asn Gln Thr Asp Lys
385                 390                 395                 400
Pro Ser Ile Leu Pro Gln Phe Lys Arg Asn Lys Ala Gln Glu Asn Ser
                405                 410                 415
Lys Leu Asp Glu Lys Val Glu Glu Pro Lys Thr Ser Glu Lys Val Glu
                420                 425                 430
```

```
Lys Glu Lys Leu Ser Glu Thr Gly Asn Ser Thr Ser Asn Ser Thr Leu
            435                 440                 445

Glu Glu Val Pro Thr Val Asp Pro Val Gln Glu Lys Val Ala Lys Phe
    450                 455                 460

Ala Glu Ser Tyr Gly Met Lys Leu Glu Asn Val Leu Phe Asn Met Asp
465                 470                 475                 480

Gly Thr Ile Glu Leu Tyr Leu Pro Ser Gly Glu Val Ile Lys Lys Asn
                485                 490                 495

Met Ala Asp Phe Thr Gly Glu Ala Pro Gln Gly Asn Gly Glu Asn Lys
            500                 505                 510

Pro Ser Glu Asn Gly Lys Val Ser Thr Gly Thr Val Glu Asn Gln Pro
            515                 520                 525

Thr Glu Asn Lys Pro Ala Asp Ser Leu Pro Glu Ala Pro Asn Glu Lys
    530                 535                 540

Pro Val Lys Pro Glu Asn Ser Thr Asp Asn Gly Met Leu Asn Pro Glu
545                 550                 555                 560

Gly Asn Val Gly Ser Asp Pro Met Leu Asp Pro Ala Leu Glu Glu Ala
                565                 570                 575

Pro Ala Val Asp Pro Val Gln Glu Lys Leu Glu Lys Phe Thr Ala Ser
            580                 585                 590

Tyr Gly Leu Gly Leu Asp Ser Val Ile Phe Asn Met Asp Gly Thr Ile
                595                 600                 605

Glu Leu Arg Leu Pro Ser Gly Glu Val Ile Lys Lys Asn Leu Ser Asp
    610                 615                 620

Phe Ile Ala
625

<210> SEQ ID NO 367
<211> LENGTH: 627
<212> TYPE: PRT
<213> ORGANISM: Artificial Sequence
<220> FEATURE:
<223> OTHER INFORMATION: Unknown Organism

<400> SEQUENCE: 367

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp His Asn His Tyr Phe Phe Lys
    50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ala
    130                 135                 140

Asp Pro Ile Asp Glu His Lys Pro Val Gly Ile Gly His Ser His Ser
145                 150                 155                 160
```

```
Asn Tyr Glu Leu Phe Lys Pro Glu Gly Val Ala Lys Lys Glu Gly
                165                 170                 175

Asn Lys Val Tyr Thr Gly Glu Leu Thr Asn Val Val Asn Leu Leu
            180                 185                 190

Lys Asn Ser Thr Phe Asn Asn Gln Asn Phe Thr Leu Ala Asn Gly Gln
        195                 200                 205

Lys Arg Val Ser Phe Ser Phe Pro Glu Leu Glu Lys Lys Leu Gly
    210                 215                 220

Ile Asn Met Leu Val Lys Leu Ile Thr Pro Asp Gly Lys Val Leu Glu
225                 230                 235                 240

Lys Val Ser Gly Lys Val Phe Glu Gly Val Gly Asn Ile Ala Asn
                245                 250                 255

Phe Glu Leu Asp Gln Pro Tyr Leu Pro Gly Gln Thr Phe Lys Tyr Thr
            260                 265                 270

Ile Ala Ser Lys Asp Tyr Pro Glu Val Ser Tyr Asp Gly Thr Phe Thr
        275                 280                 285

Val Pro Thr Ser Leu Ala Tyr Lys Met Ala Ser Gln Thr Ile Phe Tyr
    290                 295                 300

Pro Phe His Ala Gly Asp Thr Tyr Leu Arg Val Asn Pro Gln Phe Ala
305                 310                 315                 320

Val Pro Lys Gly Thr Asp Ala Leu Val Arg Val Phe Asp Glu Phe His
                325                 330                 335

Gly Asn Ala Tyr Leu Glu Asn Asn Tyr Lys Val Gly Glu Ile Lys Leu
            340                 345                 350

Pro Ile Pro Lys Leu Asn Gln Gly Thr Thr Arg Thr Ala Gly Asn Lys
        355                 360                 365

Ile Pro Val Thr Phe Met Ala Asn Ala Tyr Leu Asp Asn Gln Ser Thr
    370                 375                 380

Tyr Ile Val Glu Val Pro Ile Leu Glu Lys Glu Asn Gln Thr Asp Lys
385                 390                 395                 400

Pro Ser Ile Leu Pro Gln Phe Lys Arg Asn Lys Ala Gln Glu Asn Ser
                405                 410                 415

Lys Leu Asp Glu Lys Val Glu Glu Pro Lys Thr Ser Glu Lys Val Glu
            420                 425                 430

Lys Glu Lys Leu Ser Glu Thr Gly Asn Ser Thr Ser Asn Ser Thr Leu
        435                 440                 445

Glu Glu Val Pro Thr Val Asp Pro Val Gln Glu Lys Val Ala Lys Phe
450                 455                 460

Ala Glu Ser Tyr Gly Met Lys Leu Glu Asn Val Leu Phe Asn Met Asp
465                 470                 475                 480

Gly Thr Ile Glu Leu Tyr Leu Pro Ser Gly Glu Val Ile Lys Lys Asn
                485                 490                 495

Met Ala Asp Phe Thr Gly Glu Ala Pro Gln Gly Asn Gly Glu Asn Lys
            500                 505                 510

Pro Ser Glu Asn Gly Lys Val Ser Thr Gly Thr Val Glu Asn Gln Pro
        515                 520                 525

Thr Glu Asn Lys Pro Ala Asp Ser Leu Pro Glu Ala Pro Asn Glu Lys
    530                 535                 540

Pro Val Lys Pro Glu Asn Ser Thr Asp Asn Gly Met Leu Asn Pro Glu
545                 550                 555                 560

Gly Asn Val Gly Ser Asp Pro Met Leu Asp Pro Ala Leu Glu Glu Ala
                565                 570                 575
```

```
Pro Ala Val Asp Pro Val Gln Glu Lys Leu Glu Lys Phe Thr Ala Ser
            580                 585                 590

Tyr Gly Leu Gly Leu Asp Ser Val Ile Phe Asn Met Asp Gly Thr Ile
        595                 600                 605

Glu Leu Arg Leu Pro Ser Gly Glu Val Ile Lys Asn Leu Ser Asp
    610                 615                 620

Phe Ile Ala
625

<210> SEQ ID NO 368
<211> LENGTH: 621
<212> TYPE: PRT
<213> ORGANISM: Artificial Sequence
<220> FEATURE:
<223> OTHER INFORMATION: Unknown Organism

<400> SEQUENCE: 368

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser Tyr Phe Phe Lys Lys Asp Leu Thr Glu Glu
    50                  55                  60

Gln Ile Lys Ala Ala Gln Lys His Leu Glu Glu Val Lys Thr Ser His
65                  70                  75                  80

Asn Gly Leu Asp Ser Leu Ser Ser His Glu Gln Asp Tyr Pro Gly Asn
                85                  90                  95

Ala Lys Glu Met Lys Asp Leu Asp Lys Lys Ile Glu Glu Lys Ile Ala
            100                 105                 110

Gly Ile Met Lys Gln Tyr Gly Val Lys Arg Glu Ser Ile Val Val Asn
        115                 120                 125

Lys Glu Lys Asn Ala Ile Ile Tyr Pro Ala Asp Pro Ile Asp Glu His
    130                 135                 140

Lys Pro Val Gly Ile Gly His Ser His Ser Asn Tyr Glu Leu Phe Lys
145                 150                 155                 160

Pro Glu Glu Gly Val Ala Lys Lys Glu Gly Asn Lys Val Tyr Thr Gly
                165                 170                 175

Glu Glu Leu Thr Asn Val Val Asn Leu Leu Lys Asn Ser Thr Phe Asn
            180                 185                 190

Asn Gln Asn Phe Thr Leu Ala Asn Gly Gln Lys Arg Val Ser Phe Ser
        195                 200                 205

Phe Pro Pro Glu Leu Glu Lys Lys Leu Gly Ile Asn Met Leu Val Lys
    210                 215                 220

Leu Ile Thr Pro Asp Gly Lys Val Leu Glu Lys Val Ser Gly Lys Val
225                 230                 235                 240

Phe Gly Glu Gly Val Gly Asn Ile Ala Asn Phe Glu Leu Asp Gln Pro
                245                 250                 255

Tyr Leu Pro Gly Gln Thr Phe Lys Tyr Thr Ile Ala Ser Lys Asp Tyr
            260                 265                 270

Pro Glu Val Ser Tyr Asp Gly Thr Phe Thr Val Pro Thr Ser Leu Ala
        275                 280                 285

Tyr Lys Met Ala Ser Gln Thr Ile Phe Tyr Pro Phe His Ala Gly Asp
    290                 295                 300
```

-continued

```
Thr Tyr Leu Arg Val Asn Pro Gln Phe Ala Val Pro Lys Gly Thr Asp
305                 310                 315                 320

Ala Leu Val Arg Val Phe Asp Glu Phe His Gly Asn Ala Tyr Leu Glu
                325                 330                 335

Asn Asn Tyr Lys Val Gly Glu Ile Lys Leu Pro Ile Pro Lys Leu Asn
            340                 345                 350

Gln Gly Thr Thr Arg Thr Ala Gly Asn Lys Ile Pro Val Thr Phe Met
        355                 360                 365

Ala Asn Ala Tyr Leu Asp Asn Gln Ser Thr Tyr Ile Val Glu Val Pro
    370                 375                 380

Ile Leu Glu Lys Glu Asn Gln Thr Asp Lys Pro Ser Ile Leu Pro Gln
385                 390                 395                 400

Phe Lys Arg Asn Lys Ala Gln Glu Asn Ser Lys Leu Asp Glu Lys Val
                405                 410                 415

Glu Glu Pro Lys Thr Ser Glu Lys Val Glu Lys Leu Ser Glu
            420                 425                 430

Thr Gly Asn Ser Thr Ser Asn Ser Thr Leu Glu Glu Val Pro Thr Val
        435                 440                 445

Asp Pro Val Gln Glu Lys Val Ala Lys Phe Ala Glu Ser Tyr Gly Met
    450                 455                 460

Lys Leu Glu Asn Val Leu Phe Asn Met Asp Gly Thr Ile Glu Leu Tyr
465                 470                 475                 480

Leu Pro Ser Gly Glu Val Ile Lys Lys Asn Met Ala Asp Phe Thr Gly
                485                 490                 495

Glu Ala Pro Gln Gly Asn Gly Glu Asn Lys Pro Ser Glu Asn Gly Lys
            500                 505                 510

Val Ser Thr Gly Thr Val Glu Asn Gln Pro Thr Glu Asn Lys Pro Ala
        515                 520                 525

Asp Ser Leu Pro Glu Ala Pro Asn Glu Lys Pro Val Lys Pro Glu Asn
    530                 535                 540

Ser Thr Asp Asn Gly Met Leu Asn Pro Glu Gly Asn Val Gly Ser Asp
545                 550                 555                 560

Pro Met Leu Asp Pro Ala Leu Glu Glu Ala Pro Ala Val Asp Pro Val
                565                 570                 575

Gln Glu Lys Leu Glu Lys Phe Thr Ala Ser Tyr Gly Leu Gly Leu Asp
            580                 585                 590

Ser Val Ile Phe Asn Met Asp Gly Thr Ile Glu Leu Arg Leu Pro Ser
        595                 600                 605

Gly Glu Val Ile Lys Lys Asn Leu Ser Asp Phe Ile Ala
    610                 615                 620

<210> SEQ ID NO 369
<211> LENGTH: 906
<212> TYPE: PRT
<213> ORGANISM: Artificial Sequence
<220> FEATURE:
<223> OTHER INFORMATION: Unknown Organism

<400> SEQUENCE: 369

Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45
```

-continued

```
Ser Gly Phe Val Met Ser His Gly Asp Ser Asn His Tyr Phe Phe Lys
 50                  55                  60

Lys Asp Leu Thr Glu Glu Gln Ile Lys Ala Ala Gln Lys His Leu Glu
 65                  70                  75                  80

Glu Val Lys Thr Ser His Asn Gly Leu Asp Ser Leu Ser Ser His Glu
                 85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
    130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
    210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
    290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
    370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
                405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
        435                 440                 445

Thr Ser Asn Ser Thr Leu Glu Glu Val Pro Thr Val Asp Pro Val Gln
    450                 455                 460

Glu Lys Val Ala Lys Phe Ala Glu Ser Tyr Gly Met Lys Leu Glu Asn
```

-continued

```
            465                 470                 475                 480
Val Leu Phe Asn Met Asp Gly Thr Ile Glu Leu Tyr Leu Pro Ser Gly
                    485                 490                 495
Glu Val Ile Lys Lys Asn Met Ala Asp Phe Thr Gly Glu Ala Pro Gln
                500                 505                 510
Gly Asn Gly Glu Asn Lys Pro Ser Glu Asn Gly Lys Val Ser Thr Gly
                515                 520                 525
Thr Val Glu Asn Gln Pro Thr Glu Asn Lys Pro Ala Asp Ser Leu Pro
            530                 535                 540
Glu Ala Pro Asn Glu Lys Pro Val Lys Pro Glu Asn Ser Thr Asp Asn
545                 550                 555                 560
Gly Met Leu Asn Pro Glu Gly Asn Val Gly Ser Asp Pro Met Leu Asp
                    565                 570                 575
Pro Ala Leu Glu Glu Ala Pro Ala Val Asp Pro Val Gln Glu Lys Leu
                580                 585                 590
Glu Lys Phe Thr Ala Ser Tyr Gly Leu Gly Leu Asp Ser Val Ile Phe
                595                 600                 605
Asn Met Asp Gly Thr Ile Glu Leu Arg Leu Pro Ser Gly Glu Val Ile
            610                 615                 620
Lys Lys Asn Leu Ser Asp Phe Ile Ala Gly Pro Gln Ile Thr Tyr Thr
625                 630                 635                 640
Asp Asp Glu Ile Gln Val Ala Lys Leu Ala Gly Lys Tyr Thr Thr Glu
                    645                 650                 655
Asp Gly Tyr Ile Phe Asp Thr Ser Trp Ile Lys Lys Asp Ser Leu Ser
                660                 665                 670
Glu Ala Glu Arg Ala Ala Ala Gln Ala Tyr Ala Lys Glu Lys Gly Leu
                675                 680                 685
Thr Pro Pro Ser Thr Asp His Gln Asp Ser Gly Asn Thr Glu Ala Lys
            690                 695                 700
Gly Ala Glu Ala Ile Tyr Asn Arg Val Lys Ala Ala Lys Lys Val Pro
705                 710                 715                 720
Leu Asp Arg Met Pro Tyr Asn Leu Gln Tyr Thr Val Glu Val Lys Asn
                    725                 730                 735
Gly Ser Leu Ile Ile Pro His Tyr Asp His Tyr His Asn Ile Lys Phe
                740                 745                 750
Glu Trp Phe Asp Glu Gly Leu Tyr Glu Ala Pro Lys Gly Tyr Ser Leu
                755                 760                 765
Glu Asp Leu Leu Ala Thr Val Lys Tyr Tyr Val Glu Pro Arg Asn Ala
            770                 775                 780
Ser Asp His Val Arg Lys Asn Lys Ala Asp Gln Asp Ser Lys Pro Asp
785                 790                 795                 800
Glu Asp Lys Glu His Asp Glu Val Ser Glu Pro Thr His Pro Glu Ser
                    805                 810                 815
Asp Glu Lys Glu Asn His Ala Gly Leu Asn Pro Ser Ala Asp Asn Leu
                820                 825                 830
Tyr Lys Pro Ser Thr Asp Thr Glu Glu Thr Glu Glu Ala Glu Asp
            835                 840                 845
Thr Thr Asp Glu Ala Glu Ile Pro Gly Thr Pro Ser Ile Arg Gln Asn
            850                 855                 860
Ala Met Glu Thr Leu Thr Gly Leu Lys Ser Ser Leu Leu Leu Gly Thr
865                 870                 875                 880
Lys Asp Asn Asn Thr Ile Ser Ala Glu Val Asp Ser Leu Leu Ala Leu
                    885                 890                 895
```

-continued

```
Leu Lys Glu Ser Gln Pro Ala Pro Ile Gln
            900                 905

<210> SEQ ID NO 370
<211> LENGTH: 906
<212> TYPE: PRT
<213> ORGANISM: Artificial Sequence
<220> FEATURE:
<223> OTHER INFORMATION: Unknown Organism

<400> SEQUENCE: 370

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Gln Ala Tyr
        35                  40                  45

Ala Lys Glu Lys Gly Leu Thr Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro His Tyr Asp His
            100                 105                 110

Tyr His Asn Ile Lys Phe Glu Trp Phe Asp Glu Gly Leu Tyr Glu Ala
        115                 120                 125

Pro Lys Gly Tyr Ser Leu Glu Asp Leu Leu Ala Thr Val Lys Tyr Tyr
    130                 135                 140

Val Glu Pro Arg Asn Ala Ser Asp His Val Arg Lys Asn Lys Ala Asp
145                 150                 155                 160

Gln Asp Ser Lys Pro Asp Glu Asp Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
        195                 200                 205

Glu Glu Glu Ala Glu Asp Thr Thr Asp Glu Ala Glu Ile Pro Gly Thr
    210                 215                 220

Pro Ser Ile Arg Gln Asn Ala Met Glu Thr Leu Thr Gly Leu Lys Ser
225                 230                 235                 240

Ser Leu Leu Gly Thr Lys Asp Asn Asn Thr Ile Ser Ala Glu Val
                245                 250                 255

Asp Ser Leu Leu Ala Leu Leu Lys Glu Ser Gln Pro Ala Pro Ile Gln
            260                 265                 270

Gly Pro Gln Ile Gly Gln Pro Thr Leu Pro Asn Asn Ser Leu Ala Thr
        275                 280                 285

Pro Ser Pro Ser Leu Pro Ile Asn Pro Gly Thr Ser His Glu Lys His
    290                 295                 300

Glu Glu Asp Gly Tyr Gly Phe Asp Ala Asn Arg Ile Ile Ala Glu Asp
305                 310                 315                 320

Glu Ser Gly Phe Val Met Ser His Gly Asp Ser Asn His Tyr Phe Phe
                325                 330                 335

Lys Lys Asp Leu Thr Glu Glu Gln Ile Lys Ala Ala Gln Lys His Leu
            340                 345                 350
```

-continued

```
Glu Glu Val Lys Thr Ser His Asn Gly Leu Asp Ser Leu Ser Ser His
        355                 360                 365
Glu Gln Asp Tyr Pro Gly Asn Ala Lys Glu Met Lys Asp Leu Asp Lys
    370                 375                 380
Lys Ile Glu Glu Lys Ile Ala Gly Ile Met Lys Gln Tyr Gly Val Lys
385                 390                 395                 400
Arg Glu Ser Ile Val Val Asn Lys Glu Lys Asn Ala Ile Ile Tyr Pro
                405                 410                 415
Ser Gly Asp His His His Ala Asp Pro Ile Asp Glu His Lys Pro Val
            420                 425                 430
Gly Ile Gly His Ser His Ser Asn Tyr Glu Leu Phe Lys Pro Glu Glu
        435                 440                 445
Gly Val Ala Lys Lys Glu Gly Asn Lys Val Tyr Thr Gly Glu Glu Leu
    450                 455                 460
Thr Asn Val Val Asn Leu Leu Lys Asn Ser Thr Phe Asn Asn Gln Asn
465                 470                 475                 480
Phe Thr Leu Ala Asn Gly Gln Lys Arg Val Ser Phe Ser Phe Pro Pro
                485                 490                 495
Glu Leu Glu Lys Lys Leu Gly Ile Asn Met Leu Val Lys Leu Ile Thr
            500                 505                 510
Pro Asp Gly Lys Val Leu Glu Lys Val Ser Gly Lys Val Phe Gly Glu
        515                 520                 525
Gly Val Gly Asn Ile Ala Asn Phe Glu Leu Asp Gln Pro Tyr Leu Pro
    530                 535                 540
Gly Gln Thr Phe Lys Tyr Thr Ile Ala Ser Lys Asp Tyr Pro Glu Val
545                 550                 555                 560
Ser Tyr Asp Gly Thr Phe Thr Val Pro Thr Ser Leu Ala Tyr Lys Met
                565                 570                 575
Ala Ser Gln Thr Ile Phe Tyr Pro Phe His Ala Gly Asp Thr Tyr Leu
            580                 585                 590
Arg Val Asn Pro Gln Phe Ala Val Pro Lys Gly Thr Asp Ala Leu Val
        595                 600                 605
Arg Val Phe Asp Glu Phe His Gly Asn Ala Tyr Leu Glu Asn Asn Tyr
    610                 615                 620
Lys Val Gly Glu Ile Lys Leu Pro Ile Pro Lys Leu Asn Gln Gly Thr
625                 630                 635                 640
Thr Arg Thr Ala Gly Asn Lys Ile Pro Val Thr Phe Met Ala Asn Ala
                645                 650                 655
Tyr Leu Asp Asn Gln Ser Thr Tyr Ile Val Glu Val Pro Ile Leu Glu
            660                 665                 670
Lys Glu Asn Gln Thr Asp Lys Pro Ser Ile Leu Pro Gln Phe Lys Arg
        675                 680                 685
Asn Lys Ala Gln Glu Asn Ser Lys Leu Asp Glu Lys Val Glu Pro
    690                 695                 700
Lys Thr Ser Glu Lys Val Glu Lys Glu Lys Leu Ser Glu Thr Gly Asn
705                 710                 715                 720
Ser Thr Ser Asn Ser Thr Leu Glu Glu Val Pro Thr Val Asp Pro Val
                725                 730                 735
Gln Glu Lys Val Ala Lys Phe Ala Glu Ser Tyr Gly Met Lys Leu Glu
            740                 745                 750
Asn Val Leu Phe Asn Met Asp Gly Thr Ile Glu Leu Tyr Leu Pro Ser
        755                 760                 765
```

-continued

```
Gly Glu Val Ile Lys Lys Asn Met Ala Asp Phe Thr Gly Glu Ala Pro
    770                 775                 780
Gln Gly Asn Gly Glu Asn Lys Pro Ser Glu Asn Gly Lys Val Ser Thr
785                 790                 795                 800
Gly Thr Val Glu Asn Gln Pro Thr Glu Asn Lys Pro Ala Asp Ser Leu
                805                 810                 815
Pro Glu Ala Pro Asn Glu Lys Pro Val Lys Pro Glu Asn Ser Thr Asp
            820                 825                 830
Asn Gly Met Leu Asn Pro Glu Gly Asn Val Gly Ser Asp Pro Met Leu
        835                 840                 845
Asp Pro Ala Leu Glu Glu Ala Pro Ala Val Asp Pro Val Gln Glu Lys
    850                 855                 860
Leu Glu Lys Phe Thr Ala Ser Tyr Gly Leu Gly Leu Asp Ser Val Ile
865                 870                 875                 880
Phe Asn Met Asp Gly Thr Ile Glu Leu Arg Leu Pro Ser Gly Glu Val
                885                 890                 895
Ile Lys Lys Asn Leu Ser Asp Phe Ile Ala
            900                 905

<210> SEQ ID NO 371
<211> LENGTH: 906
<212> TYPE: PRT
<213> ORGANISM: Artificial Sequence
<220> FEATURE:
<223> OTHER INFORMATION: Unknown Organism

<400> SEQUENCE: 371

Met Gln Ile Gly Gln Pro Thr Leu Pro Asn Asn Ser Leu Ala Thr Pro
1               5                   10                  15
Ser Pro Ser Leu Pro Ile Asn Pro Gly Thr Ser His Glu Lys His Glu
            20                  25                  30
Glu Asp Gly Tyr Gly Phe Asp Ala Asn Arg Ile Ile Ala Glu Asp Glu
        35                  40                  45
Ser Gly Phe Val Met Ser Ser Gly Asp Ser Asn His Tyr Phe Phe Lys
    50                  55                  60
Lys Asp Leu Thr Glu Glu Gln Ile Lys Ala Ala Gln Lys His Leu Glu
65                  70                  75                  80
Glu Val Lys Thr Ser His Asn Gly Leu Asp Ser Leu Ser Ser His Glu
                85                  90                  95
Gln Asp Tyr Pro Gly Asn Ala Lys Glu Met Lys Asp Leu Asp Lys Lys
            100                 105                 110
Ile Glu Glu Lys Ile Ala Gly Ile Met Lys Gln Tyr Gly Val Lys Arg
        115                 120                 125
Glu Ser Ile Val Val Asn Lys Glu Lys Asn Ala Ile Ile Tyr Pro Ser
    130                 135                 140
Gly Asp Gly His His Ala Asp Pro Ile Asp Glu His Lys Pro Val Gly
145                 150                 155                 160
Ile Gly His Ser His Ser Asn Tyr Glu Leu Phe Lys Pro Glu Glu Gly
                165                 170                 175
Val Ala Lys Lys Glu Gly Asn Lys Val Tyr Thr Gly Glu Glu Leu Thr
            180                 185                 190
Asn Val Val Asn Leu Leu Lys Asn Ser Thr Phe Asn Asn Gln Asn Phe
        195                 200                 205
Thr Leu Ala Asn Gly Gln Lys Arg Val Ser Phe Ser Phe Pro Pro Glu
    210                 215                 220
```

-continued

```
Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
            245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
            325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
370                 375                 380

Leu Asp Asn Gln Ser Thr Tyr Ile Val Glu Val Pro Ile Leu Glu Lys
385                 390                 395                 400

Glu Asn Gln Thr Asp Lys Pro Ser Ile Leu Pro Gln Phe Lys Arg Asn
            405                 410                 415

Lys Ala Gln Glu Asn Ser Lys Leu Asp Glu Lys Val Glu Glu Pro Lys
            420                 425                 430

Thr Ser Glu Lys Val Glu Lys Glu Lys Leu Ser Glu Thr Gly Asn Ser
        435                 440                 445

Thr Ser Asn Ser Thr Leu Glu Glu Val Pro Thr Val Asp Pro Val Gln
450                 455                 460

Glu Lys Val Ala Lys Phe Ala Glu Ser Tyr Gly Met Lys Leu Glu Asn
465                 470                 475                 480

Val Leu Phe Asn Met Asp Gly Thr Ile Glu Leu Tyr Leu Pro Ser Gly
            485                 490                 495

Glu Val Ile Lys Lys Asn Met Ala Asp Phe Thr Gly Glu Ala Pro Gln
        500                 505                 510

Gly Asn Gly Glu Asn Lys Pro Ser Glu Asn Gly Lys Val Ser Thr Gly
        515                 520                 525

Thr Val Glu Asn Gln Pro Thr Glu Asn Lys Pro Ala Asp Ser Leu Pro
530                 535                 540

Glu Ala Pro Asn Glu Lys Pro Val Lys Pro Glu Asn Ser Thr Asp Asn
545                 550                 555                 560

Gly Met Leu Asn Pro Glu Gly Asn Val Gly Ser Asp Pro Met Leu Asp
            565                 570                 575

Pro Ala Leu Glu Glu Ala Pro Ala Val Asp Pro Val Gln Glu Lys Leu
            580                 585                 590

Glu Lys Phe Thr Ala Ser Tyr Gly Leu Gly Leu Asp Ser Val Ile Phe
        595                 600                 605

Asn Met Asp Gly Thr Ile Glu Leu Arg Leu Pro Ser Gly Glu Val Ile
610                 615                 620

Lys Lys Asn Leu Ser Asp Phe Ile Ala Gly Pro Gln Ile Thr Tyr Thr
625                 630                 635                 640

Asp Asp Glu Ile Gln Val Ala Lys Leu Ala Gly Lys Tyr Thr Thr Glu
```

```
                    645                 650                 655
Asp Gly Tyr Ile Phe Asp Thr Ser Trp Ile Lys Lys Asp Ser Leu Ser
            660                 665                 670

Glu Ala Glu Arg Ala Ala Gln Ala Tyr Ala Lys Glu Lys Gly Leu
        675                 680                 685

Thr Pro Pro Ser Thr Asp His Gln Asp Ser Gly Asn Thr Glu Ala Lys
        690                 695                 700

Gly Ala Glu Ala Ile Tyr Asn Arg Val Lys Ala Ala Lys Lys Val Pro
705                 710                 715                 720

Leu Asp Arg Met Pro Tyr Asn Leu Gln Tyr Thr Val Glu Val Lys Asn
                725                 730                 735

Gly Ser Leu Ile Ile Pro His Tyr Asp His Tyr His Asn Ile Lys Phe
            740                 745                 750

Glu Trp Phe Asp Glu Gly Leu Tyr Glu Ala Pro Lys Gly Tyr Ser Leu
        755                 760                 765

Glu Asp Leu Leu Ala Thr Val Lys Tyr Tyr Val Glu Pro Arg Asn Ala
770                 775                 780

Ser Asp His Val Arg Lys Asn Lys Ala Asp Gln Asp Ser Lys Pro Asp
785                 790                 795                 800

Glu Asp Lys Glu His Asp Glu Val Ser Glu Pro Thr His Pro Glu Ser
                805                 810                 815

Asp Glu Lys Glu Asn His Ala Gly Leu Asn Pro Ser Ala Asp Asn Leu
            820                 825                 830

Tyr Lys Pro Ser Thr Asp Thr Glu Glu Thr Glu Glu Ala Glu Asp
        835                 840                 845

Thr Thr Asp Glu Ala Glu Ile Pro Gly Thr Pro Ser Ile Arg Gln Asn
850                 855                 860

Ala Met Glu Thr Leu Thr Gly Leu Lys Ser Ser Leu Leu Gly Thr
865                 870                 875                 880

Lys Asp Asn Asn Thr Ile Ser Ala Glu Val Asp Ser Leu Leu Ala Leu
                885                 890                 895

Leu Lys Glu Ser Gln Pro Ala Pro Ile Gln
            900                 905

<210> SEQ ID NO 372
<211> LENGTH: 906
<212> TYPE: PRT
<213> ORGANISM: Artificial Sequence
<220> FEATURE:
<223> OTHER INFORMATION: Unknown Organism

<400> SEQUENCE: 372

Met Gln Ile Thr Tyr Thr Asp Asp Glu Ile Gln Val Ala Lys Leu Ala
1               5                   10                  15

Gly Lys Tyr Thr Thr Glu Asp Gly Tyr Ile Phe Asp Thr Ser Trp Ile
            20                  25                  30

Lys Lys Asp Ser Leu Ser Glu Ala Glu Arg Ala Ala Gln Ala Tyr
        35                  40                  45

Ala Lys Glu Lys Gly Leu Thr Pro Pro Ser Thr Asp His Gln Asp Ser
    50                  55                  60

Gly Asn Thr Glu Ala Lys Gly Ala Glu Ala Ile Tyr Asn Arg Val Lys
65                  70                  75                  80

Ala Ala Lys Lys Val Pro Leu Asp Arg Met Pro Tyr Asn Leu Gln Tyr
                85                  90                  95

Thr Val Glu Val Lys Asn Gly Ser Leu Ile Ile Pro His Tyr Asp His
```

```
                    100                 105                 110
Tyr His Asn Ile Lys Phe Glu Trp Phe Asp Glu Gly Leu Tyr Glu Ala
            115                 120                 125

Pro Lys Gly Tyr Ser Leu Glu Asp Leu Leu Ala Thr Val Lys Tyr Tyr
            130                 135                 140

Val Glu Pro Arg Asn Ala Ser Asp His Val Arg Lys Asn Lys Ala Asp
145                 150                 155                 160

Gln Asp Ser Lys Pro Asp Glu Lys Glu His Asp Glu Val Ser Glu
                165                 170                 175

Pro Thr His Pro Glu Ser Asp Glu Lys Glu Asn His Ala Gly Leu Asn
            180                 185                 190

Pro Ser Ala Asp Asn Leu Tyr Lys Pro Ser Thr Asp Thr Glu Glu Thr
            195                 200                 205

Glu Glu Glu Ala Glu Asp Thr Thr Asp Glu Ala Glu Ile Pro Gly Thr
            210                 215                 220

Pro Ser Ile Arg Gln Asn Ala Met Glu Thr Leu Thr Gly Leu Lys Ser
225                 230                 235                 240

Ser Leu Leu Leu Gly Thr Lys Asp Asn Thr Ile Ser Ala Glu Val
                245                 250                 255

Asp Ser Leu Leu Ala Leu Leu Lys Glu Ser Gln Pro Ala Pro Ile Gln
            260                 265                 270

Gly Pro Gln Ile Gly Gln Pro Thr Leu Pro Asn Asn Ser Leu Ala Thr
            275                 280                 285

Pro Ser Pro Ser Leu Pro Ile Asn Pro Gly Thr Ser His Glu Lys His
            290                 295                 300

Glu Glu Asp Gly Tyr Gly Phe Asp Ala Asn Arg Ile Ile Ala Glu Asp
305                 310                 315                 320

Glu Ser Gly Phe Val Met Ser Ser Gly Asp Ser Asn His Tyr Phe Phe
                325                 330                 335

Lys Lys Asp Leu Thr Glu Glu Gln Ile Lys Ala Ala Gln Lys His Leu
            340                 345                 350

Glu Glu Val Lys Thr Ser His Asn Gly Leu Asp Ser Leu Ser Ser His
            355                 360                 365

Glu Gln Asp Tyr Pro Gly Asn Ala Lys Glu Met Lys Asp Leu Asp Lys
            370                 375                 380

Lys Ile Glu Glu Lys Ile Ala Gly Ile Met Lys Gln Tyr Gly Val Lys
385                 390                 395                 400

Arg Glu Ser Ile Val Val Asn Lys Glu Lys Asn Ala Ile Ile Tyr Pro
                405                 410                 415

Ser Gly Asp Gly His His Ala Asp Pro Ile Asp Glu His Lys Pro Val
            420                 425                 430

Gly Ile Gly His Ser His Ser Asn Tyr Glu Leu Phe Lys Pro Glu Glu
            435                 440                 445

Gly Val Ala Lys Lys Glu Gly Asn Lys Val Tyr Thr Gly Glu Glu Leu
            450                 455                 460

Thr Asn Val Val Asn Leu Leu Lys Asn Ser Thr Phe Asn Asn Gln Asn
465                 470                 475                 480

Phe Thr Leu Ala Asn Gly Gln Lys Arg Val Ser Phe Ser Phe Pro Pro
                485                 490                 495

Glu Leu Glu Lys Lys Leu Gly Ile Asn Met Leu Val Lys Leu Ile Thr
            500                 505                 510

Pro Asp Gly Lys Val Leu Glu Lys Val Ser Gly Lys Val Phe Gly Glu
            515                 520                 525
```

```
Gly Val Gly Asn Ile Ala Asn Phe Glu Leu Asp Gln Pro Tyr Leu Pro
        530                 535                 540
Gly Gln Thr Phe Lys Tyr Thr Ile Ala Ser Lys Asp Tyr Pro Glu Val
545                 550                 555                 560
Ser Tyr Asp Gly Thr Phe Thr Val Pro Thr Ser Leu Ala Tyr Lys Met
                565                 570                 575
Ala Ser Gln Thr Ile Phe Tyr Pro Phe His Ala Gly Asp Thr Tyr Leu
            580                 585                 590
Arg Val Asn Pro Gln Phe Ala Val Pro Lys Gly Thr Asp Ala Leu Val
        595                 600                 605
Arg Val Phe Asp Glu Phe His Gly Asn Ala Tyr Leu Glu Asn Asn Tyr
    610                 615                 620
Lys Val Gly Glu Ile Lys Leu Pro Ile Pro Lys Leu Asn Gln Gly Thr
625                 630                 635                 640
Thr Arg Thr Ala Gly Asn Lys Ile Pro Val Thr Phe Met Ala Asn Ala
                645                 650                 655
Tyr Leu Asp Asn Gln Ser Thr Tyr Ile Val Glu Val Pro Ile Leu Glu
            660                 665                 670
Lys Glu Asn Gln Thr Asp Lys Pro Ser Ile Leu Pro Gln Phe Lys Arg
        675                 680                 685
Asn Lys Ala Gln Glu Asn Ser Lys Leu Asp Glu Lys Val Glu Glu Pro
    690                 695                 700
Lys Thr Ser Glu Lys Val Glu Lys Glu Lys Leu Ser Glu Thr Gly Asn
705                 710                 715                 720
Ser Thr Ser Asn Ser Thr Leu Glu Glu Val Pro Thr Val Asp Pro Val
                725                 730                 735
Gln Glu Lys Val Ala Lys Phe Ala Glu Ser Tyr Gly Met Lys Leu Glu
            740                 745                 750
Asn Val Leu Phe Asn Met Asp Gly Thr Ile Glu Leu Tyr Leu Pro Ser
        755                 760                 765
Gly Glu Val Ile Lys Lys Asn Met Ala Asp Phe Thr Gly Glu Ala Pro
    770                 775                 780
Gln Gly Asn Gly Glu Asn Lys Pro Ser Glu Asn Gly Lys Val Ser Thr
785                 790                 795                 800
Gly Thr Val Glu Asn Gln Pro Thr Glu Asn Lys Pro Ala Asp Ser Leu
                805                 810                 815
Pro Glu Ala Pro Asn Glu Lys Pro Val Lys Pro Glu Asn Ser Thr Asp
            820                 825                 830
Asn Gly Met Leu Asn Pro Glu Gly Asn Val Gly Ser Asp Pro Met Leu
        835                 840                 845
Asp Pro Ala Leu Glu Glu Ala Pro Ala Val Asp Pro Val Gln Glu Lys
    850                 855                 860
Leu Glu Lys Phe Thr Ala Ser Tyr Gly Leu Gly Leu Asp Ser Val Ile
865                 870                 875                 880
Phe Asn Met Asp Gly Thr Ile Glu Leu Arg Leu Pro Ser Gly Glu Val
                885                 890                 895
Ile Lys Lys Asn Leu Ser Asp Phe Ile Ala
            900                 905

<210> SEQ ID NO 373
<211> LENGTH: 906
<212> TYPE: PRT
<213> ORGANISM: Artificial Sequence
<220> FEATURE:
```

<223> OTHER INFORMATION: Unknown Organism

<400> SEQUENCE: 373

```
Met Gln Ile Gly Gln Pro Thr Leu Pro Asn Asn Ser Leu Ala Thr Pro
1               5                   10                  15

Ser Pro Ser Leu Pro Ile Asn Pro Gly Thr Ser His Glu Lys His Glu
            20                  25                  30

Glu Asp Gly Tyr Gly Phe Asp Ala Asn Arg Ile Ile Ala Glu Asp Glu
        35                  40                  45

Ser Gly Phe Val Met Ser His Gly Asp Ser Asn His Tyr Phe Phe Lys
50                  55                  60

Lys Asp Leu Thr Glu Glu Gln Ile Lys Ala Ala Gln Lys His Leu Glu
65                  70                  75                  80

Glu Val Lys Thr Ser His Asn Gly Leu Asp Ser Leu Ser Ser His Glu
                85                  90                  95

Gln Asp Tyr Pro Gly Asn Ala Lys Glu Met Lys Asp Leu Asp Lys Lys
            100                 105                 110

Ile Glu Glu Lys Ile Ala Gly Ile Met Lys Gln Tyr Gly Val Lys Arg
        115                 120                 125

Glu Ser Ile Val Val Asn Lys Glu Lys Asn Ala Ile Ile Tyr Pro Ser
130                 135                 140

Gly Asp His His His Ala Asp Pro Ile Asp Glu His Lys Pro Val Gly
145                 150                 155                 160

Ile Gly His Ser His Ser Asn Tyr Glu Leu Phe Lys Pro Glu Glu Gly
                165                 170                 175

Val Ala Lys Lys Glu Gly Asn Lys Val Tyr Thr Gly Glu Glu Leu Thr
            180                 185                 190

Asn Val Val Asn Leu Leu Lys Asn Ser Thr Phe Asn Asn Gln Asn Phe
        195                 200                 205

Thr Leu Ala Asn Gly Gln Lys Arg Val Ser Phe Ser Phe Pro Pro Glu
210                 215                 220

Leu Glu Lys Lys Leu Gly Ile Asn Met Leu Val Lys Leu Ile Thr Pro
225                 230                 235                 240

Asp Gly Lys Val Leu Glu Lys Val Ser Gly Lys Val Phe Gly Glu Gly
                245                 250                 255

Val Gly Asn Ile Ala Asn Phe Glu Leu Asp Gln Pro Tyr Leu Pro Gly
            260                 265                 270

Gln Thr Phe Lys Tyr Thr Ile Ala Ser Lys Asp Tyr Pro Glu Val Ser
        275                 280                 285

Tyr Asp Gly Thr Phe Thr Val Pro Thr Ser Leu Ala Tyr Lys Met Ala
290                 295                 300

Ser Gln Thr Ile Phe Tyr Pro Phe His Ala Gly Asp Thr Tyr Leu Arg
305                 310                 315                 320

Val Asn Pro Gln Phe Ala Val Pro Lys Gly Thr Asp Ala Leu Val Arg
                325                 330                 335

Val Phe Asp Glu Phe His Gly Asn Ala Tyr Leu Glu Asn Asn Tyr Lys
            340                 345                 350

Val Gly Glu Ile Lys Leu Pro Ile Pro Lys Leu Asn Gln Gly Thr Thr
        355                 360                 365

Arg Thr Ala Gly Asn Lys Ile Pro Val Thr Phe Met Ala Asn Ala Tyr
370                 375                 380

Leu Asp Asn Gln Ser Thr Tyr Ile Val Glu Val Pro Ile Leu Glu Lys
385                 390                 395                 400
```

-continued

```
Glu Asn Gln Thr Asp Lys Pro Ser Ile Leu Pro Gln Phe Lys Arg Asn
                405                 410                 415
Lys Ala Gln Glu Asn Ser Lys Leu Asp Glu Lys Val Glu Glu Pro Lys
            420                 425                 430
Thr Ser Glu Lys Val Glu Lys Glu Lys Leu Ser Glu Thr Gly Asn Ser
        435                 440                 445
Thr Ser Asn Ser Thr Leu Glu Glu Val Pro Thr Val Asp Pro Val Gln
450                 455                 460
Glu Lys Val Ala Lys Phe Ala Glu Ser Tyr Gly Met Lys Leu Glu Asn
465                 470                 475                 480
Val Leu Phe Asn Met Asp Gly Thr Ile Glu Leu Tyr Leu Pro Ser Gly
                485                 490                 495
Glu Val Ile Lys Lys Asn Met Ala Asp Phe Thr Gly Glu Ala Pro Gln
            500                 505                 510
Gly Asn Gly Glu Asn Lys Pro Ser Glu Asn Gly Lys Val Ser Thr Gly
        515                 520                 525
Thr Val Glu Asn Gln Pro Thr Glu Asn Lys Pro Ala Asp Ser Leu Pro
530                 535                 540
Glu Ala Pro Asn Glu Lys Pro Val Lys Pro Glu Asn Ser Thr Asp Asn
545                 550                 555                 560
Gly Met Leu Asn Pro Glu Gly Asn Val Gly Ser Asp Pro Met Leu Asp
                565                 570                 575
Pro Ala Leu Glu Glu Ala Pro Ala Val Asp Pro Val Gln Glu Lys Leu
            580                 585                 590
Glu Lys Phe Thr Ala Ser Tyr Gly Leu Gly Leu Asp Ser Val Ile Phe
        595                 600                 605
Asn Met Asp Gly Thr Ile Glu Leu Arg Leu Pro Ser Gly Glu Val Ile
610                 615                 620
Lys Lys Asn Leu Ser Asp Phe Ile Ala Gly Pro Gln Ile Thr Tyr Thr
625                 630                 635                 640
Asp Asp Glu Ile Gln Val Ala Lys Leu Ala Gly Lys Tyr Thr Thr Glu
                645                 650                 655
Asp Gly Tyr Ile Phe Asp Thr Ser Trp Ile Lys Lys Asp Ser Leu Ser
            660                 665                 670
Glu Ala Glu Arg Ala Ala Gln Ala Tyr Ala Lys Glu Lys Gly Leu
        675                 680                 685
Thr Pro Pro Ser Thr Asp His Gln Asp Ser Gly Asn Thr Glu Ala Lys
690                 695                 700
Gly Ala Glu Ala Ile Tyr Asn Arg Val Lys Ala Ala Lys Lys Val Pro
705                 710                 715                 720
Leu Asp Arg Met Pro Tyr Asn Leu Gln Tyr Thr Val Glu Val Lys Asn
                725                 730                 735
Gly Ser Leu Ile Ile Pro Ser Tyr Asp His Tyr His Asn Ile Lys Phe
            740                 745                 750
Glu Trp Phe Asp Glu Gly Leu Tyr Glu Ala Pro Lys Gly Tyr Ser Leu
        755                 760                 765
Glu Asp Leu Leu Ala Thr Val Lys Tyr Tyr Val Glu Pro Arg Asn Ala
770                 775                 780
Ser Asp His Val Arg Lys Asn Lys Ala Asp Gln Asp Ser Lys Pro Asp
785                 790                 795                 800
Glu Asp Lys Glu His Asp Glu Val Ser Glu Pro Thr His Pro Glu Ser
                805                 810                 815
Asp Glu Lys Glu Asn His Ala Gly Leu Asn Pro Ser Ala Asp Asn Leu
```

-continued

```
                820                 825                 830
Tyr Lys Pro Ser Thr Asp Thr Glu Glu Thr Glu Glu Ala Glu Asp
        835                 840                 845

Thr Thr Asp Glu Ala Glu Ile Pro Gly Thr Pro Ser Ile Arg Gln Asn
850                 855                 860

Ala Met Glu Thr Leu Thr Gly Leu Lys Ser Ser Leu Leu Gly Thr
865                 870                 875                 880

Lys Asp Asn Asn Thr Ile Ser Ala Glu Val Asp Ser Leu Leu Ala Leu
                885                 890                 895

Leu Lys Glu Ser Gln Pro Ala Pro Ile Gln
        900                 905

<210> SEQ ID NO 374
<211> LENGTH: 259
<212> TYPE: PRT
<213> ORGANISM: Artificial Sequence
<220> FEATURE:
<223> OTHER INFORMATION: Unknown Organism

<400> SEQUENCE: 374

Met Leu Ala Gly Lys Tyr Thr Thr Glu Asp Gly Tyr Ile Phe Asp Thr
1               5                   10                  15

Ser Trp Ile Lys Lys Asp Ser Leu Ser Glu Ala Glu Arg Ala Ala Ala
            20                  25                  30

Gln Ala Tyr Ala Lys Glu Lys Gly Leu Thr Pro Pro Ser Thr Asp His
        35                  40                  45

Gln Asp Ser Gly Asn Thr Glu Ala Lys Gly Ala Glu Ala Ile Tyr Asn
    50                  55                  60

Arg Val Lys Ala Ala Lys Lys Val Pro Leu Asp Arg Met Pro Tyr Asn
65                  70                  75                  80

Leu Gln Tyr Thr Val Glu Val Lys Asn Gly Ser Leu Ile Ile Pro His
                85                  90                  95

Tyr Asp His Tyr His Asn Ile Lys Phe Glu Trp Phe Asp Glu Gly Leu
            100                 105                 110

Tyr Glu Ala Pro Lys Gly Tyr Ser Leu Glu Asp Leu Leu Ala Thr Val
        115                 120                 125

Lys Tyr Tyr Val Glu Pro Arg Asn Ala Ser Asp His Val Arg Lys Asn
    130                 135                 140

Lys Ala Asp Gln Asp Ser Lys Pro Asp Glu Asp Lys Glu His Asp Glu
145                 150                 155                 160

Val Ser Glu Pro Thr His Pro Glu Ser Asp Glu Lys Glu Asn His Ala
                165                 170                 175

Gly Leu Asn Pro Ser Ala Asp Asn Leu Tyr Lys Pro Ser Thr Asp Thr
            180                 185                 190

Glu Glu Thr Glu Glu Glu Ala Glu Asp Thr Thr Asp Glu Ala Glu Ile
        195                 200                 205

Pro Gly Thr Pro Ser Ile Arg Gln Asn Ala Met Glu Thr Leu Thr Gly
    210                 215                 220

Leu Lys Ser Ser Leu Leu Gly Thr Lys Asp Asn Asn Thr Ile Ser
225                 230                 235                 240

Ala Glu Val Asp Ser Leu Leu Ala Leu Leu Lys Glu Ser Gln Pro Ala
                245                 250                 255

Pro Ile Gln

<210> SEQ ID NO 375
```

<211> LENGTH: 268
<212> TYPE: PRT
<213> ORGANISM: Artificial Sequence
<220> FEATURE:
<223> OTHER INFORMATION: Unknown Organism

<400> SEQUENCE: 375

```
Met Gln Ile Thr Tyr Thr Asp Asp Glu Ile Gln Val Ala Lys Leu Ala
1               5                   10                  15
Gly Lys Tyr Thr Thr Glu Asp Gly Tyr Ile Phe Asp Thr Ser Trp Ile
            20                  25                  30
Lys Lys Asp Ser Leu Ser Glu Ala Glu Arg Ala Ala Ala Gln Ala Tyr
        35                  40                  45
Ala Lys Glu Lys Gly Leu Thr Pro Pro Ser Thr Asp His Gln Asp Ser
    50                  55                  60
Gly Asn Thr Glu Ala Lys Gly Ala Glu Ala Ile Tyr Asn Arg Val Lys
65                  70                  75                  80
Ala Ala Lys Lys Val Pro Leu Asp Arg Met Pro Tyr Asn Leu Gln Tyr
                85                  90                  95
Thr Val Glu Val Lys Asn Gly Ser Leu Ile Ile Pro Pro Gly Asn Ile
            100                 105                 110
Lys Phe Glu Trp Phe Asp Glu Gly Leu Tyr Glu Ala Pro Lys Gly Tyr
        115                 120                 125
Ser Leu Glu Asp Leu Leu Ala Thr Val Lys Tyr Tyr Val Glu Pro Arg
    130                 135                 140
Asn Ala Ser Asp His Val Arg Lys Asn Lys Ala Asp Gln Asp Ser Lys
145                 150                 155                 160
Pro Asp Glu Asp Lys Glu His Asp Glu Val Ser Glu Pro Thr His Pro
                165                 170                 175
Glu Ser Asp Glu Lys Glu Asn His Ala Gly Leu Asn Pro Ser Ala Asp
            180                 185                 190
Asn Leu Tyr Lys Pro Ser Thr Asp Thr Glu Thr Glu Glu Glu Glu Ala
        195                 200                 205
Glu Asp Thr Thr Asp Glu Ala Glu Ile Pro Gly Thr Pro Ser Ile Arg
    210                 215                 220
Gln Asn Ala Met Glu Thr Leu Thr Gly Leu Lys Ser Ser Leu Leu Leu
225                 230                 235                 240
Gly Thr Lys Asp Asn Asn Thr Ile Ser Ala Glu Val Asp Ser Leu Leu
                245                 250                 255
Ala Leu Leu Lys Glu Ser Gln Pro Ala Pro Ile Gln
            260                 265
```

<210> SEQ ID NO 376
<211> LENGTH: 999
<212> TYPE: PRT
<213> ORGANISM: Artificial Sequence
<220> FEATURE:
<223> OTHER INFORMATION: Unknown Organism
<221> NAME/KEY: MISC_FEATURE
<222> LOCATION: (1)..(1)
<223> OTHER INFORMATION: Xaa = Methionine or nothing
<221> NAME/KEY: MISC_FEATURE
<222> LOCATION: (430)..(430)
<223> OTHER INFORMATION: Xaa = Glycine or nothing
<221> NAME/KEY: MISC_FEATURE
<222> LOCATION: (431)..(431)
<223> OTHER INFORMATION: Xaa = Proline or nothing

<400> SEQUENCE: 376

Xaa Asp Ile Asp Ser Leu Leu Lys Gln Leu Tyr Lys Leu Pro Leu Ser

```
  1               5                  10                 15
Gln Arg His Val Glu Ser Asp Gly Leu Ile Phe Asp Pro Ala Gln Ile
                20                 25                 30

Thr Ser Arg Thr Ala Arg Gly Val Ala Val Pro His Gly Asn His Tyr
                35                 40                 45

His Phe Ile Pro Tyr Glu Gln Met Ser Glu Leu Glu Lys Arg Ile Ala
                50                 55                 60

Arg Ile Ile Pro Leu Arg Tyr Arg Ser Asn His Trp Val Pro Asp Ser
65                  70                 75                 80

Arg Pro Glu Glu Pro Ser Pro Gln Pro Thr Pro Glu Pro Ser Pro Ser
                85                 90                 95

Pro Gln Pro Ala Pro Asn Pro Gln Pro Ala Pro Ser Asn Pro Ile Asp
                100                105                110

Glu Lys Leu Val Lys Glu Ala Val Arg Lys Val Gly Asp Gly Tyr Val
                115                120                125

Phe Glu Glu Asn Gly Val Ser Arg Tyr Ile Pro Ala Lys Asn Leu Ser
                130                135                140

Ala Glu Thr Ala Ala Gly Ile Asp Ser Lys Leu Ala Lys Gln Glu Ser
145                 150                155                160

Leu Ser His Lys Leu Gly Ala Lys Lys Thr Asp Leu Pro Ser Ser Asp
                165                170                175

Arg Glu Phe Tyr Asn Lys Ala Tyr Asp Leu Leu Ala Arg Ile His Gln
                180                185                190

Asp Leu Leu Asp Asn Lys Gly Arg Gln Val Asp Phe Glu Ala Leu Asp
                195                200                205

Asn Leu Leu Glu Arg Leu Lys Asp Val Ser Ser Asp Lys Val Lys Leu
210                 215                220

Val Asp Asp Ile Leu Ala Phe Leu Ala Pro Ile Arg His Pro Glu Arg
225                 230                235                240

Leu Gly Lys Pro Asn Ala Gln Ile Thr Tyr Thr Asp Asp Glu Ile Gln
                245                250                255

Val Ala Lys Leu Ala Gly Lys Tyr Thr Thr Glu Asp Gly Tyr Ile Phe
                260                265                270

Asp Pro Arg Asp Ile Thr Ser Asp Glu Gly Asp Ala Tyr Val Thr Pro
                275                280                285

His Met Thr His Ser His Trp Ile Lys Lys Asp Ser Leu Ser Glu Ala
                290                295                300

Glu Arg Ala Ala Ala Gln Ala Tyr Ala Lys Glu Lys Gly Leu Thr Pro
305                 310                315                320

Pro Ser Thr Asp His Gln Asp Ser Gly Asn Thr Glu Ala Lys Gly Ala
                325                330                335

Glu Ala Ile Tyr Asn Arg Val Lys Ala Lys Lys Val Pro Leu Asp
                340                345                350

Arg Met Pro Tyr Asn Leu Gln Tyr Thr Val Glu Val Lys Asn Gly Ser
                355                360                365

Leu Ile Ile Pro His Tyr Asp His Tyr His Asn Ile Lys Phe Glu Trp
                370                375                380

Phe Asp Glu Gly Leu Tyr Glu Ala Pro Lys Gly Tyr Thr Leu Glu Asp
385                 390                395                400

Leu Leu Ala Thr Val Lys Tyr Tyr Val Glu His Pro Asn Glu Arg Pro
                405                410                415

His Ser Asp Asn Gly Phe Gly Asn Ala Ser Asp His Val Xaa Xaa Asp
                420                425                430
```

-continued

```
Leu Thr Glu Glu Gln Ile Lys Ala Ala Gln Lys His Leu Glu Val
        435                 440                 445
Lys Thr Ser His Asn Gly Leu Asp Ser Leu Ser His Glu Gln Asp
450                 455                 460
Tyr Pro Gly Asn Ala Lys Glu Met Lys Asp Leu Asp Lys Lys Ile Glu
465                 470                 475                 480
Glu Lys Ile Ala Gly Ile Met Lys Gln Tyr Gly Val Lys Arg Glu Ser
            485                 490                 495
Ile Val Val Asn Lys Glu Lys Asn Ala Ile Ile Tyr Pro His Gly Asp
                500                 505                 510
His His His Ala Asp Pro Ile Asp Glu His Lys Pro Val Gly Ile Gly
        515                 520                 525
His Ser His Ser Asn Tyr Glu Leu Phe Lys Pro Glu Gly Val Ala
    530                 535                 540
Lys Lys Glu Gly Asn Lys Val Tyr Thr Gly Glu Glu Leu Thr Asn Val
545                 550                 555                 560
Val Asn Leu Leu Lys Asn Ser Thr Phe Asn Asn Gln Asn Phe Thr Leu
                565                 570                 575
Ala Asn Gly Gln Lys Arg Val Ser Phe Ser Phe Pro Pro Glu Leu Glu
            580                 585                 590
Lys Lys Leu Gly Ile Asn Met Leu Val Lys Leu Ile Thr Pro Asp Gly
        595                 600                 605
Lys Val Leu Glu Lys Val Ser Gly Lys Val Phe Gly Glu Gly Val Gly
    610                 615                 620
Asn Ile Ala Asn Phe Glu Leu Asp Gln Pro Tyr Leu Pro Gly Gln Thr
625                 630                 635                 640
Phe Lys Tyr Thr Ile Ala Ser Lys Asp Tyr Pro Glu Val Ser Tyr Asp
                645                 650                 655
Gly Thr Phe Thr Val Pro Thr Ser Leu Ala Tyr Lys Met Ala Ser Gln
            660                 665                 670
Thr Ile Phe Tyr Pro Phe His Ala Gly Asp Thr Tyr Leu Arg Val Asn
        675                 680                 685
Pro Gln Phe Ala Val Pro Lys Gly Thr Asp Ala Leu Val Arg Val Phe
    690                 695                 700
Asp Glu Phe His Gly Asn Ala Tyr Leu Glu Asn Asn Tyr Lys Val Gly
705                 710                 715                 720
Glu Ile Lys Leu Pro Ile Pro Lys Leu Asn Gln Gly Thr Thr Arg Thr
                725                 730                 735
Ala Gly Asn Lys Ile Pro Val Thr Phe Met Ala Asn Ala Tyr Leu Asp
            740                 745                 750
Asn Gln Ser Thr Tyr Ile Val Glu Val Pro Ile Leu Glu Lys Glu Asn
        755                 760                 765
Gln Thr Asp Lys Pro Ser Ile Leu Pro Gln Phe Lys Arg Asn Lys Ala
    770                 775                 780
Gln Glu Asn Ser Lys Leu Asp Glu Lys Val Glu Glu Pro Lys Thr Ser
785                 790                 795                 800
Glu Lys Val Glu Lys Glu Lys Leu Ser Glu Thr Gly Asn Ser Thr Ser
                805                 810                 815
Asn Ser Thr Leu Glu Glu Val Pro Thr Val Asp Pro Val Gln Glu Lys
            820                 825                 830
Val Ala Lys Phe Ala Glu Ser Tyr Gly Met Lys Leu Glu Asn Val Leu
        835                 840                 845
```

```
Phe Asn Met Asp Gly Thr Ile Glu Leu Tyr Leu Pro Ser Gly Glu Val
    850                 855                 860

Ile Lys Lys Asn Met Ala Asp Phe Thr Gly Glu Ala Pro Gln Gly Asn
865                 870                 875                 880

Gly Glu Asn Lys Pro Ser Glu Asn Gly Lys Val Ser Thr Gly Thr Val
                885                 890                 895

Glu Asn Gln Pro Thr Glu Asn Lys Pro Ala Asp Ser Leu Pro Glu Ala
                900                 905                 910

Pro Asn Glu Lys Pro Val Lys Pro Glu Asn Ser Thr Asp Asn Gly Met
            915                 920                 925

Leu Asn Pro Glu Gly Asn Val Gly Ser Asp Pro Met Leu Asp Pro Ala
    930                 935                 940

Leu Glu Glu Ala Pro Ala Val Asp Pro Val Gln Glu Lys Leu Glu Lys
945                 950                 955                 960

Phe Thr Ala Ser Tyr Gly Leu Gly Leu Asp Ser Val Ile Phe Asn Met
                965                 970                 975

Asp Gly Thr Ile Glu Leu Arg Leu Pro Ser Gly Glu Val Ile Lys Lys
                980                 985                 990

Asn Leu Ser Asp Phe Ile Ala
        995

<210> SEQ ID NO 377
<211> LENGTH: 999
<212> TYPE: PRT
<213> ORGANISM: Artificial Sequence
<220> FEATURE:
<223> OTHER INFORMATION: Unknown Organism
<221> NAME/KEY: MISC_FEATURE
<222> LOCATION: (1)..(1)
<223> OTHER INFORMATION: Xaa = Methionine or nothing
<221> NAME/KEY: MISC_FEATURE
<222> LOCATION: (570)..(570)
<223> OTHER INFORMATION: Xaa = Glycine or nothing
<221> NAME/KEY: MISC_FEATURE
<222> LOCATION: (571)..(571)
<223> OTHER INFORMATION: Xaa = Proine or nothing

<400> SEQUENCE: 377

Xaa Asp Leu Thr Glu Glu Gln Ile Lys Ala Ala Gln Lys His Leu Glu
1               5                   10                  15

Glu Val Lys Thr Ser His Asn Gly Leu Asp Ser Leu Ser Ser His Glu
            20                  25                  30

Gln Asp Tyr Pro Gly Asn Ala Lys Glu Met Lys Asp Leu Asp Lys Lys
        35                  40                  45

Ile Glu Glu Lys Ile Ala Gly Ile Met Lys Gln Tyr Gly Val Lys Arg
50                  55                  60

Glu Ser Ile Val Val Asn Lys Glu Lys Asn Ala Ile Ile Tyr Pro His
65                  70                  75                  80

Gly Asp His His His Ala Asp Pro Ile Asp Glu His Lys Pro Val Gly
                85                  90                  95

Ile Gly His Ser His Ser Asn Tyr Glu Leu Phe Lys Pro Glu Glu Gly
            100                 105                 110

Val Ala Lys Lys Glu Gly Asn Lys Val Tyr Thr Gly Glu Glu Leu Thr
        115                 120                 125

Asn Val Val Asn Leu Leu Lys Asn Ser Thr Phe Asn Asn Gln Asn Phe
130                 135                 140

Thr Leu Ala Asn Gly Gln Lys Arg Val Ser Phe Ser Phe Pro Pro Glu
145                 150                 155                 160
```

-continued

```
Leu Glu Lys Lys Leu Gly Ile Asn Met Leu Val Lys Leu Ile Thr Pro
            165                 170                 175

Asp Gly Lys Val Leu Glu Lys Val Ser Gly Lys Val Phe Gly Glu Gly
            180                 185                 190

Val Gly Asn Ile Ala Asn Phe Glu Leu Asp Gln Pro Tyr Leu Pro Gly
            195                 200                 205

Gln Thr Phe Lys Tyr Thr Ile Ala Ser Lys Asp Tyr Pro Glu Val Ser
            210                 215                 220

Tyr Asp Gly Thr Phe Thr Val Pro Thr Ser Leu Ala Tyr Lys Met Ala
225                 230                 235                 240

Ser Gln Thr Ile Phe Tyr Pro Phe His Ala Gly Asp Thr Tyr Leu Arg
            245                 250                 255

Val Asn Pro Gln Phe Ala Val Pro Lys Gly Thr Asp Ala Leu Val Arg
            260                 265                 270

Val Phe Asp Glu Phe His Gly Asn Ala Tyr Leu Glu Asn Asn Tyr Lys
            275                 280                 285

Val Gly Glu Ile Lys Leu Pro Ile Pro Lys Leu Asn Gln Gly Thr Thr
            290                 295                 300

Arg Thr Ala Gly Asn Lys Ile Pro Val Thr Phe Met Ala Asn Ala Tyr
305                 310                 315                 320

Leu Asp Asn Gln Ser Thr Tyr Ile Val Glu Val Pro Ile Leu Glu Lys
            325                 330                 335

Glu Asn Gln Thr Asp Lys Pro Ser Ile Leu Pro Gln Phe Lys Arg Asn
            340                 345                 350

Lys Ala Gln Glu Asn Ser Lys Leu Asp Glu Lys Val Glu Glu Pro Lys
            355                 360                 365

Thr Ser Glu Lys Val Glu Lys Glu Lys Leu Ser Glu Thr Gly Asn Ser
            370                 375                 380

Thr Ser Asn Ser Thr Leu Glu Glu Val Pro Thr Val Asp Pro Val Gln
385                 390                 395                 400

Glu Lys Val Ala Lys Phe Ala Glu Ser Tyr Gly Met Lys Leu Glu Asn
            405                 410                 415

Val Leu Phe Asn Met Asp Gly Thr Ile Glu Leu Tyr Leu Pro Ser Gly
            420                 425                 430

Glu Val Ile Lys Lys Asn Met Ala Asp Phe Thr Gly Glu Ala Pro Gln
            435                 440                 445

Gly Asn Gly Glu Asn Lys Pro Ser Glu Asn Gly Lys Val Ser Thr Gly
450                 455                 460

Thr Val Glu Asn Gln Pro Thr Glu Asn Lys Pro Ala Asp Ser Leu Pro
465                 470                 475                 480

Glu Ala Pro Asn Glu Lys Pro Val Lys Pro Glu Asn Ser Thr Asp Asn
            485                 490                 495

Gly Met Leu Asn Pro Glu Gly Asn Val Gly Ser Asp Pro Met Leu Asp
            500                 505                 510

Pro Ala Leu Glu Glu Ala Pro Ala Val Asp Pro Val Gln Glu Lys Leu
            515                 520                 525

Glu Lys Phe Thr Ala Ser Tyr Gly Leu Gly Leu Asp Ser Val Ile Phe
            530                 535                 540

Asn Met Asp Gly Thr Ile Glu Leu Arg Leu Pro Ser Gly Glu Val Ile
545                 550                 555                 560

Lys Lys Asn Leu Ser Asp Phe Ile Ala Xaa Xaa Asp Ile Asp Ser Leu
            565                 570                 575

Leu Lys Gln Leu Tyr Lys Leu Pro Leu Ser Gln Arg His Val Glu Ser
```

-continued

```
              580                 585                 590
Asp Gly Leu Ile Phe Asp Pro Ala Gln Ile Thr Ser Arg Thr Ala Arg
        595                 600                 605

Gly Val Ala Val Pro His Gly Asn His Tyr His Phe Ile Pro Tyr Glu
610                 615                 620

Gln Met Ser Glu Leu Glu Lys Arg Ile Ala Arg Ile Ile Pro Leu Arg
625                 630                 635                 640

Tyr Arg Ser Asn His Trp Val Pro Asp Ser Arg Pro Glu Glu Pro Ser
                645                 650                 655

Pro Gln Pro Thr Pro Glu Pro Ser Pro Ser Pro Gln Pro Ala Pro Asn
            660                 665                 670

Pro Gln Pro Ala Pro Ser Asn Pro Ile Asp Glu Lys Leu Val Lys Glu
        675                 680                 685

Ala Val Arg Lys Val Gly Asp Gly Tyr Val Phe Glu Glu Asn Gly Val
    690                 695                 700

Ser Arg Tyr Ile Pro Ala Lys Asn Leu Ser Ala Glu Thr Ala Ala Gly
705                 710                 715                 720

Ile Asp Ser Lys Leu Ala Lys Gln Glu Ser Leu Ser His Lys Leu Gly
                725                 730                 735

Ala Lys Lys Thr Asp Leu Pro Ser Ser Asp Arg Glu Phe Tyr Asn Lys
            740                 745                 750

Ala Tyr Asp Leu Leu Ala Arg Ile His Gln Asp Leu Leu Asp Asn Lys
        755                 760                 765

Gly Arg Gln Val Asp Phe Glu Ala Leu Asp Asn Leu Leu Glu Arg Leu
    770                 775                 780

Lys Asp Val Ser Ser Asp Lys Val Lys Leu Val Asp Asp Ile Leu Ala
785                 790                 795                 800

Phe Leu Ala Pro Ile Arg His Pro Glu Arg Leu Gly Lys Pro Asn Ala
                805                 810                 815

Gln Ile Thr Tyr Thr Asp Asp Glu Ile Gln Val Ala Lys Leu Ala Gly
            820                 825                 830

Lys Tyr Thr Thr Glu Asp Gly Tyr Ile Phe Asp Pro Arg Asp Ile Thr
        835                 840                 845

Ser Asp Glu Gly Asp Ala Tyr Val Thr Pro His Met Thr His Ser His
    850                 855                 860

Trp Ile Lys Lys Asp Ser Leu Ser Glu Ala Glu Arg Ala Ala Ala Gln
865                 870                 875                 880

Ala Tyr Ala Lys Glu Lys Gly Leu Thr Pro Pro Ser Thr Asp His Gln
                885                 890                 895

Asp Ser Gly Asn Thr Glu Ala Lys Gly Ala Glu Ala Ile Tyr Asn Arg
            900                 905                 910

Val Lys Ala Ala Lys Lys Val Pro Leu Asp Arg Met Pro Tyr Asn Leu
        915                 920                 925

Gln Tyr Thr Val Glu Val Lys Asn Gly Ser Leu Ile Ile Pro His Tyr
    930                 935                 940

Asp His Tyr His Asn Ile Lys Phe Glu Trp Phe Asp Glu Gly Leu Tyr
945                 950                 955                 960

Glu Ala Pro Lys Gly Tyr Thr Leu Glu Asp Leu Leu Ala Thr Val Lys
                965                 970                 975

Tyr Tyr Val Glu His Pro Asn Glu Arg Pro His Ser Asp Asn Gly Phe
            980                 985                 990

Gly Asn Ala Ser Asp His Val
        995
```

-continued

<210> SEQ ID NO 378
<211> LENGTH: 1378
<212> TYPE: PRT
<213> ORGANISM: Artificial Sequence
<220> FEATURE:
<223> OTHER INFORMATION: Unknown Organism
<221> NAME/KEY: MISC_FEATURE
<222> LOCATION: (1)..(1)
<223> OTHER INFORMATION: Xaa = Methionine or nothing
<221> NAME/KEY: MISC_FEATURE
<222> LOCATION: (570)..(570)
<223> OTHER INFORMATION: Xaa = Glycine or nothing
<221> NAME/KEY: MISC_FEATURE
<222> LOCATION: (571)..(571)
<223> OTHER INFORMATION: Xaa = Proline or nothing

<400> SEQUENCE: 378

Xaa Glu Asn Ile Ser Ser Leu Leu Arg Glu Leu Tyr Ala Lys Pro Leu
1               5                   10                  15

Ser Glu Arg His Val Glu Ser Asp Gly Leu Ile Phe Asp Pro Ala Gln
            20                  25                  30

Ile Thr Ser Arg Thr Ala Arg Gly Val Ala Val Pro His Gly Asn His
        35                  40                  45

Tyr His Phe Ile Pro Tyr Glu Gln Met Ser Glu Leu Glu Lys Arg Ile
    50                  55                  60

Ala Arg Ile Ile Pro Leu Arg Tyr Arg Ser Asn His Trp Val Pro Asp
65                  70                  75                  80

Ser Arg Pro Glu Gln Pro Ser Pro Gln Ser Thr Pro Glu Pro Ser Pro
                85                  90                  95

Ser Leu Gln Pro Ala Pro Asn Pro Gln Pro Ala Pro Ser Asn Pro Ile
            100                 105                 110

Asp Glu Lys Leu Val Lys Glu Ala Val Arg Lys Val Gly Asp Gly Tyr
        115                 120                 125

Val Phe Glu Glu Asn Gly Val Ser Arg Tyr Ile Pro Ala Lys Asp Leu
    130                 135                 140

Ser Ala Glu Thr Ala Ala Gly Ile Asp Ser Lys Leu Ala Lys Gln Glu
145                 150                 155                 160

Ser Leu Ser His Lys Leu Gly Ala Lys Lys Thr Asp Leu Pro Ser Ser
                165                 170                 175

Asp Arg Glu Phe Tyr Asn Lys Ala Tyr Asp Leu Leu Ala Arg Ile His
            180                 185                 190

Gln Asp Leu Leu Asp Asn Lys Gly Arg Gln Val Asp Phe Glu Val Leu
        195                 200                 205

Asp Asn Leu Leu Glu Arg Leu Lys Asp Val Ser Ser Asp Lys Val Lys
    210                 215                 220

Leu Val Asp Asp Ile Leu Ala Phe Leu Ala Pro Ile Arg His Pro Glu
225                 230                 235                 240

Arg Leu Gly Lys Pro Asn Ala Gln Ile Thr Tyr Thr Asp Asp Glu Ile
                245                 250                 255

Gln Val Ala Lys Leu Ala Gly Lys Tyr Thr Thr Glu Asp Gly Tyr Ile
            260                 265                 270

Phe Asp Pro Arg Asp Ile Thr Ser Asp Glu Gly Asp Ala Tyr Val Thr
        275                 280                 285

Pro His Met Thr His Ser His Trp Ile Lys Lys Asp Ser Leu Ser Glu
    290                 295                 300

Ala Glu Arg Ala Ala Ala Gln Tyr Ala Lys Glu Lys Gly Leu Thr
305                 310                 315                 320

-continued

Pro Pro Ser Thr Asp His Gln Asp Ser Gly Asn Thr Glu Ala Lys Gly
            325                 330                 335

Ala Glu Ala Ile Tyr Asn Arg Val Lys Ala Ala Lys Lys Val Pro Leu
            340                 345                 350

Asp Arg Met Pro Tyr Asn Leu Gln Tyr Thr Val Glu Val Lys Asn Gly
            355                 360                 365

Ser Leu Ile Ile Pro His Tyr Asp His Tyr His Asn Ile Lys Phe Glu
    370                 375                 380

Trp Phe Asp Glu Gly Leu Tyr Glu Ala Pro Lys Gly Tyr Ser Leu Glu
385                 390                 395                 400

Asp Leu Leu Ala Thr Val Lys Tyr Tyr Val Glu His Pro Asn Glu Arg
            405                 410                 415

Pro His Ser Asp Asn Gly Phe Gly Asn Ala Ser Asp His Val Arg Lys
            420                 425                 430

Asn Lys Ala Asp Gln Asp Ser Lys Pro Asp Glu Asp Lys Glu His Asp
            435                 440                 445

Glu Val Ser Glu Pro Thr His Pro Glu Ser Asp Glu Lys Glu Asn His
    450                 455                 460

Ala Gly Leu Asn Pro Ser Ala Asp Asn Leu Tyr Lys Pro Ser Thr Asp
465                 470                 475                 480

Thr Glu Glu Thr Glu Glu Ala Glu Asp Thr Thr Asp Glu Ala Glu
            485                 490                 495

Ile Pro Gln Val Glu Asn Ser Val Ile Asn Ala Lys Ile Ala Asp Ala
            500                 505                 510

Glu Ala Leu Leu Glu Lys Val Thr Asp Pro Ser Ile Arg Gln Asn Ala
            515                 520                 525

Met Glu Thr Leu Thr Gly Leu Lys Ser Ser Leu Leu Leu Gly Thr Lys
    530                 535                 540

Asp Asn Asn Thr Ile Ser Ala Glu Val Asp Ser Leu Leu Ala Leu Leu
545                 550                 555                 560

Lys Glu Ser Gln Pro Ala Pro Ile Gln Xaa Xaa Asn Met Gln Pro Ser
            565                 570                 575

Gln Leu Ser Tyr Ser Ser Thr Ala Ser Asp Asn Asn Thr Gln Ser Val
            580                 585                 590

Ala Lys Gly Ser Thr Ser Lys Pro Ala Asn Lys Ser Glu Asn Leu Gln
            595                 600                 605

Ser Leu Leu Lys Glu Leu Tyr Asp Ser Pro Ser Ala Gln Arg Tyr Ser
    610                 615                 620

Glu Ser Asp Gly Leu Val Phe Asp Pro Ala Lys Ile Ile Ser Arg Thr
625                 630                 635                 640

Pro Asn Gly Val Ala Ile Pro His Gly Asp His Tyr His Phe Ile Pro
            645                 650                 655

Tyr Ser Lys Leu Ser Ala Leu Glu Glu Lys Ile Ala Arg Met Val Pro
            660                 665                 670

Ile Ser Gly Thr Gly Ser Thr Val Ser Thr Asn Ala Lys Pro Asn Glu
            675                 680                 685

Val Val Ser Ser Leu Gly Ser Leu Ser Asn Pro Ser Ser Leu Thr
    690                 695                 700

Thr Ser Lys Glu Leu Ser Ser Ala Ser Asp Gly Tyr Ile Phe Asn Pro
705                 710                 715                 720

Lys Asp Ile Val Glu Glu Thr Ala Thr Ala Tyr Ile Val Arg His Gly
            725                 730                 735

-continued

```
Asp His Phe His Tyr Ile Pro Lys Ser Asn Gln Ile Gly Gln Pro Thr
                740                 745                 750

Leu Pro Asn Asn Ser Leu Ala Thr Pro Ser Pro Ser Leu Pro Ile Asn
                755                 760                 765

Pro Gly Thr Ser His Glu Lys His Glu Glu Asp Gly Tyr Gly Phe Asp
            770                 775                 780

Ala Asn Arg Ile Ile Ala Glu Asp Glu Ser Gly Phe Val Met Ser His
785                 790                 795                 800

Gly Asp His Asn His Tyr Phe Phe Lys Lys Asp Leu Thr Glu Glu Gln
                805                 810                 815

Ile Lys Ala Ala Gln Lys His Leu Glu Glu Val Lys Thr Ser His Asn
                820                 825                 830

Gly Leu Asp Ser Leu Ser Ser His Glu Gln Asp Tyr Pro Gly Asn Ala
                835                 840                 845

Lys Glu Met Lys Asp Leu Asp Lys Lys Ile Glu Lys Ile Ala Gly
                850                 855                 860

Ile Met Lys Gln Tyr Gly Val Lys Arg Glu Ser Ile Val Val Asn Lys
865                 870                 875                 880

Glu Lys Asn Ala Ile Ile Tyr Pro His Gly Asp His His Ala Asp
                885                 890                 895

Pro Ile Asp Glu His Lys Pro Val Gly Ile Gly His Ser His Ser Asn
                900                 905                 910

Tyr Glu Leu Phe Lys Pro Glu Glu Gly Val Ala Lys Lys Glu Gly Asn
                915                 920                 925

Lys Val Tyr Thr Gly Glu Glu Leu Thr Asn Val Val Asn Leu Leu Lys
                930                 935                 940

Asn Ser Thr Phe Asn Asn Gln Asn Phe Thr Leu Ala Asn Gly Gln Lys
945                 950                 955                 960

Arg Val Ser Phe Ser Phe Pro Pro Glu Leu Glu Lys Lys Leu Gly Ile
                965                 970                 975

Asn Met Leu Val Lys Leu Ile Thr Pro Asp Gly Lys Val Leu Glu Lys
                980                 985                 990

Val Ser Gly Lys Val Phe Gly Glu Gly Val Gly Asn Ile Ala Asn Phe
                995                 1000                1005

Glu Leu Asp Gln Pro Tyr Leu Pro Gly Gln Thr Phe Lys Tyr Thr
            1010                1015                1020

Ile Ala Ser Lys Asp Tyr Pro Glu Val Ser Tyr Asp Gly Thr Phe
            1025                1030                1035

Thr Val Pro Thr Ser Leu Ala Tyr Lys Met Ala Ser Gln Thr Ile
            1040                1045                1050

Phe Tyr Pro Phe His Ala Gly Asp Thr Tyr Leu Arg Val Asn Pro
            1055                1060                1065

Gln Phe Ala Val Pro Lys Gly Thr Asp Ala Leu Val Arg Val Phe
            1070                1075                1080

Asp Glu Phe His Gly Asn Ala Tyr Leu Glu Asn Tyr Lys Val
            1085                1090                1095

Gly Glu Ile Lys Leu Pro Ile Pro Lys Leu Asn Gln Gly Thr Thr
            1100                1105                1110

Arg Thr Ala Gly Asn Lys Ile Pro Val Thr Phe Met Ala Asn Ala
            1115                1120                1125

Tyr Leu Asp Asn Gln Ser Thr Tyr Ile Val Glu Val Pro Ile Leu
            1130                1135                1140

Glu Lys Glu Asn Gln Thr Asp Lys Pro Ser Ile Leu Pro Gln Phe
```

-continued

```
              1145                1150                1155

Lys Arg Asn Lys Ala Gln Glu  Asn Ser Lys Leu Asp  Glu Lys Val
        1160                1165                1170

Glu Glu Pro Lys Thr Ser Glu  Lys Val Glu Lys Glu  Lys Leu Ser
        1175                1180                1185

Glu Thr Gly Asn Ser Thr Ser  Asn Ser Thr Leu Glu  Glu Val Pro
        1190                1195                1200

Thr Val Asp Pro Val Gln Glu  Lys Val Ala Lys Phe  Ala Glu Ser
        1205                1210                1215

Tyr Gly Met Lys Leu Glu Asn  Val Leu Phe Asn Met  Asp Gly Thr
        1220                1225                1230

Ile Glu Leu Tyr Leu Pro Ser  Gly Glu Val Ile Lys  Lys Asn Met
        1235                1240                1245

Ala Asp Phe Thr Gly Glu Ala  Pro Gln Gly Asn Gly  Glu Asn Lys
        1250                1255                1260

Pro Ser Glu Asn Gly Lys Val  Ser Thr Gly Thr Val  Glu Asn Gln
        1265                1270                1275

Pro Thr Glu Asn Lys Pro Ala  Asp Ser Leu Pro Glu  Ala Pro Asn
        1280                1285                1290

Glu Lys Pro Val Lys Pro Glu  Asn Ser Thr Asp Asn  Gly Met Leu
        1295                1300                1305

Asn Pro Glu Gly Asn Val Gly  Ser Asp Pro Met Leu  Asp Pro Ala
        1310                1315                1320

Leu Glu Glu Ala Pro Ala Val  Asp Pro Val Gln Glu  Lys Leu Glu
        1325                1330                1335

Lys Phe Thr Ala Ser Tyr Gly  Leu Gly Leu Asp Ser  Val Ile Phe
        1340                1345                1350

Asn Met Asp Gly Thr Ile Glu  Leu Arg Leu Pro Ser  Gly Glu Val
        1355                1360                1365

Ile Lys Lys Asn Leu Ser Asp  Phe Ile Ala
        1370                1375
```

<210> SEQ ID NO 379
<211> LENGTH: 1152
<212> TYPE: PRT
<213> ORGANISM: Artificial Sequence
<220> FEATURE:
<223> OTHER INFORMATION: Unknown Organism
<221> NAME/KEY: MISC_FEATURE
<222> LOCATION: (1)..(1)
<223> OTHER INFORMATION: Xaa = Methionine or nothing
<221> NAME/KEY: MISC_FEATURE
<222> LOCATION: (344)..(344)
<223> OTHER INFORMATION: Xaa = Glycine or nothing
<221> NAME/KEY: MISC_FEATURE
<222> LOCATION: (345)..(345)
<223> OTHER INFORMATION: Xaa = Proline or nothing

<400> SEQUENCE: 379

```
Xaa Asp Ile Leu Ala Phe Leu Ala Pro Ile Arg His Pro Glu Arg Leu
1               5                   10                  15

Gly Lys Pro Asn Ala Gln Ile Thr Tyr Thr Asp Asp Glu Ile Gln Val
            20                  25                  30

Ala Lys Leu Ala Gly Lys Tyr Thr Thr Glu Asp Gly Tyr Ile Phe Asp
        35                  40                  45

Pro Arg Asp Ile Thr Ser Asp Glu Gly Asp Ala Tyr Val Thr Pro His
    50                  55                  60

Met Thr His Ser His Trp Ile Lys Lys Asp Ser Leu Ser Glu Ala Glu
```

-continued

```
            65                  70                  75                  80
Arg Ala Ala Gln Ala Tyr Ala Lys Glu Lys Gly Leu Thr Pro Pro
                85                  90                  95
Ser Thr Asp His Gln Asp Ser Gly Asn Thr Glu Ala Lys Gly Ala Glu
                100                 105                 110
Ala Ile Tyr Asn Arg Val Lys Ala Ala Lys Lys Val Pro Leu Asp Arg
                115                 120                 125
Met Pro Tyr Asn Leu Gln Tyr Thr Val Glu Val Lys Asn Gly Ser Leu
        130                 135                 140
Ile Ile Pro His Tyr Asp His Tyr His Asn Ile Lys Phe Glu Trp Phe
145                 150                 155                 160
Asp Glu Gly Leu Tyr Glu Ala Pro Lys Gly Tyr Ser Leu Glu Asp Leu
                165                 170                 175
Leu Ala Thr Val Lys Tyr Tyr Val Glu His Pro Asn Glu Arg Pro His
                180                 185                 190
Ser Asp Asn Gly Phe Gly Asn Ala Ser Asp His Val Arg Lys Asn Lys
                195                 200                 205
Ala Asp Gln Asp Ser Lys Pro Asp Glu Asp Lys Glu His Asp Glu Val
        210                 215                 220
Ser Glu Pro Thr His Pro Glu Ser Asp Glu Lys Glu Asn His Ala Gly
225                 230                 235                 240
Leu Asn Pro Ser Ala Asp Asn Leu Tyr Lys Pro Ser Thr Asp Thr Glu
                245                 250                 255
Glu Thr Glu Glu Glu Ala Glu Asp Thr Thr Asp Glu Ala Glu Ile Pro
                260                 265                 270
Gln Val Glu Asn Ser Val Ile Asn Ala Lys Ile Ala Asp Ala Glu Ala
                275                 280                 285
Leu Leu Glu Lys Val Thr Asp Pro Ser Ile Arg Gln Asn Ala Met Glu
        290                 295                 300
Thr Leu Thr Gly Leu Lys Ser Ser Leu Leu Gly Thr Lys Asp Asn
305                 310                 315                 320
Asn Thr Ile Ser Ala Glu Val Asp Ser Leu Leu Ala Leu Leu Lys Glu
                325                 330                 335
Ser Gln Pro Ala Pro Ile Gln Xaa Xaa Asn Met Gln Pro Ser Gln Leu
                340                 345                 350
Ser Tyr Ser Ser Thr Ala Ser Asp Asn Asn Thr Gln Ser Val Ala Lys
                355                 360                 365
Gly Ser Thr Ser Lys Pro Ala Asn Lys Ser Glu Asn Leu Gln Ser Leu
                370                 375                 380
Leu Lys Glu Leu Tyr Asp Ser Pro Ser Ala Gln Arg Tyr Ser Glu Ser
385                 390                 395                 400
Asp Gly Leu Val Phe Asp Pro Ala Lys Ile Ile Ser Arg Thr Pro Asn
                405                 410                 415
Gly Val Ala Ile Pro His Gly Asp His Tyr His Phe Ile Pro Tyr Ser
                420                 425                 430
Lys Leu Ser Ala Leu Glu Glu Lys Ile Ala Arg Met Val Pro Ile Ser
                435                 440                 445
Gly Thr Gly Ser Thr Val Ser Thr Asn Ala Lys Pro Asn Glu Val Val
        450                 455                 460
Ser Ser Leu Gly Ser Leu Ser Ser Asn Pro Ser Ser Leu Thr Thr Ser
465                 470                 475                 480
Lys Glu Leu Ser Ser Ala Ser Asp Gly Tyr Ile Phe Asn Pro Lys Asp
                485                 490                 495
```

-continued

```
Ile Val Glu Glu Thr Ala Thr Ala Tyr Ile Val Arg His Gly Asp His
            500                 505                 510
Phe His Tyr Ile Pro Lys Ser Asn Gln Ile Gly Gln Pro Thr Leu Pro
            515                 520                 525
Asn Asn Ser Leu Ala Thr Pro Ser Pro Ser Leu Pro Ile Asn Pro Gly
            530                 535                 540
Thr Ser His Glu Lys His Glu Glu Asp Gly Tyr Gly Phe Asp Ala Asn
545                 550                 555                 560
Arg Ile Ile Ala Glu Asp Ser Gly Phe Val Met Ser His Gly Asp
                    565                 570                 575
His Asn His Tyr Phe Phe Lys Lys Asp Leu Thr Glu Glu Gln Ile Lys
            580                 585                 590
Ala Ala Gln Lys His Leu Glu Val Lys Thr Ser His Asn Gly Leu
            595                 600                 605
Asp Ser Leu Ser Ser His Glu Gln Asp Tyr Pro Gly Asn Ala Lys Glu
            610                 615                 620
Met Lys Asp Leu Asp Lys Lys Ile Glu Glu Lys Ile Ala Gly Ile Met
625                 630                 635                 640
Lys Gln Tyr Gly Val Lys Arg Glu Ser Ile Val Val Asn Lys Glu Lys
                    645                 650                 655
Asn Ala Ile Ile Tyr Pro His Gly Asp His His Ala Asp Pro Ile
            660                 665                 670
Asp Glu His Lys Pro Val Gly Ile Gly His Ser His Ser Asn Tyr Glu
            675                 680                 685
Leu Phe Lys Pro Glu Glu Gly Val Ala Lys Lys Glu Gly Asn Lys Val
            690                 695                 700
Tyr Thr Gly Glu Glu Leu Thr Asn Val Val Asn Leu Leu Lys Asn Ser
705                 710                 715                 720
Thr Phe Asn Asn Gln Asn Phe Thr Leu Ala Asn Gly Gln Lys Arg Val
                    725                 730                 735
Ser Phe Ser Phe Pro Pro Glu Leu Glu Lys Lys Leu Gly Ile Asn Met
                    740                 745                 750
Leu Val Lys Leu Ile Thr Pro Asp Gly Lys Val Leu Glu Lys Val Ser
            755                 760                 765
Gly Lys Val Phe Gly Glu Gly Val Gly Asn Ile Ala Asn Phe Glu Leu
            770                 775                 780
Asp Gln Pro Tyr Leu Pro Gly Gln Thr Phe Lys Tyr Thr Ile Ala Ser
785                 790                 795                 800
Lys Asp Tyr Pro Glu Val Ser Tyr Asp Gly Thr Phe Thr Val Pro Thr
                    805                 810                 815
Ser Leu Ala Tyr Lys Met Ala Ser Gln Thr Ile Phe Tyr Pro Phe His
            820                 825                 830
Ala Gly Asp Thr Tyr Leu Arg Val Asn Pro Gln Phe Ala Val Pro Lys
            835                 840                 845
Gly Thr Asp Ala Leu Val Arg Val Phe Asp Glu Phe His Gly Asn Ala
            850                 855                 860
Tyr Leu Glu Asn Asn Tyr Lys Val Gly Glu Ile Lys Leu Pro Ile Pro
865                 870                 875                 880
Lys Leu Asn Gln Gly Thr Thr Arg Thr Ala Gly Asn Lys Ile Pro Val
                    885                 890                 895
Thr Phe Met Ala Asn Ala Tyr Leu Asp Asn Gln Ser Thr Tyr Ile Val
            900                 905                 910
```

-continued

```
Glu Val Pro Ile Leu Glu Lys Glu Asn Gln Thr Asp Lys Pro Ser Ile
            915                 920                 925

Leu Pro Gln Phe Lys Arg Asn Lys Ala Gln Glu Asn Ser Lys Leu Asp
        930                 935                 940

Glu Lys Val Glu Glu Pro Lys Thr Ser Glu Lys Val Glu Lys Glu Lys
945                 950                 955                 960

Leu Ser Glu Thr Gly Asn Ser Thr Ser Asn Ser Thr Leu Glu Glu Val
            965                 970                 975

Pro Thr Val Asp Pro Val Gln Glu Lys Val Ala Lys Phe Ala Glu Ser
            980                 985                 990

Tyr Gly Met Lys Leu Glu Asn Val Leu Phe Asn Met Asp Gly Thr Ile
            995                1000                1005

Glu Leu Tyr Leu Pro Ser Gly Glu Val Ile Lys Lys Asn Met Ala
        1010                1015                1020

Asp Phe Thr Gly Glu Ala Pro Gln Gly Asn Gly Glu Asn Lys Pro
        1025                1030                1035

Ser Glu Asn Gly Lys Val Ser Thr Gly Thr Val Glu Asn Gln Pro
        1040                1045                1050

Thr Glu Asn Lys Pro Ala Asp Ser Leu Pro Glu Ala Pro Asn Glu
        1055                1060                1065

Lys Pro Val Lys Pro Glu Asn Ser Thr Asp Asn Gly Met Leu Asn
        1070                1075                1080

Pro Glu Gly Asn Val Gly Ser Asp Pro Met Leu Asp Pro Ala Leu
        1085                1090                1095

Glu Glu Ala Pro Ala Val Asp Pro Val Gln Glu Lys Leu Glu Lys
        1100                1105                1110

Phe Thr Ala Ser Tyr Gly Leu Gly Leu Asp Ser Val Ile Phe Asn
        1115                1120                1125

Met Asp Gly Thr Ile Glu Leu Arg Leu Pro Ser Gly Glu Val Ile
        1130                1135                1140

Lys Lys Asn Leu Ser Asp Phe Ile Ala
        1145                1150
```

<210> SEQ ID NO 380
<211> LENGTH: 1139
<212> TYPE: PRT
<213> ORGANISM: Artificial Sequence
<220> FEATURE:
<223> OTHER INFORMATION: Unknown Organism
<221> NAME/KEY: MISC_FEATURE
<222> LOCATION: (1)..(1)
<223> OTHER INFORMATION: Xaa = Methionine or nothing
<221> NAME/KEY: MISC_FEATURE
<222> LOCATION: (570)..(570)
<223> OTHER INFORMATION: Xaa = Glycine or nothing
<221> NAME/KEY: MISC_FEATURE
<222> LOCATION: (571)..(571)
<223> OTHER INFORMATION: Xaa = Proline or nothing

<400> SEQUENCE: 380

```
Xaa Glu Asn Ile Ser Ser Leu Leu Arg Glu Leu Tyr Ala Lys Pro Leu
1               5                   10                  15

Ser Glu Arg His Val Glu Ser Asp Gly Leu Ile Phe Asp Pro Ala Gln
            20                  25                  30

Ile Thr Ser Arg Thr Ala Arg Gly Val Ala Val Pro His Gly Asn His
        35                  40                  45

Tyr His Phe Ile Pro Tyr Glu Gln Met Ser Glu Leu Glu Lys Arg Ile
    50                  55                  60
```

```
Ala Arg Ile Ile Pro Leu Arg Tyr Arg Ser Asn His Trp Val Pro Asp
 65                  70                  75                  80

Ser Arg Pro Glu Gln Pro Ser Pro Gln Ser Thr Pro Glu Pro Ser Pro
                 85                  90                  95

Ser Leu Gln Pro Ala Pro Asn Pro Gln Pro Ala Pro Ser Asn Pro Ile
            100                 105                 110

Asp Glu Lys Leu Val Lys Glu Ala Val Arg Lys Val Gly Asp Gly Tyr
        115                 120                 125

Val Phe Glu Glu Asn Gly Val Ser Arg Tyr Ile Pro Ala Lys Asp Leu
    130                 135                 140

Ser Ala Glu Thr Ala Ala Gly Ile Asp Ser Lys Leu Ala Lys Gln Glu
145                 150                 155                 160

Ser Leu Ser His Lys Leu Gly Ala Lys Lys Thr Asp Leu Pro Ser Ser
                165                 170                 175

Asp Arg Glu Phe Tyr Asn Lys Ala Tyr Asp Leu Leu Ala Arg Ile His
            180                 185                 190

Gln Asp Leu Leu Asp Asn Lys Gly Arg Gln Val Asp Phe Glu Val Leu
        195                 200                 205

Asp Asn Leu Leu Glu Arg Leu Lys Asp Val Ser Ser Asp Lys Val Lys
    210                 215                 220

Leu Val Asp Asp Ile Leu Ala Phe Leu Ala Pro Ile Arg His Pro Glu
225                 230                 235                 240

Arg Leu Gly Lys Pro Asn Ala Gln Ile Thr Tyr Thr Asp Asp Glu Ile
                245                 250                 255

Gln Val Ala Lys Leu Ala Gly Lys Tyr Thr Thr Glu Asp Gly Tyr Ile
            260                 265                 270

Phe Asp Pro Arg Asp Ile Thr Ser Asp Glu Gly Asp Ala Tyr Val Thr
        275                 280                 285

Pro His Met Thr His Ser His Trp Ile Lys Lys Asp Ser Leu Ser Glu
    290                 295                 300

Ala Glu Arg Ala Ala Ala Gln Ala Tyr Ala Lys Glu Lys Gly Leu Thr
305                 310                 315                 320

Pro Pro Ser Thr Asp His Gln Asp Ser Gly Asn Thr Glu Ala Lys Gly
                325                 330                 335

Ala Glu Ala Ile Tyr Asn Arg Val Lys Ala Ala Lys Lys Val Pro Leu
            340                 345                 350

Asp Arg Met Pro Tyr Asn Leu Gln Tyr Thr Val Glu Val Lys Asn Gly
        355                 360                 365

Ser Leu Ile Ile Pro His Tyr Asp His Tyr His Asn Ile Lys Phe Glu
    370                 375                 380

Trp Phe Asp Glu Gly Leu Tyr Glu Ala Pro Lys Gly Tyr Ser Leu Glu
385                 390                 395                 400

Asp Leu Leu Ala Thr Val Lys Tyr Tyr Val Glu His Pro Asn Glu Arg
                405                 410                 415

Pro His Ser Asp Asn Gly Phe Gly Asn Ala Ser Asp His Val Arg Lys
            420                 425                 430

Asn Lys Ala Asp Gln Asp Ser Lys Pro Asp Glu Lys Glu His Asp
        435                 440                 445

Glu Val Ser Glu Pro Thr His Pro Glu Ser Asp Glu Lys Glu Asn His
    450                 455                 460

Ala Gly Leu Asn Pro Ser Ala Asp Asn Leu Tyr Lys Pro Ser Thr Asp
465                 470                 475                 480

Thr Glu Glu Thr Glu Glu Glu Ala Glu Asp Thr Thr Asp Glu Ala Glu
```

-continued

```
                485                 490                 495
Ile Pro Gln Val Glu Asn Ser Val Ile Asn Ala Lys Ile Ala Asp Ala
            500                 505                 510
Glu Ala Leu Leu Glu Lys Val Thr Asp Pro Ser Ile Arg Gln Asn Ala
            515                 520                 525
Met Glu Thr Leu Thr Gly Leu Lys Ser Ser Leu Leu Gly Thr Lys
            530                 535                 540
Asp Asn Asn Thr Ile Ser Ala Glu Val Asp Ser Leu Leu Ala Leu Leu
545                 550                 555                 560
Lys Glu Ser Gln Pro Ala Pro Ile Gln Xaa Xaa Asp Leu Thr Glu Glu
                565                 570                 575
Gln Ile Lys Ala Ala Gln Lys His Leu Glu Glu Val Lys Thr Ser His
            580                 585                 590
Asn Gly Leu Asp Ser Leu Ser Ser His Glu Gln Asp Tyr Pro Gly Asn
            595                 600                 605
Ala Lys Glu Met Lys Asp Leu Asp Lys Lys Ile Glu Glu Lys Ile Ala
            610                 615                 620
Gly Ile Met Lys Gln Tyr Gly Val Lys Arg Glu Ser Ile Val Val Asn
625                 630                 635                 640
Lys Glu Lys Asn Ala Ile Ile Tyr Pro His Gly Asp His His His Ala
                645                 650                 655
Asp Pro Ile Asp Glu His Lys Pro Val Gly Ile Gly His Ser His Ser
            660                 665                 670
Asn Tyr Glu Leu Phe Lys Pro Glu Gly Val Ala Lys Lys Glu Gly
            675                 680                 685
Asn Lys Val Tyr Thr Gly Glu Glu Leu Thr Asn Val Val Asn Leu Leu
            690                 695                 700
Lys Asn Ser Thr Phe Asn Asn Gln Asn Phe Thr Leu Ala Asn Gly Gln
705                 710                 715                 720
Lys Arg Val Ser Phe Ser Pro Pro Glu Leu Lys Lys Leu Gly
                725                 730                 735
Ile Asn Met Leu Val Lys Leu Ile Thr Pro Asp Gly Lys Val Leu Glu
            740                 745                 750
Lys Val Ser Gly Lys Val Phe Gly Glu Gly Val Gly Asn Ile Ala Asn
            755                 760                 765
Phe Glu Leu Asp Gln Pro Tyr Leu Pro Gly Gln Thr Phe Lys Tyr Thr
            770                 775                 780
Ile Ala Ser Lys Asp Tyr Pro Glu Val Ser Tyr Asp Gly Thr Phe Thr
785                 790                 795                 800
Val Pro Thr Ser Leu Ala Tyr Lys Met Ala Ser Gln Thr Ile Phe Tyr
                805                 810                 815
Pro Phe His Ala Gly Asp Thr Tyr Leu Arg Val Asn Pro Gln Phe Ala
            820                 825                 830
Val Pro Lys Gly Thr Asp Ala Leu Val Arg Val Phe Asp Glu Phe His
            835                 840                 845
Gly Asn Ala Tyr Leu Glu Asn Tyr Lys Val Gly Glu Ile Lys Leu
            850                 855                 860
Pro Ile Pro Lys Leu Asn Gln Gly Thr Thr Arg Thr Ala Gly Asn Lys
865                 870                 875                 880
Ile Pro Val Thr Phe Met Ala Asn Ala Tyr Leu Asp Asn Gln Ser Thr
                885                 890                 895
Tyr Ile Val Glu Val Pro Ile Leu Glu Lys Glu Asn Gln Thr Asp Lys
            900                 905                 910
```

```
Pro Ser Ile Leu Pro Gln Phe Lys Arg Asn Lys Ala Gln Glu Asn Ser
        915                 920                 925

Lys Leu Asp Glu Lys Val Glu Pro Lys Thr Ser Glu Lys Val Glu
    930                 935                 940

Lys Glu Lys Leu Ser Glu Thr Gly Asn Ser Thr Ser Asn Ser Thr Leu
945                 950                 955                 960

Glu Glu Val Pro Thr Val Asp Pro Val Gln Lys Val Ala Lys Phe
                965                 970                 975

Ala Glu Ser Tyr Gly Met Lys Leu Glu Asn Val Leu Phe Asn Met Asp
            980                 985                 990

Gly Thr Ile Glu Leu Tyr Leu Pro Ser Gly Glu Val Ile Lys Lys Asn
        995                1000                1005

Met Ala Asp Phe Thr Gly Glu Ala Pro Gln Gly Asn Gly Glu Asn
    1010                1015                1020

Lys Pro Ser Glu Asn Gly Lys Val Ser Thr Gly Thr Val Glu Asn
    1025                1030                1035

Gln Pro Thr Glu Asn Lys Pro Ala Asp Ser Leu Pro Glu Ala Pro
    1040                1045                1050

Asn Glu Lys Pro Val Lys Pro Glu Asn Ser Thr Asp Asn Gly Met
    1055                1060                1065

Leu Asn Pro Glu Gly Asn Val Gly Ser Asp Pro Met Leu Asp Pro
    1070                1075                1080

Ala Leu Glu Glu Ala Pro Ala Val Asp Pro Val Gln Glu Lys Leu
    1085                1090                1095

Glu Lys Phe Thr Ala Ser Tyr Gly Leu Gly Leu Asp Ser Val Ile
    1100                1105                1110

Phe Asn Met Asp Gly Thr Ile Glu Leu Arg Leu Pro Ser Gly Glu
    1115                1120                1125

Val Ile Lys Lys Asn Leu Ser Asp Phe Ile Ala
    1130                1135

<210> SEQ ID NO 381
<211> LENGTH: 1238
<212> TYPE: PRT
<213> ORGANISM: Artificial Sequence
<220> FEATURE:
<223> OTHER INFORMATION: Unknown Organism
<221> NAME/KEY: MISC_FEATURE
<222> LOCATION: (1)..(1)
<223> OTHER INFORMATION: Xaa = Methionine or nothing
<221> NAME/KEY: MISC_FEATURE
<222> LOCATION: (430)..(430)
<223> OTHER INFORMATION: Xaa = Glycine or nothing
<221> NAME/KEY: MISC_FEATURE
<222> LOCATION: (431)..(431)
<223> OTHER INFORMATION: Xaa = Proline or nothing

<400> SEQUENCE: 381

Xaa Asp Ile Asp Ser Leu Leu Lys Gln Leu Tyr Lys Leu Pro Leu Ser
1               5                   10                  15

Gln Arg His Val Glu Ser Asp Gly Leu Ile Phe Asp Pro Ala Gln Ile
            20                  25                  30

Thr Ser Arg Thr Ala Arg Gly Val Ala Val Pro His Gly Asn His Tyr
        35                  40                  45

His Phe Ile Pro Tyr Glu Gln Met Ser Glu Leu Glu Lys Arg Ile Ala
    50                  55                  60

Arg Ile Ile Pro Leu Arg Tyr Arg Ser Asn His Trp Val Pro Asp Ser
65                  70                  75                  80
```

-continued

```
Arg Pro Glu Glu Pro Ser Pro Gln Pro Thr Pro Glu Pro Ser Pro Ser
                85                  90                  95

Pro Gln Pro Ala Pro Asn Pro Gln Pro Ala Pro Ser Asn Pro Ile Asp
            100                 105                 110

Glu Lys Leu Val Lys Glu Ala Val Arg Lys Val Gly Asp Gly Tyr Val
        115                 120                 125

Phe Glu Glu Asn Gly Val Ser Arg Tyr Ile Pro Ala Lys Asn Leu Ser
    130                 135                 140

Ala Glu Thr Ala Ala Gly Ile Asp Ser Lys Leu Ala Lys Gln Glu Ser
145                 150                 155                 160

Leu Ser His Lys Leu Gly Ala Lys Lys Thr Asp Leu Pro Ser Ser Asp
                165                 170                 175

Arg Glu Phe Tyr Asn Lys Ala Tyr Asp Leu Leu Ala Arg Ile His Gln
            180                 185                 190

Asp Leu Leu Asp Asn Lys Gly Arg Gln Val Asp Phe Glu Ala Leu Asp
        195                 200                 205

Asn Leu Leu Glu Arg Leu Lys Asp Val Ser Ser Asp Lys Val Lys Leu
    210                 215                 220

Val Asp Asp Ile Leu Ala Phe Leu Ala Pro Ile Arg His Pro Glu Arg
225                 230                 235                 240

Leu Gly Lys Pro Asn Ala Gln Ile Thr Tyr Thr Asp Glu Ile Gln
                245                 250                 255

Val Ala Lys Leu Ala Gly Lys Tyr Thr Thr Glu Asp Gly Tyr Ile Phe
            260                 265                 270

Asp Pro Arg Asp Ile Thr Ser Asp Glu Gly Asp Ala Tyr Val Thr Pro
        275                 280                 285

His Met Thr His Ser His Trp Ile Lys Lys Asp Ser Leu Ser Glu Ala
    290                 295                 300

Glu Arg Ala Ala Ala Gln Ala Tyr Ala Lys Glu Lys Gly Leu Thr Pro
305                 310                 315                 320

Pro Ser Thr Asp His Gln Asp Ser Gly Asn Thr Glu Ala Lys Gly Ala
                325                 330                 335

Glu Ala Ile Tyr Asn Arg Val Lys Ala Ala Lys Lys Val Pro Leu Asp
            340                 345                 350

Arg Met Pro Tyr Asn Leu Gln Tyr Thr Val Glu Val Lys Asn Gly Ser
        355                 360                 365

Leu Ile Ile Pro His Tyr Asp His Tyr His Asn Ile Lys Phe Glu Trp
    370                 375                 380

Phe Asp Glu Gly Leu Tyr Glu Ala Pro Lys Gly Tyr Thr Leu Glu Asp
385                 390                 395                 400

Leu Leu Ala Thr Val Lys Tyr Tyr Val Glu His Pro Asn Glu Arg Pro
                405                 410                 415

His Ser Asp Asn Gly Phe Gly Asn Ala Ser Asp His Val Xaa Xaa Asn
            420                 425                 430

Met Gln Pro Ser Gln Leu Ser Tyr Ser Ser Thr Ala Ser Asp Asn Asn
        435                 440                 445

Thr Gln Ser Val Ala Lys Gly Ser Thr Ser Lys Pro Ala Asn Lys Ser
    450                 455                 460

Glu Asn Leu Gln Ser Leu Leu Lys Glu Leu Tyr Asp Ser Pro Ser Ala
465                 470                 475                 480

Gln Arg Tyr Ser Glu Ser Asp Gly Leu Val Phe Asp Pro Ala Lys Ile
                485                 490                 495
```

-continued

```
Ile Ser Arg Thr Pro Asn Gly Val Ala Ile Pro His Gly Asp His Tyr
            500                 505                 510
His Phe Ile Pro Tyr Ser Lys Leu Ser Ala Leu Glu Glu Lys Ile Ala
            515                 520                 525
Arg Met Val Pro Ile Ser Gly Thr Gly Ser Thr Val Ser Thr Asn Ala
            530                 535                 540
Lys Pro Asn Glu Val Val Ser Ser Leu Gly Ser Leu Ser Ser Asn Pro
545                 550                 555                 560
Ser Ser Leu Thr Thr Ser Lys Glu Leu Ser Ser Ala Ser Asp Gly Tyr
                565                 570                 575
Ile Phe Asn Pro Lys Asp Ile Val Glu Thr Ala Thr Ala Tyr Ile
            580                 585                 590
Val Arg His Gly Asp His Phe His Tyr Ile Pro Lys Ser Asn Gln Ile
            595                 600                 605
Gly Gln Pro Thr Leu Pro Asn Asn Ser Leu Ala Thr Pro Ser Pro Ser
            610                 615                 620
Leu Pro Ile Asn Pro Gly Thr Ser His Glu Lys His Glu Glu Asp Gly
625                 630                 635                 640
Tyr Gly Phe Asp Ala Asn Arg Ile Ile Ala Glu Asp Glu Ser Gly Phe
                645                 650                 655
Val Met Ser His Gly Asp His Asn His Tyr Phe Phe Lys Lys Asp Leu
            660                 665                 670
Thr Glu Glu Gln Ile Lys Ala Ala Gln Lys His Leu Glu Glu Val Lys
            675                 680                 685
Thr Ser His Asn Gly Leu Asp Ser Leu Ser Ser His Glu Gln Asp Tyr
            690                 695                 700
Pro Gly Asn Ala Lys Glu Met Lys Asp Leu Asp Lys Lys Ile Glu Glu
705                 710                 715                 720
Lys Ile Ala Gly Ile Met Lys Gln Tyr Gly Val Lys Arg Glu Ser Ile
            725                 730                 735
Val Val Asn Lys Glu Lys Asn Ala Ile Ile Tyr Pro His Gly Asp His
            740                 745                 750
His His Ala Asp Pro Ile Asp Glu His Lys Pro Val Gly Ile Gly His
            755                 760                 765
Ser His Ser Asn Tyr Glu Leu Phe Lys Pro Glu Glu Gly Val Ala Lys
            770                 775                 780
Lys Glu Gly Asn Lys Val Tyr Thr Gly Glu Glu Leu Thr Asn Val Val
785                 790                 795                 800
Asn Leu Leu Lys Asn Ser Thr Phe Asn Asn Gln Asn Phe Thr Leu Ala
            805                 810                 815
Asn Gly Gln Lys Arg Val Ser Phe Ser Phe Pro Pro Glu Leu Glu Lys
            820                 825                 830
Lys Leu Gly Ile Asn Met Leu Val Lys Leu Ile Thr Pro Asp Gly Lys
            835                 840                 845
Val Leu Glu Lys Val Ser Gly Lys Val Phe Glu Gly Val Gly Asn
            850                 855                 860
Ile Ala Asn Phe Glu Leu Asp Gln Pro Tyr Leu Pro Gly Gln Thr Phe
865                 870                 875                 880
Lys Tyr Thr Ile Ala Ser Lys Asp Tyr Pro Glu Val Ser Tyr Asp Gly
                885                 890                 895
Thr Phe Thr Val Pro Thr Ser Leu Ala Tyr Lys Met Ala Ser Gln Thr
            900                 905                 910
Ile Phe Tyr Pro Phe His Ala Gly Asp Thr Tyr Leu Arg Val Asn Pro
```

```
                    915                 920                 925
Gln Phe Ala Val Pro Lys Gly Thr Asp Ala Leu Val Arg Val Phe Asp
    930                 935                 940

Glu Phe His Gly Asn Ala Tyr Leu Glu Asn Asn Tyr Lys Val Gly Glu
945                 950                 955                 960

Ile Lys Leu Pro Ile Pro Lys Leu Asn Gln Gly Thr Thr Arg Thr Ala
                965                 970                 975

Gly Asn Lys Ile Pro Val Thr Phe Met Ala Asn Ala Tyr Leu Asp Asn
                980                 985                 990

Gln Ser Thr Tyr Ile Val Glu Val  Pro Ile Leu Glu Lys  Glu Asn Gln
            995                 1000                1005

Thr Asp  Lys Pro Ser Ile Leu  Pro Gln Phe Lys Arg  Asn Lys Ala
1010                1015                1020

Gln Glu  Asn Ser Lys Leu Asp  Glu Lys Val Glu Glu  Pro Lys Thr
1025                1030                1035

Ser Glu  Lys Val Glu Lys Glu  Lys Leu Ser Glu Thr  Gly Asn Ser
1040                1045                1050

Thr Ser  Asn Ser Thr Leu Glu  Glu Val Pro Thr Val  Asp Pro Val
1055                1060                1065

Gln Glu  Lys Val Ala Lys Phe  Ala Glu Ser Tyr Gly  Met Lys Leu
1070                1075                1080

Glu Asn  Val Leu Phe Asn Met  Asp Gly Thr Ile Glu  Leu Tyr Leu
1085                1090                1095

Pro Ser  Gly Glu Val Ile Lys  Lys Asn Met Ala Asp  Phe Thr Gly
1100                1105                1110

Glu Ala  Pro Gln Gly Asn Gly  Glu Asn Lys Pro Ser  Glu Asn Gly
1115                1120                1125

Lys Val  Ser Thr Gly Thr Val  Glu Asn Gln Pro Thr  Glu Asn Lys
1130                1135                1140

Pro Ala  Asp Ser Leu Pro Glu  Ala Pro Asn Glu Lys  Pro Val Lys
1145                1150                1155

Pro Glu  Asn Ser Thr Asp Asn  Gly Met Leu Asn Pro  Glu Gly Asn
1160                1165                1170

Val Gly  Ser Asp Pro Met Leu  Asp Pro Ala Leu Glu  Glu Ala Pro
1175                1180                1185

Ala Val  Asp Pro Val Gln Glu  Lys Leu Glu Lys Phe  Thr Ala Ser
1190                1195                1200

Tyr Gly  Leu Gly Leu Asp Ser  Val Ile Phe Asn Met  Asp Gly Thr
1205                1210                1215

Ile Glu  Leu Arg Leu Pro Ser  Gly Glu Val Ile Lys  Lys Asn Leu
1220                1225                1230

Ser Asp  Phe Ile Ala
1235

<210> SEQ ID NO 382
<211> LENGTH: 1365
<212> TYPE: PRT
<213> ORGANISM: Artificial Sequence
<220> FEATURE:
<223> OTHER INFORMATION: Unknown Organism
<221> NAME/KEY: MISC_FEATURE
<222> LOCATION: (1)..(1)
<223> OTHER INFORMATION: Xaa = Methionine or nothing
<221> NAME/KEY: MISC_FEATURE
<222> LOCATION: (557)..(557)
<223> OTHER INFORMATION: Xaa = Glycine or nothing
<221> NAME/KEY: MISC_FEATURE
```

-continued

```
<222> LOCATION: (558)..(558)
<223> OTHER INFORMATION: Xaa = Proline or nothing

<400> SEQUENCE: 382
```

| | | | | | | | | | | | | | | |
|---|---|---|---|---|---|---|---|---|---|---|---|---|---|---|
| Xaa | Asp | Ile | Asp | Ser | Leu | Leu | Lys | Gln | Leu | Tyr | Lys | Leu | Pro | Leu | Ser |
| 1 | | | | 5 | | | | | 10 | | | | | 15 | |
| Gln | Arg | His | Val | Glu | Ser | Asp | Gly | Leu | Ile | Phe | Asp | Pro | Ala | Gln | Ile |
| | | | 20 | | | | | 25 | | | | | 30 | | |
| Thr | Ser | Arg | Thr | Ala | Arg | Gly | Val | Ala | Val | Pro | His | Gly | Asn | His | Tyr |
| | | 35 | | | | | 40 | | | | | 45 | | | |
| His | Phe | Ile | Pro | Tyr | Glu | Gln | Met | Ser | Glu | Leu | Glu | Lys | Arg | Ile | Ala |
| 50 | | | | | 55 | | | | | 60 | | | | | |
| Arg | Ile | Ile | Pro | Leu | Arg | Tyr | Arg | Ser | Asn | His | Trp | Val | Pro | Asp | Ser |
| 65 | | | | 70 | | | | | 75 | | | | | 80 | |
| Arg | Pro | Glu | Glu | Pro | Ser | Pro | Gln | Pro | Thr | Pro | Glu | Pro | Ser | Pro | Ser |
| | | | | 85 | | | | | 90 | | | | | 95 | |
| Pro | Gln | Pro | Ala | Pro | Asn | Pro | Gln | Pro | Ala | Pro | Ser | Asn | Pro | Ile | Asp |
| | | | 100 | | | | | 105 | | | | | 110 | | |
| Glu | Lys | Leu | Val | Lys | Glu | Ala | Val | Arg | Lys | Val | Gly | Asp | Gly | Tyr | Val |
| | | 115 | | | | | 120 | | | | | 125 | | | |
| Phe | Glu | Glu | Asn | Gly | Val | Ser | Arg | Tyr | Ile | Pro | Ala | Lys | Asn | Leu | Ser |
| 130 | | | | | 135 | | | | | 140 | | | | | |
| Ala | Glu | Thr | Ala | Ala | Gly | Ile | Asp | Ser | Lys | Leu | Ala | Lys | Gln | Glu | Ser |
| 145 | | | | | 150 | | | | | 155 | | | | | 160 |
| Leu | Ser | His | Lys | Leu | Gly | Ala | Lys | Lys | Thr | Asp | Leu | Pro | Ser | Ser | Asp |
| | | | | 165 | | | | | 170 | | | | | 175 | |
| Arg | Glu | Phe | Tyr | Asn | Lys | Ala | Tyr | Asp | Leu | Leu | Ala | Arg | Ile | His | Gln |
| | | | 180 | | | | | 185 | | | | | 190 | | |
| Asp | Leu | Leu | Asp | Asn | Lys | Gly | Arg | Gln | Val | Asp | Phe | Glu | Ala | Leu | Asp |
| | | | 195 | | | | | 200 | | | | | 205 | | |
| Asn | Leu | Leu | Glu | Arg | Leu | Lys | Asp | Val | Ser | Ser | Asp | Lys | Val | Lys | Leu |
| | 210 | | | | | 215 | | | | | 220 | | | | |
| Val | Asp | Asp | Ile | Leu | Ala | Phe | Leu | Ala | Pro | Ile | Arg | His | Pro | Glu | Arg |
| 225 | | | | | 230 | | | | | 235 | | | | | 240 |
| Leu | Gly | Lys | Pro | Asn | Ala | Gln | Ile | Thr | Tyr | Thr | Asp | Glu | Ile | Gln |
| | | | | 245 | | | | | 250 | | | | | 255 | |
| Val | Ala | Lys | Leu | Ala | Gly | Lys | Tyr | Thr | Thr | Glu | Asp | Gly | Tyr | Ile | Phe |
| | | | 260 | | | | | 265 | | | | | 270 | | |
| Asp | Pro | Arg | Asp | Ile | Thr | Ser | Asp | Glu | Gly | Asp | Ala | Tyr | Val | Thr | Pro |
| | | 275 | | | | | 280 | | | | | 285 | | | |
| His | Met | Thr | His | Ser | His | Trp | Ile | Lys | Lys | Asp | Ser | Leu | Ser | Glu | Ala |
| 290 | | | | | 295 | | | | | 300 | | | | | |
| Glu | Arg | Ala | Ala | Ala | Gln | Ala | Tyr | Ala | Lys | Glu | Lys | Gly | Leu | Thr | Pro |
| 305 | | | | 310 | | | | | 315 | | | | | 320 | |
| Pro | Ser | Thr | Asp | His | Gln | Asp | Ser | Gly | Asn | Thr | Glu | Ala | Lys | Gly | Ala |
| | | | | 325 | | | | | 330 | | | | | 335 | |
| Glu | Ala | Ile | Tyr | Asn | Arg | Val | Lys | Ala | Ala | Lys | Lys | Val | Pro | Leu | Asp |
| | | | 340 | | | | | 345 | | | | | 350 | | |
| Arg | Met | Pro | Tyr | Asn | Leu | Gln | Tyr | Thr | Val | Glu | Val | Lys | Asn | Gly | Ser |
| | | | | 355 | | | | | 360 | | | | | 365 | |
| Leu | Ile | Ile | Pro | His | Tyr | Asp | His | Tyr | His | Asn | Ile | Lys | Phe | Glu | Trp |
| | 370 | | | | | 375 | | | | | 380 | | | | |
| Phe | Asp | Glu | Gly | Leu | Tyr | Glu | Ala | Pro | Lys | Gly | Tyr | Thr | Leu | Glu | Asp |
| 385 | | | | | 390 | | | | | 395 | | | | | 400 |

-continued

```
Leu Leu Ala Thr Val Lys Tyr Tyr Val Glu His Pro Asn Glu Arg Pro
                405                 410                 415
His Ser Asp Asn Gly Phe Gly Asn Ala Ser Asp His Val Gln Arg Asn
            420                 425                 430
Lys Asn Gly Gln Ala Asp Thr Asn Gln Thr Glu Lys Pro Ser Glu Glu
        435                 440                 445
Lys Pro Gln Thr Glu Lys Pro Glu Glu Thr Pro Arg Glu Glu Lys
450                 455                 460
Pro Gln Ser Glu Lys Pro Glu Ser Pro Lys Pro Thr Glu Glu Pro Glu
465                 470                 475                 480
Glu Glu Ser Pro Glu Glu Ser Glu Glu Pro Gln Val Glu Thr Glu Lys
                485                 490                 495
Val Glu Glu Lys Leu Arg Glu Ala Glu Asp Leu Leu Gly Lys Ile Gln
            500                 505                 510
Asp Pro Ile Ile Lys Ser Asn Ala Lys Glu Thr Leu Thr Gly Leu Lys
        515                 520                 525
Asn Asn Leu Leu Phe Gly Thr Gln Asp Asn Asn Thr Ile Met Ala Glu
    530                 535                 540
Ala Glu Lys Leu Leu Ala Leu Leu Lys Glu Ser Lys Xaa Xaa Asn Met
545                 550                 555                 560
Gln Pro Ser Gln Leu Ser Tyr Ser Ser Thr Ala Ser Asp Asn Asn Thr
                565                 570                 575
Gln Ser Val Ala Lys Gly Ser Thr Ser Lys Pro Ala Asn Lys Ser Glu
            580                 585                 590
Asn Leu Gln Ser Leu Leu Lys Glu Leu Tyr Asp Ser Pro Ser Ala Gln
        595                 600                 605
Arg Tyr Ser Glu Ser Asp Gly Leu Val Phe Asp Pro Ala Lys Ile Ile
    610                 615                 620
Ser Arg Thr Pro Asn Gly Val Ala Ile Pro His Gly Asp His Tyr His
625                 630                 635                 640
Phe Ile Pro Tyr Ser Lys Leu Ser Ala Leu Glu Glu Lys Ile Ala Arg
                645                 650                 655
Met Val Pro Ile Ser Gly Thr Gly Ser Thr Val Ser Thr Asn Ala Lys
            660                 665                 670
Pro Asn Glu Val Val Ser Ser Leu Gly Ser Leu Ser Asn Pro Ser
        675                 680                 685
Ser Leu Thr Thr Ser Lys Glu Leu Ser Ser Ala Ser Asp Gly Tyr Ile
    690                 695                 700
Phe Asn Pro Lys Asp Ile Val Glu Glu Thr Ala Thr Ala Tyr Ile Val
705                 710                 715                 720
Arg His Gly Asp His Phe His Tyr Ile Pro Lys Ser Asn Gln Ile Gly
                725                 730                 735
Gln Pro Thr Leu Pro Asn Asn Ser Leu Ala Thr Pro Ser Pro Ser Leu
            740                 745                 750
Pro Ile Asn Pro Gly Thr Ser His Glu Lys His Glu Glu Asp Gly Tyr
        755                 760                 765
Gly Phe Asp Ala Asn Arg Ile Ile Ala Glu Asp Glu Ser Gly Phe Val
    770                 775                 780
Met Ser His Gly Asp His Asn His Tyr Phe Phe Lys Lys Asp Leu Thr
785                 790                 795                 800
Glu Glu Gln Ile Lys Ala Ala Gln Lys His Leu Glu Glu Val Lys Thr
                805                 810                 815
```

-continued

Ser His Asn Gly Leu Asp Ser Leu Ser Ser His Glu Gln Asp Tyr Pro
             820                 825                 830

Gly Asn Ala Lys Glu Met Lys Asp Leu Asp Lys Lys Ile Glu Lys
         835                 840                 845

Ile Ala Gly Ile Met Lys Gln Tyr Gly Val Lys Arg Glu Ser Ile Val
     850                 855                 860

Val Asn Lys Glu Lys Asn Ala Ile Ile Tyr Pro His Gly Asp His His
865                 870                 875                 880

His Ala Asp Pro Ile Asp Glu His Lys Pro Val Gly Ile Gly His Ser
             885                 890                 895

His Ser Asn Tyr Glu Leu Phe Lys Pro Glu Gly Val Ala Lys Lys
         900                 905                 910

Glu Gly Asn Lys Val Tyr Thr Gly Glu Leu Thr Asn Val Val Asn
         915                 920                 925

Leu Leu Lys Asn Ser Thr Phe Asn Asn Gln Asn Phe Thr Leu Ala Asn
930                 935                 940

Gly Gln Lys Arg Val Ser Phe Ser Phe Pro Glu Leu Glu Lys Lys
945                 950                 955                 960

Leu Gly Ile Asn Met Leu Val Lys Leu Ile Thr Pro Asp Gly Lys Val
             965                 970                 975

Leu Glu Lys Val Ser Gly Lys Val Phe Gly Glu Gly Val Gly Asn Ile
         980                 985                 990

Ala Asn Phe Glu Leu Asp Gln Pro Tyr Leu Pro Gly Gln Thr Phe Lys
         995                 1000                1005

Tyr Thr Ile Ala Ser Lys Asp Tyr Pro Glu Val Ser Tyr Asp Gly
     1010                1015                1020

Thr Phe Thr Val Pro Thr Ser Leu Ala Tyr Lys Met Ala Ser Gln
     1025                1030                1035

Thr Ile Phe Tyr Pro Phe His Ala Gly Asp Thr Tyr Leu Arg Val
     1040                1045                1050

Asn Pro Gln Phe Ala Val Pro Lys Gly Thr Asp Ala Leu Val Arg
     1055                1060                1065

Val Phe Asp Glu Phe His Gly Asn Ala Tyr Leu Glu Asn Asn Tyr
     1070                1075                1080

Lys Val Gly Glu Ile Lys Leu Pro Ile Pro Lys Leu Asn Gln Gly
     1085                1090                1095

Thr Thr Arg Thr Ala Gly Asn Lys Ile Pro Val Thr Phe Met Ala
     1100                1105                1110

Asn Ala Tyr Leu Asp Asn Gln Ser Thr Tyr Ile Val Glu Val Pro
     1115                1120                1125

Ile Leu Glu Lys Glu Asn Gln Thr Asp Lys Pro Ser Ile Leu Pro
     1130                1135                1140

Gln Phe Lys Arg Asn Lys Ala Gln Glu Asn Ser Lys Leu Asp Glu
     1145                1150                1155

Lys Val Glu Glu Pro Lys Thr Ser Glu Lys Val Glu Lys Glu Lys
     1160                1165                1170

Leu Ser Glu Thr Gly Asn Ser Thr Ser Asn Ser Thr Leu Glu Glu
     1175                1180                1185

Val Pro Thr Val Asp Pro Val Gln Glu Lys Val Ala Lys Phe Ala
     1190                1195                1200

Glu Ser Tyr Gly Met Lys Leu Glu Asn Val Leu Phe Asn Met Asp
     1205                1210                1215

Gly Thr Ile Glu Leu Tyr Leu Pro Ser Gly Glu Val Ile Lys Lys

-continued

```
                1220                1225                1230
Asn Met Ala Asp Phe Thr Gly Glu Ala Pro Gln Gly Asn Gly Glu
            1235                1240                1245

Asn Lys Pro Ser Glu Asn Gly Lys Val Ser Thr Gly Thr Val Glu
        1250                1255                1260

Asn Gln Pro Thr Glu Asn Lys Pro Ala Asp Ser Leu Pro Glu Ala
    1265                1270                1275

Pro Asn Glu Lys Pro Val Lys Pro Glu Asn Ser Thr Asp Asn Gly
1280                1285                1290

Met Leu Asn Pro Glu Gly Asn Val Gly Ser Asp Pro Met Leu Asp
    1295                1300                1305

Pro Ala Leu Glu Glu Ala Pro Ala Val Asp Pro Val Gln Glu Lys
        1310                1315                1320

Leu Glu Lys Phe Thr Ala Ser Tyr Gly Leu Gly Leu Asp Ser Val
            1325                1330                1335

Ile Phe Asn Met Asp Gly Thr Ile Glu Leu Arg Leu Pro Ser Gly
        1340                1345                1350

Glu Val Ile Lys Lys Asn Leu Ser Asp Phe Ile Ala
            1355                1360                1365
```

<210> SEQ ID NO 383
<211> LENGTH: 1126
<212> TYPE: PRT
<213> ORGANISM: Artificial Sequence
<220> FEATURE:
<223> OTHER INFORMATION: Unknown Organism
<221> NAME/KEY: MISC_FEATURE
<222> LOCATION: (1)..(1)
<223> OTHER INFORMATION: Xaa = Methionine or nothing
<221> NAME/KEY: MISC_FEATURE
<222> LOCATION: (557)..(557)
<223> OTHER INFORMATION: Xaa = Glycine or nothing
<221> NAME/KEY: MISC_FEATURE
<222> LOCATION: (558)..(558)
<223> OTHER INFORMATION: Xaa = Proline or nothing

<400> SEQUENCE: 383

```
Xaa Asp Ile Asp Ser Leu Leu Lys Gln Leu Tyr Lys Leu Pro Leu Ser
1               5                   10                  15

Gln Arg His Val Glu Ser Asp Gly Leu Ile Phe Asp Pro Ala Gln Ile
            20                  25                  30

Thr Ser Arg Thr Ala Arg Gly Val Ala Val Pro His Gly Asn His Tyr
        35                  40                  45

His Phe Ile Pro Tyr Glu Gln Met Ser Glu Leu Glu Lys Arg Ile Ala
    50                  55                  60

Arg Ile Ile Pro Leu Arg Tyr Arg Ser Asn His Trp Val Pro Asp Ser
65                  70                  75                  80

Arg Pro Glu Glu Pro Ser Pro Gln Pro Thr Pro Glu Pro Ser Pro Ser
                85                  90                  95

Pro Gln Pro Ala Pro Asn Pro Gln Pro Ala Pro Ser Asn Pro Ile Asp
            100                 105                 110

Glu Lys Leu Val Lys Glu Ala Val Arg Lys Val Gly Asp Gly Tyr Val
        115                 120                 125

Phe Glu Glu Asn Gly Val Ser Arg Tyr Ile Pro Ala Lys Asn Leu Ser
    130                 135                 140

Ala Glu Thr Ala Ala Gly Ile Asp Ser Lys Leu Ala Lys Gln Glu Ser
145                 150                 155                 160

Leu Ser His Lys Leu Gly Ala Lys Lys Thr Asp Leu Pro Ser Ser Asp
```

-continued

```
                165                 170                 175
Arg Glu Phe Tyr Asn Lys Ala Tyr Asp Leu Leu Ala Arg Ile His Gln
            180                 185                 190
Asp Leu Leu Asp Asn Lys Gly Arg Gln Val Asp Phe Glu Ala Leu Asp
        195                 200                 205
Asn Leu Leu Glu Arg Leu Lys Asp Val Ser Ser Asp Lys Val Lys Leu
    210                 215                 220
Val Asp Asp Ile Leu Ala Phe Leu Ala Pro Ile Arg His Pro Glu Arg
225                 230                 235                 240
Leu Gly Lys Pro Asn Ala Gln Ile Thr Tyr Thr Asp Asp Glu Ile Gln
                245                 250                 255
Val Ala Lys Leu Ala Gly Lys Tyr Thr Thr Glu Asp Gly Tyr Ile Phe
            260                 265                 270
Asp Pro Arg Asp Ile Thr Ser Asp Glu Gly Asp Ala Tyr Val Thr Pro
        275                 280                 285
His Met Thr His Ser His Trp Ile Lys Lys Asp Ser Leu Ser Glu Ala
    290                 295                 300
Glu Arg Ala Ala Ala Gln Ala Tyr Ala Lys Glu Lys Gly Leu Thr Pro
305                 310                 315                 320
Pro Ser Thr Asp His Gln Asp Ser Gly Asn Thr Glu Ala Lys Gly Ala
                325                 330                 335
Glu Ala Ile Tyr Asn Arg Val Lys Ala Ala Lys Lys Val Pro Leu Asp
            340                 345                 350
Arg Met Pro Tyr Asn Leu Gln Tyr Thr Val Glu Val Lys Asn Gly Ser
        355                 360                 365
Leu Ile Ile Pro His Tyr Asp His Tyr His Asn Ile Lys Phe Glu Trp
    370                 375                 380
Phe Asp Glu Gly Leu Tyr Glu Ala Pro Lys Gly Tyr Thr Leu Glu Asp
385                 390                 395                 400
Leu Leu Ala Thr Val Lys Tyr Tyr Val Glu His Pro Asn Glu Arg Pro
                405                 410                 415
His Ser Asp Asn Gly Phe Gly Asn Ala Ser Asp His Val Gln Arg Asn
            420                 425                 430
Lys Asn Gly Gln Ala Asp Thr Asn Gln Thr Glu Lys Pro Ser Glu Glu
        435                 440                 445
Lys Pro Gln Thr Glu Lys Pro Glu Glu Thr Pro Arg Glu Glu Lys
    450                 455                 460
Pro Gln Ser Glu Lys Pro Glu Ser Pro Lys Pro Thr Glu Glu Pro Glu
465                 470                 475                 480
Glu Glu Ser Pro Glu Glu Ser Glu Glu Pro Gln Val Glu Thr Glu Lys
                485                 490                 495
Val Glu Glu Lys Leu Arg Glu Ala Glu Asp Leu Leu Gly Lys Ile Gln
            500                 505                 510
Asp Pro Ile Ile Lys Ser Asn Ala Lys Glu Thr Leu Thr Gly Leu Lys
        515                 520                 525
Asn Asn Leu Leu Phe Gly Thr Gln Asp Asn Asn Thr Ile Met Ala Glu
    530                 535                 540
Ala Glu Lys Leu Leu Ala Leu Leu Lys Glu Ser Lys Xaa Xaa Asp Leu
545                 550                 555                 560
Thr Glu Glu Gln Ile Lys Ala Ala Gln Lys His Leu Glu Glu Val Lys
                565                 570                 575
Thr Ser His Asn Gly Leu Asp Ser Leu Ser Ser His Glu Gln Asp Tyr
            580                 585                 590
```

```
Pro Gly Asn Ala Lys Glu Met Lys Asp Leu Asp Lys Lys Ile Glu Glu
            595                 600                 605

Lys Ile Ala Gly Ile Met Lys Gln Tyr Gly Val Lys Arg Glu Ser Ile
    610                 615                 620

Val Val Asn Lys Glu Lys Asn Ala Ile Ile Tyr Pro His Gly Asp His
625                 630                 635                 640

His His Ala Asp Pro Ile Asp Glu His Lys Pro Val Gly Ile Gly His
                645                 650                 655

Ser His Ser Asn Tyr Glu Leu Phe Lys Pro Glu Glu Val Ala Lys
            660                 665                 670

Lys Glu Gly Asn Lys Val Tyr Thr Gly Glu Glu Leu Thr Asn Val Val
            675                 680                 685

Asn Leu Leu Lys Asn Ser Thr Phe Asn Asn Gln Asn Phe Thr Leu Ala
            690                 695                 700

Asn Gly Gln Lys Arg Val Ser Phe Ser Phe Pro Pro Glu Leu Glu Lys
705                 710                 715                 720

Lys Leu Gly Ile Asn Met Leu Val Lys Leu Ile Thr Pro Asp Gly Lys
            725                 730                 735

Val Leu Glu Lys Val Ser Gly Lys Val Phe Gly Glu Gly Val Gly Asn
            740                 745                 750

Ile Ala Asn Phe Glu Leu Asp Gln Pro Tyr Leu Pro Gly Gln Thr Phe
            755                 760                 765

Lys Tyr Thr Ile Ala Ser Lys Asp Tyr Pro Glu Val Ser Tyr Asp Gly
            770                 775                 780

Thr Phe Thr Val Pro Thr Ser Leu Ala Tyr Lys Met Ala Ser Gln Thr
785                 790                 795                 800

Ile Phe Tyr Pro Phe His Ala Gly Asp Thr Tyr Leu Arg Val Asn Pro
                805                 810                 815

Gln Phe Ala Val Pro Lys Gly Thr Asp Ala Leu Val Arg Val Phe Asp
                820                 825                 830

Glu Phe His Gly Asn Ala Tyr Leu Glu Asn Asn Tyr Lys Val Gly Glu
            835                 840                 845

Ile Lys Leu Pro Ile Pro Lys Leu Asn Gln Gly Thr Thr Arg Thr Ala
850                 855                 860

Gly Asn Lys Ile Pro Val Thr Phe Met Ala Asn Ala Tyr Leu Asp Asn
865                 870                 875                 880

Gln Ser Thr Tyr Ile Val Glu Val Pro Ile Leu Glu Lys Glu Asn Gln
                885                 890                 895

Thr Asp Lys Pro Ser Ile Leu Pro Gln Phe Lys Arg Asn Lys Ala Gln
                900                 905                 910

Glu Asn Ser Lys Leu Asp Glu Lys Val Glu Pro Lys Thr Ser Glu
            915                 920                 925

Lys Val Glu Lys Glu Lys Leu Ser Glu Thr Gly Asn Ser Thr Ser Asn
            930                 935                 940

Ser Thr Leu Glu Glu Val Pro Thr Val Asp Pro Val Gln Glu Lys Val
945                 950                 955                 960

Ala Lys Phe Ala Glu Ser Tyr Gly Met Lys Leu Glu Asn Val Leu Phe
                965                 970                 975

Asn Met Asp Gly Thr Ile Glu Leu Tyr Leu Pro Ser Gly Glu Val Ile
            980                 985                 990

Lys Lys Asn Met Ala Asp Phe Thr Gly Glu Ala Pro Gln Gly Asn Gly
            995                 1000                1005
```

-continued

```
Glu Asn Lys Pro Ser Glu Asn Gly Lys Val Ser Thr Gly Thr Val
    1010                1015                1020

Glu Asn Gln Pro Thr Glu Asn Lys Pro Ala Asp Ser Leu Pro Glu
    1025                1030                1035

Ala Pro Asn Glu Lys Pro Val Lys Pro Glu Asn Ser Thr Asp Asn
    1040                1045                1050

Gly Met Leu Asn Pro Glu Gly Asn Val Gly Ser Asp Pro Met Leu
    1055                1060                1065

Asp Pro Ala Leu Glu Glu Ala Pro Ala Val Asp Pro Val Gln Glu
    1070                1075                1080

Lys Leu Glu Lys Phe Thr Ala Ser Tyr Gly Leu Gly Leu Asp Ser
    1085                1090                1095

Val Ile Phe Asn Met Asp Gly Thr Ile Glu Leu Arg Leu Pro Ser
    1100                1105                1110

Gly Glu Val Ile Lys Lys Asn Leu Ser Asp Phe Ile Ala
    1115                1120                1125

<210> SEQ ID NO 384
<211> LENGTH: 913
<212> TYPE: PRT
<213> ORGANISM: Artificial Sequence
<220> FEATURE:
<223> OTHER INFORMATION: Unknown Organism
<221> NAME/KEY: MISC_FEATURE
<222> LOCATION: (1)..(1)
<223> OTHER INFORMATION: Xaa = Methionine or nothing
<221> NAME/KEY: MISC_FEATURE
<222> LOCATION: (344)..(344)
<223> OTHER INFORMATION: Xaa = Glycine or nothing
<221> NAME/KEY: MISC_FEATURE
<222> LOCATION: (345)..(345)
<223> OTHER INFORMATION: Xaa = Proline or nothing

<400> SEQUENCE: 384

Xaa Asp Ile Leu Ala Phe Leu Ala Pro Ile Arg His Pro Glu Arg Leu
1               5                   10                  15

Gly Lys Pro Asn Ala Gln Ile Thr Tyr Thr Asp Asp Glu Ile Gln Val
                20                  25                  30

Ala Lys Leu Ala Gly Lys Tyr Thr Thr Glu Asp Gly Tyr Ile Phe Asp
            35                  40                  45

Pro Arg Asp Ile Thr Ser Asp Glu Gly Asp Ala Tyr Val Thr Pro His
    50                  55                  60

Met Thr His Ser His Trp Ile Lys Lys Asp Ser Leu Ser Glu Ala Glu
65                  70                  75                  80

Arg Ala Ala Ala Gln Ala Tyr Ala Lys Glu Lys Gly Leu Thr Pro Pro
                85                  90                  95

Ser Thr Asp His Gln Asp Ser Gly Asn Thr Glu Ala Lys Gly Ala Glu
            100                 105                 110

Ala Ile Tyr Asn Arg Val Lys Ala Ala Lys Lys Val Pro Leu Asp Arg
        115                 120                 125

Met Pro Tyr Asn Leu Gln Tyr Thr Val Glu Val Lys Asn Gly Ser Leu
    130                 135                 140

Ile Ile Pro His Tyr Asp His Tyr His Asn Ile Lys Phe Glu Trp Phe
145                 150                 155                 160

Asp Glu Gly Leu Tyr Glu Ala Pro Lys Gly Tyr Ser Leu Glu Asp Leu
                165                 170                 175

Leu Ala Thr Val Lys Tyr Tyr Val Glu His Pro Asn Glu Arg Pro His
            180                 185                 190
```

-continued

```
Ser Asp Asn Gly Phe Gly Asn Ala Ser Asp His Val Arg Lys Asn Lys
        195                 200                 205
Ala Asp Gln Asp Ser Lys Pro Asp Glu Asp Lys Glu His Asp Glu Val
210                 215                 220
Ser Glu Pro Thr His Pro Glu Ser Asp Glu Lys Glu Asn His Ala Gly
225                 230                 235                 240
Leu Asn Pro Ser Ala Asp Asn Leu Tyr Lys Pro Ser Thr Asp Thr Glu
                245                 250                 255
Glu Thr Glu Glu Glu Ala Glu Asp Thr Thr Asp Glu Ala Glu Ile Pro
                260                 265                 270
Gln Val Glu Asn Ser Val Ile Asn Ala Lys Ile Ala Asp Ala Glu Ala
            275                 280                 285
Leu Leu Glu Lys Val Thr Asp Pro Ser Ile Arg Gln Asn Ala Met Glu
        290                 295                 300
Thr Leu Thr Gly Leu Lys Ser Ser Leu Leu Gly Thr Lys Asp Asn
305                 310                 315                 320
Asn Thr Ile Ser Ala Glu Val Asp Ser Leu Leu Ala Leu Leu Lys Glu
                325                 330                 335
Ser Gln Pro Ala Pro Ile Gln Xaa Xaa Asp Leu Thr Glu Glu Gln Ile
                340                 345                 350
Lys Ala Ala Gln Lys His Leu Glu Glu Val Lys Thr Ser His Asn Gly
            355                 360                 365
Leu Asp Ser Leu Ser Ser His Glu Gln Asp Tyr Pro Gly Asn Ala Lys
        370                 375                 380
Glu Met Lys Asp Leu Asp Lys Lys Ile Glu Glu Lys Ile Ala Gly Ile
385                 390                 395                 400
Met Lys Gln Tyr Gly Val Lys Arg Glu Ser Ile Val Val Asn Lys Glu
                405                 410                 415
Lys Asn Ala Ile Ile Tyr Pro His Gly Asp His His Ala Asp Pro
            420                 425                 430
Ile Asp Glu His Lys Pro Val Gly Ile Gly His Ser His Ser Asn Tyr
        435                 440                 445
Glu Leu Phe Lys Pro Glu Glu Gly Val Ala Lys Glu Gly Asn Lys
        450                 455                 460
Val Tyr Thr Gly Glu Glu Leu Thr Asn Val Val Asn Leu Leu Lys Asn
465                 470                 475                 480
Ser Thr Phe Asn Asn Gln Asn Phe Thr Leu Ala Asn Gly Gln Lys Arg
                485                 490                 495
Val Ser Phe Ser Phe Pro Pro Glu Leu Glu Lys Lys Leu Gly Ile Asn
                500                 505                 510
Met Leu Val Lys Leu Ile Thr Pro Asp Gly Lys Val Leu Glu Lys Val
            515                 520                 525
Ser Gly Lys Val Phe Gly Glu Gly Val Gly Asn Ile Ala Asn Phe Glu
        530                 535                 540
Leu Asp Gln Pro Tyr Leu Pro Gly Gln Thr Phe Lys Tyr Thr Ile Ala
545                 550                 555                 560
Ser Lys Asp Tyr Pro Glu Val Ser Tyr Asp Gly Thr Phe Thr Val Pro
                565                 570                 575
Thr Ser Leu Ala Tyr Lys Met Ala Ser Gln Thr Ile Phe Tyr Pro Phe
                580                 585                 590
His Ala Gly Asp Thr Tyr Leu Arg Val Asn Pro Gln Phe Ala Val Pro
            595                 600                 605
Lys Gly Thr Asp Ala Leu Val Arg Val Phe Asp Glu Phe His Gly Asn
```

-continued

```
            610                 615                 620
Ala Tyr Leu Glu Asn Asn Tyr Lys Val Gly Glu Ile Lys Leu Pro Ile
625                 630                 635                 640
Pro Lys Leu Asn Gln Gly Thr Thr Arg Thr Ala Gly Asn Lys Ile Pro
                645                 650                 655
Val Thr Phe Met Ala Asn Ala Tyr Leu Asp Asn Gln Ser Thr Tyr Ile
                660                 665                 670
Val Glu Val Pro Ile Leu Glu Lys Glu Asn Gln Thr Asp Lys Pro Ser
                675                 680                 685
Ile Leu Pro Gln Phe Lys Arg Asn Lys Ala Gln Glu Asn Ser Lys Leu
                690                 695                 700
Asp Glu Lys Val Glu Glu Pro Lys Thr Ser Glu Lys Val Glu Lys Glu
705                 710                 715                 720
Lys Leu Ser Glu Thr Gly Asn Ser Thr Ser Asn Ser Thr Leu Glu Glu
                725                 730                 735
Val Pro Thr Val Asp Pro Val Gln Glu Lys Val Ala Lys Phe Ala Glu
                740                 745                 750
Ser Tyr Gly Met Lys Leu Glu Asn Val Leu Phe Asn Met Asp Gly Thr
                755                 760                 765
Ile Glu Leu Tyr Leu Pro Ser Gly Glu Val Ile Lys Lys Asn Met Ala
                770                 775                 780
Asp Phe Thr Gly Glu Ala Pro Gln Gly Asn Gly Glu Asn Lys Pro Ser
785                 790                 795                 800
Glu Asn Gly Lys Val Ser Thr Gly Thr Val Glu Asn Gln Pro Thr Glu
                805                 810                 815
Asn Lys Pro Ala Asp Ser Leu Pro Glu Ala Pro Asn Glu Lys Pro Val
                820                 825                 830
Lys Pro Glu Asn Ser Thr Asp Asn Gly Met Leu Asn Pro Glu Gly Asn
                835                 840                 845
Val Gly Ser Asp Pro Met Leu Asp Pro Ala Leu Glu Glu Ala Pro Ala
                850                 855                 860
Val Asp Pro Val Gln Glu Lys Leu Glu Lys Phe Thr Ala Ser Tyr Gly
865                 870                 875                 880
Leu Gly Leu Asp Ser Val Ile Phe Asn Met Asp Gly Thr Ile Glu Leu
                885                 890                 895
Arg Leu Pro Ser Gly Glu Val Ile Lys Lys Asn Leu Ser Asp Phe Ile
                900                 905                 910
Ala
```

STREPTOCOCCUS ANTIGENS

This application claims the benefit of U.S. provisional application 60/212,683 filed Jun. 20, 2000 which is herein incorporated by reference.

FIELD OF THE INVENTION

The present invention is related to antigens, epitopes and antibodies directed to these epitopes, more particularly polypeptide antigens of *streptococcus pneumoniae* pathogen which may be useful for prophylaxis, diagnostic or treatment of streptococcal infection.

BACKGROUND OF THE INVENTION

*S. pneumoniae* is an important agent of disease in man especially among infants, the elderly and immunocompromised persons. It is a bacterium frequently isolated from patients with invasive diseases such as bacteraemia/septicaemia, pneumonia, meningitis with high morbidity and mortality throughout the world. Even with appropriate antibiotic therapy, pneumococcal infections still result in many deaths. Although the advent of antimicrobial drugs has reduced the overall mortality from pneumococcal disease, the presence of resistant pneumococcal organisms has become a major problem in the world today. Effective pneumococcal vaccines could have a major impact on the morbidity and mortality associated with *S. pneumoniae* disease. Such vaccines would also potentially be useful to prevent otitis media in infants and young children.

Efforts to develop a pneumococcal vaccine have generally concentrated on generating immune responses to the pneumococcal capsular polysaccharide. More than 80 pneumococcal capsular serotypes have been identified on the basis of antigenic differences. The currently available pneumococcal vaccine, comprising 23 capsular polysaccharides that most frequently caused disease, has significant shortcomings related primarily to the poor immunogenicity of some capsular polysaccharides, the diversity of the serotypes and the differences in the distribution of serotypes over time, geographic areas and age groups. In particular, the failure of existing vaccines and capsular conjugate vaccines currently in development to protect young children against all serotypes spurres evaluation of other *S. pneumoniae* components. Although immunogenicity of capsular polysaccharides can be improved, serotype specificity will still represent a major limitation of polysaccharide-based vaccines. The use of a antigenically conserved immunogenic pneumococcal protein antigen, either by itself or in combination with additional components, offers the possibility of a protein-based pneumococcal vaccine.

PCT WO 98/18930 published May 7, 1998 entitled "*Streptococcus Pneumoniae* antigens and vaccines" describes certain polypeptides which are claimed to be antigenic. However, no biological activity of these polypeptides is reported. Similarly, no sequence conservation is reported, which is a necessary species common vaccine candidate.

PCT WO 00/39299 describes polypeptides and polynucleotides encoding these polypeptides. PCT WO 00/39299 demonstrates that polypeptides designated as BVH-3 and BVH-11 provide protection against fatal experimental infection with pneumococci.

Therefore there remains an unmet need for *Streptococcus* antigens that may be used as components for the prophylaxis, diagnostic and/or therapy of *Streptococcus* infection.

SUMMARY OF THE INVENTION

An isolated polynucleotide comprising a polynucleotide chosen from;
(a) a polynucleotide encoding a polypeptide having at least 70% identity to a second polypeptide chosen from: table A, B, D, E or H;
(b) a polynucleotide encoding a polypeptide having at least 95% identity to a second polypeptide chosen from: table A, B, D, E or H;
(c) a polynucleotide encoding a polypeptide having an amino sequence chosen from table A, B, D, E or H; or fragments, analogs or derivatives thereof;
(d) a polynucleotide encoding a polypeptide chosen from: table A, B, D, E or H;
(e) a polynucleotide encoding a polypeptide capable of generating antibodies having binding specificity for a polypeptide having a sequence chosen from: table A, B, D, E or H;
(f) a polynucleotide encoding an epitope bearing portion of a polypeptide chosen from table A, B, D, E or H; and
(g) a polynycleotide complementary to a polynucleotide in (a), (b), (c), (d),(e) or (f).

In other aspects, there are provided novel polypeptides encoded by polynucleotides of the invention, pharmaceutical or vaccine composition, vectors comprising polynucleotides of the invention operably linked to an expression control region, as well as host cells transfected with said vectors and methods of producing polypeptides comprising culturing said host cells under conditions suitable for expression.

BRIEF DESCRIPTION OF THE DRAWINGS

FIG. 1 is the DNA sequence of SP64 BVH-3 gene; SEQ ID NO: 1.

FIG. 2 is a DNA sequence containing the complete SP64 BVH-3 gene at nucleotides 1777 to 4896; SEQ ID NO: 2.

FIG. 3 is the DNA sequence of SP64 BVH-11 gene; SEQ ID NO: 3.

FIG. 4 is a DNA sequence containing the complete SP64 BVH-11 gene at nucleotides 45 to 2567; SEQ ID NO: 4.

FIG. 5 is a DNA sequence containing the complete SP64 BVH-11-2 gene at nucleotides 114 to 2630; SEQ ID NO: 5.

FIG. 6 is the amino acid sequence of SP64 BVH-3 polypeptide; SEQ ID NO: 6.

FIG. 7 is the amino acid sequence of SP64 BVH-11 polypeptide; SEQ ID NO: 7.

FIG. 8 is the amino acid sequence of SP64 BVH-11-2 polypeptide; SEQ ID NO: 8.

FIG. 9 is the DNA sequence of SP63 BVH-3 gene; SEQ ID NO:9.

FIG. 10 is the amino acid sequence of SP63 BVH-3 polypeptide; SEQ ID NO: 10.

FIG. 11 is the amino acid sequence of 4D4.9 polypeptide; SEQ ID NO: 11.

FIG. 12 is the amino acid sequence of 7G11.7 polypeptide; SEQ ID NO: 12.

FIG. 13 is the amino acid sequence of 7G11.9 polypeptide; SEQ ID NO: 13.

FIG. 14 is the amino acid sequence of 4D3.4 polypeptide; SEQ ID NO: 14.

FIG. 15 is the amino acid sequence of 8E3.1 polypeptide; SEQ ID NO: 15.

FIG. 16 is the amino acid sequence of 1G2.2 polypeptide; SEQ ID NO: 16.

FIG. 17 is the amino acid sequence of 10C12.7 polypeptide; SEQ ID NO: 17.

FIG. 18 is the amino acid sequence of 14F6.3 polypeptide; SEQ ID NO: 18.

FIG. 19 is the amino acid sequence of B12D8.2 polypeptide; SEQ ID NO: 19.

FIG. 20 is the amino acid sequence of 7F4.1 polypeptide; SEQ ID NO: 20.

FIG. 21 is the amino acid sequence of 10D7.5 polypeptide; SEQ ID NO: 21.

FIG. 22 is the amino acid sequence of 10G9.3 polypeptide, 10A2.2 polypeptide and B11B8.1 polypeptide; SEQ ID NO: 22.

FIG. 23 is the amino acid sequence of 11B8.4 polypeptide; SEQ ID NO: 23.

FIG. 24 is the amino acid sequence of Mab H11B-11B8 target epitope; SEQ ID 163.

FIG. 29 is a schematic representation of the BVH-11-2 protein and the location of protective surface epitopes recognized by certain monoclonal antibodies.

FIG. 31 depicts the comparison of the amino acid sequences of BVH-3M (sp64) and BVH-3 (Sp63) proteins by using the program Clustal W from MacVector sequence analysis software (version 6.5.3). Underneath the alignment, there is a consensus line where * and . characters indicate identical and similar amino acid residues, respectively.

FIG. 32 depicts the comparison of the amino acid sequences of BVH-3, BVH-11 and BVH-11-2 proteins by using the program Clustal W from MacVector sequence analysis software (version 6.5.3). Underneath the alignment, there is a consensus line where * and . characters indicate identical and similar amino acid residues, respectively.

FIG. 33 is the DNA sequence of the NEW43 gene (SEQ ID No 257).

FIG. 34 is the deduced amino acid sequence of NEW43 polypeptide (SEQ ID No 258).

DETAILED DESCRIPTION OF THE INVENTION

Figure 25:
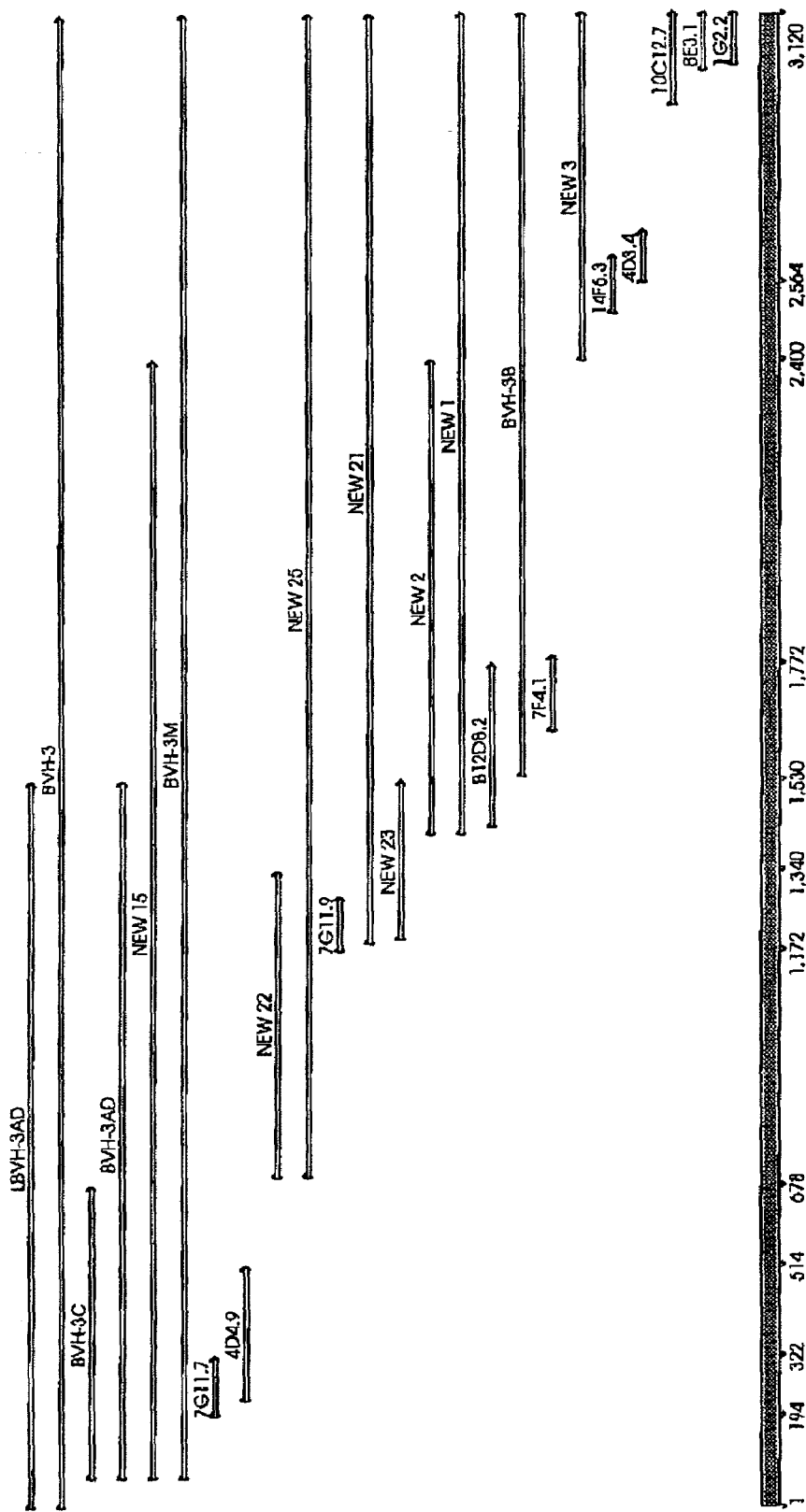
FIG. 25 is a schematic representation of the BVH-3 gene as well as location of gene sequences coding for the full length and truncated polypeptides. The relationships between DNA fragments are shown with respect to each other.

It was determined that portions of the BVH-3 and BVH-11 polypeptides were internal. Other portions were not present in important strains such as encapsulated *s. pneumonia* causing disease strains. It would be advantageous to have a polypeptide that comprises a portion that is not internal. When large portions of a polypeptide are internal, these portions are not exposed on the bacteria. However, these portions can be very immunogenic in a recombinant polypeptide and will not confer protection against infections. It would also be advantageous to have a polypeptide that comprises a portion that is present in most strains.

The present invention is concerned with polypeptides in which undesired portions have been deleted and/or modified in order to obtain a specific immune response.

In accordance with the present invention, there are also provided polypeptides or polynucleotides encoding such polypeptides comprising protective domains.

Surprisingly, when the undesired portion of the polypeptides are deleted or modified, the polypeptides have desired biological properties. This is surprising in view of the fact that some of these portions were described as being epitope bearing portion in the patent application PCT WO 98/18930. In other publications such as PCT WO 00/37105, portions identified as histidine triad and coil coiled regions were said to be of importance. The present inventors have found that variants of the polypeptide BVH-3 and BVH-11 in which certain portions were deleted and/or modified and chimeras of these polypeptides have biological properties and generate a specific immune response.

According to one aspect, the present invention provides an isolated polynucleotide encoding a polypeptide having at least 70% identity to a second polypeptide comprising a sequence as disclosed in the present application, the tables and figures.

In accordance with one aspect of the present invention, there is provided an isolated polynucleotide comprising a polynucleotide chosen from;

(a) a polynucleotide encoding a polypeptide having at least 70% identity to a second polypeptide chosen from: table B, E or H;

(b) a polynucleotide encoding a polypeptide having at least 95% identity to a second polypeptide chosen from: table B, E or H;

(c) a polynucleotide encoding a polypeptide having an amino sequence chosen from table B, E or H or fragments, analogs or derivatives thereof;

(d) a polynucleotide encoding a polypeptide chosen from: table B, E or H;

(e) a polynucleotide encoding a polypeptide capable of generating antibodies having binding specificity for a polypeptide having a sequence chosen from: table B, E or H, (f) a polynucleotide encoding an epitope bearing portion of a polypeptide chosen from table B, E or H; and (g) a polynucleotide complementary to a polynucleotide in (a), (b), (c), (d), (e) or (f).

According to one aspect, the present invention provides an isolated polynucleotide encoding a polypeptide having at least 70% identity to a second polypeptide comprising a sequence chosen from table A, B, D, E, G or H or fragments, analogues or derivatives thereof.

According to one aspect, the present invention provides an isolated polynucleotide encoding a polypeptide having at least 95% identity to a second polypeptide comprising a sequence chosen from table A, B, D, E, G or H or fragments, analogues or derivatives thereof.

According to one aspect, the present invention relates to polypeptides characterised by the amino acid sequence chosen from table A, B, D, E, G or H or fragments, analogues or derivatives thereof.

According to one aspect, the present invention provides an isolated polynucleotide encoding a polypeptide having at least 70% identity to a second polypeptide comprising a sequence chosen from table A, B, D, E, G or H.

According to one aspect, the present invention provides an isolated polynucleotide encoding a polypeptide having at least 95% identity to a second polypeptide comprising a sequence chosen from table A, B, D, E, G or H.

According to one aspect, the present invention relates to polypeptides characterised by the amino acid sequence chosen from table A, B, D, E, G or H.

According to one aspect, the present invention provides an isolated polynucleotide encoding a polypeptide having at least 70% identity to a second polypeptide comprising a sequence chosen from table B, E or H or fragments, analogues or derivatives thereof.

According to one aspect, the present invention provides an isolated polynucleotide encoding a polypeptide having at least 95% identity to a second polypeptide comprising a sequence chosen from B, E or H or fragments, analogues or derivatives thereof.

According to one aspect, the present invention relates to polypeptides characterised by the amino acid sequence chosen from table B, E or H or fragments, analogues or derivatives thereof.

According to one aspect, the present invention provides an isolated polynucleotide encoding a polypeptide having at least 70% identity to a second polypeptide comprising a sequence chosen from table B, E or H.

According to one aspect, the present invention provides an isolated polynucleotide encoding a polypeptide having at least 95% identity to a second polypeptide comprising a sequence chosen from B, E or H.

According to one aspect, the present invention relates to polypeptides characterised by the amino acid sequence chosen from table B, E or H.

In accordance with the present invention, all nucleotides encoding polypeptides and chimeric polypeptides are within the scope of the present invention.

In a further embodiment, the polypeptides or chimeric polypeptides in accordance with the present invention are antigenic.

In a further embodiment, the polypeptides or chimeric polypeptides in accordance with the present invention are immunogenic.

In a further embodiment, the polypeptides or chimeric polypeptides in accordance with the present invention can elicit an immune response in an individual.

In a further embodiment, the present invention also relates to polypeptides which are able to raise antibodies having binding specificity to the polypeptides or chimeric polypeptides of the present invention as defined above.

In one embodiment, the polypeptides of table A (BVH-3) or table D (BVH-11) comprise at least one epitope bearing portion.

In a further embodiment, the fragments of the polypeptides of the present invention will comprise one or more epitope bearing portion identified in Table C and F. The fragment will comprises at least 15 contiguous amino acid of the polypeptide of table C and F. The fragment will comprises at least 20 contiguous amino acid of the polypeptide of table C and F.

In a further embodiment, the epitope bearing portion of the polypeptide of table A(BVH-3) comprises at least one polypeptide listed in Table C.

In a further embodiment, the epitope bearing portion of the polypeptide of table B(BVH-11) comprises at least one polypeptide listed in Table F.

An antibody that "has binding specificity" is an antibody that recognises and binds the selected polypeptide but which does not substantially recognise and bind other molecules in a sample, such as a biological sample. Specific binding can be measured using an ELISA assay in which the selected polypeptide is used as an antigen.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

As used herein, "fragments", "derivatives" or "analogues" of the polypeptides of the invention include those polypeptides in which one or more of the amino acid residues are substituted with a conserved or non-conserved amino acid residue (preferably conserved) and which may be natural or unnatural. In one embodiment, derivatives and analogues of polypeptides of the invention will have about 70% identity with those sequences illustrated in the figures or fragments thereof. That is, 70% of the residues are the same. In a further embodiment, polypeptides will have greater than 75% homology. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, derivatives and analogues of polypeptides of the invention will have less than about 20 amino acid residue substitutions, modifications or deletions and more preferably less than 10. Preferred substitutions are those known in the art as conserved i.e. the substituted residues share physical or chemical properties such as hydrophobicity, size, charge or functional groups.

The skilled person will appreciate that analogues or derivatives of the proteins or polypeptides of the invention will also find use in the context of the present invention, i.e. as antigenic/immunogenic material. Thus, for instance proteins or polypeptides which include one or more additions, deletions, substitutions or the like are encompassed by the present invention. In addition, it may be possible to replace one amino acid with another of similar "type". For instance replacing one hydrophobic amino acid with another hydrophilic amino acid.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In an alternative approach, the analogues or derivatives could be fusion proteins, incorporating moieties which render purification easier, for example by effectively tagging the desired protein or polypeptide, It may be necessary to remove the "tag" or it may be the case that the fusion protein itself retains sufficient antigenicity to be useful.

In an additional aspect of the invention there are provided antigenic/immunogenic fragments of the proteins or polypeptides of the invention, or of analogues or derivatives thereof.

The fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, analogue or derivative as described herein. The key issue, once again, is that the fragment retains the antigenic/immunogenic properties.

Thus, what is important for analogues, derivatives and fragments is that they possess at least a degree of the antigenicity/immunogenic of the protein or polypeptide from which they are derived.

In accordance with the present invention, polypeptides of the invention include both polypeptides and chimeric polypeptides.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *streptococcus* strains.

Moreover, the polypeptides of the present invention can be modified by terminal —NH$_2$ acylation (e.g. by acetylation, or thioglycolic acid amidation, terminal carboxy amidation, e.g. with ammonia or methylamine) to provide stability, increased hydrophobicity for linking or binding to a support or other molecule.

Also contemplated are hetero and homo polypeptide multimers of the polypeptide fragments, analogues and derivatives. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology.

Preferably, a fragment, analogue or derivative of a polypeptide of the invention will comprise at least one antigenic region i.e. at least one epitope.

In order to achieve the formation of antigenic polymers (i.e. synthetic multimers), polypeptides may be utilised having bishaloacetyl groups, nitroarylhalides, or the like, where the reagents being specific for thio groups. Therefore, the link between two mercapto groups of the different peptides may be a single bond or may be composed of a linking group of at least two, typically at least four, and not more than 16, but usually not more than about 14 carbon atoms.

In a particular embodiment, polypeptide fragments, analogues and derivatives of the invention do not contain a methionine (Met) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a *streptococcus* culture and subsequently sequenced to determine the initial residue of the mature protein and therefore the sequence of the mature polypeptide.

According to another aspect, there are provided vaccine compositions comprising one or more *streptococcus* polypeptides of the invention in admixture with a pharmaceutically acceptable carrier diluent or adjuvant. Suitable adjuvants include oils i.e. Freund's complete or incomplete adjuvant; salts i.e. $AlK(SO_4)_2$, $AlNa(SO_4)_2$, $AlNH_4(SO_4)_2$, silica, kaolin, carbon polynucleotides i.e. poly IC and poly AU. Preferred adjuvants include QuilA and Alhydrogel. Vaccines of the invention may be administered parenterally by injection, rapid infusion, nasopharyngeal absorption, dermoabsorption, or bucal or oral. Pharmaceutically acceptable carriers also include tetanus toxoid.

The term vaccine is also meant to include antibodies. In accordance with the present invention, there is also provided the use of one or more antibodies having binding specificity for the polypeptides of the present invention for the treatment or prophylaxis of *streptococcus* infection and/or diseases and symptoms mediated by *streptococcus* infection.

Vaccine compositions of the invention are used for the treatment or prophylaxis of *streptococcus* infection and/or diseases and symptoms mediated by *streptococcus* infection as described in P. R. Murray (Ed, in chief), E. J. Baron, M. A. Pfaller, F. C. Tenover and R. H. Yolken. Manual of Clinical Microbiology, ASM Press, Washington, D.C. sixth edition, 1995, 1482p which are herein incorporated by reference. In one embodiment, vaccine compositions of the present invention are used for the treatment or prophylaxis of meningitis, otitis media, bacteremia or pneumonia. In one embodiment, vaccine compositions of the invention are used for the treatment or prophylaxis of *streptococcus* infection and/or diseases and symptoms mediated by *streptococcus* infection, in particular *S. pneumoniae*, group A *streptococcus* (*pyogenes*), group B *streptococcus* (GBS or *agalactiae*), *dysgalactiae, uberis, nocardia* as well as *Staphylococcus aureus*. In a further embodiment, the *streptococcus* infection is *S. pneumoniae*.

In a particular embodiment, vaccines are administered to those individuals at risk of *streptococcus* infection such as infants, elderly and immunocompromised individuals.

As used in the present application, the term "individuals" include mammals. In a further embodiment, the mammal is human.

Vaccine compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

Vaccine compositions are preferably in unit dosage form of about 0.1 µg to 10 mg and more preferably 1 µg to 1 mg and most preferably 10 to 100 µg 1 to 3 times with an interval of about 1 to 6 week intervals between immunizations.

According to another aspect, there are provided polynucleotides encoding polypeptides characterised by the amino acid sequence chosen from table A, B, D, E, G or H or fragments, analogues or derivatives thereof.

According to another aspect, there are provided polynucleotides encoding polypeptides characterised by the amino acid sequence chosen from table B, E or H or fragments, analogues or derivatives thereof.

In one embodiment, polynucleotides are those illustrated in table A, B, D, E, G or H which encodes polypeptides of the invention.

In one embodiment, polynucleotides are those illustrated in table B, E or H which encodes polypeptides of the invention.

It will be appreciated that the polynucleotide sequences illustrated in the figures may be altered with degenerate codons yet still encode the polypeptides of the invention. Accordingly the present invention further provides polynucleotides which hybridise to the polynucleotide sequences herein above described (or the complement sequences thereof) having 50% identity between sequences. In one embodiment, at least 70% identity between sequences. In one embodiment, at least 75% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity.

Suitable stringent conditions for hybridation can be readily determined by one of skilled in the art (see for example Sambrook et al., (1989) Molecular cloning: A Laboratory Manual, 2$^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridise under stringent conditions to either
(a) a DNA sequence encoding a polypeptide or
(b) the complement of a DNA sequence encoding a polypeptide;

wherein said polypeptide comprising a sequence chosen from table A, B, D, E, G or H or fragments or analogues thereof.

In a further embodiment, the present invention provides polynucleotides that hybridise under stringent conditions to either
(c) a DNA sequence encoding a polypeptide or
(d) the complement of a DNA sequence encoding a polypeptide;

wherein said polypeptide comprising a sequence chosen from table B, E or H or fragments or analogues thereof.

In a further embodiment, the present invention provides polynucleotides that hybridise under stringent conditions to either
(a) a DNA sequence encoding a polypeptide or
(b) the complement of a DNA sequence encoding a polypeptide;

wherein said polypeptide comprises at least 10 contiguous amino acid residues from a polypeptide comprising a sequence chosen from table A, B, D, E, G or H or fragments or analogues thereof.

In a further embodiment, the present invention provides polynucleotides that hybridise under stringent conditions to either
(c) a DNA sequence encoding a polypeptide or
(d) the complement of a DNA sequence encoding a polypeptide;

wherein said polypeptide comprises at least 10 contiguous amino acid residues from a polypeptide comprising a sequence chosen from table B, E or H or fragments or analogues thereof.

In a further embodiment, polynucleotides are those encoding polypeptides of the invention illustrated in table A, B, D, E, G or H.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments, analogues or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2$^{nd}$ ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K., Springer-Verlag, New York, 3$^{rd}$ Edition, 1993, 380 pages; Current Protocols in Immunology, Edited by Coligan J. E. et al., John Wiley & Sons Inc., New York which are herein incorporated by reference.

For recombinant production, host cells are transfected with vectors which encode the polypeptide, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2$^{nd}$ ed, Cold Spring Harbor, N.Y., 1989; Current Protocols in Molecular Biology, Edited by Ausubel F. M. et al., John Wiley and Sons, Inc. New York incorporated herein by reference). Suitable promoters include but are not limited to LTR or SV40 promoter, E. coli lac, tac or trp promoters and the phage lambda $P_L$ promoter. Vectors will preferably incorporate an origin of replication as well as selection markers i.e. ampicilin resistance gene. Suitable bacterial vectors include pET, pQE70, pQE60, pQE-9, pbs, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlue-BacIII, pWLNEO, pSV2CAT, pOG44, pXT1, pSG, pSVK3, pBPV, pMSG and pSVL. Host cells may be bacterial i.e. *E. coli, Bacillus subtilis, Streptomyces*; fungal i.e. *Aspergillus niger, Aspergillus nidulins*; yeast i.e. Saccharomyces or eukaryotic i.e. CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptide may be expressed with or without a leader or secretion sequence. In the former case the leader may be removed using post-translational processing (see U.S. Pat. No. 4,431,739; U.S. Pat. No. 4,425,437; and U.S. Pat. No. 4,338,397 incorporated herein by reference) or be chemically removed subsequent to purifying the expressed polypeptide.

According to a further aspect, the *streptococcus* polypeptides of the invention may be used in a diagnostic test for *streptococcus* infection, in particular *S. pneumoniae* infection. Several diagnostic methods are possible, for example detecting *streptococcus* organism in a biological sample, the following procedure may be followed:

a) obtaining a biological sample from a patient;

b) incubating an antibody or fragment thereof reactive with a *streptococcus* polypeptide of the invention with the biological sample to form a mixture; and c) detecting specifically bound antibody or bound fragment in the mixture which indicates the presence of *streptococcus*.

Alternatively, a method for the detection of antibody specific to a *streptococcus* antigen in a biological sample containing or suspected of containing said antibody may be performed as follows:

a) obtaining a biological sample from a patient;

b) incubating one or more *streptococcus* polypeptides of the invention or fragments thereof with the biological sample to form a mixture; and c) detecting specifically bound antigen or bound fragment in the mixture which indicates the presence of antibody specific to *streptococcus*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the polypeptide are present in an organism.

The DNA sequences encoding polypeptides of the invention may also be used to design DNA probes for use in detecting the presence of *streptococcus* in a biological sample suspected of containing such bacteria. The detection method of this invention comprises:

a) obtaining the biological sample from a patient;

b) incubating one or more DNA probes having a DNA sequence encoding a polypeptide of the invention or fragments thereof with the biological sample to form a mixture; and c) detecting specifically bound DNA probe in the mixture which indicates the presence of *streptococcus* bacteria.

The DNA probes of this invention may also be used for detecting circulating *streptococcus* i.e. *S. pneumoniae* nucleic acids in a sample, for example using a polymerase chain reaction, as a method of diagnosing *streptococcus* infections. The probe may be synthesized using conventional techniques and may be immobilized on a solid phase, or may be labelled with a detectable label. A preferred DNA probe for this application is an oligomer having a sequence complementary to at least about 6 contiguous nucleotides of the *streptococcus pneumoniae* polypeptides of the invention.

Another diagnostic method for the detection of *streptococcus* in a patient comprises:

a) labelling an antibody reactive with a polypeptide of the invention or fragment thereof with a detectable label;

b) administering the labelled antibody or labelled fragment to the patient; and c) detecting specifically bound labelled antibody or labelled fragment in the patient which indicates the presence of *streptococcus*.

A further aspect of the invention is the use of the *streptococcus* polypeptides of the invention as immunogens for the production of specific antibodies for the diagnosis and in particular the treatment of *streptococcus* infection. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *streptococcus pneumoniae* polypeptides but is preferably specific for one.

A further aspect of the invention is the use of the antibodies directed to the *streptococcus* polypeptides of the invention for passive immunization. One could use the antibodies described in the present application. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *streptococcus pneumoniae* polypeptides but is preferably specific for one.

The following are reference tables summarizing the sequences disclosed in the present application:

TABLE A, B and C Variants and Epitope of BVH-3-

TABLE A

| Family | Polypeptide SEQ ID NO |
|---|---|
| BVH-3 | |
| New 21 | aa 396–1039 of SEQ ID. 6 |
| New 25 | aa 233–1039 of SEQ ID. 6 |
| New 40 | aa 408–1039 of SEQ ID. 6 |

TABLE B

| Family | Polypeptide SEQ ID NO |
|---|---|
| BVH-3 | |
| NEW1-mut1** | 255 |
| NEW35A | 256 |
| NEW42 | 349 |
| NEW49 | 350 |
| NEW50 | 351 |
| NEW51 | 352 |
| NEW52 | 353 |
| NEW53 | 354 |
| NEW54 | 355 |
| NEW55 | 356 |
| NEW56 | 357 |
| NEW56-mut2** | 358 |
| NEW56-mut3** | 359 |
| NEW57 | 360 |
| NEW63 | 361 |
| NEW64 | 362 |
| NEW65 | 363 |
| NEW66 | 364 |
| NEW76 | 365 |
| NEW105 | 366 |
| NEW106 | 367 |
| NEW107 | 368 |

**silent mutation, i.e. the polypeptide is the same as New1 or New 56

TABLE C

| Epitopes of BVH-3 | |
|---|---|
| 7G11.7 | 12 |
| 7G11.9 | 13 |
| B12D8.2 | 19 |
| 7F4.1 | 20 |
| 14F6.3 | 18 |
| 4D3.4 | 14 |
| 10C12.7 | 17 |
| 8E3.1 | 15 |
| 1G2.2 | 16 |

TABLE D

TABLE D, E and F Variants and Epitope of BVH-11-

| Family | Polypeptide SEQ ID NO |
|---|---|
| BVH-11 | |
| New19 | aa 497–838 of Seq. ID 8 |
| New24 | aa 227–838 of Seq. ID 8 |

TABLE E

| Family | Polypeptide SEQ ID NO |
|---|---|
| BVH-11 | |
| New 43 | 258 |
| NEW60 | 293 |
| NEW61 | 294 |
| NEW62 | 295 |
| NEW80 | 296 |
| NEW81 | 297 |
| NEW82 | 298 |
| NEW83 | 299 |
| NEW84 | 300 |
| NEW85 | 301 |
| NEW88D1 | 302 |
| NEW88D2 | 303 |
| NEW88 | 304 |

TABLE F

| epitopes of BVH-11 | |
|---|---|
| 10D7.5 | 21 |
| 10G9.3 | 22 |
| B11B8.1 | 22 |
| 10A2.2 | 22 |
| 11b8.4 | 23 |
| 3A4.1 | 24 |

TABLE G

| Family | Polypeptide SEQ ID NO | |
|---|---|---|
| Chimeras with BVH-11 and BVH-3 | | |
| New17 | M*-NEW5-G*P*-NEW1 | (376) |
| New20 | M*-NEW1-G*P*-NEW5 | (377) |
| New26 | M*-NEW10-G*P*-NEW25 | (378) |
| New27 | M*-NEW19-G*P*-NEW25 | (379) |
| New28 | M*-NEW10-G*P*-NEW1 | (380) |
| New29 | M*-NEW5-G*P*-NEW25 | (381) |
| New30 | M*-NEW4-G*P*-NEW25 | (382) |
| New31 | M*-NEW4-G*P*-NEW1 | (383) |
| NEW32 | M*-NE19-G*P*-NEW1 | (384) |

*OPTIONAL AMINO ACID

TABLE H

| Family | Polypeptide SEQ ID NO |
|---|---|
| Chimeras with BVH-11 and BVH-3 | |
| VP 89 | 369 |
| VP 90 | 370 |
| VP 91 | 371 |
| VP 92 | 372 |
| VP 93 | 373 |
| VP 94 | 332 |
| VP 108 | 333 |
| VP 109 | 334 |
| VP 110 | 335 |
| VP 111 | 336 |
| VP 112 | 337 |
| VP 113 | 338 |
| VP 114 | 339 |
| VP 115 | 340 |
| VP 116 | 341 |
| VP 117 | 342 |
| VP 119 | 343 |
| VP 120 | 344 |

TABLE H-continued

| Family | Polypeptide SEQ ID NO |
|---|---|
| VP 121 | 345 |
| VP 122 | 346 |
| VP 123 | 347 |
| VP 124 | 348 |

EXAMPLE 1

This example describes the bacterial strains, plasmids, PCR primers, recombinant proteins and hybridoma antibodies used herein.

Figure 26:
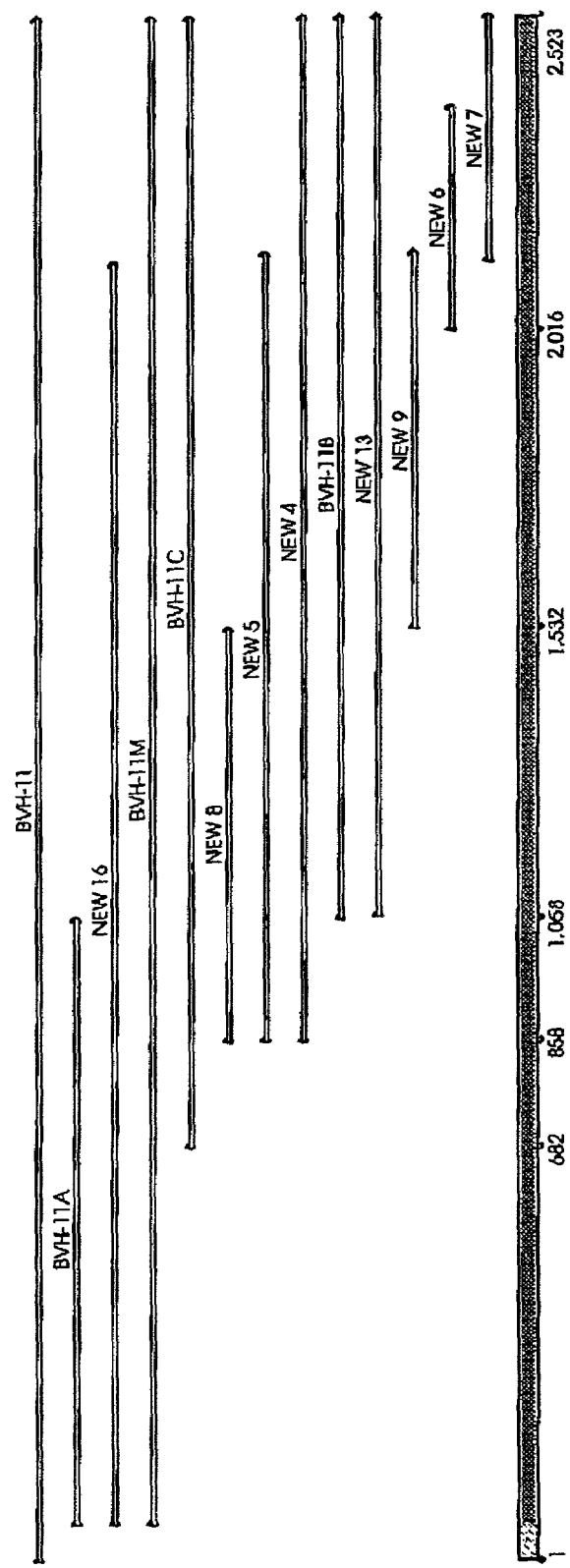
FIG. 26 is a schematic representation of the BVH-11 gene as well as location of gene sequences coding for the full length and truncated polypeptides. The relationships between DNA fragments are shown with respect to each other.
Figure 27:
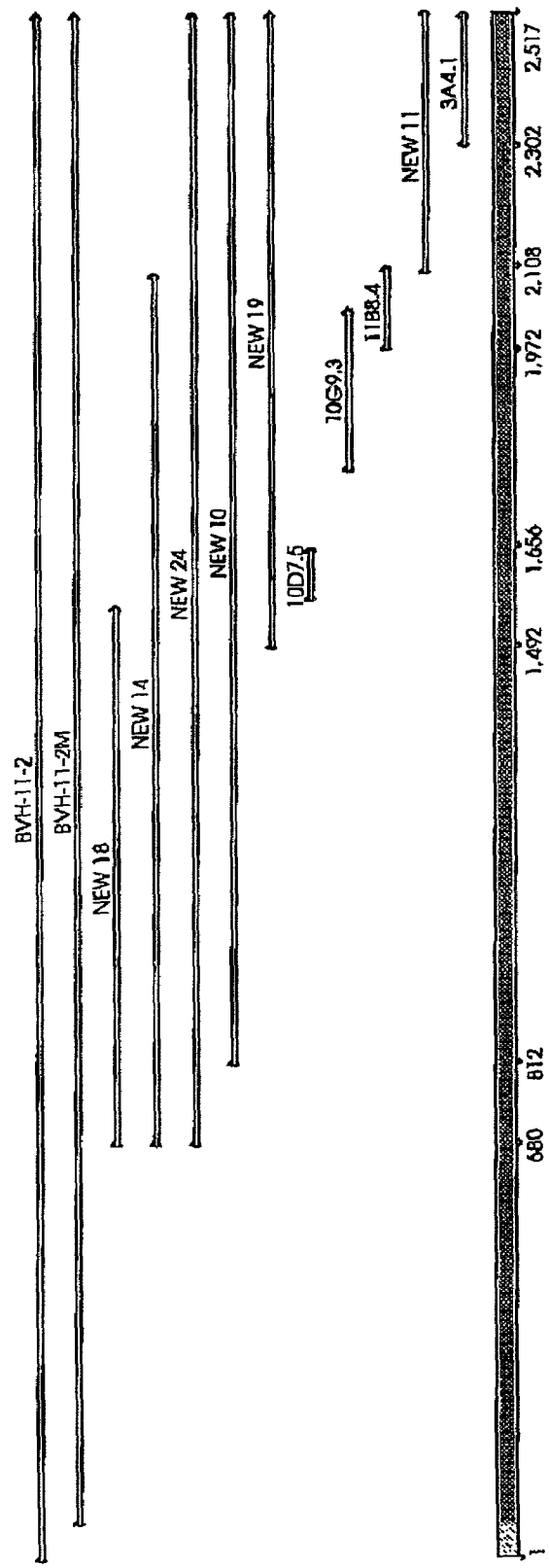
FIG. 27 is a schematic representation of the BVH-11-2 gene as well as location of gene sequences coding for the full length and truncated polypeptides. The relationships between DNA fragments are shown with respect to each other.
Figure 30:
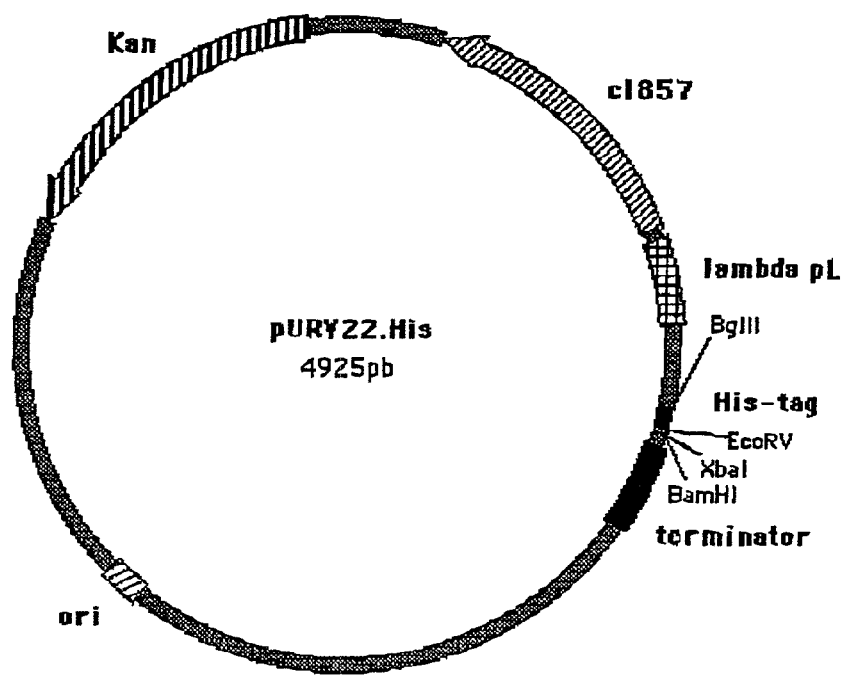
FIG. 30 is a map of plasmid pURV22.HIS. $Kan^R$, kanamycin-resistance coding region; cI857, bacteriophage λ cI857 temperature-sensitive repressor gene; lambda pL, bacteriophage λ transcription promotor; His-tag, 6-histidine coding region; terminator, T1 transcription terminator; ori, colE1 origin of replication.

*S. pneumoniae* SP64 (serogroup 6) and SP63 (serogroup 9) clinical isolates were provided by the Laboratoire de la Santé Publique du Québec, Sainte-Anne-de-Bellevue; Rx1 strain, a nonencapsulated derivative of the type 2 strain D39 and the type 3 strain WU2 were provided by David E. Briles from University of Alabama, Birmingham and the type 3 clinical isolate P4241 was provided by the Centre de Recherche en Infectiologie du Centre Hospitalier de l'Université Laval, Sainte-Foy. *E. coli* strains DH5α (Gibco BRL, Gaithesburg, Md.); AD494 (λDE3) (Novagen, Madison, Wis.) and BL21 (λDE3) (Novagen) as well as plasmid superlinker pSL301 vector (Invitrogen, San Diego, Calif.); PCMV-GH vector (gift from Dr. Stephen A. Johnston, Department for Biochemistry, University of Texas, Dallas, Tex.); pET32 and pET21 (Novagen) and pURV22.HIS expression vectors (FIG. 30) were used in this study. The pURV22.HIS vector contains a cassette of the bacteriophage λ cI857 temperature-sensitive repressor gene from which the functional $P_R$ promoter has been deleted. The inactivation of the cI857 repressor by a temperature increase from the range of 30–37° C. to 37–42° C. results in the induction of the gene under the control of promoter λPL. The PCR primers used for the generation of the recombinant plasmids had a restriction endonuclease site at the 5'end, thereby allowing directional cloning of the amplified product into the digested plasmid vector. The PCR oligonucleotide primers used are listed in the following Table 1. The location of the gene sequences coding for BVH-3, BVH-11 and BVH-11-2 gene products is summarized in the FIG. 25, FIG. 26 and FIG. 27, respectively.

Table 1. List of PCR oligonucleotide primers

TABLE 1

List of PCR oligonucleotide primers

| Primer | SEQ ID NO | Sequence 5'–3' | Nucleotide position | Restriction sites |
|---|---|---|---|---|
| OCRR 479 | 25 | cagtagatctgtgcct atgcactaaac | SEQ ID 1: 61–78 SEQ ID 9: 1–18 | BglII |
| OCRR 480 | 26 | gatctctagactactg ctattccttacgctat g | SEQ ID 2: 4909–4887 SEQ ID 9: 2528–2519 | XbaI |
| OCRR 497 | 27 | atcactcgagcattac ctggataatcctgt | SEQ ID 1: 1525–1506 | XhoI |
| OCRR 498 | 28 | ctgctaagcttatgaa agatttagat | SEQ ID 1: 1534–1548 | HindIII |
| OCRR 499 | 29 | gatactcgagctgcta ttccttac | SEQ ID 2: 4906–4893 | XhoI |
| HAMJ 172 | 30 | gaatctcgagttaagc tgctgctaattc | SEQ ID 1: 675–661 | XhoI |
| HAMJ 247 | 31 | gacgctcgagcgctat gaaatcagataaattc | SEQ ID 1: 3117–3096 | XhoI |
| HAMJ 248 | 32 | gacgctcgagggcatt acctggataatcctgt tcatg | SEQ ID 1: 1527–1501 | XhoI |
| HAMJ 249 | 33 | cagtagatctcttcat catttattgaaaagag g | SEQ ID 2: 1749–1771 | BglII |
| HAMJ 278 | 34 | ttatttcttccatatg gacttgacagaagagc aaattaag | SEQ ID 1: 1414–1437 | NdeI |
| HAMJ 279 | 35 | cgccaagcttcgctat gaaatcagataaattc | SEQ ID 1: 3117–3096 | HindIII |
| HAMJ 280 | 36 | cgccaagcttttccac aatataagtcgattga tt | SEQ ID 1: 2400–2377 | HindIII |
| HAMJ 281 | 37 | ttatttcttccatatg gaagtacctatcttgg aaaaagaa | SEQ ID 1: 2398–2421 | NdeI |
| HAMJ 300 | 38 | ttatttcttccatatg gtgcctatgcactaaa ccagc | SEQ ID 1: 62–82 | NdeI |
| HAMJ 313 | 39 | ataagaatgcggccgc ttccacaatataagtc gattgatt | SEQ ID 1: 2400–2377 | NotI |
| OCRR 487 | 40 | cagtagatctgtgctt atgaactaggtttgc | SEQ ID 3: 58–79 | BglII |
| OCRR 488 | 41 | gatcaagcttgctgct accttttacttactctc | SEQ ID 4: 2577–2556 | HindIII |
| HAMJ 171 | 42 | ctgagatatccgttat cgttcaaacc | SEQ ID 3: 1060–1075 | EcoRV |
| HAMJ 251 | 43 | ctgcaagcttttaaag gggaataatacg | SEQ ID 3: 1059–1045 | HindIII |
| HAMJ 264 | 44 | cagtagatctgcagaa gccttcctatctg | SEQ ID 3: 682–700 | BglII |
| HAMJ 282 | 45 | tcgccaagcttcgtta tcgttcaaaccattgg g | SEQ ID 3: 1060–1081 | HindIII |
| HAMJ 283 | 46 | ataagaatgcggccgc cttactctcctttaat aaagccaatagtt | SEQ ID 3: 2520–2492 | NotI |
| HAMJ 284 | 47 | catgccatggacattg atagtctcttgaaaca gc | SEQ ID 3: 856–880 | NcoI |
| HAMJ 285 | 48 | cgccaagcttcttact ctcctttaataaagcc aatag | SEQ ID 3: 2520–2494 | HindIII |
| HAMJ 286 | 49 | cgacaagcttaacatg gtcgctagcgttacc | SEQ ID 3: 2139–2119 SEQ ID 5: 2210–2190 | HindIII |
| HAMJ 287 | 50 | cataccatgggccttt atgaggcacctaag | SEQ ID 3: 2014–2034 | NcoI |
| HAMJ 288 | 51 | cgacaagcttaagtaa atcttcagcctctctc ag | SEQ ID 3: 2376–2353 | HindIII |
| HAMJ 289 | 52 | gataccatggctagcg accatgttcaaagaa | SEQ ID 3: 2125–2146 | NcoI |
| HAMJ 290 | 53 | cgccaagcttatcatc cactaacttgacttta tcac | SEQ ID 3: 1533–1508 | HindIII |
| HAMJ 291 | 54 | cataccatggatattc ttgccttcttagctcc g | SEQ ID 3: 1531–1554 | NcoI |
| HAMJ 301 | 55 | catgccatggtgctta tgaactaggtttgc | SEQ ID 3: 59–79 | NcoI |
| HAMJ 302 | 56 | cgccaagctttagcgt taccaaaaccattatc | SEQ ID 3: 2128–2107 | HindIII |
| HAMJ 160 | 57 | gtattagatctgttcc tatgaacttggtcgtc acca | SEQ ID 5: 172–196 | BglII |

TABLE 1-continued

List of PCR oligonucleotide primers

| Primer | SEQ ID NO | Sequence 5'–3' | Nucleotide position | Restriction sites |
|---|---|---|---|---|
| HAMJ 186 | 58 | cgcctctagactactg tataggagccgg | SEQ ID 5: 2613–2630 | XbaI |
| HAMJ 292 | 59 | catgccatggaaaaca tttcaagccttttacg tg | SEQ ID 5: 925–948 | NcoI |
| HAMJ 293 | 60 | cgacaagcttctgtat aggagccggttgactt tc | SEQ ID 5: 2627–2604 | HindIII |
| HAMJ 294 | 61 | catgccatggttcgta aaaataaggcagacca ag | SEQ ID 5: 2209–2232 | NcoI |
| HAMJ 297 | 62 | catgccatggaagcct attggaatgggaag | SEQ ID 5: 793–812 | NcoI |
| HAMJ 352 | 63 | catgccatggaagcct attggaatgggaagc | SEQ ID 5: 793–813 | NcoI |
| HAMJ 353 | 64 | cgccaagcttgtaggt aatttgcgcatttgg | SEQ ID 5: 1673–1653 | HindIII |
| HAMJ 354 | 65 | cgccaagcttctgtat aggagccggttgac | SEQ ID 5: 2627–2608 | HindIII |
| HAMJ 355 | 66 | catgccatggatattc ttgccttcttagctcc | SEQ ID 5: 1603–1624 | NcoI |
| HAMJ 404 | 67 | ttatttcttccatatg catggtgatcatttcc attaca | SEQ ID 1: 1186–1207 | NdeI |
| HAMJ 464 | 68 | gatgcatatgaatatg caaccgagtcagttaa gc | SEQ ID 1: 697–720 | NdeI |
| HAMJ 465 | 69 | gatgctcgagagcatc aaatccgtatccatc | SEQ ID 1: 1338–1318 | XhoI |
| HAMJ 466 | 70 | gatgcatatggatcat ttccattacattcca | SEQ ID 1: 1192–1212 | NdeI |
| HAMJ 467 | 71 | gacaagcttggcatta cctggataatcctg | SEQ ID 1: 1527–1507 | HindIII |
| HAMJ 352 | 72 | catgccatggaagcct attggaatgggaagc | SEQ ID 5: 793–813 | NcoI |
| HAMJ 470 | 73 | ataagaatgcggccgc cgctatgaaatcagat aaattc | SEQ ID 1: 3096–3117 | NotI |
| HAMJ 471 | 168 | atatgggcccctgtat aggagccggttgactt tc | SEQ ID 5: 2626–2604 | Apa I |
| HAMJ 472 | 169 | atatgggcccaatatg caaccgagtcagttaa gc | SEQ ID 1: 720–697 | Apa I |
| HAMJ 350 | 170 | atatgggcccaacatg gtcgctagcgttacc | SEQ ID 3: 2139–2119 | Apa I |
| HAMJ 351 | 171 | tcccgggcccgacttg acagaagagcaaatta ag | SEQ ID 1: 1414–1437 | Apa I |
| HAMJ 358 | 172 | catgccatgggacttg acagaagagcaaatta ag | SEQ ID 1: 1415–1437 | NcoI |
| HAMJ | 173 | tcccgggcccgctat | SEQ ID 1: | Apa I |

TABLE 1-continued

List of PCR oligonucleotide primers

| Primer | SEQ ID NO | Sequence 5'–3' | Nucleotide position | Restriction sites |
|---|---|---|---|---|
| | 359 | gaaatcagataaattc | 3116–3096 | |
| HAMJ 403 | 174 | atatgggcccgacatt gatagtctcttgaaac agc | SEQ ID 3: 856–880 | Apa I |
| HAMJ 361 | 175 | cgccaagcttaacatg gtcgctagcgttacc | SEQ ID 3: 2139–2119 | HindIII |
| HAMJ 483 | 176 | atatgggcccttact ctcctttaataaagcc aatag | SEQ ID 3: 2520–2494 | Apa I |

Molecular biology techniques were performed according to standard methods. See for example, Sambrook, J., Fritsch, E. F., Maniatis, T., "Molecular cloning. A laboratory manual" Vol. 1–2–3 (second edition) Cold Spring Harbour Laboratory Press, 1989, New York, which is herein incorporated by reference. PCR-amplified products were digested with restriction endonucleases and ligated to either linearized plasmid pSL301, pCMV-GH, pET or pURV22.HIS expression vector digested likewise or digested with enzymes that produce compatible cohesive ends. Recombinant pSL301 and recombinant pCMV-GH plasmids were digested with restriction enzymes for the in-frame cloning in pET expression vector. When pET vectors were used, clones were first stabilized in E. coli DH5α before introduction into E. coli BL21(λDE3) or AD494 (λDE3) for expression of full-length or truncated BVH-3, BVH-11 or BVH-11-2 molecules. Each of the resultant plasmid constructs was confirmed by nucleotide sequence analysis. The recombinant proteins were expressed as N-terminal fusions with the thioredoxin and His-tag (pET32 expression system); as C-terminal fusions with an His-tag (pET21 expression system); or as N-terminal fusions with an His-tag (pURV22.HIS expression system). The expressed recombinant proteins were purified from supernatant fractions obtained after centrifugation of sonicated IPTG-(pET systems) or heat-(pURV22.HIS) induced E. coli using a His-Bind metal chelation resin (QIAgen, Chatsworth, Calif.). The gene products generated from S. pneumoniae SP64 are listed in the following Table 2. The gene fragment encoding BVH-3-Sp63 protein (amino acid residues 21 to 840 on SEQ ID NO: 10) was generated from S. pneumoniae SP63 using the PCR-primer sets OCRR479-OCRR480 and the cloning vector pSL301. The recombinant pSL301-BVH-3Sp63 was digested for the in-frame cloning in pET32 vector for the expression of the BVH-3-Sp63 molecule.

TABLE 2

Lists of truncated BVH-3, BVH-11, BVH-11-2 and Chimeric gene products generated from S. pneumoniae SP64

| PCR-primer sets | Protein designation | Identification | Encoded amino acids (SEQ ID No 6) | Cloning vector |
|---|---|---|---|---|
| OCRR479–OCRR480 | BVH-3M | BVH-3 w/o ss | 21–1039 | pSL301 |
| OCRR479–OCRR497 | BVH-3AD | BVH-3 N'end w/o ss | 21–509 | pSL301 |
| HAMJ248–HAMJ249 | L-BVH-3AD | BVH-3 N'end | 1–509 | pET-21(+) |
| OCRR498–OCRR499 | BVH-3B | BVH-3 C'end | 512–1039 | pSL301 |
| OCRR479–HAMJ172 | BVH-3C | BVH-3 N'end w/o ss | 21–225 | pET-32 c(+) |
| OCRR487–OCRR488 | BVH-11M | BVH-11 w/o ss | 20–840 | pCMV-GH |
| HAMJ251–OCRR487 | BVH-11A | BVH-11 N'end w/o ss | 20–353 | pET-32 c(+) |

TABLE 2-continued

Lists of truncated BVH-3, BVH-11, BVH-11-2 and
Chimeric gene products generated from *S. pneumoniae* SP64

| PCR-primer sets | Protein designation | Identification | Encoded amino acids (SEQ ID No 6) | Cloning vector |
|---|---|---|---|---|
| HAMJ171–OCRR488 | BVH-11B | BVH-11 C'end | 354–840 | pET-32 a(+) |
| HAMJ264–OCRR488 | BVH-11C | BVH-11 C'end | 228–840 | pET-32 a(+) |
| HAMJ278–HAMJ279 | NEW1 | BVH-3 C'end | 472–1039 | pET-21b(+) |
| HAMJ278–HAMJ280 | NEW2 | BVH-3 C'end | 472–800 | pET-21b(+) |
| HAMJ281–HAMJ279 | NEW3 | BVH-3 C'end | 800–1039 | pET-21b(+) |
| HAMJ284–HAMJ285 | NEW4 | BVH-11 C'end | 286–840 | pET-21d(+) |
| HAMJ284–HAMJ286 | NEW5 | BVH-11 internal | 286–713 | pET-21d(+) |
| HAMJ287–HAMJ288 | NEW6 | BVH-11 internal | 672–792 | pET-21d(+) |
| HAMJ285–HAMJ289 | NEW7 | BVH-11 C'end | 709–840 | pET-21d(+) |
| HAMJ284–HAMJ290 | NEW8 | BVH-11 internal | 286–511 | pET-21d(+) |
| HAMJ286–HAMJ291 | NEW9 | BVH-11 internal | 511–713 | pET-21d(+) |
| HAMJ160–HAMJ186 | BVH-11-2M | BVH-11-2 w/o ss | 20–838 | pSL301 |
| HAMJ292–HAMJ293 | NEW10 | BVH-11-2 C'end | 271–838 | pET-21d(+) |
| HAMJ293–HAMJ294 | NEW11 | BVH-11-2 C'end | 699–838 | pET-21d(+) |
| HAMJ282–HAMJ283 | NEW13 | BVH-11 C'end | 354–840 | pET-21b(+) |
| HAMJ286–HAMJ297 | NEW14 | BVH-11-2 internal | 227–699 | pET-21d(+) |
| HAMJ300–HAMJ313 | NEW15 | BVH-3 N'end w/o ss | 21–800 | pET-21b(+) |
| HAMJ301–HAMJ302 | NEW16 | BVH-11 N'end w/o ss | 20–709 | pET-21d(+) |
| HAMJ352–HAMJ353 | NEW18 | BVH-11-2 internal | 227–520 | pET21d(+) |
| HAMJ354–HAMJ355 | NEW19 | BVH-11-2 C'end | 497–838 | pET21d(+) |
| HAMJ404–HAMJ279 | NEW21 | BVH-3 C'end | 396–1039 | pET21b(+) |
| HAMJ464–HAMJ465 | NEW22 | BVH-3 internal | 233–446 | pET-21a(+) |
| HAMJ466–HAMJ467 | NEW23 | BVH-3 internal | 398–509 | pET-21b(+) |
| HAMJ352–HAMJ293 | NEW24 | BVH-11-2 C'end | 227–838 | pET-21d(+) |
| HAMJ464–HAMJ470 | NEW25 | BVH-3 C'end | 233–1039 | pET-21b(+) |
| HAMJ278–HAMJ279 (NEW 1) HAMJ282–HAMJ283 (NEW 13) | NEW12 | Chimera* | M-NEW 1 -KL - NEW 13 | pET 21 b (+) |
| HAMJ284–HAMJ350 (NEW 5) HAMJ351–HAMJ279 (NEW 1) | NEW17 | Chimera* | M- NEW 5 -GP - NEW 1 | pET 21 d (+) |
| HAMJ358–HAMJ359 (NEW 1) HAMJ403–HAMJ361 (NEW 5) | NEW20 | Chimera* | M- NEW 1 -GP - NEW 5 | pET 21 d (+) |
| HAMJ292–HAMJ471 (NEW 10) HAMJ472–HAMJ470 (NEW 25) | NEW26 | Chimera* | M- NEW 10 -GP - NEW 25 | pET 21 d (+) |
| HAMJ355–HAMJ471 M- NEW 19 -GP - (NEW 19) HAMJ472–HAMJ470 (NEW 25) | NEW27 pET 21 d (+) | Chimera* |  NEW 25 |  |
| HAMJ292–HAMJ471 (NEW 10) HAMJ351–HAMJ279 (NEW 1) | NEW28 | Chimera* | M- NEW 10 -GP - NEW 1 | pET 21 d (+) |
| HAMJ284–HAMJ350 (NEW 5) HAMJ472–HAMJ470 (NEW 25) | NEW29 | Chimera* | M- NEW 5 -GP - NEW 25 | pET 21 d (+) |
| HAMJ284–HAMJ483 (NEW 4) HAMJ472–HAMJ470 (NEW 25) | NEW30 | Chimera* | M- NEW 4 -GP - NEW 25 | pET 21 d (+) |
| HAMJ284–HAMJ483 (NEW 4) HAMJ351–HAMJ279 (NEW 1) | NEW31 | Chimera* | M- NEW 4 -GP - NEW 1 | pET 21 d (+) |
| HAMJ355–HAMJ471 (NEW 19) HAMJ351–HAMJ279 (NEW 1) | NEW32 | Chimera* | M- NEW 19 -GP - NEW 1 | pET 21 d (+) | w/o ss: without signal sequence. Analysis of the BVH-3, BVH-11 and BVH-11-2 protein sequences suggested the presence of putative hydrophobic leader sequences.
*encoded amino acids for the chimeras are expressed as the gene product, additional non essential amino acids residue were added M is methionine, K is lysine, L is leucine, G is glycine and P is proline.

Monoclonal antibody (Mab)-secreting hybridomas were obtained by fusions of spleen cells from immunized mice and non-secreting, HGPRT-deficient mouse myeloma SP2/0 cells by the methods of Fazekas De St-Groth and Scheidegger (J Immunol Methods 35 : 1–21, 1980) with modifications (J. Hamel et al. J Med Microbiol 23 : 163–170, 1987). Female BALB/c mice (Charles River, St-Constant, Quebec, Canada) were immunized with either BVH-3M (thioredoxin-His•Tag-BVH-3M fusion protein/pET32 system), BVH-11M (thioredoxin-His•Tag-BVH-11M fusion protein/pET32 system), BVH-11-2M (thioredoxin-His•Tag-BVH-11-2M fusion protein/pET32 system), BVH-11B (thioredoxin-His•Tag-BVH-11B fusion protein/pET32 system), BVH-3M (His•Tag-BVH-3 fusion protein/pURV22.HIS system) or NEW1 (NEW1-His•Tag fusion protein/pET21 system) gene products from *S. pneumoniae* strain SP64 to generate the Mab series H3-, H11-, H112-, H11B-, H3V-, and HN1-, respectively. Culture supernatants of hybridomas were initially screened by enzyme-linked-immunoassay (ELISA) according to the procedure described by Hamel et al. (Supra) using plates coated with preparations of purified recombinant BVH-3, BVH-11 and/or BVH-11-2 proteins or suspensions of heat-killed *S. pneumoniae* cells. The Mab-secreting hybridomas selected for further characterization are listed in Table 3 and Table 4 from the following Example 2. The class and subclass of Mab immunoglobulins were determined by ELISA using commercially available reagents (Southern Biotechnology Associates, Birmingham, Ala.).

Furthermore, the cloning and expression of chimeric gene(s) encoding for chimeric polypeptides and the protection observed after vaccination with these chimeric polypeptides are described.

BVH-3 and BVH-11 gene fragments corresponding to the 3'end of the genes were amplified by PCR using pairs of oligonucleotides engineered to amplify gene fragments to be included in the chimeric genes. The primers used had a restriction endonuclease site at the 5' end, thereby allowing directional in-frame cloning of the amplified product into digested plasmid vectors (Table 1 and Table 2). PCR-amplified products were digested with restriction endonucleases and ligated to linearized plasmid pET21 or pSL301 vector. The resultant plasmid constructs were confirmed by nucleotide sequence analysis. The recombinant pET21 plasmids containing a PCR product were linearized by digestion with restriction enzymes for the in-frame cloning of a second DNA fragment and the generation of a chimeric gene encoding for a chimeric pneumococcal protein molecule. Recombinant pSL301 plasmids containing a PCR product were digested with restriction enzymes for the obtention of the DNA inserts. The resulting insert DNA fragments were purified and inserts corresponding to a given chimeric gene were ligated into pET21 vector for the generation of a chimeric gene. The recombinant chimeric polypeptides listed in Table 2 were as C-terminal fusion with an His-tag. The expressed recombinant proteins were purified from supernatant fractions obtained from centrifugation of sonicated IPTG-induced *E. coli* cultures using a His-Bind metal chelation resin (QIAgen, Chatsworth, Calif.).

Groups of 8 female BALB/c mice (Charles River) were immunized subcutaneously two times at three-week intervals with 25 μg of either affinity purified His•Tag-fusion protein identifed in presence of 15–20 μg of QuilA adjuvant. Ten to 14 days following the last immunization, the mice were challenged challenged intravenously with 10E5–10E6 CFU of *S. pneumoniae* type 3 strain WU2. The polypeptides and fragments are capable of eliciting a protective immune response.

TABLE 2A

| Experiment | Immunogen | Alive:Dead | Days to death post-infection |
|---|---|---|---|
| 1 | none | 0:8 | 1, 1, 1, 1, 1, 1, 1, 1 |
|  | NEW 1 | 2:6 | 1, 2, 2, 2, 2, 2, >14, >14 |
|  | NEW 13 | 1:7 | 1, 1, 3, 3, 4, 5, 5, >14 |
|  | NEW 12 | 6:2 | 3, 11, 6X >14 |
|  | BVH-3M | 1:7 | 3, 3, 3, 3, 3, 3, 3, >14 |
| 2 | none | 0:8 | 1, 1, 1, 1, 1, 1, 1, 1 |
|  | NEW 17 | 7:1 | 4, 7 X >14 |
|  | NEW 12 | 3:5 | 3, 3, 3, 4, 5, >14, >14, >14 |
| 3 | none | 0:8 | 2, 2, 2, 2, 2, 2, 2, 2 |
|  | NEW 18 | 1:7 | 2, 2, 2, 2, 3, 3, 3, 3 |
|  | NEW 19 | 8:0 | 8 X >14 |
|  | NEW 10 | 8:0 | 8 X >14 |
|  | BVH-11-2 | 8:0 | 8 X >14 |

EXAMPLE 2

This example describes the identification of peptide domains carrying target epitopes using Mabs and recombinant truncated proteins described in example 1.

Hybridomas were tested by ELISA against truncated BVH-3, BVH-11 or BVH-11-2 gene products in order to characterize the epitopes recognized by the Mabs. The truncated gene products were generated from *S. pneumoniae* SP64 strain except for BVH-3-Sp63 which was generated from *S. pneumoniae* SP63 strain. As a positive control, the reactivity of each antibody was examined with full-length BVH-3, BVH-11 or BVH-11-2 recombinant proteins. In some cases, the Mab reactivity was evaluated by Western immunoblotting after separation of the gene product by SDS-PAGE and transfer on nitrocellulose paper. The reactivities observed is set forth in the following Table 3 and Table 4.

TABLE 3

ELISA reactivity of BVH-3-reactive Mabs with a panel of eleven BVH-3 gene products and the BVH-11M molecule

| Mabs (IgG isotype) | Gene products tested | | | | | | | | | | | |
|---|---|---|---|---|---|---|---|---|---|---|---|---|
|  | BVH-3M | BVH-3AD | BVH-3B | BVH-3C | NEW 1 | NEW 2 | NEW 3 | NEW 21 | NEW 22 | NEW 23 | BVH-3 Sp63 | BVH-11M |
| H3-4F9 (1) | + | + | − | + | − | − | − | − | − | − | + | + |
| H3-4D4 (1) | + | + | − | + | − | − | − | − | − | − | + | + |
| H3-9H12 (1) | + | + | − | + | − | − | − | − | − | − | + | + |
| H3-7G2 (1) | + | + | − | − | − | − | − | − | + | − | − | − |
| H3-10A1 (1) | + | + | − | − | − | − | − | + | − | + | + | − |

TABLE 3-continued

ELISA reactivity of BVH-3-reactive Mabs with a panel of eleven BVH-3 gene products and the BVH-11M molecule

| Mabs (IgG isotype) | BVH-3M | BVH-3AD | BVH-3B | BVH-3C | NEW 1 | NEW 2 | NEW 3 | NEW 21 | NEW 22 | NEW 23 | BVH-3 Sp63 | BVH-11M |
|---|---|---|---|---|---|---|---|---|---|---|---|---|
| H3-4D3 (1) | + | − | + | − | + | − | + | + | − | − | + | − |
| H11-6E7 (1) | + | + | − | + | − | − | − | NT | NT | NT | + | + |
| H11-10H10 (2a) | + | + | − | + | − | − | − | NT | NT | NT | + | + |
| H11-7G11 (2b) | + | + | + | + | + | + | − | NT | NT | NT | + | + |
| H3V-4F3 (1) | + | − | + | − | + | − | − | + | − | − | + | − |
| H3V-2F2 (1) | + | − | + | − | + | + | − | + | − | − | + | − |
| H3V-7F4 (1) | + | − | + | − | + | + | − | + | − | − | + | − |
| H3V-7H3 (1) | + | − | + | − | + | − | + | + | − | − | + | − |
| H3V-13B8 (1) | + | − | + | − | + | − | + | + | − | − | + | − |
| H3V-9C2 (1) | + | + | − | +/− | − | − | − | − | + | − | +/− | +/− |
| H3V-9C6 (1) | + | + | − | − | − | − | − | + | − | − | − | − |
| H3V-16A7 (1) | + | + | − | − | − | − | − | + | − | + | − | − |
| H3V-15A10 (1) | + | + | + | +/− | + | + | − | + | + | + | + | +/− |
| H3V-6B3 (1/2) | + | + | NT | NT | + | + | − | + | + | − | NT | − |
| HN1-5H3 (2b) | + | − | + | NT | + | − | − | + | − | − | + | − |
| HN1-8E3 (2a) | + | − | + | NT | + | − | − | + | − | − | + | − |
| HN1-14F6 (2a) | + | − | + | NT | + | − | − | + | − | − | + | − |
| HN1-2G2 (1) | + | − | + | NT | + | + | − | + | − | − | + | − |
| HN1-12D8 (2a) | + | − | + | NT | + | + | − | + | − | − | + | − |
| HN1-14B2 (2a) | + | − | + | NT | + | + | − | + | − | − | + | − |
| HN1-1G2 (2a) | + | − | + | NT | + | − | + | + | − | − | + | − |
| HN1-10C12 (1) | + | − | + | NT | + | − | + | + | − | − | + | − |
| HN1-3E5 (1) | + | + | − | − | + | + | − | + | − | + | + | − |

NT: not tested
+/−: very low reactivity but higher than background, possible non-specific Mab binding

TABLE 4

ELISA reactivity of BVH-11 and/or BVH-11-2-reactive Mabs with a panel of fourteen BVH-11 and BVH-11-2 gene products and the BVH-3M molecule

| Mabs (IgG isotype) | BVH-11M | BVH-11A | BVH-11B | BVH-11C | NEW 5 | NEW 6 | NEW 7 | NEW 8 | NEW 9 | NEW 10 | New 11 | New 14 | New 18 | New 19 | BVH-11-2-M | BVH-3M |
|---|---|---|---|---|---|---|---|---|---|---|---|---|---|---|---|---|
| H3-4F9 (1) | + | + | − | − | − | − | − | − | − | − | − | − | − | − | + | + |
| H3-4D4 (1) | + | + | − | − | − | − | − | − | − | − | − | − | − | − | + | + |
| H3-9H12 (1) | + | + | − | − | − | − | − | − | − | − | − | − | − | − | + | + |
| H11-6E7 (1) | + | + | − | − | − | − | − | − | − | − | − | − | − | − | + | + |
| H11-10H10 (2a) | + | + | − | − | − | − | − | − | − | − | − | − | − | − | + | + |
| H11-7G11 (2b) | + | + | − | − | − | − | − | − | − | − | − | − | − | − | + | + |
| H11-1B12 (1) | + | + | − | − | − | − | − | − | − | − | − | − | − | − | + | − |
| H11-7B9 (2a) | + | + | − | − | − | − | − | − | − | − | − | − | − | − | + | − |
| H11-3H5 (1) | + | − | + | + | + | − | − | −* | − | + | − | + | + | + | − |

TABLE 4-continued

ELISA reactivity of BVH-11 and/or BVH-11-2-reactive Mabs with a panel of fourteen BVH-11 and BVH-11-2 gene products and the BVH-3M molecule

| Mabs (IgG isotype) | BVH-11M | BVH-11A | BVH-11B | BVH-11C | NEW 5 | NEW 6 | NEW 7 | NEW 8 | NEW 9 | NEW 10 | New 11 | New 14 | New 18 | New 19 | BVH-11-2-M | BVH-3M |
|---|---|---|---|---|---|---|---|---|---|---|---|---|---|---|---|---|
| H11-10B8 (1) | + | − | + | + | + | − | − | −* | − | + | − | + | + | − | + | − |
| H11-1A2 (1) | + | − | + | + | + | − | − | −* | − | + | − | + | + | − | + | − |
| H112-3A1 (1) | + | − | + | NT | + | − | − | + | − | + | − | + | + | − | + | − |
| H112-13C11 (1) | + | +/− | + | NT | + | − | − | + | − | + | − | + | + | − | + | − |
| H112-10H10 (1) | + | + | − | NT | + | − | − | + | − | + | − | + | + | − | + | − |
| H112-1D8 (2a) | + | + | − | NT | + | − | − | + | − | + | − | + | + | − | + | − |
| H112-10G9 (2b) | + | − | + | NT | + | − | − | − | + | + | − | + | − | + | + | − |
| H112-10A2 (1) | + | − | + | NT | + | − | − | +/− | + | + | − | + | − | + | + | − |
| H112-3E8 (2a) | + | − | + | NT | + | − | − | +/− | − | + | − | + | − | + | + | − |
| H112-10D7 (2a) | + | − | + | NT | + | − | − | − | − | + | − | + | − | − | + | − |
| H112-2H7 (2a) | + | + | − | NT | − | − | − | − | − | − | − | − | − | − | + | − |
| H112-6H7 (1) | + | + | − | NT | − | − | − | − | − | − | − | − | − | − | + | − |
| H112-3A4 (2a) | − | − | − | NT | − | − | − | − | − | + | + | − | − | + | + | − |
| H112-10C5 (1) | − | − | − | NT | − | − | − | − | − | + | + | − | − | + | + | − |
| H112-14H6 (1) | − | − | − | NT | − | − | − | − | − | + | + | − | − | + | + | − |
| H112-7G2 (1) | − | − | − | NT | − | − | − | − | − | + | − | + | + | − | + | − |
| H112-13H10 (2a) | − | − | − | NT | − | − | − | − | − | − | − | + | + | − | + | − |
| H112-7E8 (2b) | +/− | − | − | NT | − | − | − | − | − | − | − | − | +/− | − | + | − |
| H112-7H6 (1) | +/− | − | − | NT | − | − | − | − | − | +/− | − | − | − | − | + | − |
| H11B-5F10 (1) | + | − | + | + | + | − | − | + | − | + | − | + | − | + | + | − |
| H11B-15G2 (1) | + | − | + | + | + | − | − | + | − | + | − | + | + | − | + | − |
| H11B-13D5 (2) | + | − | + | + | + | − | − | − | + | + | − | + | − | + | + | − |
| H11B-11B8 (1) | + | − | + | + | + | − | − | − | + | + | − | + | − | + | + | − |
| H11B-7E11 (1) | + | − | + | + | + | − | − | − | − | + | − | + | − | − | + | − |
| H11B-1C9 (1) | + | − | + | + | + | − | − | − | − | + | − | + | − | − | + | − |
| H11B-5E3 (2) | + | − | + | + | − | − | + | − | − | − | − | − | − | − | − | − |
| H11B-6E8 (1) | + | − | + | + | − | − | + | − | − | − | − | − | − | − | − | − |

Figure 28:
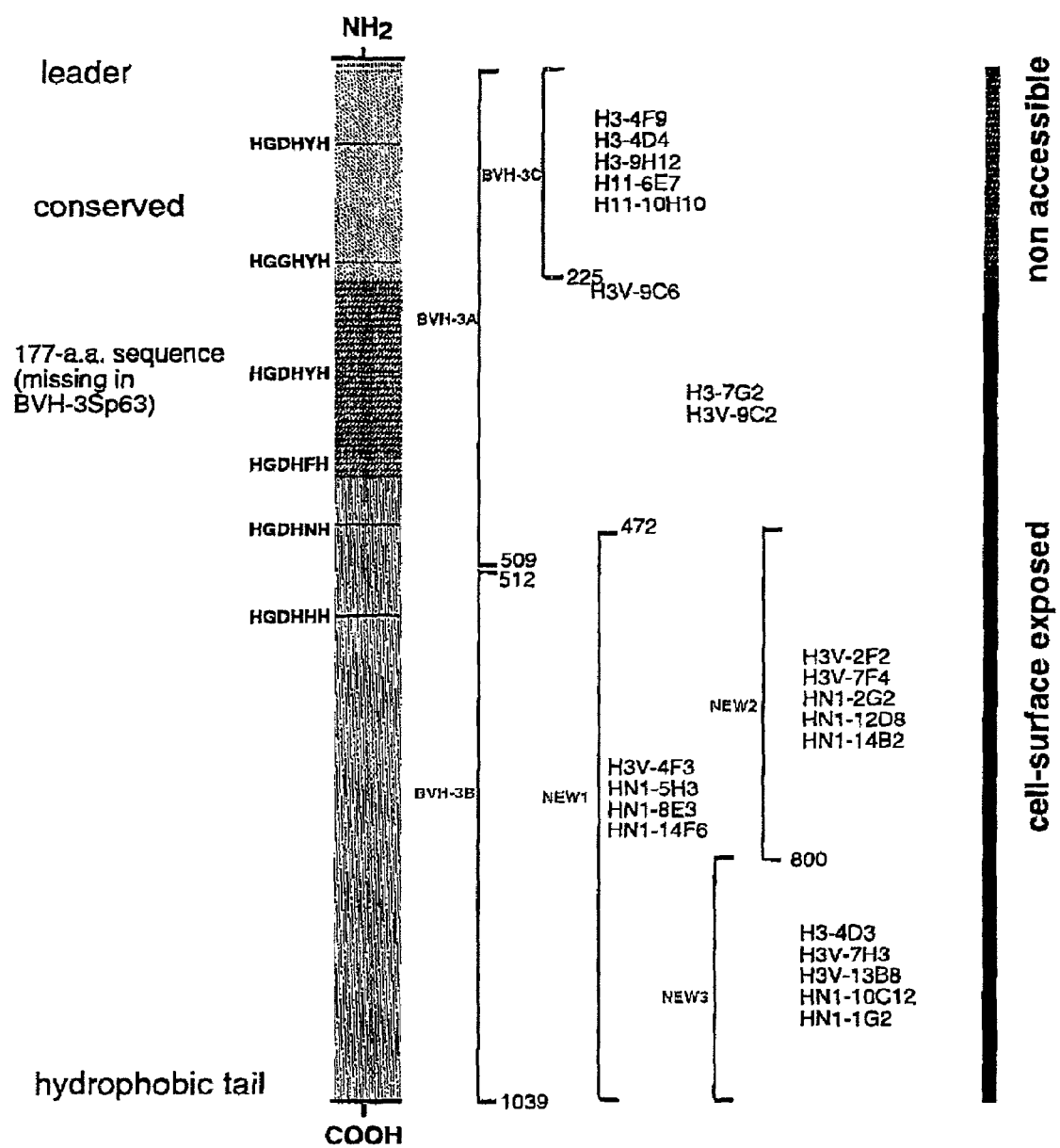
FIG. 28 is a schematic representation of the BVH-3 protein and the location of internal and surface epitopes recognized by certain monoclonal antibodies.

NT: not tested
+/−: very low reactivity but higher than background, possible non-specific Mab binding
*a strong signal was detected when tested by Western immunoblotting The deduced locations of the epitopes are summarized in FIG. 28 and FIG. 29. As can be seen from the data in Table 3, BVH-3-reactive Mabs can be divided into two groups: BVH-3A- and BVH-3B-reactive Mabs with the exception of Mabs H11-7G11 and H3V-15A10 which reacted with both, BVH-3A and BVH-3B molecules. The BVH-3A-reactive Mabs can be subdivided in two subgroups of antibodies depending of their reactivity or lack of reactivity with BVH-3C recombinant protein. Mab reactive with BVH-3C protein recognized epitopes shared by both, BVH-3 and BVH-11 proteins. As can be seen in Table 4, these BVH-3- and BVH-11-cross-reactive Mabs were also reactive with BVH-11A and BVH-11-2M recombinant proteins. BVH-3B-reactive Mabs can be subdivided into three subgroups according to their reactivity with NEW1, NEW2 and NEW3 recombinant proteins. Some Mabs were only reactive with the NEW1 protein while other Mabs were reactive with either, NEW1 and NEW2 or NEW1 and NEW3 recombinant proteins.

Mabs H11-7G11 and H3V-15A10 react with epitopes in more than one position on BVH-3. The reactivity of H11-7G11 with BVH-3AD, BVH-3B, BVH-3C, BVH-11A and BVH-11-2M molecules suggests that H11-7G11 epitope might comprised HXXHXH sequence. This sequence is repeated, respectively, 6 and 5 times in BVH-3 and BVH-11/BVH-11-2 protein sequences. The lack of reactivity of Mab H11-7G11 with NEW 10 molecule suggests that the epitope includes the HGDHXH sequence. Multiple-position mapping of H3V-15A10 epitope on BVH-3 is suggested by the reactivity of the Mab with two BVH-3 fragments that do not overlap.

Interestingly, Mabs H3-7G2, H3V-9C6 and H3V-16A7 were not reactive with BVH-3 Sp63 thus allowing the location of their corresponding epitopes on a 177-amino acid fragment comprised between amino acids 244 and 420 on BVH-3 molecule of S. pneumoniae SP64 (FIG. 31).

As can be seen from the data in Table 4, the Mabs that are reactive with BVH-11- and/or BVH-11-2 and that do not recognize BVH-3 molecules can be divided into three groups according to their reactivities with BVH-11A and NEW10 recombinant proteins. Some Mabs reacted exclusively with either BVH-11A or NEW10 protein while other Mabs were reactive with both, BVH-11A and NEW10 recombinant proteins.

EXAMPLE 3

This example describes the construction of BVH-3 and BVH-11-2 gene libraries for the mapping of epitopes.

BVH-3 and BVH-11-2 gene libraries were constructed using recombinant pCMV-GH and PSL301 plasmid DNA containing respectively, BVH-3 gene sequence spanning nucleotides 1837 to 4909 (SEQ ID NO: 2) or BVH-11-2 gene sequence spanning nucleotides 172 to 2630 (SEQ ID NO: 5) and the Novatope® library construction and screening system (Novagen). The recombinant plasmids containing BVH-3 or BVH-11-2 gene fragment were purified using QIAgen kit (Chatsworth, Calif.) and digested with the restriction enzymes BglII and XbaI respectively. The resulting BglII-XbaI DNA fragments were purified using the QIAquick gel extraction kit from QIAgen and digested with Dnase I for the generation of randomly cleaved DNA. DNA fragments of 50 to 200 bp were purified, treated with T4 DNA polymerase to blunt the target DNA ends and add a single 3'dA residue, and ligated into pSCREEN-T-Vector (Novagen) following the procedures suggested by the manufacturer (Novatope® System, Novagen). The gene libraries of E. coli clones, each of which expressing a small peptide derived from BVH-3 or BVH-11-2 genes were screened by standard colony lift methods using Mabs as immunoprobes. The colony screening was not successful with Mabs producing very high backgrounds on colony lifts. Moreover, in some cases, Mabs failed to detect epitope-expressing-colonies. The lack of reactivity can possibly be explained by the small amount of recombinant proteins produced or the recognition of conformation-dependent epitopes consisting of different protein domains. Sequencing of DNA inserts from positive clones determined the location of the segment that encodes the target epitope. The data are presented in Table 5. The peptides encoded by DNA inserts into the recombinant pSCREEN-T vector can be purified and used as immunogens as described below in Example 6.

The peptide sequences obtained from the screening of BVH-3 and BVH-11-2 gene libraries with the Mabs are in agreement with the Mab ELISA reactivities against the truncated gene products. As expected, the amino acid sequences obtained from H11-7G11 contained the sequence HGDHXH. These findings provide additional evidence for the location of epitopes recognized with the Mabs. Interestingly, although the Mabs H112-10G9, H112-10A2 and H11B-11B8 were reactive against the same peptide sequence (amino acid residues 594 to 679 on BVH-11-2 protein sequence), clones corresponding to the sequence spanning from amino acid residues 658 to 698 were only picked up by Mab H11B-11B8 thus revealing the location of H11B-11B8 epitope between amino acid residues 658 to 679 (SEQ ID NO: 163). Mabs H112-10G9, H112-10A2, and H11B-11B8 are directed against 3 distinct non overlapping epitopes located closely on the peptide sequence corresponding to amino acid residues 594 to 679 (SEQ ID NO: 22).

TABLE 5

Peptide sequences obtained from the screening of BVH-3 and BVH-11-2 gene libraries with Mabs

| Mab | Clone/ Protein designation | Nucleotide position | Amino acid position | Amino acid sequence | SEQ ID NO |
|---|---|---|---|---|---|
| H3-4D4 | 4D4.9 | SEQ ID 1: 226–509 | SEQ ID 6: 76–169 | DQGYVTSHGDHYHYYNGKVPYDALFSEELLMKDPNYQLKDA DIVNEVKGGYIIKVDGKYYVYLKDAAHADNVRTKDEINRQK QEHVKDNEKVNS | 11 |
| H11-7G11 | 7G11.7 | SEQ ID 1: 193–316 | SEQ ID 6: 64–105 | GIQAEQIVIKITDQGYVTSHGDHYHYYNGKVPYDALFSEEL L | 12 |
| H11-7G11 | 7G11.9 | SEQ ID 1: 1171–1284 | SEQ ID 6: 390–428 | TAYIVRHGDHFHYIPKSNQIGQPTLPNNSLATPSPSLPI | 13 |
| H3-4D3 | 4D3.4 | SEQ ID 1: 2565–2670 | SEQ ID 6: 855–890 | TSNSTLEEVPTVDPVQEKVAKFAESYGMKLENVLFN | 14 |
| HN1-8E3 | 8E3.1 | SEQ ID 1: 3004–3120 | SEQ ID 6: 1016–1039 | MDGTIELRLPSGEVIKKNLSDFIA | 15 |

TABLE 5-continued Peptide sequences obtained from the screening of
BVH-3 and BVH-11-2 gene libraries with Mabs

| Mab | Clone/ Protein designation | Nucleotide position | Amino acid position | Amino acid sequence | SEQ ID NO |
|---|---|---|---|---|---|
| HN1-1G2 | 1G2.2 | SEQ ID 1: 3017–3120 | SEQ ID 6: 1005–1039 | YGLGLDSVIFNMDGTIELRLPSGEVIKKNLSDFIA | 16 |
| HN1-10C12 | 10C12.7 | SEQ ID 1: 2936–3120 | SEQ ID 6: 983–1039 | PALEEAPAVDPVQEKLEKFTASYGLGLDSVIFNMDGTIELR LPSGEVIKKNLSDFIA | 17 |
| HN1-14F6 | 14F6.3 | SEQ ID 1: 2501–2618 | SEQ ID 6: 833–872 | KVEEPKTSEKVEKEKLSETGNSTSNSTLEEVPTVDPVQEK | 18 |
| HN1-12D8 | B12D8.2 | SEQ ID 1: 1433–1767 | SEQ ID 6: 512–589 | MKDLDKKIEEKIAGIMKQYGVKRESIVVNKEKNAIIYPHGD HHHADPIDEHKPVGIGHSHSNYELFKPEEGVAKKEGN | 19 |
| H3V-7F4 | 7F4.1 | SEQ ID 1: 1633–1785 | SEQ ID 6: 545–595 | AIIYPHGDHHHADPIDEHKPVGIGHSHSNYELFKPEEGVAK KEGNKVYTGE | 20 |
| H112-10D7 | 10D7.5 | SEQ ID 5: 1685–1765 | SEQ ID 8: 525–553 | IQVAKLAGKYTTEDGYIFDPRDITSDEGD | 21 |
| H112-10G9 | 10G9.3 | SEQ ID 5: 1893–2150 | SEQ ID 8: 594–679 | DHQDSGNTEAKGAEAIYNRVKAAKKVPLDRMPYNLQYTVEV KNGSLIIPHYDHYHNIKFEWFDEGLYEAPKGYSLEDLLATV KYYV | 22 |
| H112-10A2 | 10A2.2 | SEQ ID 5: 1893–2150 | SEQ ID 8: 594–679 | DHQDSGNTEAKGAEAIYNRVKAAKKVPLDRMPYNLQYTVEV KNGSLIIPHYDHYHNIKFEWFDEGLYEAPKGYSLEDLLATV KYYV | 22 |
| H11B-11B8 | B11B8.1 | SEQ ID 5: 1893–2150 | SEQ ID 8: 594–679 | DHQDSGNTEAKGAEAIYNRVKAAKKVPLDRMPYNLQYTVEV KNGSLIIPHYDHYHNIKFEWFDEGLYEAPKGYSLEDLLATV KYYV | 22 |
| H11B-11B8 | 11B8.4 | SEQ ID 5: 2085–2217 | SEQ ID 8: 658–698 | GLYEAPKGYSLEDLLATVKYYVEHPNERPHSDNGFGNASDH | 23 |
| H112-3A4 | 3A4.1 | SEQ ID 5: 2421–2626 | SEQ ID 8: 769–837 | VENSVINAKIADAEALLEKVTDPSIRQNAMETLTGLKSSLL LGTKDNNTISAEVDSLLALLKESQPAPI | 24 |

EXAMPLE 4

This example describes the immunization of animals with recombinant proteins for the generation of antibody reactive with BVH-3, BVH-11 and/or BVH-11-2.

NZW rabbits (Charles River Laboratories, St-Constant, Québec, Canada) were immunized subcutaneously at multiple sites with 50 μg or 100 μg of the purified BVH-3M, L-BVH-3AD, NEW1, NEW13, or L-BVH-11 recombinant protein in presence of 80 μg of QuilA adjuvant (Cedarlane Laboratoratories Ltd, Hornby, Canada). The rabbits were boosted two times at three-week intervals with the same antigen and blood samples were collected before each immunization and 6 to 28 days following the last immunization. The sera samples were designated preimmune, post $1^{st}$, post $2^{nd}$ or post $3^{rd}$ injection. The rabbit immune response to immunization was evaluated by ELISA using recombinant BVH-3M (BVH-3M-His•Tag fusion protein/pET21 system) or BVH-11M (BVH-11M-His•Tag fusion protein/pET21 system) proteins or suspensions of heat-killed S. pneumoniae Rx-1 cells as coating antigens. ELISA titer was defined as the reciprocal of the highest sera dilution at which absorbance $A_{410}$ value was 0.1 above the background value. Antibodies reactive with BVH-3 and/or BVH-11 epitopes were elicited following immunization in all animals as shown in the following Table 6. Antibody reactive with recombinant or pneumococcal antigens was not present in the preimmune sera. The immune response to immunization was detectable in the sera of each rabbit after a single injection of recombinant antigen. The antibody response following the second injection with either antigen tested was characterized by a strong increase in antibody titer. Interestingly, good titers of antibody reactive with S. pneumoniae cells, with an average titer of 52,000 after the third immunization, were obtained, thus establishing that native pneumococcal epitopes are expressed on the recombinant E. coli gene products. These data support the potential use of BVH-3, BVH-11 and/or BVH-11-2 gene products and the antibody raised to BVH-3, BVH-11 and/or BVH-11-2 gene products as vaccines for the prevention and the treatment of pneumococcal disease, respectively.

TABLE 6

Rabbit Antibody response to immunization with BVH-3 and BVH-11 gene products

| | | | ELISA Titer with coating antigen | | |
|---|---|---|---|---|---|
| Rabbit | Immunogen | Sera sample | BVH-3M | BVH-11M | S. pneumoniae |
| #15 | BVH-3M (50 μg) | Preimmune | NT | NT | 200 |
| | | Post-$1^{st}$ | NT | NT | 1,600 |
| | | Post-$2^{nd}$ | NT | NT | 20,000 |
| | | Post $3^{rd}$ | 512,000 | NT | 40,000 |

TABLE 6-continued

Rabbit Antibody response to immunization with BVH-3 and BVH-11 gene products

| Rabbit | Immunogen | Sera sample | ELISA Titer with coating antigen | | |
|---|---|---|---|---|---|
| | | | BVH-3M | BVH-11M | S. pneumoniae |
| #16 | BVH-3M (100 µg) | Preimmune | NT | NT | 200 |
| | | post 1st | NT | NT | 1,600 |
| | | post 2nd | NT | NT | 40,000 |
| | | post 3rd | $10^6$ | NT | 80,000 |
| #112 | L-BVH-3AD (50 µg) | Preimmune | <100 | NT | NT |
| | | post 1st | 16,000 | NT | NT |
| | | post 2nd | 512,000 | NT | NT |
| | | post 3rd | $2 \times 10^6$ | NT | 32,000 |
| #113 | New 1 (50 µg) | Preimmune | <100 | NT | NT |
| | | post 1st | 16,000 | NT | NT |
| | | post 2nd | 512,000 | NT | NT |
| | | post 3rd | $10^6$ | NT | 64,000 |
| #114 | New 13 (50 µg) | Preimmune | NT | <100 | NT |
| | | post 1st | NT | 16,000 | NT |
| | | post 2nd | NT | 64,000 | NT |
| | | post 3rd | NT | 256,000 | 32,000 |
| #116 | L-BVH-11 (50 µg) | Preimmune | NT | <100 | NT |
| | | post 1st | NT | 64,000 | NT |
| | | post 2nd | NT | $10^6$ | NT |
| | | post 3rd | NT | $2 \times 10^6$ | 64,000 |

NT: not tested

EXAMPLE 5

This example describes the protection of animals against fatal experimental pneumococcal infection by administration of antibody raised to BVH-3, BVH-11 or BVH-11-2 gene products.

High-titer Mab preparations were obtained from ascites fluid of mice inoculated intraperitoneally with Mab-secreting hybridoma cells according to the method described by Brodeur et al (J Immunol Methods 71 :265–272, 1984). Sera samples were collected from rabbits immunized with BVH-3M as described in Example 4. The rabbit sera collected after the third immunization and ascites fluid were used for the purification of antibodies by precipitation using 45 to 50% saturated ammonium sulfate. The antibody preparations were dissolved and dialyzed against phosphate-buffered saline (PBS).

CBA/N (xid) mice (National Cancer Institute, Frederick, Mass.) were injected intraperitoneally with either 0.1 ml of purified rabbit antibodies or 0.2 ml of ascites fluid before intravenous challenge with approximately 200 CFU of the type 3 S. pneumoniae strain WU2. Control mice received sterile PBS or antibodies purified from preimmune rabbit sera or sera from rabbits immunized with an unrelated N. meningitidis recombinant protein antigen. One group of mice was challenged with S. pneumoniae before the administration of anti-BVH-3 antibody. Samples of the S. pneumoniae challenge inoculum were plated on chocolate agar plates to determine the number of CFU and verify the challenge dose. The CBA/N mice were chosen because of their high susceptibility to S. pneumoniae infection. The $LD_{50}$ of WU2 injected intravenously to CBA/N mice is estimated to be $\leq 10$ CFU. Deaths were recorded at 24-h intervals for a period of at least 7 days.

The protection data obtained from mice injected with rabbit anti-BVH-3 antibody are set forth in the following Table 7. Nine out of 10 mice receiving the anti-BVH-3 antibody survived the challenge in contrast to none of 10 mice injected with control antibody or PBS buffer. The observation that antibody raised to the BVH-3-M molecule passively protected even when administered after the challenge demonstrated the ability of anti-BVH-3 antibody to prevent death even from an already established infection.

TABLE 7

Protective effects of rabbit antibody to BVH-3-M gene in CBA/N mice challenged i.v. with WU2 pneumococci

| Antibody preparation | Time of antibody administration | Alive:Dead | Days to death post-infection |
|---|---|---|---|
| Anti-BVH3M | 1 h before infection | 5:0 | >14, >14, >14, >14, >14 |
| Anti-N. meningitidis | 1 h before infection | 0:5 | 2, 2, 2, 2, 2 |
| Anti-BVH-3M | 0.5 h post-infection | 4:1 | 2, >14, >14, >14, >14 |
| None (PBS) | 1 h before infection | 0:5 | 1, 2, 2, 2, 2 |

CBA/N mice were infected with 1000 CFU of WU2 S. pneumoniae before or after intraperitoneal administration of 0.1 ml of rabbit antibody.

In an other experiment, 0.1 ml of rabbit antibody prepared from preimmune and immune sera were administered intraperitoneally to CBA/N mice four hours before intranasal challenge with 280 CFU of S. pneumoniae P4241 type 3 strain. As seen in the following Table 8, all immunized mice survived the challenge while none of 9 mice receiving preimmune sera antibody or buffer alone were alive on day 6 post-infection. S. pneumoniae hemocultures on day 11 post-challenge were negative for all surviving mice. Furthermore, 100% protection was observed in mice receiving monoclonal antibodies H112-10G9 or a mixture of H112-10G9 and H11B-7E11 which are directed against BVH-11/BVH-11-2.

TABLE 8

Protective effects of passive transfer of rabbit antibody to BVH-3-M gene product or anti-BVH-11/BVH-11-2 specific Mabs in CBA/N mice challenged i.n. with P4241 pneumococci

| Antibody preparation | Alive: Dead | Days to death post-infection |
|---|---|---|
| Anti-BVH-3M | 5:0 | >11, >11, >11, >11, >11 |
| Antibody from preimmune sera | 0:5 | 3, 3, 3, 6, 6 |
| H112 – 10G9 | 4:0 | >11, >11, >11, >11 |
| H112 – 10G9 + H11B – 7E11 | 5:0 | >11, >11, >11, >11, >11 |
| None (PBS) | 0:4 | 3, 3, 3, 3 |

Altogether, the results from Table 7 and Table 8 clearly establish that immunization of animals with a BVH-3 gene product such as BVH-3M elicited protective antibodies capable of preventing experimental bacteremia and pneumonia infections.

The protection data obtained for mice injected with ascites fluid are set forth in the following Table 9. Administration of a volume of 0.2 ml of ascites fluid of 0.2 ml of some sets of ascites fluid prevented death from experimental infection. For example, H112-3A4+H112-10G9 and H112-10G2+H112-10D7 sets of 2 Mabs conferred complete protection against experimental infection. These data indicated that antibody targetting BVH-11 and/or BVH-11-2 epitopes gave efficient protection. The Mabs H112-3A4, H112-10G9, H112-10D7, H112-10A2, H112-3E8, H112-10C5, H11B-11B8, H11B-15G2, H11B-1C9, H11B-7E11, H11B-13D5 and H11-10B8 were present in at least one protective pair of Mabs and were said to be protective and reactive against protective epitopes. The locations of protection-conferring epitopes on BVH-11-2 molecules are summarized in Table 10 and FIG. 29. Protective Mabs H112-3A4, H112-10G9, H112-10D7, H112-10A2, H112-3E8, H112-10C5, H11B-11B8, H11B-15G2, H11B-1C9, H11B-7E11, H11B-13D5 and H11-10B8 were all reactive with New 10 protein corresponding to amino acid residues 271 to 838 on the BVH-11-2 molecule. Six out of these 12 Mabs were directed against epitopes present in the NEW 19 protein and 3 protective Mabs recognized NEW 14. Interestingly, Mab H112-3A4 and H112-10C5 reacted with distinct epitopes exclusive to BVH-11-2 located at the carboxyl end comprised between amino acid residues 769 and 837. Also, Mabs H11-7G11, H11-6E7 and H3-4F9 reactive with epitopes shared by pneumococcal BVH-3, BVH-11 and BVH-11-2 molecules did not succeed to protect even if given in combination with protective H112-10G9 or H112-11B8 Mab. These Mabs recognized epitopes located at the amino end of the BVH-3, BVH-11 and BVH-11-2 molecules comprising, respectively, the first 225, 228 and 226 amino acid residues. The comparison of the BVH-3, BVH-11 and BVH-11-2 protein sequences revealed that a large number of amino acids were conserved in the amino end portion comprising these 225–228 residues with a global 72.8% identity (FIG. 32).

Altogether the data set forth in Table 9 and Table 10 suggest that the protection eliciting BVH-11- and BVH-11-2-epitopes is comprised in the carboxy terminal product containing amino acids 229 to 840 and 227 to 838, on BVH-11 and BVH-11-2 proteins, respectively.

TABLE 9

Passive immunization with BVH-11- and/or BVH-11-2-specific Mabs can protect mice from lethal experimental pneumococcal infection.

| Experiment | Mab | Alive: Dead | Days to death post-infection |
| --- | --- | --- | --- |
| 1 | H112 3A4 + H112-10G9 | 6:0 | 6X >10 |
|   | H112-3A4 + H112-10D7 | 5:1 | 4, 5X >10 |
|   | None | 0:6 | 2, 2, 2, 2, 2, 6 |
| 2 | H112-10 A2 + H112-10D7 | 5:1 | 3, 5X >10 |
|   | H112-3E8 + H112-10G9 | 6:0 | 6X >10 |
|   | None | 0:6 | 2, 2, 2, 2, 2, 2 |
| 3 | H112-10D7 + H11B-11B8 | 6:0 | 6X >10 |
|   | H112-10G9 + H11B-15G2 | 3:3 | 2, 6, 6, 3X >10 |
|   | None | 0:6 | 2, 2, 2, 2, 2, 2 |
| 4 | H112-10G9 + H112-10D7 | 5:0 | 5X >11 |
|   | None | 0:5 | 2, 2, 2, 2, 2 |
| 5 | H112-10G9 + H11-10B8 | 4:1 | 8, 4X >14 |
|   | H112-10G9 + H11B-7E11 | 5:0 | 5X >14 |
|   | None | 0:3 | 1, 2, 2 |
| 6 | H112-10G9 + H11B-1C9 | 4:1 | 4, 4X >14 |
|   | None | 0:3 | 2, 2, 2 |
| 7 | H112-10C5 + H11B-13D5 | 5:0 | 5X >14 |
|   | None | 3:3 | 2, 2, 2 |

CBA/N mice were injected intraperitoneally with a total of 0.2 ml of ascites fluid 4 hours before intravenous challenge with S. pneumoniae WU2.

TABLE 10

Deduced locations of protection-conferring epitopes on BVH-11-2 molecules.

| Mabs | Protection | Gene products carrying Mab-epitope |
| --- | --- | --- |
| H112-3A4 | + | NEW 19 and NEW 11 |
| H112-10G9 | + | NEW 19 |
| H112-10D7 | + | NEW 14 and NEW 10 |
| H112-10A2 | + | NEW 19 |
| H112-3E8 | + | NEW 19 |
| H11B-11B8 | + | NEW 19 |
| H11B-15G2 | + | NEW 18 |
| H11B-7E11 | + | NEW 14 and NEW 10 |
| H11-10B8 | + | NEW 18 |
| H11B-1C9 | + | NEW 14 and NEW 10 |
| H112-3A1 | − | NEW 18 and NEW 8 |
| H112-10H10 | − | NEW 18 and NEW 8 |
| H112-2H7 | − | BVH-11-2M |
| H112-6H7 | − | BVH-11-2M |
| H11-7G11 | − | BVH-11A and BVH-3C |
| H11-6E7 | − | BVH-11A and BVH-3C |
| H112-10C5 | + | NEW 19, NEW11 and 3A4.1 |
| H11B-13D5 | + | NEW 19 |
| H112-7G2 | − | NEW 18 |
| H112-7E8 | − | BVH-11-2M |
| H3-4F9 | − | BVH-11A and BVH-3C |

Altogether the data presented in this example substantiate the potential use of antibodies raised to BVH-3, BVH-11 or BVH-11-2 molecules as therapeutic means to prevent, diagnose or treat S. pneumoniae diseases.

EXAMPLE 6

This example describes the localization of surface-exposed peptide domains using Mabs described in Example 1.

S. pneumoniae type 3 strain WU2 was grown in Todd Hewitt (TH) broth (Difco Laboratories, Detroit Mich.) enriched with 0.5% Yeast extract (Difco Laboratories) at 37° C. in a 8% $CO_2$ atmosphere to give an $OD_{600}$ of 0.260 (~$10^8$ CFU/ml). The bacterial suspension was then aliquoted in 1 ml samples and the S. pneumoniae cells were pelleted by centrifugation and resuspended in hybridoma culture supernatants. The bacterial suspensions were then incubated for 2 h at 4° C. Samples were washed twice in blocking buffer [PBS containing 2% bovine serum albumin (BSA)], and then 1 ml of goat fluorescein (FITC)-conjugated anti-mouse IgG+IgM diluted in blocking buffer was added. After an additional incubation of 60 min at room temperature, samples were washed twice in blocking buffer and fixed with 0.25% formaldehyde in PBS buffer for 18–24 h at 4° C. Cells were washed once in PBS buffer and resuspended in 500 μl of PBS buffer. Cells were kept in the dark at 4° C. until analyzed by flow cytometry (Epics® XL; Beckman Coulter, Inc.). Ten thousands (10,000) cells were analyzed per sample and the results were expressed as % Fluorescence and Fluorescence index (FI) values. The % Fluorescence is the number of fluorescein-labelled S. pneumoniae cells divided by 100 and the FI value is the median fluorescence value of pneumococci treated with Mab supernatant divided by the fluorescence value of pneumococci treated with the conjugate alone or with a control unrelated Mab. A FI value of 1 indicated that the Mab has not been detected at the surface of the bacteria whereas a FI value higher than 2 was considered positive when at least 10% of the pneumococcal cells were labelled and indicated that the Mab was reactive with cell-surface exposed epitopes. The following Table 11 summarized the data obtained with the Mabs tested by flow cytometry.

Flow cytometric analysis revealed that the Mabs reactive with BVH-3C and/or BVH-11A molecules did not bind to the cell surface. In contrast, with the exception of Mabs H3V-9C6 and H3V-16A7, the Mabs reactive with NEW 1, NEW 2, NEW 3, NEW 22 or NEW 23 BVH-3 gene products were detected at the surface of pneumococci. These data indicated that the first 225 amino acid residues located at the amino end of BVH-3 are internal. The lack of binding of Mabs H3V-9C6 and H3V-16A7 suggest some portions of the sequence corresponding to the 177-amino acids absent from the BVH-3 molecule of *S. pneumoniae* SP63 appears not to be accessible to antibodies.

Results from BVH-11- and/or BVH-11-2-reactive Mabs revealed that there is a good correlation between surface-exposure and protection. All Mabs reactive with internal epitopes as determined by the flow cytometry assay were not protective whereas all the protective Mabs described in Example 5 gave a positive signal in flow cytometry. Although an FI value of 9.0 and a % Fluorescence of 81.2 were obtained with Mab H11-7G11, this Mab was not shown to protect. Additional assays can be used to further evaluate whether this Mab and its corresponding epitope might participate in anti-infectious immunity.

TABLE 11

Results from the binding of Mabs at the surface of *S. pneumoniae* by flow cytometry analysis

| Mab | % Fluorescence | FI | Binding | Gene products carrying Mab-epitope |
|---|---|---|---|---|
| H3-4F9 | 3.4 | 1.2 | − | BVH-3C and BVH-11A |
| H3-4D4 | 3.4 | 1.2 | − | BVH-3C and BVH-11A |
| H3-9H12 | 2.5 | 1.1 | − | BVH-3C and BVH-11A |
| H3-7G2 | 66.2 | 6.3 | + | NEW 22 |
| H3-10A1 | 58.8 | 5.6 | + | NEW 23 |
| H3-4D3 | 33.2 | 3.5 | + | NEW 3 |
| H3V-4F3 | 24.4 | 2.9 | + | NEW 1 |
| H3V-2F2 | 15.6 | 2.4 | + | NEW 2 |
| H3V-7F4 | 58.7 | 5.6 | + | NEW 2 |
| H3V-7H3 | 68.8 | 6.9 | + | NEW 3 |
| H3V-13B8 | 75.0 | 7.7 | + | NEW 3 |
| H3V-9C2 | 66.4 | 6.2 | + | NEW 22 |
| H3V-9C6 | 2.9 | 1.0 | − | NEW 22 |
| H3V-16A7 | 6.6 | 1.7 | − | NEW 23 |
| H3V-15A10 | 58.7 | 5.7 | + | NEW 22 and NEW 23 |
| HN1-5H3 | 43.4 | 5.3 | + | NEW 1 |
| HN1-8E3 | 57.4 | 6.6 | + | NEW 1 |
| HN1-14F6 | 57.8 | 6.7 | + | NEW 1 |
| HN1-2G2 | 54.8 | 6.3 | + | NEW 2 |
| HN1-12D8 | 14.3 | 3.0 | + | NEW 2 |
| HN1-14B2 | 11.5 | 2.7 | + | NEW 2 |
| HN1-1G2 | 59.9 | 7.0 | + | NEW 3 |
| HN1-10C12 | 13.6 | 2.8 | + | NEW 3 |
| H11-6E7 | 4.9 | 1.2 | − | BVH-3C and BVH-11A |
| H11-10H10 | 6.5 | 1.6 | − | BVH-3C and BVH-11A |
| H11-7G11 | 81.2 | 9.0 | + | BVH-3C and NEW 2 |
| H11-1B12 | 3.1 | 1.2 | − | BVH-11A |
| H11-7B9 | 2.4 | 1.1 | − | BVH-11A |
| H11-10B8 | 81.1 | 9.1 | + | NEW 18 and NEW 8 |
| H11-1A2 | 84.4 | 10 | + | NEW 18 and NEW 8 |
| H11-3H5 | 84.0 | 9.8 | + | NEW 18 and NEW 8 |
| H112-13C11 | 49.3 | 5.9 | + | NEW 18 and NEW 8 |
| H112-10H10 | 0.4 | 1.0 | − | BVH-11A and NEW 18 |
| H112-1D8 | 0.4 | 1.0 | − | BVH-11A and NEW 18 |
| H112-10G9 | 78.9 | 10.4 | + | NEW 19 |
| H112-10A2 | 75.5 | 9.6 | + | NEW 19 |
| H112-3E8 | 62.5 | 7.5 | + | NEW 19 |
| H112-10D7 | 64.5 | 7.7 | + | NEW 14 |
| H112-2H7 | 0.7 | 1.1 | − | BVH-11A |
| H112-6H7 | 0.3 | 1.0 | − | BVH-11A |
| H112-3A4 | 70.1 | 8.9 | + | NEW 11 |
| H112-10C5 | 86.3 | 9.2 | + | NEW 11 AND 3A4.1 |
| H112-14H6 | 89.6 | 11 | + | NEW 11 |
| H112-14H6 | 0.8 | 1.4 | − | NEW 11 |
| H112-7G2 | 4.7 | 2.0 | − | NEW 18 |
| H112-13H10 | 0.5 | 1.0 | − | NEW 18 |
| H112-7E8 | 0.4 | 1.0 | − | BVH-11-2M |
| H112-7H6 | 0.2 | 1.0 | − | BVH-11-2M |
| H11B-5F10 | 3.1 | 1.1 | − | NEW 18 |
| H11B-15G2 | 60.2 | 5.7 | + | NEW 18 and NEW 8 |
| H11B-13D5 | 75.7 | 8.3 | + | NEW 19 |
| H11B-11B8 | 78.4 | 8.3 | + | NEW 19 |
| H11B-7E11 | 32.3 | 3.5 | + | NEW 14 |
| H11B-1C9 | 57.3 | 5.5 | + | NEW 14 |
| H11B-5E3 | 1.8 | 1.0 | − | NEW 7 |
| H11B-6E8 | 2.4 | 1.0 | − | NEW 7 |

EXAMPLE 7

This example describes the immunization of animals with peptide epitopes of BVH-3 and BVH-11-2.

The recombinant pSCREEN-T vector (Novagen, Madison, Wis.) containing DNA fragment (nucleotides 2421 to 2626 on SEQ ID NO: 5) encoding the Mab 3A4-epitope (SEQ ID NO: 24) was transformed by electroporation (Gene Pulser II apparatus, BIO-RAD Labs, Mississauga, Canada) into *E. coli* Tuner (λDE3) pLysS [BL21 (F' ompT hsdSB (rB−mB−) gal dcm lacYI pLysS (Cm$^r$)] (Novagen). In this strain, the expression of the fusion protein is controlled by the T7 promoter which is recognized by the T7 RNA polymerase (present on the λDE3 prophage, itself under the control of the lac promoter inducible by isopropyl-β-D-thiogalactopyranoside (IPTG). The pLysS plasmid reduces the basal fusion protein expression level by coding for a T7 lysozyme, which is a natural inhibitor of the T7 RNA polymerase.

The transformants were grown at 37° C. with 250 RPM agitation in LB broth (peptone 10 g/l, yeast extract 5 g/l, NaCl 5 g/l) supplemented with 50 mM glucose, 100 μg/ml carbenicillin and 34 μg/ml chloramphenicol, until the absorbance at 600 nm reached a value of 0,7. The overexpression of T7 gene 10 protein-His•Tag-3A4.1 fusion protein was then induced by the addition of IPTG to a final concentration of 1 mM and further incubation at 25° C. with 250 RPM agitation for 3 hours. Induced cells from a 800-ml culture were pelleted by centrifugation and frozen at −70° C. The fusion protein was purified from the soluble cell fraction by affinity chromatography based on the binding of a six histidine residues sequence (His-Tag) to divalent cations (Ni$^{2+}$) immobilized on a metal chelation Ni-NTA resin (Qiagen, Mississauga, Canada). Briefly, the pelleted cells were thawed and resuspended in Tris buffered sucrose solution (50 mM Tris, 25% (w/v) sucrose) and frozen at −70° C. for 15 minutes. Cells were incubated 15 minutes on ice in the presence of 2 mg/ml lysozyme before disruption by sonication. The lysate was centrifuged at 12000 RPM for 30 minutes and Nickel charged Ni-NTA resin (QIAgen) was added to the supernatant for an overnight incubation at 4° C., with 100 RPM agitation. After washing the resin with a buffer consisting of 20 mM Tris, 500 mM NaCl, 20 mM imidazole pH 7,9, the fusion 3A4.1 protein was eluted with the same buffer supplemented with 250 mM imidazole. The removal of the salt and imidazole was done by dialysis against PBS at 4° C. The protein concentration was determined with BCA protein assay reagent kit (Perce, Rockford, Ill.) and adjusted to 760 µg/ml.

To evaluate whether immunization with an epitope peptide sequence could confer protection against disease, groups of 6 female CBA/N (xid) mice (National Cancer Institute) are immunized subcutaneously three times at three-week intervals with affinity purified T7gene10 protein-His•Tag-3A4.1 fusion protein or, as control, with QuilA adjuvant alone in PBS. Twelve to fourteen days following the third immunization, the mice are challenged intravenously with S. pneumoniae WU2 strain or intranasally with P4241 strain. Samples of the S. pneumoniae challenge inoculum are plated on chocolate agar plates to determine the number of CFU and to verify the challenge dose. The challenge dose are approximalety 300 CFU. Deaths are recorded daily for a period of 14 days and on day 14 post-challenge, the surviving mice are sacrificed and blood samples tested for the presence of S. pneumoniae organisms. The 3A4.1 protein or other tested protein is said protective when the number of mice surviving the infection or the median number of days to death is significantly greater in the 3A4.1-immunized group compared to the control mock-immunized group.

EXAMPLE 8

This example illustrates the improvement of the antibody response to pneumococci using BVH-3 fragments and variants thereof.

The combined results obtained from studies of Mab reactivity with truncated gene products, epitope-expressing colonies and live intact pneumococci presented in examples 2, 3 and 6, allowed to delineate between surface-exposed and internal epitopes. The epitopes detected by Mabs that efficiently bound to pneumococci cells mapped to a region comprised between amino acid residues 223 to 1039 of BVH-3 described in SEQ ID NO 6. The existence of protective epitopes in the BVH-3-carboxyl half was confirmed by demonstrating that mice immunized with NEW1 molecule were protected from fatal infection with P4241 strain.

Gene sequence comparison revealed that in some strains, the region of BVH-3 encoding for amino acids 244 to 420 as described in SEQ ID NO6 is absent thus suggesting the lack of utility of this sequence in vaccine to prevent disease caused by such strains (SEQ ID NO: 9 versus SEQ ID NO: 1). Further BVH-3 fragments or variants thereof were designed in the purpose to develop a universal highly effective vaccine that would target the immune response to ubiquitous surface-exposed protective epitopes. BVH-3 gene fragments designated NEW1 (encoding amino acid residues 472 to 1039 from SEQ ID NO: 6) and NEW40 (encoding amino acid residues 408 to 1039 from SEQ ID NO: 6) were amplified from the S. pneumoniae strain SP64 by PCR using pairs of oligonucleotides engineered for the amplification of the appropriate gene fragment. Each of the primers had a restriction endonuclease site at the 5'end, thereby allowing directional in-frame cloning of the amplified product into the digested plasmid vector. PCR-amplified products were digested with restriction endonucleases and ligated to linearized plasmid pET21 (Novagen) expression vector digested likewise. Oligonucleotide primers HAMJ489 (ccgaattccatatgcaaattgggcaaccgactc; NdeI) and HAMJ279 (cgccaagcttcgctatgaaatcagataaattc; HindIII) were used for the NEW 40 construction. Clones were first stabilized in E. coli DH5α before introduction into E. coli BL21 (λDE3) for expression of the truncated gene products. Variants from NEW1 and NEW40 were generated by mutagenesis using the Quickchange Site-Directed Mutagenesis kit from Stratagene and the oligonucleotides designed to incorporate the appropriate mutation. The presence of 6 histidine tag residues on the C-terminus of the recombinant molecules simplified the purification of the proteins by nickel chromatography. The following tables 12 and 13 describe the sequences of the primers used for the mutagenesis experiments and the variant gene products generated, respectively. Mutagenesis experiments using primer sets 39, 40, 46, 47 or 48 resulted in silent changes and were performed in the purpose of improving the expression of the desired gene or gene fragment since it was observed that during the course of expression, BVH-3 gene and fragments of, shorter secondary translation initiation products were coexpressed.

TABLE 12

List of PCR oligonucleotide primer sets used for site-directed mutagenesis on BVH-3 gene truncates

| Primer set | Primer identification | SEQ ID No | Primer SEQUENCE 5' - - -> 3' |
|---|---|---|---|
| 9 | HAMJ513 | 177 | GAATCAGGTTTTGTCATGAGTTCCGGAGACCACAATCATTATTTC |
|   | HAMJ514 | 178 | GAAATAATGATTGTGGTCTCCGGAACTCATGACAAAACCTGATTC |
| 10 | HAMJ515 | 179 | GTCATGAGTTCCGGAGACTCCAATCATTATTTCTTCAAGAAGG |
|   | HAMJ516 | 180 | CCTTCTTGAAGAAATAATGATTGGAGTCTCCGGAACTCATGAC |
| 11 | HAMJ517 | 181 | ATGAGTTCGGAGACTCCAATTCTTATTTCTTCAAGAAGGACTTG |
|   | HAMJ518 | 182 | CAAGTCCTTCTTGAAGAAATAAGAATTGGAGTCTCCGGAACTCAT |

TABLE 12-continued

List of PCR oligonucleotide primer sets used for site-directed mutagenesis on BVH-3 gene truncates

| Primer set | Primer identification | SEQ ID No | Primer SEQUENCE 5' - - -> 3' |
|---|---|---|---|
| 14 | CHAN51 | 183 | GCGATTATTTATCCGTCTGGAGATCACCATCATGC |
|  | CHAN52 | 184 | GCATGATGGTGATCTCCAGACGGATAAATAATCGC |
| 17 | CHAN53 | 185 | CCGTCTGGAGATGGCCATCATGCAGATCCG |
|  | CHAN54 | 186 | CGGATCTGCATGATGGCCATCTCCAGACGG |
| 19 | CHAN47 | 187 | CCGCAGGGAGATAAGCGTCATGCAGATCCGATTG |
|  | CHAN48 | 188 | CAATCGGATCTGCATGACGCTTATCTCCCTGCGG |
| 20 | CHAN55 | 189 | CCGTCTGGAGATGGCACTCATGCAGATCCGATTG |
|  | CHAN56 | 190 | CAATCGGATCTGCATGAGTGCCATCTCCAGACGG |
| 22 | CHAN57 | 191 | CCGTCTGGAGATGGCACTTCTGCAGATCCGATTGATG |
|  | CHAN58 | 192 | CATCAATCGGATCTGCAGAAGTGCCATCTCCAGACGG |
| 23 | HAMJ523 | 193 | CCGCATGGAGATGGCCATCATGCAGATCCG |
|  | HAMJ524 | 194 | CGGATCTGCATGATGGCCATCTCCATGCGG |
| 24 | HAMJ526 | 195 | GTCATGAGTCACGGAGACTCCAATCATTATTTCTTCAAGAAGG |
|  | HAMJ527 | 196 | CCTTCTTGAAGAAATAATGATTGGAGTCTCCGTGACTCATGAC |
| 25 | HAMJ528 | 197 | ATGAGTCACGGAGACCACAATTCTTATTTCTTCAAGAAGGACTTG |
|  | HAMJ529 | 198 | CAAGTCCTTCTTGAAGAAATAAGAATTGTGGTCTCCGTGACTCAT |
| 29 | HAMJ569 | 199 | TACCTCATTATGACTCTTACTCTAACATCAAATTTGAGTGGTTTG |
|  | HAMJ570 | 200 | CAAACCACTCAAATTTGATGTTAGAGTAAGAGTCATAATGAGGTA |
| 30 | HAMJ571 | 201 | TACCTTCTTATGACCATTACTCTAACATCAAATTTGAGTGGTTTG |
|  | HAMJ572 | 202 | AAACCACTCAAATTTGATGTTAGAGTAATGGTCATAAGAAGGTA |
| 31 | HAMJ573 | 203 | AACGGTAGTTTAATCATACCTTCTAAAGACCATTACCATAACATC |
|  | HAMJ574 | 204 | GATGTTATGGTAATGGTCTTTAGAAGGTATGATTAAACTACCGTT |
| 32 | HAMJ575 | 205 | CGGTAGTTTAATCATACCTCATAAGGACTCTTACCATAACATCAAA |
|  | HAMJ576 | 206 | TTTGATGTTATGGTAAGAGTCCTTATGAGGTATGATTAAACTACCG |
| 33 | HAMJ577 | 207 | AACGGTAGTTTAATCATACCTGACCATTACCATAACATCAAATTTG |
|  | HAMJ578 | 208 | CAAATTTGATGTTATGGTAATGGTCAGGTATGATTAAACTACCGTT |
| 34 | HAMJ579 | 209 | AACGGTAGTTTAATCATACCTTACCATAACATCAAATTTGAGTGG |
|  | HAMJ580 | 210 | CCACTCAAATTTGATGTTATGGTAAGGTATGATTAAACTACCGTT |
| 35 | HAMJ581 | 211 | ACCGGTAGTTTAATCATACCTAACATCAAATTTGAGTGGTTTGAC |
|  | HAMJ582 | 212 | GTCAAACCACTCAAATTTGATGTTAGGTATGATTAAACTACCGTT |
| 37 | HAMJ536 | 213 | CCTATGTAACTCCACATATAACCCATAGCCACTGG |
|  | HAMJ537 | 214 | CCAGTGGCTATGGGTTATATGTGGAGTTACATAGG |
| 39 | HAMJ550 | 215 | CGTGAAAGTATTGTCGTAAATAAAGAAAAAAATGCG |
|  | HAMJ551 | 216 | CGCATTTTTTTCTTTATTTACGACAATACTTTCACG |
| 40 | HAMJ586 | 217 | CATGAAGAAGATGGTTACGGTTTCGATGCTAACCGTATTATCGCTGAAG |
|  | HAMJ587 | 218 | CTTCAGCGATAATACGGTTAGCATCGAAACCGTAACCATCTTCTTCTG |
| 41 | HAMJ588 | 219 | GAATCAGGTTTTGTCATGAGTGACCACAATCATTATTTCTTC |
|  | HAMJ589 | 220 | GAAGAAATAATGATTGTGGTCACTCATGACAAAACCTGATTC |
| 42 | HAMJ590 | 221 | GAAGATGAATCAGGTTTTGTCATGAGTAATCATTATTTCTTCAAG |
|  | HAMJ591 | 222 | CTTGAAGAAATAATGATTACTCATGACAAAACCTGATTCATCTTC |
| 43 | HAMJ592 | 223 | GAAGATGAATCAGGTTTTGTCATGAGTTATTCTTCAAGAAGGAC |
|  | HAMJ593 | 224 | GTCCTTCTTGAAGAATAACTCATGACAAAACCTGATTCATCTTC |
| 44 | HAMJ594 | 225 | AAAATGCGATTATTTATCCGCACCATCATGCAGATCCGATTG |
|  | HAMJ595 | 226 | CAATCGGATCTGCATGATGGTGCGGATAAATAATCGCATTTT |
| 45 | HAMJ600 | 227 | AAAATGCGATTATTTATCCGGCAGATCCGATTGATGAACATAAAC |
|  | HAMJ601 | 228 | GTTTATGTTCATCAATCGGATCTGCCGGATAAATAATCGCATTTT |
| 46 | HAMJ604 | 229 | GATGCTAACCGTATAATCGCCGAAGACGAATCAGGTTTTGTCATG |
|  | HAMJ605 | 230 | CATGACAAAACCTGATTCGTCTTCGGCGATTATACGGTTAGCATC |

TABLE 12-continued

List of PCR oligonucleotide primer sets used for site-directed mutagenesis on BVH-3 gene truncates

| Primer set | Primer identification | SEQ ID No | Primer SEQUENCE 5' - - -> 3' |
|---|---|---|---|
| 47 | HAMJ606 | 231 | CGCCGAAGACGAATCCGGCTTTGTAATGAGTCACGGAGACTCC |
|  | HAMJ607 | 232 | GGAGTCTCCGTGACTCATTACAAAGCCGGATTCGTCTTCGGCG |
| 48 | HAMJ608 | 233 | CATCTCATGAACAGGATTATCCCGGCAACGCCAAAGAAATGAAAG |
|  | HAMJ609 | 234 | CTTTCATTTCTTTGGCGTTGCCGGGATAATCCTGTTCATGAGATG |

TABLE 13

Lists of truncated variant BVH-3 gene products generated from *S. pneumoniae* SP64

| Protein designation | Gene/ Protein SEQ ID NO | Protein Identification* | PCR primer set (ref. table 12) | Gene used for mutagenesis |
|---|---|---|---|---|
| NEW1-mut1** | 255 | NEW1 | 39 | NEW1 |
| NEW35A | 256 | NEW1 550-SGDGTS-555 | 14, 17, 20, 22 | NEW1 |
| NEW42 | 349 | NEW40 55-SGDSNS-60 144-SGDGTS-149 | 9, 10, 11, 14, 17, 20, 22 | NEW40 |
| NEW49 | 350 | NEW40 55-SGDHNH-60 | 9 | NEW40 |
| NEW50 | 351 | NEW40 55-SGDSNH-60 | 10 | NEW49 |
| NEW51 | 352 | NEW40 55-SGDHNH-60 144-SGDHHH-149 | 14 | NEW49 |
| NEW52 | 353 | NEW40 55-SGDSNH-60 144-SGDGHH-149 | 10, 17 | NEW51 |
| NEW53 | 354 | NEW40 55-HGDHNH-60 144-SGDHHH-149 | 14 | NEW40 |
| NEW54 | 355 | NEW40 55-SGDHNH-60 144-SGDGHH-149 | 17 | NEW53 |
| NEW55 | 356 | NEW1 550-HGDGHH-555 | 23 | NEW1 |
| NEW56 | 357 | NEW40 55-HGDSNH-60 144-SGDHHH-149 | 24 | NEW53 |
| NEW56-mut2** | 358 | NEW56 | 40 | NEW56 |
| NEW56-mut3** | 359 | NEW56 | 46, 47, 48 | NEW56 |
| NEW57 | 360 | NEW40 55-HGDHNS-60 144-SGDHHH-149 | 25 | NEW53 |
| NEW63 | 361 | NEW40 55-HGDSNH-60 144-HGDHHH-149 | 24 | NEW40 |
| NEW64 | 362 | NEW40 55-HGDHNS-60 144-HGDHHH-149 | 25 | NEW40 |
| NEW65 | 363 | NEW40 55-HGDSNH-60 144-HGDGHH-149 | 23 | NEW63 |
| NEW66 | 364 | NEW40 55-HGDHNS-60 144-HGDGHH-149 | 23 | NEW64 |
| NEW76 | 365 | NEW40 55-HGDHNS-60 144-SGDGHH-149 | 17 | NEW64 |
| NEW105 | 366 | NEW40 55-_____-60 | 41, 42, 43 | NEW40 |
| NEW106 | 367 | New40 144-_____-149 | 44, 45 | NEW40 |
| NEW107 | 368 | NEW40 55-_____-60 144-_____-149 | 44, 45 | NEW105 |

*The underlined amino acid residues represent the modification in protein sequence. Nucleotides/amino acid residues are deleted in NEW105, NEW106 and NEW107 constructs.
**silent mutation, i.e. the polypeptide is the same as New1.

Groups of 7 or 8 female BALB/c mice (Charles River) immunized as described earlier in example 1 were used for protection experiments against intranasal challenge with virulent *S. pneumoniae* P4241 strain. The mice were observed for 10 to 14 days post-infection. Data from Table 15 clearly indicate that the NEW35A molecule was equivalent to the parental NEW1 in term of protection. Interestingly, high survival rates where obtained for NEW40- and NEW56-immunized groups with 7 and 8 survivors out of 8 animals, respectively. Similarly, NEW25 comprising amino acid residues 233 to 1039 protected 7 out of 8 animals from lethal infection.

TABLE 14

Protection mediated by BVH-3 fragments or variants thereof in experimental pneumonia

| Experi-ment | Immunogen | Alive:Dead | Days to death post-infection |
|---|---|---|---|
| 1 | Quil A | 0:8 | 4, 4, 4, 4, 4, 4, 4, 4 |
| | NEW 1 | 5:3 | 5, 7, 7, >14, >14, >14, >14, >14 |
| | NEW 35A | 5:2 | 9, 10, >14, >14, >14, >14, >14 |
| | NEW 40 | 7:1 | 13, >14, >14, >14, >14, >14, >14, >14 |
| | BVH-3M | 4:4 | 7, 8, 10, 12, >14, >14, >14, >14 |

TABLE 14-continued

Protection mediated by BVH-3 fragments or variants thereof in experimental pneumonia

| Experiment | Immunogen | Alive:Dead | Days to death post-infection |
|---|---|---|---|
| 2 | Quil A | 0:8 | 3, 3, 4, 4, 4, 4, 4, 4 |
|   | NEW 52 | 4:4 | 7, 7, 8, 9, >10, >10, >10, >10 |
|   | NEW 56 | 8:0 | 8 X >10 |
|   | NEW 40 | 7:1 | 6, >10, >10, >10, >10, >10, >10 |
| 3 | Quil A | 0:8 | 3, 3, 4, 4, 4, 4, 4, 4 |
|   | NEW 25 | 7:1 | 6, >13, >13, >13, >13, >13, >13 |

Additionally, flow cytometry analyses of the binding capacity of the sera antibodies from the vaccinated animals revealed that NEW40 and NEW56 antibodies labelled live intact pneumococci more efficiently than antibodies raised to BVH-3M (Table 15).

TABLE 15

Binding of mouse sera antibodies at the surface of *S. pneumoniae* type 3 strain WU2 as measured by flow cytometry.

| Antisera | Fluorescence index | | | |
|---|---|---|---|---|
|  | Experiment 1 | Experiment 2 | Experiment 3 | Mean ± SE |
| BVH-3M | 9.2 | 11.4 | 14.5 | 11.7 ± 1.5 |
| NEW1 | 11.5 | 10.1 | nd* | 10.8 ± 0.7 |
| NEW35A | 14.3 | 12.9 | nd | 13.6 ± 0.7 |
| NEW40 | 20.4 | 19.1 | 20.2 | 19.9 ± 0.4 |
| NEW56 | nd | 16.7 | 20.2 | 18.5 ± 1.8 |
| NEW52 | nd | 16.6 | 19.3 | 18.0 ± 1.4 |
| Adjuvant alone | 1.9 | 1.6 | 1.2 | 1.6 ± 0.2 | nd*: not done

Cytometry results are expressed as fluorescence index value where the fluorescence index is the median fluorescence value of pneumococci treated with test sera divided by the background fluorescence value of pneumococci treated with the fluorescein conjugate alone. In these flow cytometric assays, all sera were used at a dilution of 1:50 and the sera from mice immunized with BVH-3C fragment or QuilA adjuvant alone gave a value similar to the background value.

Altogether the protection and pneumococci antibody binding data indicate that vaccination using NEW1 or NEW40 molecules and variants thereof, directs the immune response to conserved protective surface-exposed epitopes.

EXAMPLE 9

This example describes the cloning and expression of a chimeric deletant BVH-11-2 gene encoding for a chimeric polypeptide corresponding to BVH-11-2 conserved protective surface-exposed epitopes present in most if not all *S. pneumoniae* strains.

BVH-11-2 gene fragments corresponding to 4 gene regions, were amplified by PCR using pairs of oligonucleotides engineered to amplify fragments originating from SEQ ID NO: 5 spanning nucleotides 1662 to 1742, 1806 to 2153, 2193 to 2414 and 2484 to 2627 from *S. pneumoniae* strain Sp64 BVH-11-2 gene.

The primers used, HAMJ490-491, HAMJ492-HAMJ493, HAMJ494-HAMJ495, HAMJ496-HAMJ354 had a restriction endonuclease site at the 5' end, thereby allowing directional in-frame cloning of the amplified product into the digested pET21b(+) plasmid vector (Table 16). PCR-amplified products were digested with restriction endonucleases and ligated to linearized plasmid pSL301 vector digested likewise except for the PCR-amplified fragment obtained with the primer pair HAMJ490-HAMJ491. The HAMJ490-HAMJ491 PCR-amplified product was purified from agarose gel using a QIAquick gel extraction kit from QIAgen (Chatsworth, Calif.) and ligated into pGEM-T plasmid vector without any prior restriction endonuclease digestion. The resultant plasmid constructs were confirmed by nucleotide sequence analysis. The recombinant plasmids containing each of the four were digested with restriction endonucleases corresponding with the 5' end of each primer pair used for the PCR-amplification. The fragments were purified from agarose gel like described earlier and were all ligated to linearized plasmid pET21b (+) digested with the restriction enzymes NdeI and HindIII for the in-frame cloning of the four different regions of the BVH11-2 gene. Clones were first stabilized in *E. coli* DH5α before introduction into *E. coli* BL21 (λDE3) for expression of a chimeric pneumococcal protein molecule.

The resulting NEW43 gene sequence (SEQ ID No 257) is described in FIG. 33.

The deduced amino acid sequence of NEW43 protein (SEQ ID No 258) is described in FIG. 34.

TABLE 16

List of PCR oligonucleotide primers used to construct the NEW43, VP43S and NEW86

| Primer | SEQ ID NO | Sequence 5' - 3' | Nucleotide position | Restriction sites |
|---|---|---|---|---|
| HAMJ490 | 259 | ccgaattccatatgcaaat tacctacactgatgatg | SEQ ID 5: 1662–1683 | NdeI |
| HAMJ491 | 260 | ggactagtatcaaagatat aaccgtcttc | SEQ ID 5: 1742–1722 | SpeI |
| HAMJ492 | 261 | ggactagttggattaaaaa agatagtttgtctg | SEQ ID 5: 1806–1830 | SpeI |

TABLE 16-continued

List of PCR oligonucleotide primers used to construct the NEW43, VP43S and NEW86

| Primer | SEQ ID NO | Sequence 5' – 3' | Nucleotide position | Restriction sites |
|---|---|---|---|---|
| HAMJ493 | 262 | ttcccgcggttcgacatag tacttgacagtcg | SEQ ID 5: 2153–2131 | SacII |
| HAMJ494 | 263 | ttcccgcggaacgctagtg accatgttcg | SEQ ID 5: 2193–2212 | SacII |
| HAMJ495 | 264 | cggggtaccaggaatttca gcctcatctgtg | SEQ ID 5: 2414–2393 | KpnI |
| HAMJ496 | 265 | cccggtaccctagtatta gacaaaatgctatggag | SEQ ID 5: 2484–2510 | KpnI |
| HAMJ354 | 65 | cgccaagcttctgtatagg agccggttgac | SEQ ID 5: 2627–2608 | HindIII |
| HAMJ583 | 266 | ggatcccgggaggtatgat taaactaccg | SEQ ID 5: 2039–2021 | SmaI |
| HAMJ584 | 267 | catgcccgggaacatcaaa tttgagtggtttgac | SEQ ID 5: 2058–2081 | SmaI |
| HAMJ610 | 268 | cttgatcgacatatgttgg caggcaagtacacaacag | SEQ ID 5: 1701–1722 | NdeI |

TABLE 17

List of truncated BVH-11-2 gene fragments generated from *S. pneumoniae* SP64 for the construction of NEW43

| PCR-primer sets | Gene fragment designation | Corresponding amino acid residues on SEQ ID NO: 8 | Cloning vector |
|---|---|---|---|
| HAMJ490–HAMJ491 | NEW43a | 517–543 | pGEM-T |
| HAMJ492–HAMJ493 | NEW43b | 565–680 | pSL301 |
| HAMJ494–HAMJ495 | NEW43c | 694–767 | pSL301 |
| HAMJ496–HAMJ354 | NEW43d | 791–838 | pSL301 |

TABLE 18

Properties of NEW86 and VP43S genes generated from NEW43 gene

| PCR-primer sets | Gene/Protein designation | Identification |
|---|---|---|
| HAMJ610–HAMJ354 | VP43S | NEW43 C'end corresponding to residues 15–272) (SEQ ID NO: 374) |
| HAMJ490–HAMJ583 HAMJ584–HAMJ354 | NEW86 | NEW43 109-_PG_-114 (SEQ ID NO: 375) |

NEW43-derived molecules designated VP43S and NEW86 were generated from gene amplification and cloning experiments using PCR primers described in Tables 16 and 18 and pET21 expression plasmid vector. Variants from NEW43 were generated by mutagenesis using the Quickchange Site-Directed Mutagenesis kit from Stratagene and the oligonucleotides designed to incorporate the appropriate mutation. The presence of 6 histidine tag residues on the C-terminus of the recombinant molecules simplified the purification of the proteins by nickel chromatography. The following tables 19 and 20 describe the sequences of the primers used for the mutagenesis experiments the NEW43 variant gene products generated, respectively.

TABLE 19

List of PCR oligonucleotide primer sets used for site-directed mutagenesis on NEW43 gene

| Primer set | Primer identification | SEQ ID NO | Primer SEQUENCE 5' - - -> 3' |
|---|---|---|---|
| 1 | HAMJ497 | 269 | AACGGTAGTTTAATCATACCTTCTTATGACCATTACCATAACATC |
|   | HAMJ498 | 270 | GATGTTATGGTAATGGTCATAAGAAGGTATGATTAAACTACCGTT |

TABLE 19-continued

List of PCR oligonucleotide primer sets used for site-directed mutagenesis on NEW43 gene

| Primer set | Primer identification | SEQ ID NO | Primer SEQUENCE 5' - - -> 3' |
|---|---|---|---|
| 2 | HAMJ499 | 271 | AATCATACCTTCTTATGACTCTTACCATAACATCAAATTTGAGTG |
| | HAMJ500 | 272 | CACTCAAATTTGATGTTATGGTAAGAGTCATAAGAAGGTATGATT |
| 3 | HAMJ501 | 273 | TACCTTCTTATGACTCTTACTCTAACATCAAATTTGAGTGGTTTG |
| | HAMJ502 | 274 | CAAACCACTCAAATTTGATGTTAGAGTAAGAGTCATAAGAAGGTA |
| 26 | HAMJ530 | 275 | AATCATACCTCATTATGACTCTTACCATAACATCAAATTTGAGTG |
| | HAMJ531 | 276 | CACTCAAATTTGATGTTATGGTAAGAGTCATAATGAGGTATGATT |
| 27 | HAMJ532 | 277 | TACCTCATTATGACCATTACTCTAACATCAAATTTGAGTGGTTTG |
| | HAMJ533 | 278 | CAAACCACTCAAATTTGATGTTAGAGTAATGGTCATAATGAGGTA |
| 29 | HAMJ569 | 279 | TACCTCATTATGACTCTTACTCTAACATCAAATTTGAGTGGTTTG |
| | HAMJ570 | 280 | CAAACCACTCAAATTTGATGTTAGAGTAAGAGTCATAATGAGGTA |
| 30 | HAMJ571 | 281 | TACCTTCTTATGACCATTACTCTAACATCAAATTTGAGTGGTTTG |
| | HAMJ572 | 282 | AAACCACTCAAATTTGATGTTAGAGTAATGGTCATAAGAAGGTA |
| 31 | HAMJ573 | 283 | AACGGTAGTTTAATCATACCTTCTAAAGACCATTACCATAACATC |
| | HAMJ574 | 284 | GATGTTATGGTAATGGTCTTTAGAAGGTATGATTAAACTACCGTT |
| 32 | HAMJ575 | 285 | CGGTAGTTTAATCATACCTCATAAGGACTCTTACCATAACATCAAA |
| | HAMJ576 | 286 | TTTGATGTTATGGTAAGAGTCCTTATGAGGTATGATTAAACTACCG |
| 33 | HAMJ577 | 287 | AACGGTAGTTTAATCATACCTGACCATTACCATAACATCAAATTTG |
| | HAMJ578 | 288 | CAAATTTGATGTTATGGTAATGGTCAGGTATGATTAAACTACCGTT |
| 34 | HAMJ579 | 289 | AACGGTAGTTTAATCATACCTTACCATAACATCAAATTTGAGTGG |
| | HAMJ580 | 290 | CCACTCAAATTTGATGTTATGGTAAGGTATGATTAAACTACCGTT |
| 35 | HAMJ581 | 291 | ACCGGTAGTTTAATCATACCTAACATCAAATTTGAGTGGTTTGAC |
| | HAMJ582 | 292 | GTCAAACCACTCAAATTTGATGTTAGGTATGATTAAACTACCGTT |

TABLE 20

List of NEW43 variant gene products generated from *S. pneumoniae* SP64

| Polypeptide designation | Polypeptide SEQ ID NO | Polypeptide identification* | PCR primer set (ref. table 22) | Gene used for mutagenesis |
|---|---|---|---|---|
| NEW60 | 293 | NEW43 109-SYDHYH-114 | 1 | NEW43 |
| NEW61 | 294 | NEW43 109-HYDSYH-114 | 26 | NEW43 |
| NEW62 | 295 | NEW43 109-HYDHYS-114 | 27 | NEW43 |
| NEW80 | 296 | NEW43 109-SYDSYH-114 | 2 | NEW60 |
| NEW81 | 297 | NEW43 109-SYDSYS-114 | 3 | NEW80 |
| NEW82 | 298 | NEW43 109-HYDSYS-114 | 29 | NEW61 |
| NEW83 | 299 | NEW43 109-SYDHYS-114 | 30 | NEW60 |
| NEW84 | 300 | NEW43 109-SKDHYH-114 | 31 | NEW60 |
| NEW85 | 301 | NEW43 109-HKDSYH-114 | 32 | NEW61 |
| NEW88D1 | 302 | NEW43 109-__DHYH-114 | 33 | NEW43 |
| NEW88D2 | 303 | NEW43 109-___YH-114 | 34 | NEW88D1 |
| NEW88 | 304 | NEW43 109-_____-114 | 35 | NEW88D2 |

*The underlined amino acid residues represent the modification in protein sequence. Nucleotides/amino acid residues are deleted in NEW88D1, NEW88D2 and NEW88 constructs.

Groups of 7 or 8 female BALB/c mice (Charles River) immunized as described earlier in example 1 were used for protection experiments against intranasal challenge with virulent *S. pneumoniae* P4241 strain. Data from Table 21 clearly indicate that NEW 19, NEW43 and variants thereof provided protection against experimental pneumonia.

TABLE 21

Protection mediated by NEW 19 and NEW 43 fragments or variants thereof in experimental pneumonia

| Experiment | Immunogen | Alive: Dead | Median day alive |
|---|---|---|---|
| 1 | Quil A | 0:8 | 4, 4, 4, 4, 4, 4, 4, 5 |
| | NEW 19 | 7:1 | 5, 7X >14 |
| | NEW 43 | 8:0 | 8X >14 |
| 2 | Quil A | 0:8 | 4, 4, 4, 4, 4, 5, 5, 5 |
| | NEW 43 | 7:1 | 8, 7X >14 |
| | NEW 80 | 6:2 | 5, 6, 6X >14 |
| | NEW 83 | 6:2 | 8, 10, 6X >14 |
| 3 | Quil A | 0:8 | 4, 4, 4, 4, 5, 5, 5, 5 |
| | NEW 43 | 7:1 | 5, 7X >8 |
| | NEW 88D1 | 5:3 | 5, 6, 6, 6X >8 |
| | NEW 88D2 | 5:3 | 6, 6, 6, 6X >8 |
| | NEW 88 | 7:1 | 6, 7X >8 |
| 3 | Quil A | 0:8 | 4, 4, 4, 5, 5, 5, 5, 6 |
| | NEW 60 | 8:0 | 8X >8 |
| | NEW 84 | 8:0 | 8X >8 |
| | NEW 85 | 5:3 | 5, 7, 7, 5X >8 |
| | NEW 86 | 5:3 | 5, 6, 6, 5X >8 |

EXAMPLE 10

This example describes the cloning and expression of chimeric genes encoding for a chimeric protein corresponding to the carboxy-terminal region of BVH-3 or variants thereof in fusion, at either the carboxyl end or the amino end, to NEW43 or variants thereof.

The chimeric genes comprising a BVH-3 truncate variant gene and a NEW43 or NEW43 variant gene have been designed following the procedure described in example 1. The polypeptides encoded by these chimeric genes are listed in the table 22. Briefly, gene fragments to be included in a chimeric gene were amplified by PCR using pairs of oligonucleotides engineered so that the primers had a restriction endonuclease site at the 5' end, thereby allowing directional in-frame cloning of the amplified product into digested plasmid vectors (Table 23 and Table 24). PCR-amplified products were digested with restriction endonucleases and ligated to linearized plasmid pSL301 vector. The resultant plasmid construct were confirmed by nucleotide sequence analysis. The recombinant pSL301 plasmids containing a PCR product were redigested with the same endonuclease restriction enzyme for the obtention of the DNA inserts. The resulting insert DNA fragments were purified and inserts corresponding to a given chimeric gene were ligated into pURV22-NdeI vector for the generation of a chimeric gene. The expressed recombinant proteins were purified from supernatant fractions obtained from centrifugation of sonicated heat-induced *E. coli* cultures using multiple chromatographic purification steps.

TABLE 22

List of polypeptides encoded by chimeric genes comprising a BVH-3 truncate variant gene and a NEW43 or NEW43 variant gene

| Polypeptide designation | SEQ ID NO | Identification |
|---|---|---|
| VP 89 | 369 | M-New56 -GP- New43* |
| VP 90 | 370 | M-New43 -GP- New56 |
| VP 91 | 371 | M-New52 -GP- New43 |
| VP 92 | 372 | M-New43 -GP- New52 |
| VP 93 | 373 | M-New56 -GP- New60 |
| VP 94 | 332 | M-New60 -GP- New56 |
| VP108 | 333 | M-New56 -GP- New88 |
| VP109 | 334 | M-New88 -GP- New56 |
| VP110 | 335 | M-New60 -GP- New105 |
| VP111 | 336 | M-New60 -GP- New107 |
| VP112 | 337 | M-New88 -GP- New105 |
| VP113 | 338 | M-New88 -GP- New107 |
| VP114 | 339 | M-New80 -GP- New105 |
| VP115 | 340 | M-New80 -GP- New107 |
| VP116 | 341 | M-New83 -GP- New105 |
| VP117 | 342 | M-New83 -GP- New107 |
| VP119 | 343 | M-New43S- GP-New105 |
| VP120 | 344 | M-New43S- GP-New107 |
| VP121 | 345 | M-New80S- GP-New105 |
| VP122 | 346 | M-New80S- GP-New107 |
| VP123 | 347 | M-New88S- GP-New105 |
| VP124 | 348 | M-New88S- GP-New107 |

*Encoded amino acids for the chimeras are expressed as the gene product, additional amino acid residues were added. M is methionine, G is glycine and P is proline.

TABLE 23

List of PCR oligonucleotide primer pairs designed for the generation of the chimeric genes encoding the polypeptides listed in Table 22.

| Primer set | PCR-primer identification | Gene used for PCR amplification | Corresponding position of the gene fragment on the chimeric protein molecule |
|---|---|---|---|
| 49 | HAMJ490–HAMJ471 | Variant New43 | N-terminal |
| 50 | HAMJ564–HAMJ556 | Variant New43 | C-terminal |
| 51 | HAMJ489–HAMJ359 | Variant New40 | N-terminal |
| 52 | HAMJ559–HAMJ557 | Variant New40 | C-terminal |
| 53 | HAMJ610–HAMJ471 | Variant New43S | N-terminal |

TABLE 24

List of PCR oligonucleotide primers designed for the generation of the chimeric genes encoding the polypeptides listed in Table 22.

| Primer | SEQ ID NO | Sequence 5' - 3' | Restriction site |
|---|---|---|---|
| HAMJ490 | 259 | ccgaattccatatgcaaattacctacactgatgatg | NdeI |
| HAMJ471 | 168 | atatgggcccctgtataggagccggttgactttc | ApaI |
| HAMJ564 | 327 | atatgggccccaaattacctacactgatgatgagattcagg | ApaI |
| HAMJ556 | 328 | ataagaatgcggccgcctactgtataggagccggttgactttc | NotI |
| HAMJ489 | 329 | ccgaattccatatgcaaattgggcaaccgactc | NdeI |
| HAMJ359 | 173 | tcccgggccccgctatgaaatcagataaattc | ApaI |
| HAMJ559 | 330 | atatgggccccaaattgggcaaccgactc | ApaI |
| HAMJ354 | 65 | cgccaagcttctgtataggagccggttgac | HindIII |
| HAMJ610 | 268 | cttgatcgacatatgttggcaggcaagtacacaacag | NdeI |
| HAMJ557 | 331 | ataagaatgcggccgcttacgctatgaaatcagataaattc | NotI |
| HAMJ279 | 35 | cgccaagcttcgctatgaaatcagataaattc | HindIII |

What is claimed is:

1. An isolated polypeptide having the amino acid sequence of SEQ ID NO:332 or a polypeptide having at least 85% sequence similarity to SEQ ID NO:332 wherein the polypeptide elicits an immune response when administered to an individual.

2. An isolated polypeptide which has the amino acid sequence of SEQ ID NO:332.

3. A vaccine composition comprising a polypeptide according to claim 1 and a pharmaceutically acceptable carrier, diluent or adjuvant.

4. A vaccine composition comprising a polypeptide according to claim 2 and a pharmaceutically acceptable carrier, diluent or adjuvant.

5. A method of treating or preventing *Streptococcus pneumoniae* infection in an animal comprising administering to the animal a therapeutically or prophylactically effective amount of a vaccine composition according to claim 3.

6. A method of treating or preventing *Streptococcus pneumoniae* infection in an animal comprising administering to the animal a therapeutically or prophylactically effective amount of a vaccine composition according to claim 4.

* * * * *